US012508065B2

(12) United States Patent
Johnson et al.

(10) Patent No.: US 12,508,065 B2
(45) Date of Patent: Dec. 30, 2025

(54) METHOD OF TREATING TISSUE USING END EFFECTOR WITH ULTRASONIC AND ELECTROSURGICAL FEATURES

(71) Applicant: Cilag GmbH International, Zug (CH)

(72) Inventors: Gregory W. Johnson, Minneapolis, MN (US); Jason R. Lesko, Cincinnati, OH (US); Frederick L. Estera, Cincinnati, OH (US); Amy M. Krumm, Cincinnati, OH (US); Catherine A. Corbett, Cincinnati, OH (US); William B. Weisenburgh, II, Maineville, OH (US); Barry C. Worrell, Centerville, OH (US); Mark A. Davison, Maineville, OH (US); Chad P. Boudreaux, Cincinnati, OH (US); John A. Hibner, Mason, OH (US); Nathan Cummings, Worcester, MA (US); Ellen Burkart, Cincinnati, OH (US); William D. Dannaher, Cincinnati, OH (US); Christina M. Hough, Cincinnati, OH (US); Joseph Isosaki, Cincinnati, OH (US); Craig N. Faller, Batavia, OH (US); Shan Wan, Mason, OH (US); Adam N. Brown, Lebanon, OH (US); Candice Otrembiak, Loveland, OH (US); Eitan T. Wiener, Cincinnati, OH (US); Jeffrey D. Messerly, Cincinnati, OH (US); Kai Chen, Millburn, NJ (US); Matthew C. Miller, Cincinnati, OH (US); William E. Clem, Bozeman, MT (US)

(73) Assignee: Cilag GmbH International, Zug (CH)

( * ) Notice: Subject to any disclaimer, the term of this patent is extended or adjusted under 35 U.S.C. 154(b) by 900 days.

(21) Appl. No.: 17/410,361

(22) Filed: Aug. 24, 2021

(65) Prior Publication Data

US 2022/0039861 A1 Feb. 10, 2022

Related U.S. Application Data

(63) Continuation of application No. 15/355,892, filed on Nov. 18, 2016, now abandoned.

(Continued)

(51) Int. Cl.
*A61B 18/12* (2006.01)
*A61B 18/14* (2006.01)

(Continued)

(52) U.S. Cl.
CPC ................................ *A61B 18/1445* (2013.01); *A61B 2017/00389* (2013.01); *A61B 2017/2825* (2013.01);

(Continued)

(58) Field of Classification Search
CPC .... A61B 17/320092; A61B 2018/1455; A61B 2018/142; A61B 2018/126; A61B 18/1206; A61B 18/1442
See application file for complete search history.

(56) References Cited

U.S. PATENT DOCUMENTS 3,938,527 A 2/1976 Rioux et al.
5,269,780 A * 12/1993 Roos .................. A61B 18/1442 606/50

(Continued)

FOREIGN PATENT DOCUMENTS

CN 101040799 A 9/2007
CN 102497827 A 6/2012

(Continued)

OTHER PUBLICATIONS

Chinese Office Action and Search Report dated Jun. 16, 2020, for Application No. 20680072340.2, 17 pages.

(Continued)

*Primary Examiner* — Daniel W Fowler
(74) *Attorney, Agent, or Firm* — Frost Brown Todd LLP

(57) ABSTRACT

An end effector of an instrument is positioned in a patient. An ultrasonic blade of the end effector is positioned against tissue in the patient. The ultrasonic blade is activated to vibrate ultrasonically while the ultrasonic blade is positioned (Continued)

against tissue. At least one electrode of the end effector is positioned against tissue in the patient. The at least one electrode is activated to apply RF electrosurgical energy to tissue against which the at least one electrode is positioned against tissue.

19 Claims, 68 Drawing Sheets

Related U.S. Application Data

(60) Provisional application No. 62/365,543, filed on Jul. 22, 2016, provisional application No. 62/324,428, filed on Apr. 19, 2016, provisional application No. 62/265,611, filed on Dec. 10, 2015.

(51) Int. Cl.
*A61B 17/00* (2006.01)
*A61B 17/28* (2006.01)
*A61B 17/29* (2006.01)
*A61B 17/32* (2006.01)
*A61B 18/00* (2006.01)

(52) U.S. Cl.
CPC ................. *A61B 2017/2945* (2013.01); *A61B 2017/320073* (2017.08); *A61B 2017/320078* (2017.08); *A61B 2017/320094* (2017.08); *A61B 2017/320095* (2017.08); *A61B 2018/00607* (2013.01); *A61B 2018/00994* (2013.01); *A61B 2018/126* (2013.01); *A61B 2018/1452* (2013.01)

(56) References Cited

U.S. PATENT DOCUMENTS

| | | | | |
|---|---|---|---|---|
| 5,322,055 | A | 6/1994 | Davison et al. | |
| 5,324,299 | A | 6/1994 | Davison et al. | |
| 5,873,873 | A | 2/1999 | Smith et al. | |
| 5,891,141 | A * | 4/1999 | Rydell | A61B 18/1485 606/45 |
| 5,980,510 | A | 11/1999 | Tsonton et al. | |
| 6,132,427 | A * | 10/2000 | Jones | A61B 18/1402 606/41 |
| 6,152,923 | A * | 11/2000 | Ryan | A61B 18/1445 606/42 |
| 6,283,981 | B1 | 9/2001 | Beaupre | |
| 6,309,400 | B2 | 10/2001 | Beaupre | |
| 6,325,811 | B1 | 12/2001 | Messerly | |
| 6,423,082 | B1 | 7/2002 | Houser et al. | |
| 6,500,176 | B1 | 12/2002 | Truckai et al. | |
| 6,773,444 | B2 | 8/2004 | Messerly | |
| 6,783,524 | B2 | 8/2004 | Anderson et al. | |
| 7,052,496 | B2 * | 5/2006 | Yamauchi | A61B 18/1442 606/49 |
| 7,112,201 | B2 | 9/2006 | Truckai et al. | |
| 7,125,409 | B2 | 10/2006 | Truckai et al. | |
| 7,169,146 | B2 | 1/2007 | Truckai et al. | |
| 7,186,253 | B2 | 3/2007 | Truckai et al. | |
| 7,189,233 | B2 | 3/2007 | Truckai et al. | |
| 7,220,951 | B2 | 5/2007 | Truckai et al. | |
| 7,309,849 | B2 | 12/2007 | Truckai et al. | |
| 7,311,709 | B2 | 12/2007 | Truckai et al. | |
| 7,354,440 | B2 | 4/2008 | Truckai et al. | |
| 7,381,209 | B2 | 6/2008 | Truckai et al. | |
| 7,544,200 | B2 | 6/2009 | Houser | |
| 7,645,278 | B2 | 1/2010 | Ichihashi et al. | |
| 7,819,866 | B2 | 10/2010 | Bednarek | |
| 8,057,498 | B2 | 11/2011 | Robertson | |
| 8,461,744 | B2 | 6/2013 | Wiener et al. | |
| 8,591,536 | B2 | 11/2013 | Robertson | |
| 8,623,027 | B2 | 1/2014 | Price et al. | |
| 8,663,220 | B2 | 3/2014 | Wiener et al. | |
| 8,911,460 | B2 | 12/2014 | Neurohr et al. | |
| 8,986,302 | B2 | 3/2015 | Aldridge et al. | |
| 9,017,326 | B2 | 4/2015 | DiNardo et al. | |
| 9,023,071 | B2 | 5/2015 | Miller et al. | |
| 9,095,367 | B2 | 8/2015 | Olson et al. | |
| 9,237,900 | B2 | 1/2016 | Boudreaux et al. | |
| 9,381,058 | B2 | 7/2016 | Houser et al. | |
| 9,393,037 | B2 | 7/2016 | Olson et al. | |
| 9,724,120 | B2 | 8/2017 | Faller et al. | |
| 10,028,765 | B2 | 7/2018 | Hibner et al. | |
| 10,660,692 | B2 | 5/2020 | Lesko et al. | |
| 2002/0128649 | A1 * | 9/2002 | Bacher | A61B 18/1445 606/51 |
| 2003/0171747 | A1 | 9/2003 | Kanehira et al. | |
| 2004/0087943 | A1 | 5/2004 | Dycus et al. | |
| 2004/0143256 | A1 | 7/2004 | Bednarek | |
| 2005/0004570 | A1 | 1/2005 | Chapman et al. | |
| 2005/0033278 | A1 | 2/2005 | McClurken et al. | |
| 2005/0113827 | A1 | 5/2005 | Dumbauld | |
| 2005/0192612 | A1 * | 9/2005 | Houser | A61B 17/320092 606/169 |
| 2006/0079874 | A1 | 4/2006 | Faller et al. | |
| 2007/0078458 | A1 | 4/2007 | Dumbauld et al. | |
| 2007/0191713 | A1 | 8/2007 | Eichmann et al. | |
| 2007/0270798 | A1 | 11/2007 | Lu et al. | |
| 2007/0282333 | A1 | 12/2007 | Fortson et al. | |
| 2008/0132887 | A1 | 6/2008 | Masuda et al. | |
| 2008/0200940 | A1 | 8/2008 | Eichmann et al. | |
| 2008/0234711 | A1 * | 9/2008 | Houser | A61B 17/320068 606/169 |
| 2008/0243213 | A1 * | 10/2008 | Takashino | A61B 18/1445 607/115 |
| 2008/0294222 | A1 | 11/2008 | Schechter | |
| 2010/0292691 | A1 | 11/2010 | Brogna | |
| 2011/0015660 | A1 | 1/2011 | Wiener et al. | |
| 2012/0116265 | A1 | 5/2012 | Houser et al. | |
| 2012/0116391 | A1 | 5/2012 | Houser et al. | |
| 2012/0203143 | A1 * | 8/2012 | Sanai | A61B 17/320092 601/3 |
| 2013/0046303 | A1 | 2/2013 | Evans et al. | |
| 2013/0103030 | A1 * | 4/2013 | Garrison | A61B 18/1442 606/45 |
| 2013/0150848 | A1 | 6/2013 | Yasunaga | |
| 2014/0005667 | A1 * | 1/2014 | Stulen | A61B 18/1445 606/45 |
| 2014/0135804 | A1 | 5/2014 | Weisenburgh, II et al. | |
| 2014/0275977 | A1 * | 9/2014 | Curley | A61M 5/007 600/431 |
| 2014/0276785 | A1 | 9/2014 | Batchelor et al. | |
| 2015/0080924 | A1 | 3/2015 | Stulen et al. | |
| 2015/0141981 | A1 | 5/2015 | Price et al. | |
| 2015/0148835 | A1 * | 5/2015 | Faller | A61B 17/320068 |
| 2017/0164972 | A1 | 6/2017 | Johnson et al. | |
| 2017/0164997 | A1 | 6/2017 | Johnson et al. | |
| 2020/0315686 | A1 | 10/2020 | Lesko et al. | |
| 2022/0039858 | A1 | 2/2022 | Johnson et al. | |

FOREIGN PATENT DOCUMENTS

| | | | |
|---|---|---|---|
| WO | WO 2008/118709 | A1 | 10/2008 |
| WO | WO 2013/115036 | A1 | 1/2013 |
| WO | WO 2017/100423 | A2 | 6/2017 |
| WO | WO 2017/100427 | A2 | 6/2017 |

OTHER PUBLICATIONS

International Search Report and Written Opinion dated Sep. 25, 2017, for International Application No. PCT/US2016/065570, 15 pages.
International Search Report and Written Opinion dated Sep. 25, 2017, for International Application No. PCT/US2016/065575, 13 pages.
International Search Report and Written Opinion dated Feb. 2, 2018, for International Application No. PCT/US2017/057871, 11 pages.
Japanese Notification of Reasons for Refusal dated Nov. 17, 2020, for Application No. 2018-530107, 4 pages.

(56) References Cited

OTHER PUBLICATIONS

U.S. Appl. No. 61/410,603, filed Nov. 5, 2010.
U.S. Appl. No. 62/265,611, filed Dec. 10, 2015.
U.S. Appl. No. 62/324,428, filed Apr. 19, 2016.
U.S. Appl. No. 62/365,543, filed Jul. 22, 2016.

* cited by examiner

METHOD OF TREATING TISSUE USING END EFFECTOR WITH ULTRASONIC AND ELECTROSURGICAL FEATURES

PRIORITY

This application is a continuation of U.S. patent application Ser. No. 15/355,892, entitled "Method of Treating Tissue Using End Effector with Ultrasonic and Electrosurgical Features," filed Nov. 18, 2016, and published as U.S. Pub. No. 2017/0164997 on Jun. 15, 2017.

U.S. patent application Ser. No. 15/355,892 claims priority to U.S. Provisional Pat. App. No. 62/265,611, entitled "End Effector for Instrument with Ultrasonic and Electrosurgical Features," filed Dec. 10, 2015, the disclosure of which is incorporated by reference herein.

U.S. patent application Ser. No. 15/355,892 also claims priority to U.S. Provisional Pat. App. No. 62/324,428, entitled "End Effector for Instrument with Ultrasonic and Electrosurgical Features," filed Apr. 19, 2016, the disclosure of which is incorporated by reference herein.

U.S. patent application Ser. No. 15/355,892 also claims priority to U.S. Provisional Pat. App. No. 62/365,543, entitled "End Effector for Instrument with Ultrasonic and Electrosurgical Features," filed Jul. 22, 2016, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No.

6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," issued as U.S. Pat. No. 9,095,367 on Aug. 4, 2015, the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 98 depicts a perspective view of the tube assembly of FIG. 97;

FIG. 99 depicts a side view of a proximal portion of the tube assembly of FIG. 95, showing electrical connections of the tube assembly with electrical components;

FIG. 100 depicts a perspective view of the proximal portion of the tube assembly of FIG. 99;

FIG. 101 depicts a perspective view of an exemplary actuation ring usable with the end effector of FIG. 91 to open and close the end effector;

FIG. 102 depicts a cross-section view of another exemplary end effector that may be incorporated into the instrument of FIG. 1;

FIG. 103 depicts a bottom view of an exemplary clamp pad of the end effector of FIG. 102;

FIG. 104 depicts a bottom view of another exemplary clamp pad of the end effector of FIG. 102;

FIG. 105 depicts a side view of another exemplary end effector, shown in a shear device;

FIG. 106 depicts a cross-section view of the end effector of FIG. 105 taken along the distal section at line A-A of FIG. 105;

FIG. 107 depicts a cross-section view of the end effector of FIG. 105 taken along the proximal section at line B-B of FIG. 105;

FIG. 108 depicts a cross-section view of another version of the end effector of FIG. 105 taken along the distal section at line A-A of FIG. 105;

FIG. 109 depicts a cross-section view of the end effector of FIG. 108 taken along the proximal section at line B-B of FIG. 105;

Figure 1:
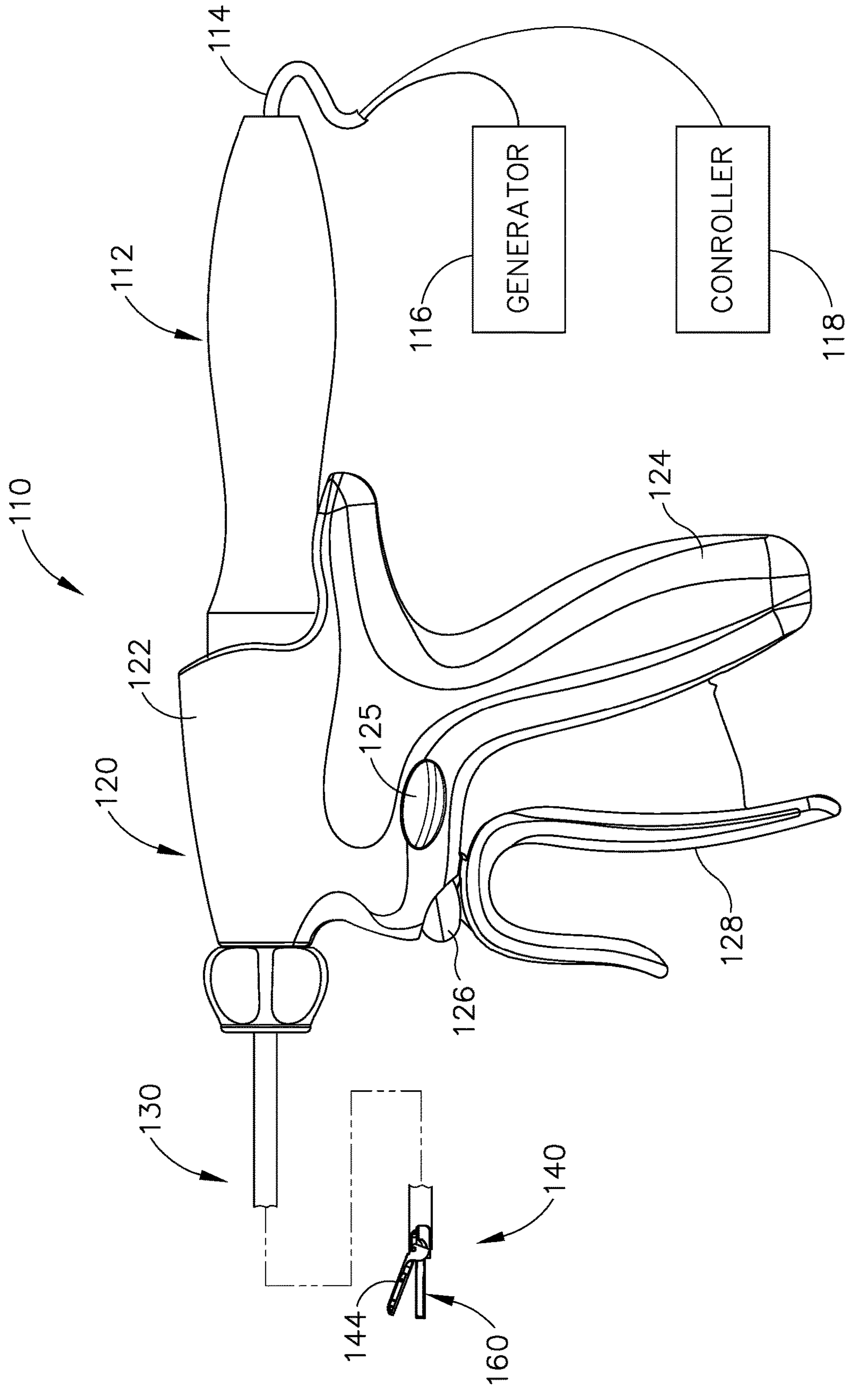
FIG. 1 depicts a side elevational view of an exemplary surgical instrument.
Figure 2A:
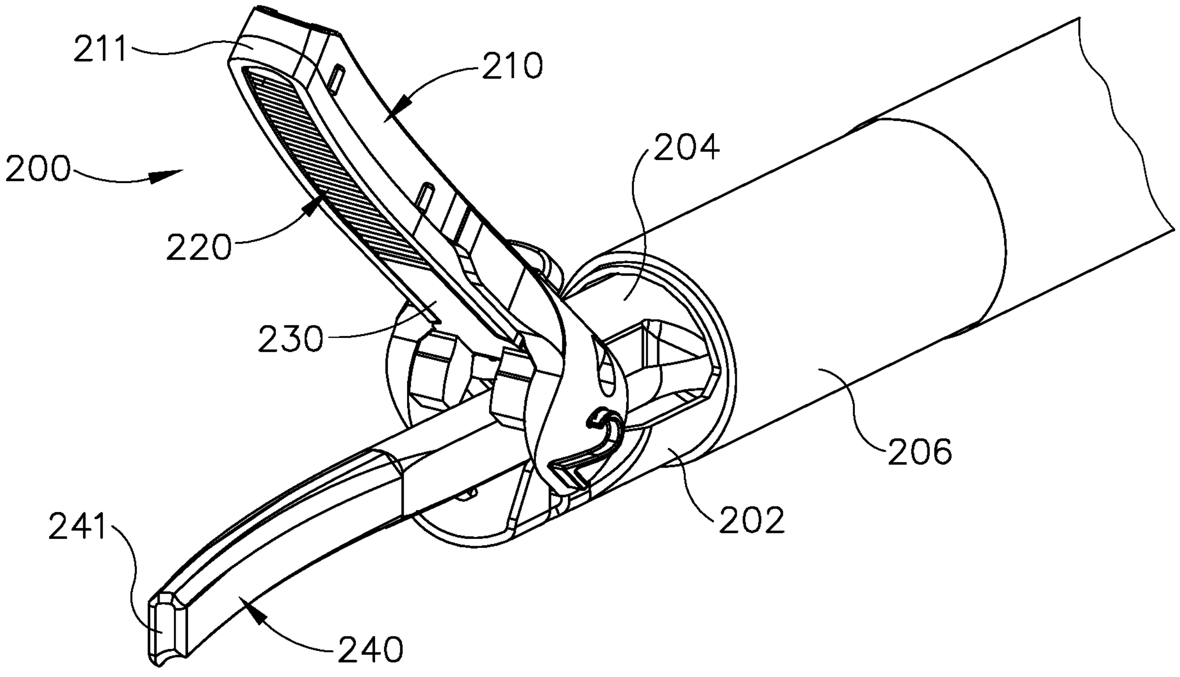
FIG. 2A depicts a perspective view of an exemplary end effector that may be incorporated into the instrument of FIG. 1, with the end effector in an open configuration.
Figure 2B:
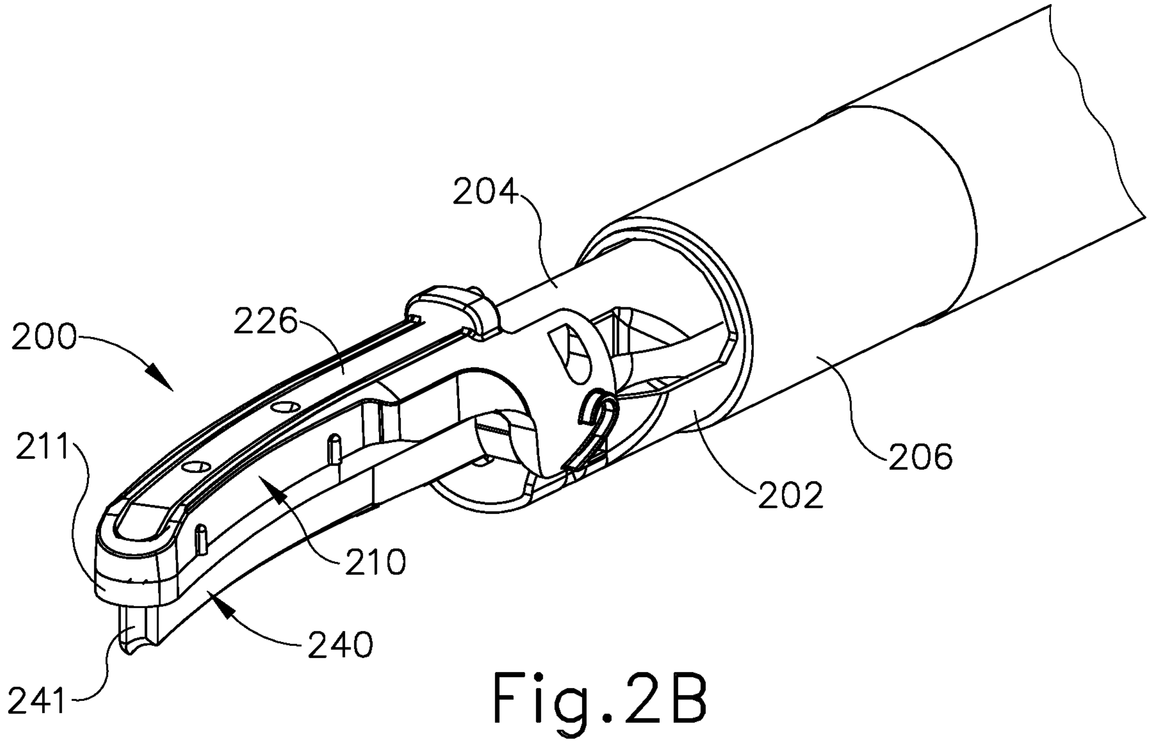
FIG. 2B depicts a perspective view of the end effector of FIG. 2A, with the end effector in a closed configuration.
Figure 105:
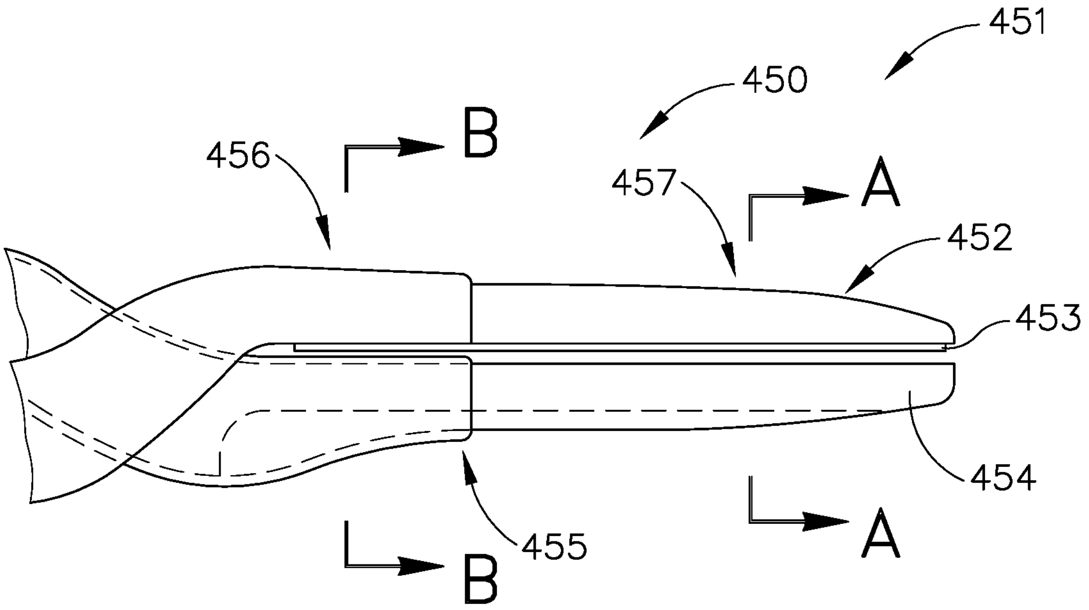
Figure 110:
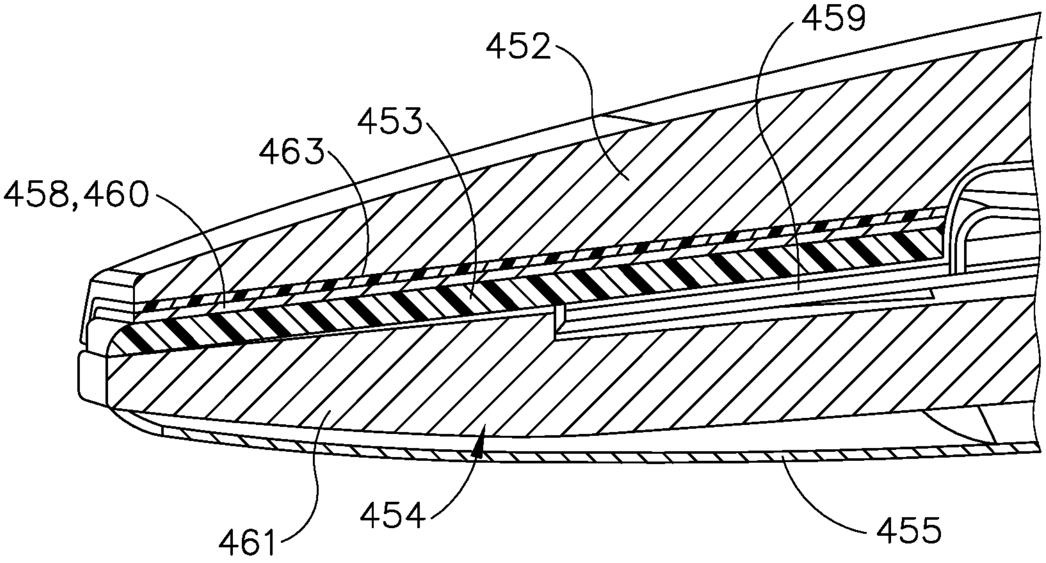
Figure 111:
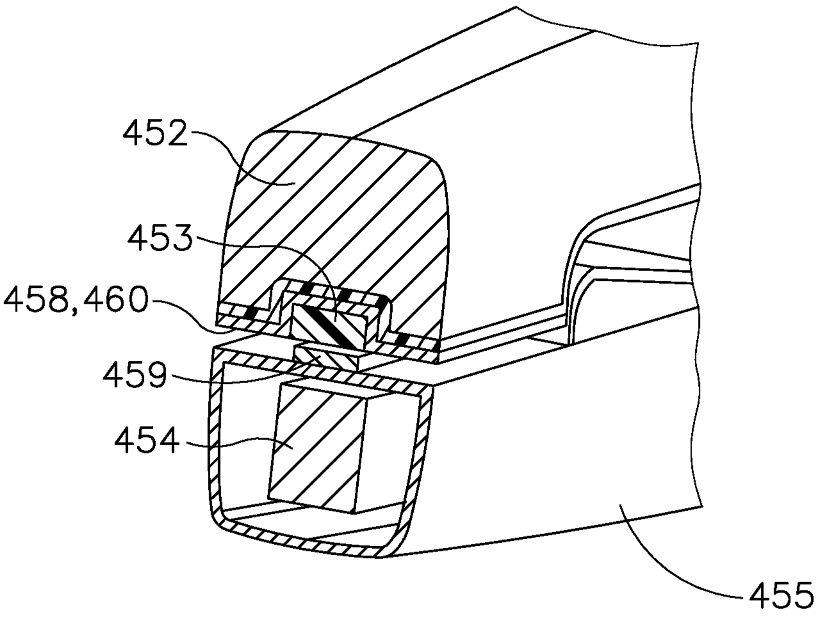
Figure 112:
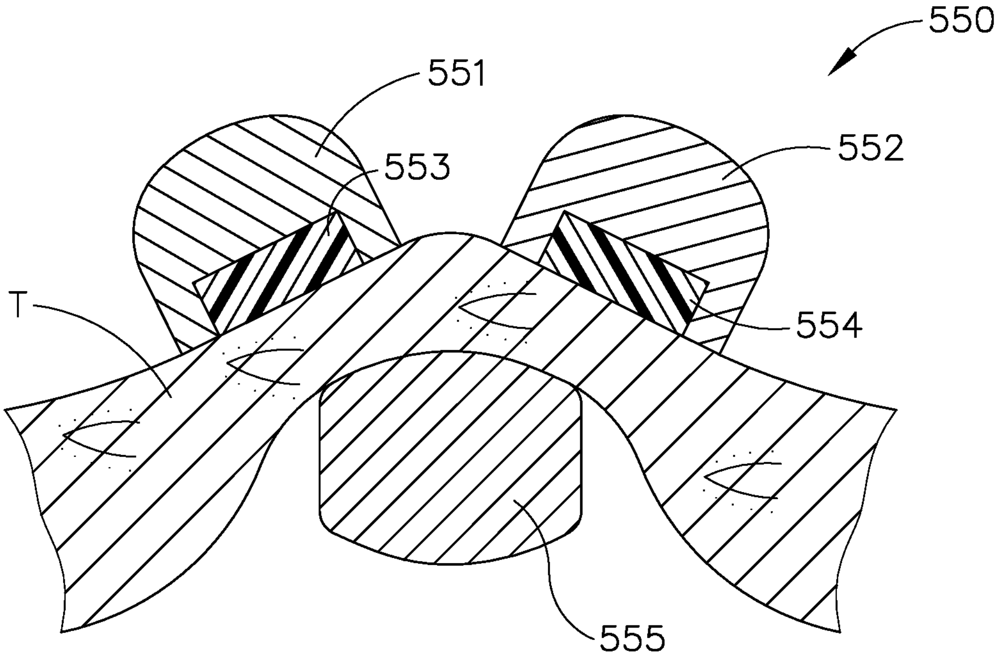
Figure 113:
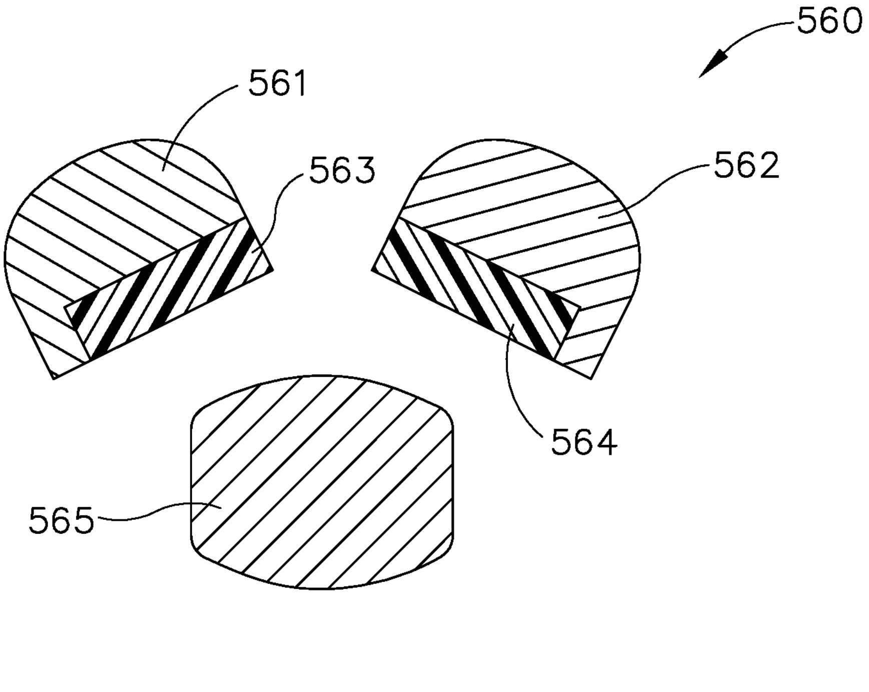
Figure 114:
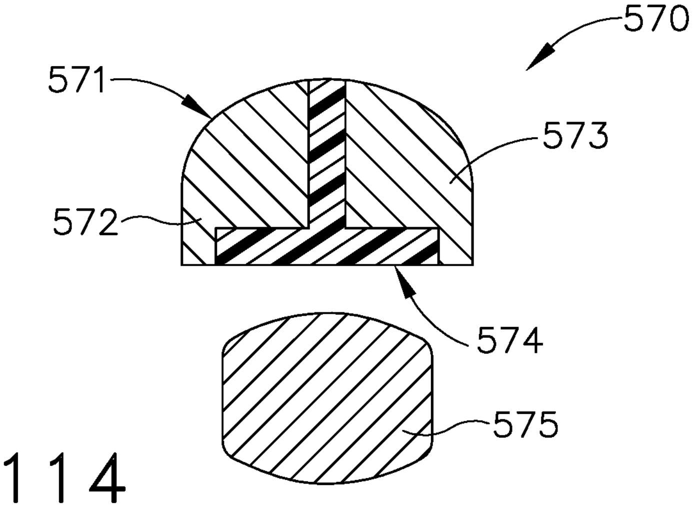
Figure 115:
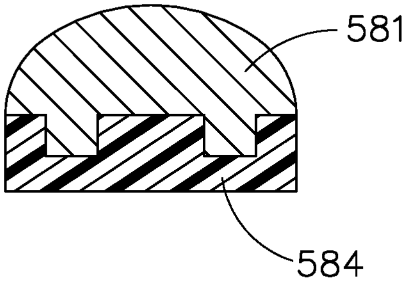
Figure 116:
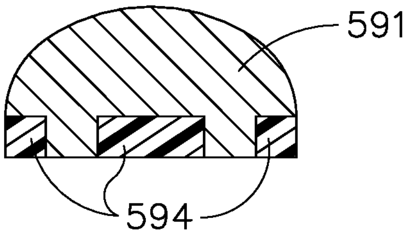
Figure 117:
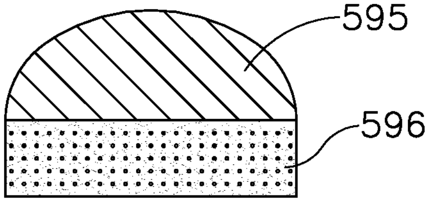

FIG. 110 depicts a perspective view in side cross-section of another version of the end effector of FIG. 105;

FIG. 111 depicts a perspective view in end cross-section of the end effector of FIG. 110;

FIG. 112 depicts a cross-section view of another exemplary end effector that may be incorporated into the instrument of FIG. 1;

FIG. 113 depicts a cross-section view of another exemplary end effector that may be incorporated into the instrument of FIG. 1;

FIG. 114 depicts a cross-section view of another exemplary end effector that may be incorporated into the instrument of FIG. 1;

FIG. 115 depicts a cross-section view of an exemplary alternative clamp pad to clamp arm arrangement that may be incorporated into the instrument of FIG. 1;

FIG. 116 depicts a cross-section view of another exemplary alternative clamp pad to clamp arm arrangement that may be incorporated into the instrument of FIG. 1; and FIG. 117 depicts a cross-section view of another exemplary alternative clamp pad to clamp arm arrangement that may be incorporated into the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms “proximal” and “distal” are defined herein relative to a human or robotic operator of the surgical instrument. The term “proximal” refers the position of an element closer to the human or robotic operator of the surgical instrument and further away from the surgical end effector of the surgical instrument. The term “distal” refers to the position of an element closer to the surgical end effector of the surgical instrument and further away from the human or robotic operator of the surgical instrument.

I. Exemplary Ultrasonic Surgical Instrument with Integrated RF Energy

FIG. 1 illustrates an exemplary ultrasonic surgical instrument (110). At least part of instrument (110) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2015; U.S. Pub. No. 2012/0116265; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (110) is operable to cut tissue and seal or weld tissue (e.g., a blood vessel, etc.) substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (110) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (110), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (125, 126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 1.

An ultrasonic transducer assembly (112) extends proximally from body (122) of handle assembly (120) in the present example. In some other versions, transducer assembly (112) is fully integrated within body (122). Transducer assembly (112) receives electrical power from generator (116) and converts that power into ultrasonic vibrations through piezoelectric principles. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, it should be understood that controller (118) and generator (116) may be integrated together in a single unit. By way of example only, generator (116) may comprise a GEN04, GEN11, or GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad that is secured to the underside of clamp arm (144), facing blade (160). By way of example only, the clamp pad may be formed of a polytetrafluoroethylene (PTFE) material and/or any other suitable material(s). By way of further example only, the clamp pad may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of trigger (128) toward pistol grip (124). Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the acoustic waveguide and blade (160) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

End effector (140) of the present example is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (110) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

Buttons (125, 126) may provide the operator with varied control of the energy that is applied to tissue through end effector (140). For instance, in some versions, button (125) may be activated to apply RF electrosurgical energy to tissue; while button (126) may be activated to apply ultrasonic energy to tissue. As another merely illustrative example, button (125) may be activated to apply ultrasonic energy to tissue at a low power level (e.g., without also applying RF electrosurgical energy to tissue, applying RF electrosurgical energy to tissue simultaneously, or applying RF electrosurgical energy to tissue in a sequence with the ultrasonic energy); while button (126) may be activated to apply ultrasonic energy to tissue at a high power level (e.g., without also applying RF electrosurgical energy to tissue, applying RF electrosurgical energy to tissue simultaneously, or applying RF electrosurgical energy to tissue in a sequence with the ultrasonic energy). In addition or in the alternative, buttons (125, 126) may provide functionality in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. Other suitable ways in which buttons (125, 126) may provide operation of instrument (110) will be apparent to those of ordinary skill in the art in view of the teachings herein.

II. Exemplary End Effector Configurations

As noted above, end effector (140) may include various kinds of electrode configurations to apply RF electrosurgical energy to tissue. It should also be understood that ultrasonic blade (160) may have various structural configurations. These various structural configurations of ultrasonic blade (160) may provide different kinds of effects on tissue. In particular, the particular structural configuration of ultrasonic blade (160) may influence the way in which ultrasonic blade (160) applies ultrasonic energy to tissue. For instance, some ultrasonic blade (160) configurations may provide better ultrasonic cutting of tissue while other ultrasonic blade (160) configurations may provide better ultrasonic sealing of tissue. The relationships between the structural configurations of the electrode(s) and ultrasonic blade (160) may also influence the way in which end effector (140) applies RF electrosurgical energy to tissue. The following discussion provides various examples of different end effector configurations. It should be understood that any of the various end effectors described below may be readily incorporated into instrument (110), in place of end effector (140).

It should also be understood that all of the end effectors described below may include features that are configured to ensure that a minimum gap is defined between the variation of clamp arm (144) and the variation of blade (160), even when the variation of end effector (140) is in a fully closed configuration. Such a minimum gap will prevent the variation of clamp arm (144) from contacting the variation of blade (160), which will prevent formation of a short circuit between an electrode of the variation of clamp arm (144) and the variation of blade (160). This may be particularly important when the variation of end effector is being used to provide bipolar RF electrosurgical energy to tissue, with the electrode of the variation of clamp arm (144) providing one pole for the RF electrosurgical energy and the variation of blade (160) providing the other pole for the RF electrosurgical energy. A minimum gap may also selected to prevent arcing of such energy, where the arcing might otherwise occur when a gap is sized below the predetermined minimum amount. By way of example only, a minimum gap may be provided in accordance with at least some of the teachings of U.S. patent application Ser. No. 14/928,375, entitled "Ultrasonic Surgical Instrument Clamp Arm with Proximal Nodal Pad," filed Oct. 30, 2015, issued as U.S. Pat. No. 10,028,765 on Jul. 25, 2018, the disclosure of which is incorporated by reference herein. Other suitable ways in which a minimum gap may be provided will be apparent to those of ordinary skill in the art in view of the teachings herein.

A. End Effector with Blade Having Narrow Width and Peaked Contact Surface

FIGS. 2A-3B and 10-11 show one merely illustrative example of an end effector (200) that may be readily incorporated into instrument (110) in place of end effector (140). End effector (200) of this example comprises a clamp arm (210) and an ultrasonic blade (240). Clamp arm (210) is configured to pivot relative to blade (240) between an open position (FIGS. 2A and 3A) and a closed position (FIGS. 2B and 3B) to selectively receive and clamp tissue in end effector (200). To provide this pivotal movement, clamp arm (210) is pivotably coupled with an outer tube (202) at one pivot point; and with inner tube (204) at another pivot point. Thus, relative longitudinal movement between tubes (202, 204) provides pivotal movement of clamp arm (210). In some versions, outer tube (202) is configured to translate longitudinally relative to inner tube (204), while inner tube (204) remains longitudinally stationary, to provide pivotal movement of clamp arm (210). In some other versions, inner tube (204) is configured to translate longitudinally relative to outer tube (202), while outer tube (202) remains longitudinally stationary, to provides pivotal movement of clamp arm (210). Whichever tube (202, 204) is movable, the movable tube (202, 204) may be coupled with trigger (128) such that pivotal movement of trigger (128) relative to pistol grip (124) may provide the longitudinal movement of the movable tube (202, 204). Various suitable ways in which trigger (128) may be coupled with the movable tube (202, 204) will be apparent to those of ordinary skill in the art in view of the teachings herein. It should also be understood that tubes (202, 204) may form part of shaft assembly (130).

Figure 4:
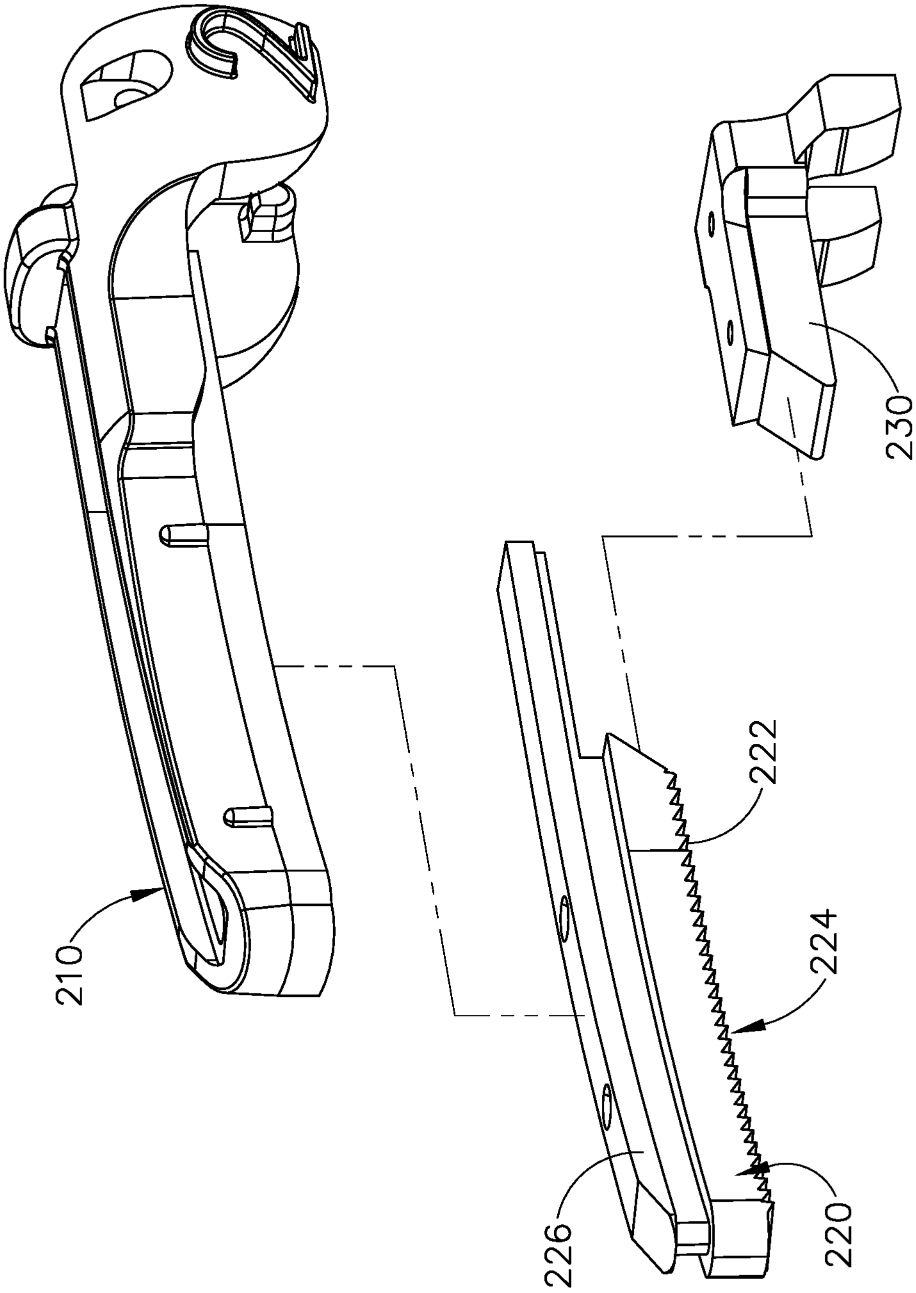
FIG. 4 depicts an exploded perspective view of a clamp arm assembly of the end effector of FIG. 2A.
Figure 5:
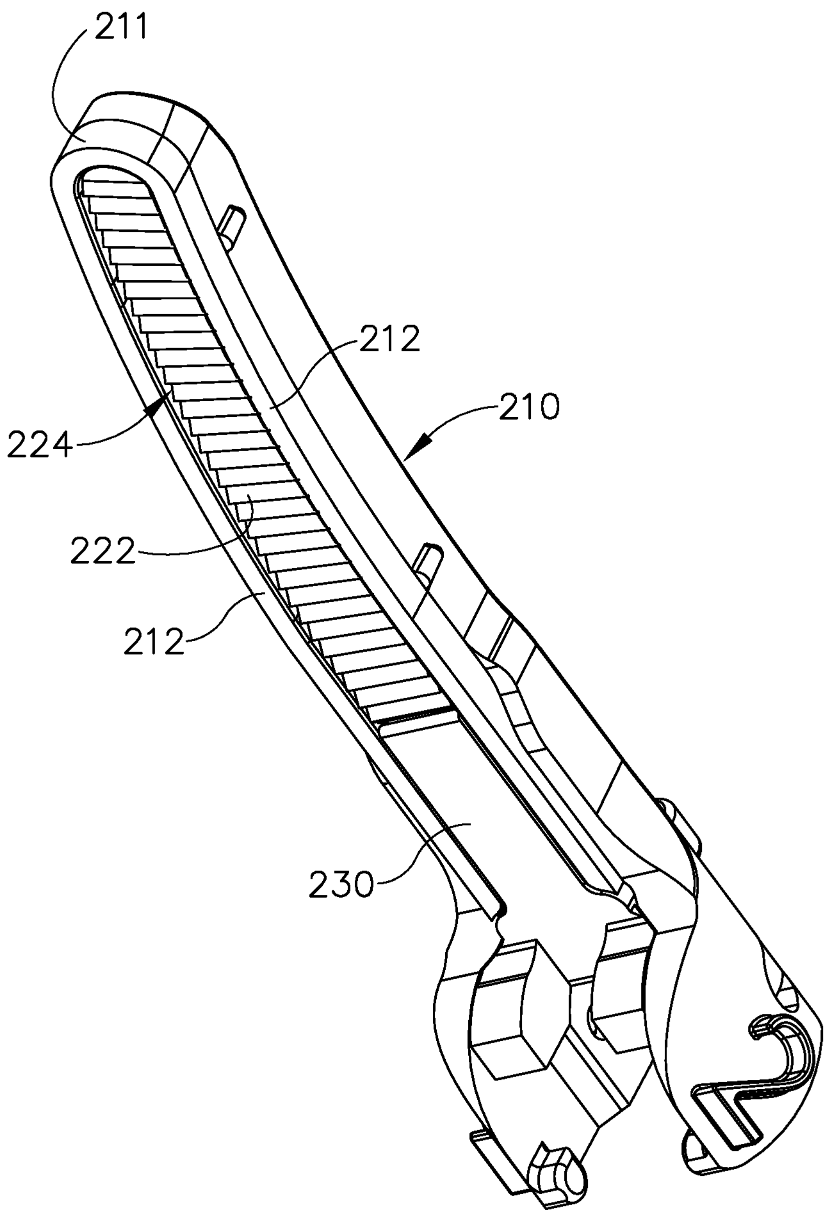
FIG. 5 depicts a perspective view of the clamp arm assembly of FIG. 4.

As best seen in FIGS. 2A-2B and 4-5, clamp arm (210) of the present example includes a clamp pad (220) and a clamp pad retainer member (230). As best seen in FIG. 5, clamp arm (210) further includes a U-shaped electrode surface (212). Clamp pad (220) includes a plurality of teeth (222) and valleys (224) that assist in gripping tissue that is clamped between clamp arm (210) and blade (240). As best seen in FIG. 4, clamp pad (220) includes a rail (226) that allows clamp pad (220) to be slid into the body of clamp arm (210). Retainer member (230) is also configured to be secured to the body of clamp arm (210), proximal to clamp pad (220), to thereby further secure clamp pad (220) to the body of clamp arm (210). It should also be understood that retainer member (230) may engage the sides of blade (240) in order to ensure proper lateral/yaw alignment of clamp arm (210) relative to blade (240) during closure of clamp arm (210). By way of example only, retainer member (230) may provide such alignment in accordance with at least some of the teachings of U.S. patent application Ser. No. 14/928,375, entitled “Ultrasonic Surgical Instrument Clamp Arm with Proximal Nodal Pad,” filed Oct. 30, 2015, issued as U.S. Pat. No. 10,028,765 on Jul. 25, 2018, the disclosure of which is incorporated by reference herein. Other suitable ways in which end effector (200) may provide proper alignment between clamp arm (210) and blade (240) will be apparent to those of ordinary skill in the art in view of the teachings herein. Similarly, other suitable ways in which clamp pad (220) may be secured to the body of clamp arm (210) will be apparent to those of ordinary skill in the art in view of the teachings herein.

As best seen in FIG. 5, electrode surface (212) extends all the way around the distal end (211) of clamp arm (210), surrounding the outer perimeter of clamp pad (220). In the present example, electrode surface (212) is flush with the ridges of teeth (222), such that valleys (224) are recessed relative to electrode surface (212). In some alternative versions, the ridges of teeth (222) are recessed relative to electrode surface (212). In some other alternative versions, the ridges of teeth (222) are proud relative to electrode surface (212), such that electrode surface is recessed relative to the ridges of teeth (222). Other suitable relationships will be apparent to those of ordinary skill in the art in view of the teachings herein.

Electrode surface (212) is coupled with generator (116) and controller (118) such that electrode surface (212) is configured to provide one pole of bipolar RF electrosurgical energy to tissue. In the present example, blade (240) is configured to provide the other pole of bipolar RF electrosurgical energy to tissue. Thus, electrode surface (212) and blade (240) cooperate to apply bipolar RF electrosurgical energy to tissue. Various suitable ways in which electrode surface (212) and blade (240) may be coupled with generator (116) and controller (118) to apply bipolar RF electrosurgical energy to tissue will be apparent to those of ordinary skill in the art in view of the teachings herein. In some versions, outer tube (202) provides an electrical path between electrode surface (212) and generator (116). In some such versions, a sheath (206) may be disposed about outer tube (202). Such a sheath (206) may be formed of an electrically insulative material, such that sheath (206) shields the operator from the electrical path provided along outer tube (202).

Figure 6:
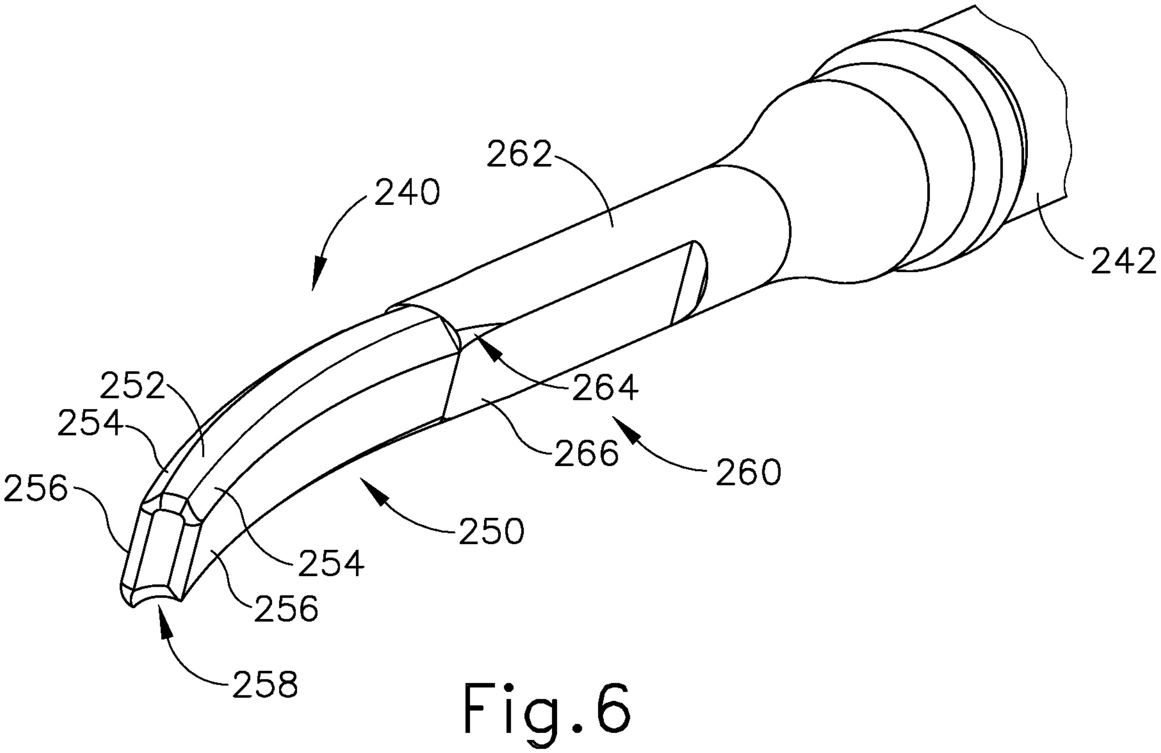
FIG. 6 depicts a perspective view of an ultrasonic blade of the end effector of FIG. 2A.

FIGS. 6-9 show blade (240) in greater detail. As best seen in FIG. 6, blade (240) is curved, such that blade (240) extends along a path that curvingly deviates from the longitudinal axis defined by acoustic waveguide (242). Clamp arm (210) follows the same curve. In some versions, blade (240) and clamp arm (210) are straight instead of being curved. It should be understood that acoustic waveguide (242) may be coupled with transducer (112); and that acoustic waveguide (242) may form part of shaft assembly (130). In particular, acoustic waveguide (242) may be coaxially positioned within tubes (202, 204) described above. Blade (240) includes a distal portion (250) and a proximal portion (260). Distal portion (250) is located within a region of end effector (200) that is intended to grasp and manipulate tissue. In particular, distal portion (250) is located at a region associated with the length of clamp pad (220). Proximal portion (260) is located within a region of end effector (200) that is not intended to grasp and manipulate tissue. In particular, proximal portion (260) is located at a region associated with the length of retainer member (230). In the present example, end effector (200) is configured such that tissue may nevertheless be received between proximal portion (260) and retainer member (230) when end effector (200) is in a fully open configuration. In some other versions, end effector (200) includes stops or other features that prevent tissue from reaching the region between proximal portion (260) and retainer member (230).

Figure 7:
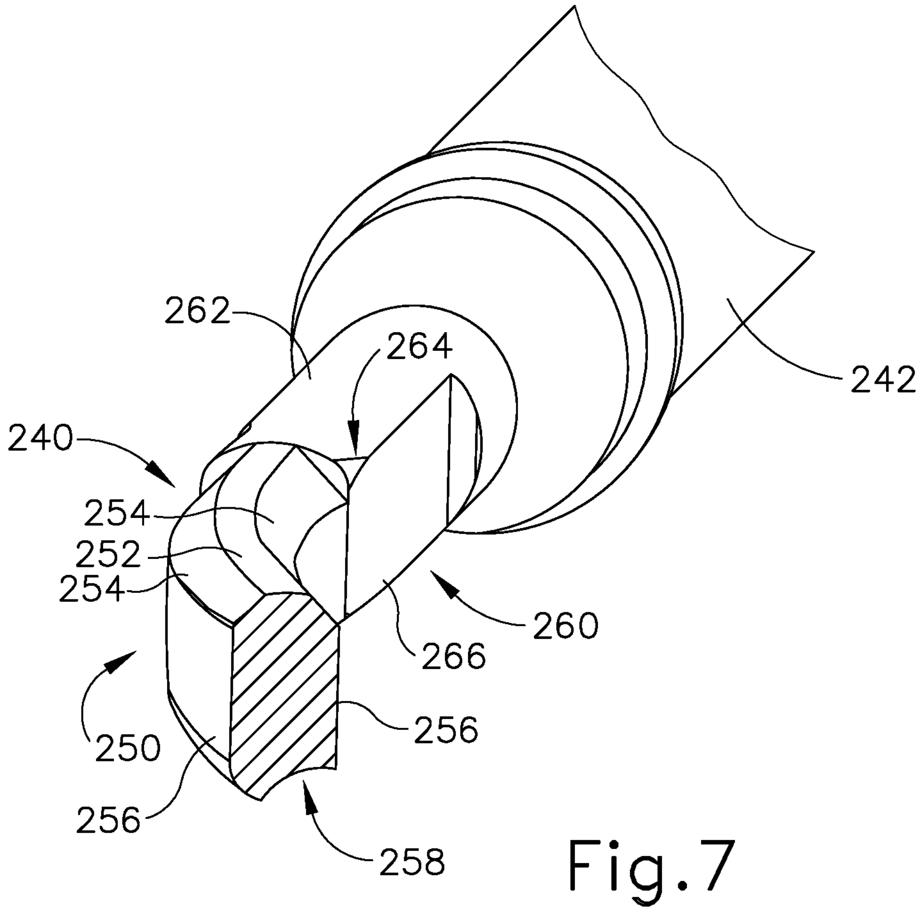
FIG. 7 depicts a perspective cross-sectional view of the ultrasonic blade of FIG. 6, with the cross-section taken at a distal portion of the ultrasonic blade.
Figure 8:
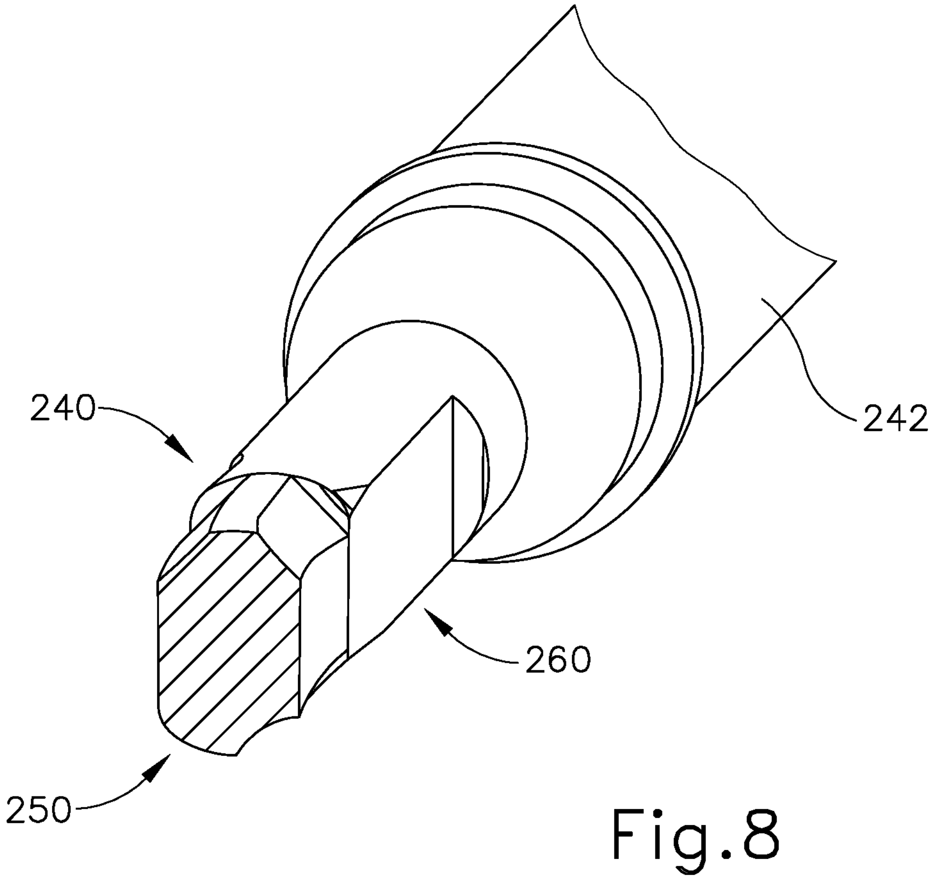
FIG. 8 depicts a perspective cross-sectional view of the ultrasonic blade of FIG. 6, with the cross-section taken at an intermediate portion of the ultrasonic blade.

As best seen in FIGS. 7-8, distal portion (250) of blade (240) has an upper contact surface (252) flanked by a pair of oblique surfaces (254); as well as a pair of laterally presented surfaces (256). The bottom of blade (240) includes a concave cutout (258). In some versions, upper contact surface (252) is flat. In some other versions, upper contact surface (252) is curved. Oblique surfaces (254) are flat in this example, though other versions may have oblique surfaces (254) that are curved or have some other surface geometry. Laterally presented surfaces (256) are also flat in this example, though other versions may have surfaces (256) that are curved, angled, or have some other surface geometry. Concave cutout (258) is configured to provide blade (240) with back-cutting capabilities as is known in the art. It should be understood that cutout (258) may be configured in numerous ways; and may even be omitted if desired.

Figure 9:
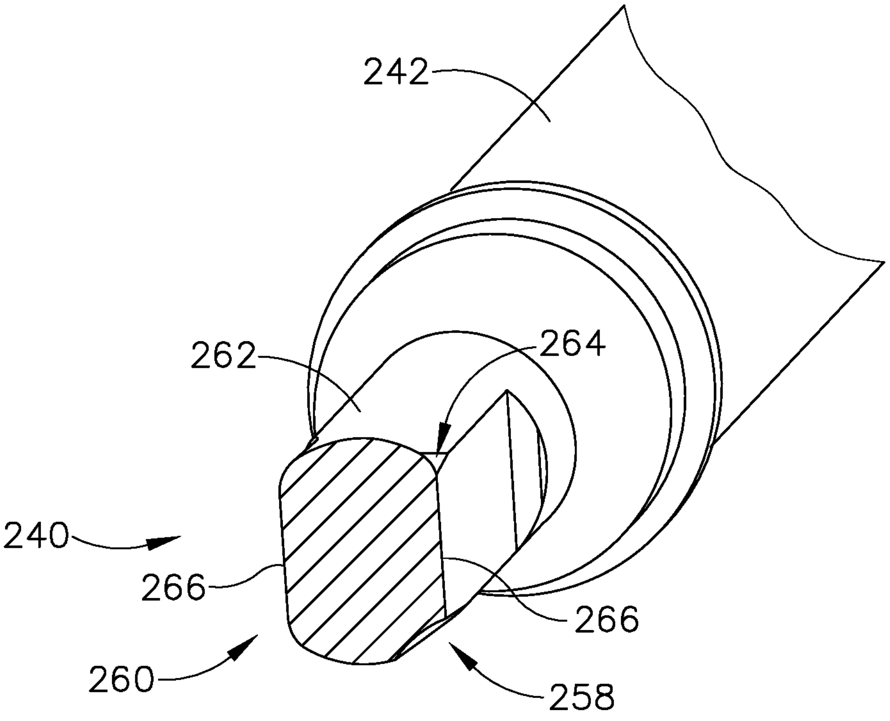
FIG. 9 depicts a perspective cross-sectional view of the ultrasonic blade of FIG. 6, with the cross-section taken at a proximal portion of the ultrasonic blade.

As best seen in FIGS. 6 and 9, proximal portion (260) of blade (240) has an upper curved surface (262), a pair of chamfers (264), and a pair of laterally presented surfaces (266). In the present example, chamfers (264) extend along only part of the length of proximal portion (260), at the distal end of proximal portion (260). In some other versions, chamfers (264) extend along the full length of proximal portion (260). As also shown in FIG. 9, at least a portion of cutout (258) extends into at least a portion of the length of proximal portion (260). In some other versions, cutout (258) stops short of proximal portion (260), such that cutout (258) does not extend into any portion of the length of proximal portion (260). In still other versions cutout (258) extends along the full length of proximal portion (260).

Figure 3A:
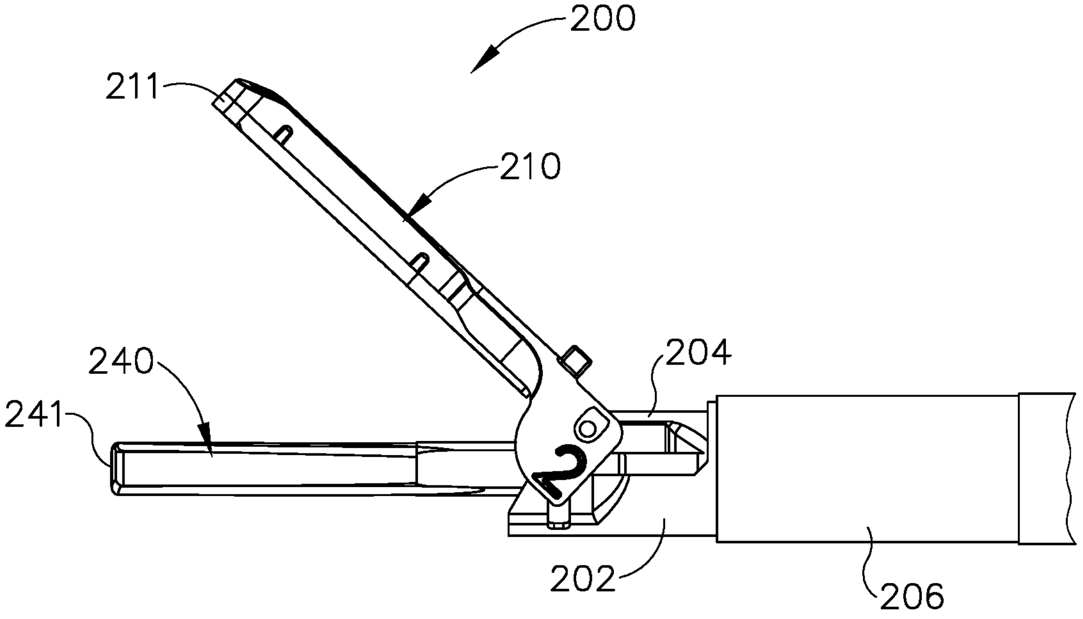
FIG. 3A depicts a side elevational view of the end effector of FIG. 2A, with the end effector in the open configuration.
Figure 3B:
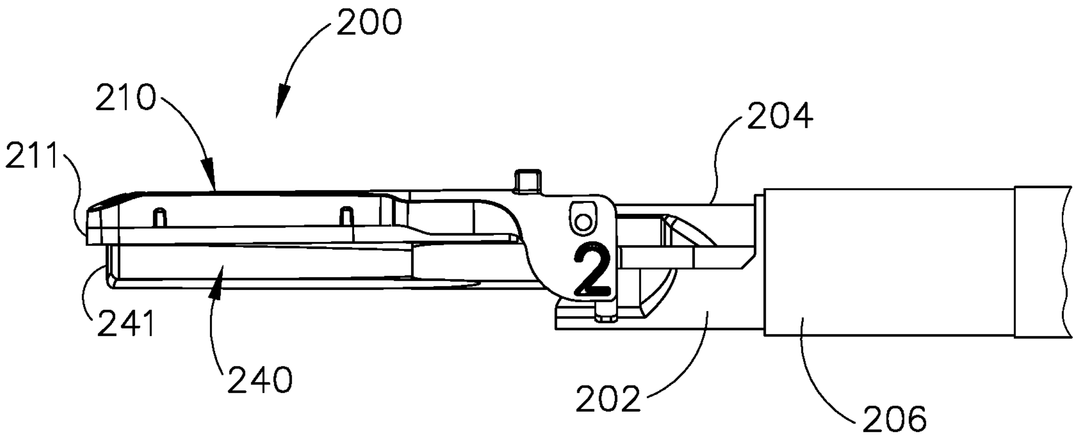
FIG. 3B depicts a side elevational view of the end effector of FIG. 2A, with the end effector in the closed configuration.
Figure 10:
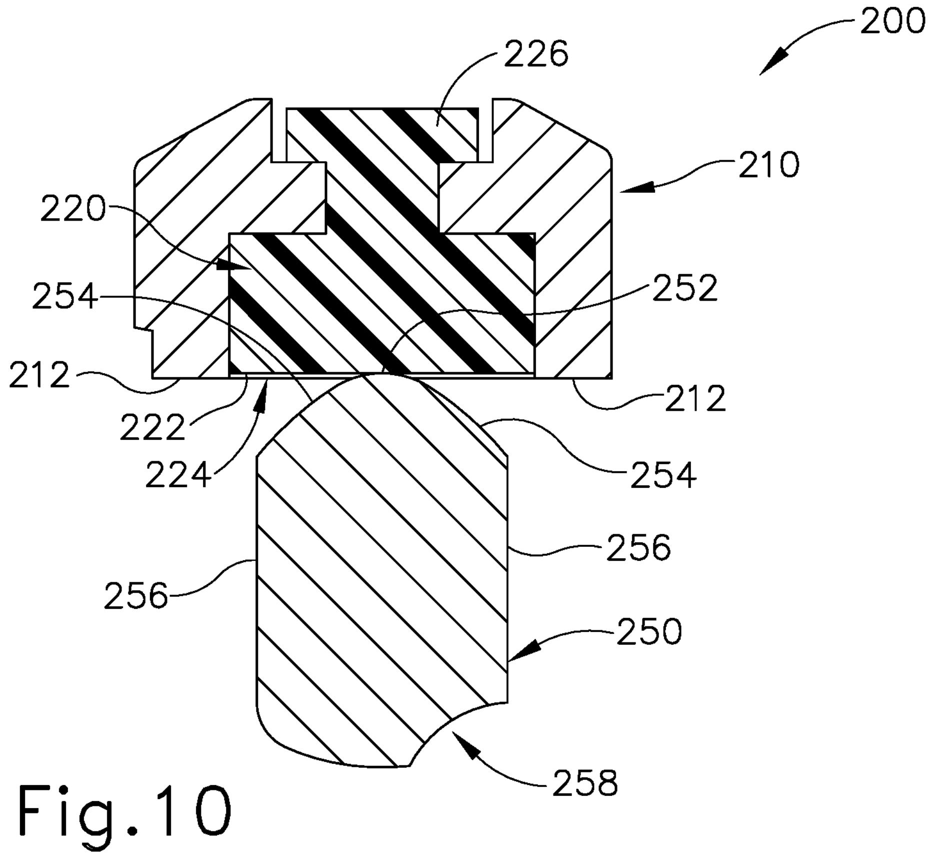
FIG. 10 depicts a cross-sectional end view of the end effector of FIG. 2A, with the end effector in the closed configuration.

FIGS. 2A-3B and 10 show the relationships between the structures of clamp arm (210) and blade (240). In particular, FIGS. 2B and 3B show how the distal end (211) of clamp arm (210) extends distally past the distal end (241) of blade (240). This ensures that electrode surface (212) (best seen in FIGS. 5 and 10) may be used to fully seal the full perimeter of a cut line formed in tissue that has been severed by blade (240). FIG. 10 shows how the lateral portions of electrode surface (212) are positioned laterally outwardly relative to surfaces (256) of distal portion (250) of blade (240). In other words, the width separating the lateral portions of electrode surface (212) is greater than the width separating surfaces (256), such that distal portion (250) of blade (240) is narrower than clamp arm (210).

Figure 11:
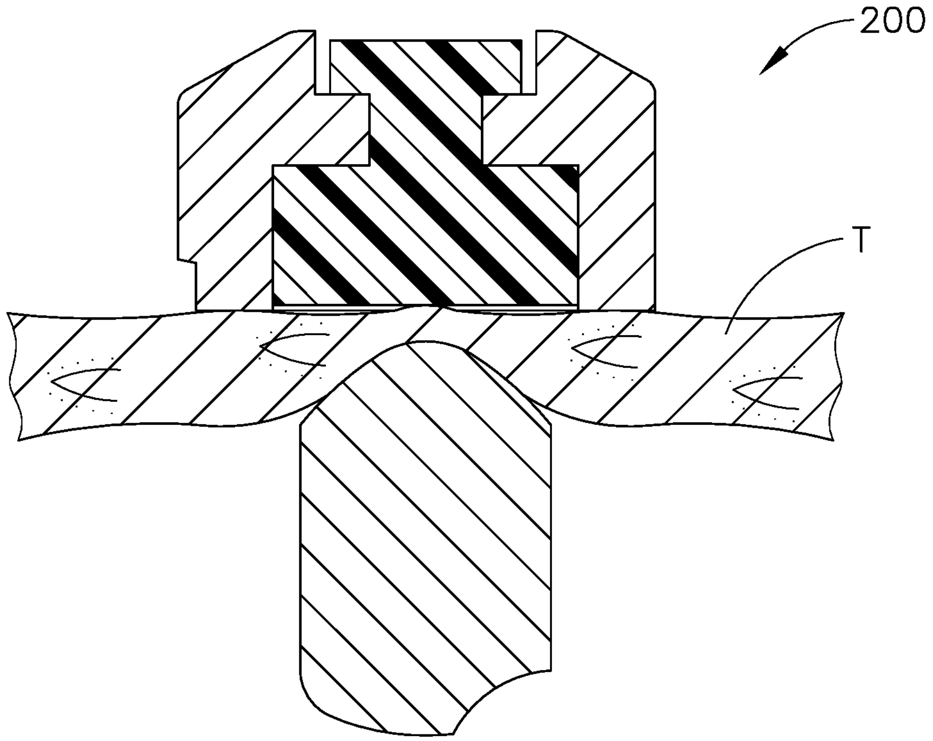
FIG. 11 depicts a cross-sectional end view of the end effector of FIG. 2A, with the end effector compressing tissue between the clamp arm and the ultrasonic blade.

FIG. 11 shows how end effector (200) would engage tissue (T) with end effector (200) in the closed configuration. While just a single layer of tissue (T) is shown in this example, it should be understood that two or more layers of tissue (T) may be captured in end effector (200) in some examples. As shown, the compression forces on the tissue (T) are focused in the region between upper contact surface (252) and clamp pad (220). These compression forces are directed mainly along the same vertical plane along which clamp arm (210) pivots toward blade (240). The tissue (T) is also contacted by oblique surfaces (254). However, the compression provided by oblique surfaces (254) is lower than the compression provided by upper contact surface (252). Moreover, the compression forces imposed on the tissue (T) by oblique surfaces (254) are directed obliquely outwardly, mainly toward electrode surfaces (212). It should be understood that the above-described manner in which end effector (200) engages tissue (T) may provide ultrasonic severing of tissue (T) in the region between upper contact surface (252) and clamp pad (220); with combined ultrasonic and RF electrosurgical sealing of tissue (T) in the regions between oblique surfaces (254) and electrode surfaces (212).

B. End Effector with Blade Having Wide Width and Curved Contact Surface

Figure 12A:
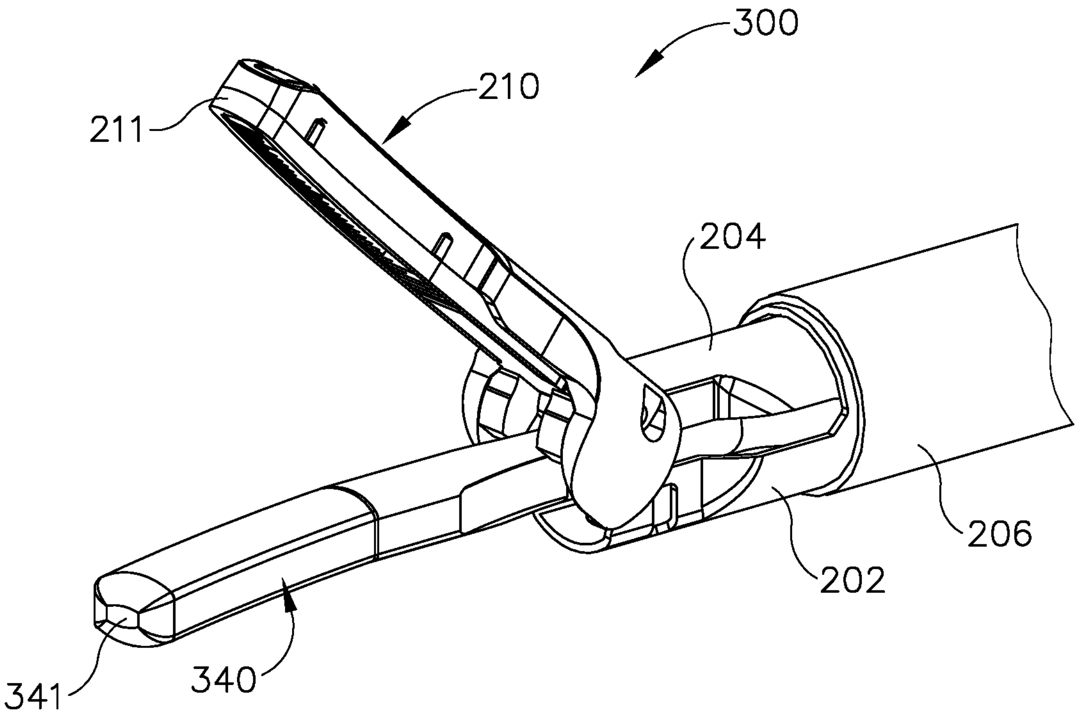
FIG. 12A depicts a perspective view of another exemplary end effector that may be incorporated into the instrument of FIG. 1, with the end effector in an open configuration.
Figure 12B:
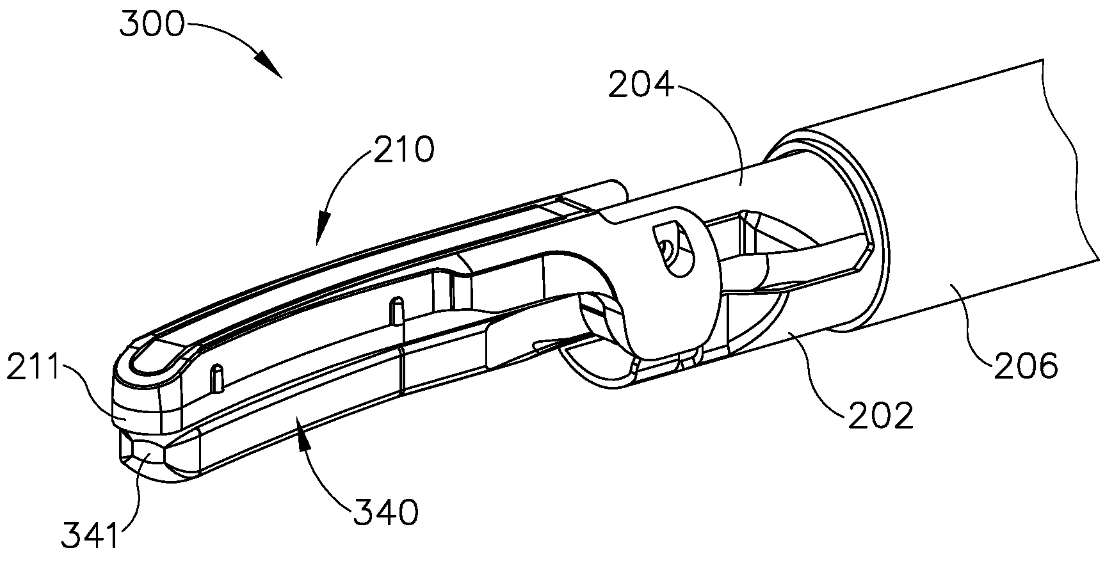
FIG. 12B depicts a perspective view of the end effector of FIG. 12A, with the end effector in a closed configuration.
Figure 16:
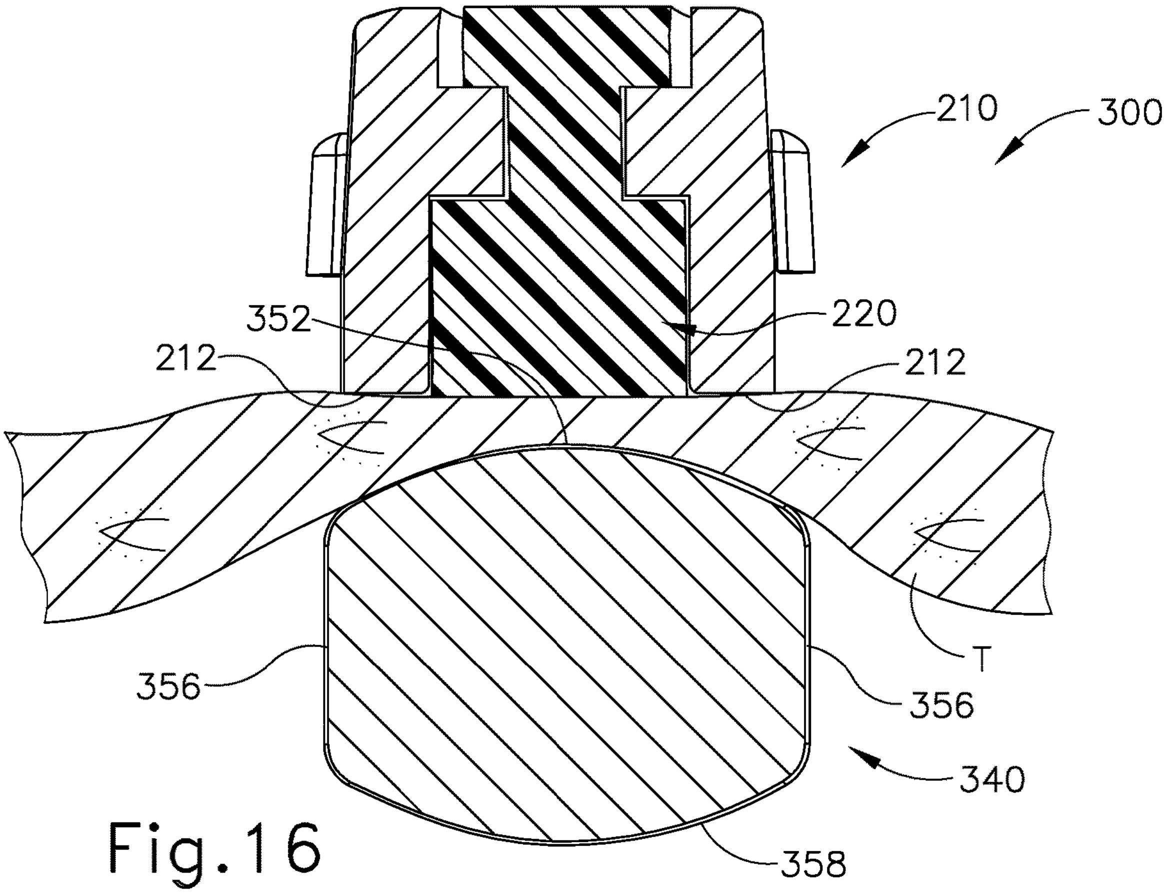
FIG. 16 depicts a cross-sectional end view of the end effector of FIG. 12A, with the end effector compressing tissue between the clamp arm and the ultrasonic blade.

FIGS. 12A-12B and 16 show another exemplary end effector (300) that may be readily incorporated into instrument (110) in place of end effector (140). End effector (300) of this example comprises clamp arm (210) and an ultrasonic blade (340). Clamp arm (210) of end effector (300) is configured and operable just like clamp arm (210) of end effector (200) as described above. Therefore, the details of clamp arm (210) will not be repeated here.

Figure 13:
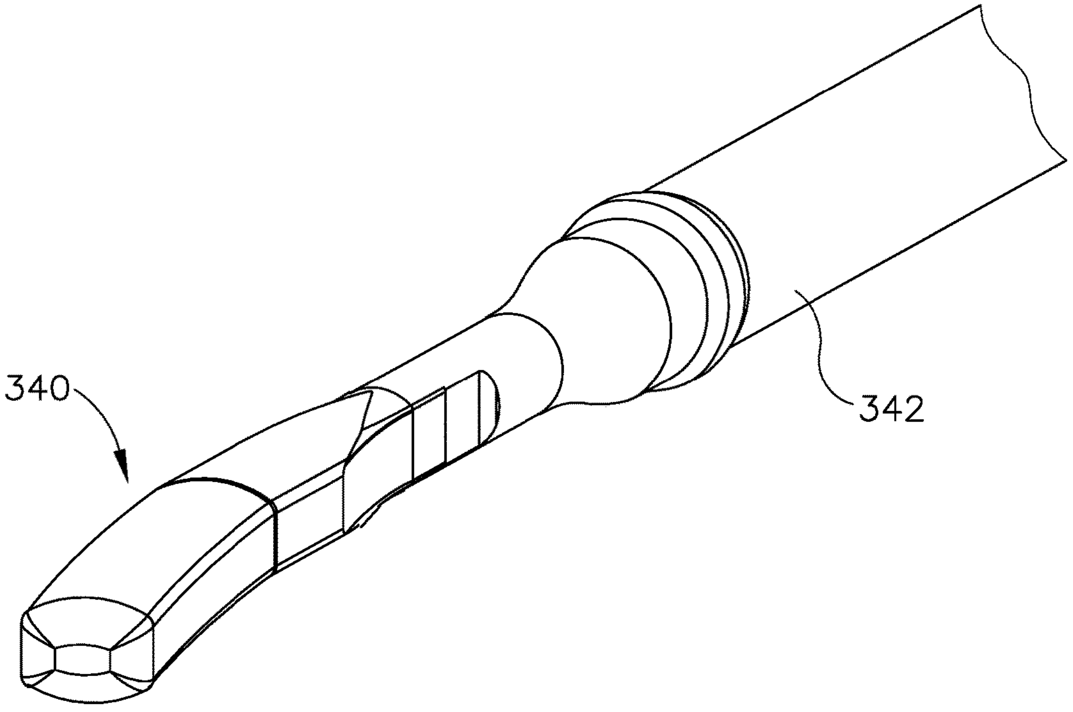
FIG. 13 depicts a perspective view of an ultrasonic blade of the end effector of FIG. 12A.
Figure 14:
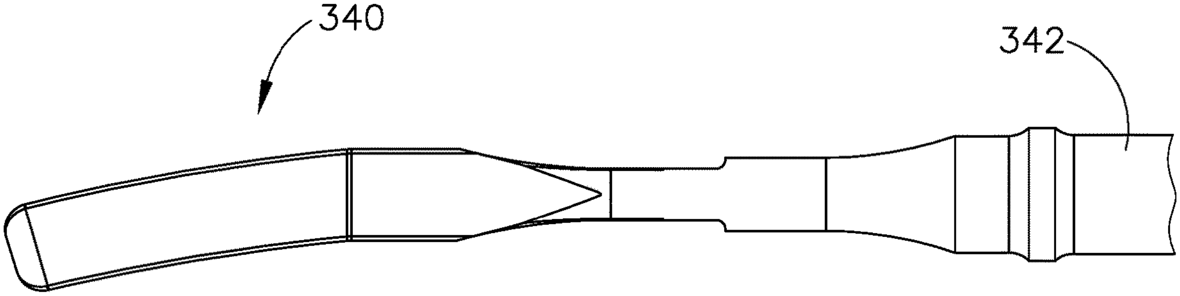
FIG. 14 depicts a top plan view of the ultrasonic blade of FIG. 13.
Figure 15:
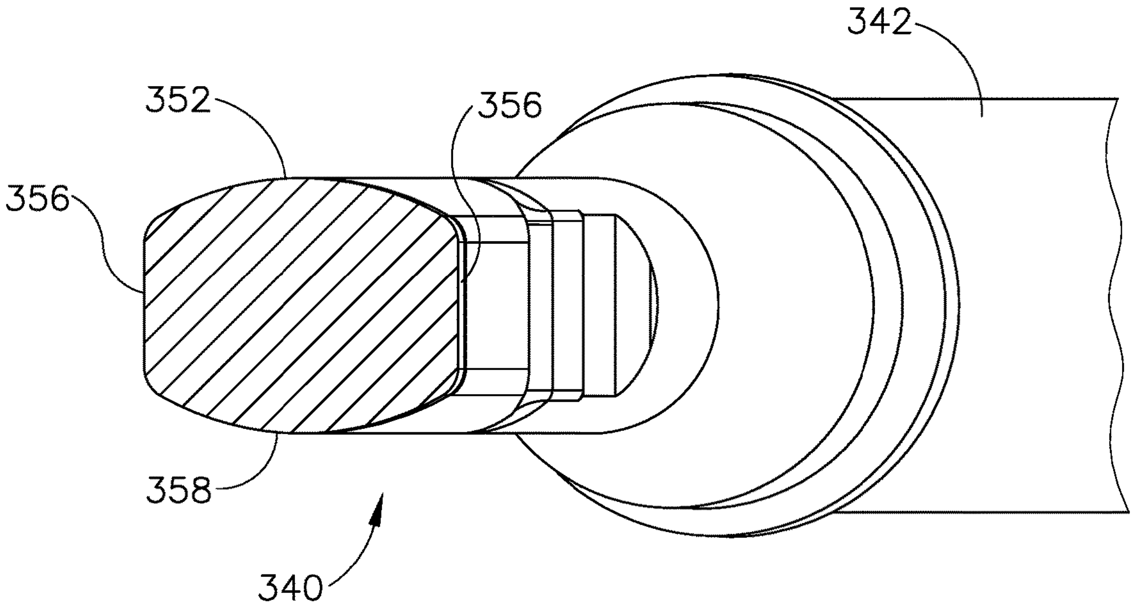
FIG. 15 depicts a perspective cross-sectional view of the ultrasonic blade of FIG. 13, with the cross-section taken at an intermediate portion of the ultrasonic blade.

FIGS. 13-15 show blade (340) in greater detail. As best seen in FIG. 14, blade (340) is curved, such that blade (340) extends along a path that curvingly deviates from the longitudinal axis defined by acoustic waveguide (342). Clamp arm (210) follows the same curve. In some versions, blade (340) and clamp arm (210) are straight instead of being curved. It should be understood that acoustic waveguide (342) may be coupled with transducer (112); and that acoustic waveguide (342) may form part of shaft assembly (130). In particular, acoustic waveguide (342) may be coaxially positioned within tubes (202, 204) described above. As best seen in FIG. 15, blade (340) includes a curved upper contact surface (352), a pair of flat laterally presented surfaces (356), and a curved lower surface (358). In some alternative versions, lower surface (358) may include a cutout similar to cutout (258) described above. It should also be understood that surfaces (356) may be curved, angled, or have any other suitable surface geometry.

FIGS. 12A-12B and 16 show the relationships between the structures of clamp arm (210) and blade (340). In particular, FIG. 12B shows how the distal end (211) of clamp arm (210) extends distally past the distal end (341) of blade (340). This ensures that electrode surface (212) may be used to fully seal the full perimeter of a cut line formed in tissue that has been severed by blade (350). FIG. 16 shows how the lateral portions of electrode surface (212) terminate laterally at the same vertical planes defined by surfaces (356) of blade (340). In other words, the width of clamp arm (210) is equal to the width of blade (340).

FIG. 16 also shows how end effector (300) would engage tissue (T) with end effector (300) in the closed configuration. While just a single layer of tissue (T) is shown in this example, it should be understood that two or more layers of tissue (T) may be captured in end effector (300) in some examples. As shown, the compression forces on the tissue (T) are focused in the region at and near the peak of the curve defined by upper contact surface (352). These compression forces are directed mainly along the same vertical plane along which clamp arm (210) pivots toward blade (350). The tissue (T) is also contacted by the laterally outboard region of upper contact surface (352) (i.e., the regions that are closest to lateral surfaces (356)). However, the compression provided at these outermost regions of upper contact surface (352) is lower than the compression provided by the laterally central region of upper contact surface (352). Moreover, the compression forces imposed on the tissue (T) by outermost regions of upper contact surface (352) are directed obliquely outwardly, mainly toward electrode surfaces (212). It should be understood that the above-described manner in which end effector (300) engages tissue (T) may provide ultrasonic severing of tissue (T) in the laterally central region between upper contact surface (352) and clamp pad (220); with combined ultrasonic and RF electrosurgical sealing of tissue (T) in the outer regions between upper contact surface (352) and electrode surfaces (212).

C. End Effector with Clamp Arm Having Electrode Skirt

Figure 17:
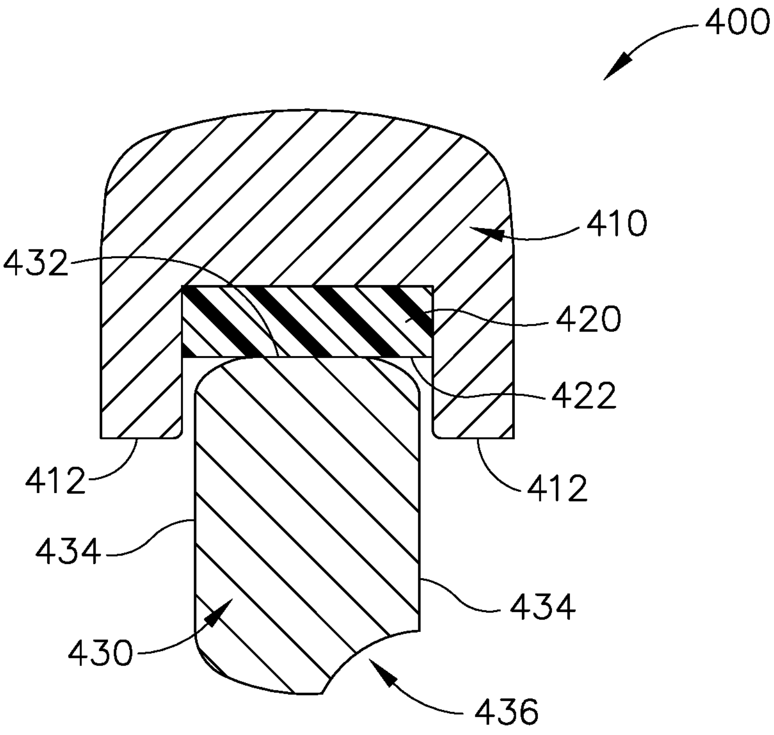
FIG. 17 depicts a cross-sectional end view of another exemplary end effector that may be incorporated into the instrument of FIG. 1, with the end effector in a closed configuration.

FIG. 17 shows another exemplary end effector (400) that may be readily incorporated into instrument (110) in place of end effector (140). End effector (400) of this example comprises a clamp arm (410) and an ultrasonic blade (430). Clamp arm (410) is operable to pivot toward and away from blade (430) in the manner described above. Clamp arm (410) of this example comprises a clamp pad (420) and electrode surfaces (412) that are laterally outboard of clamp pad (420). Clamp pad (420) has a flat tissue engagement surface (422) that is recessed relative to electrode surfaces (412). Electrode surfaces (412) are at the bottoms of arms that are configured to receive blade (430). Blade (430) of this example includes a generally flat upper surface (432), a pair of generally flat outer surfaces (434), and a lower cutout (436). While surfaces (432, 434) are generally flat, and surfaces (434) are perpendicular to surface (432), blade (430) provides curved transitions from surface (432) to surfaces (434) in this example. Thus, the upper region of blade (430) (i.e., the region that faces clamp arm (410)) has rounded corners instead of sharp corners. It should also be understood that surfaces (434) may be curved, angled, or have any other suitable surface geometry.

In the present example, the lateral portions of electrode surface (412) are positioned laterally outwardly relative to surfaces (434) of blade (430). In other words, the width separating the lateral portions of electrode surface (412) is greater than the width separating surfaces (434), such that blade (430) is narrower than clamp arm (410). End effector (400) is configured to compress tissue between surface (432) and clamp pad (420), and thereby ultrasonically sever the tissue in a region that is laterally positioned between electrode surfaces (412). End effector (400) is further operable to provide ultrasonic and RF electrosurgical sealing of tissue in regions of tissue that are contacted by electrode surfaces (412), which would include tissue that is laterally outward from the cut line formed by upper surface (432) and clamp pad (420).

D. End Effector with Clamp Pad Having Proud Contact Surface

Figure 18:
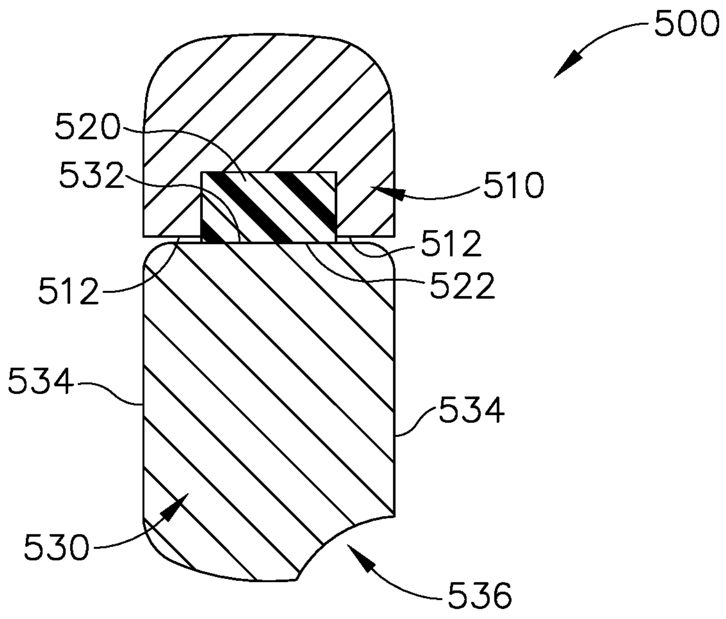
FIG. 18 depicts a cross-sectional end view of another exemplary end effector that may be incorporated into the instrument of FIG. 1, with the end effector in a closed configuration.

FIG. 18 shows another exemplary end effector (500) that may be readily incorporated into instrument (110) in place of end effector (140). End effector (500) of this example comprises a clamp arm (510) and an ultrasonic blade (530). Clamp arm (510) is operable to pivot toward and away from blade (530) in the manner described above. Clamp arm (510) of this example comprises a clamp pad (520) and electrode surfaces (512) that are laterally outboard of clamp pad (520). Clamp pad (520) is also proud relative to electrode surfaces (512), such that electrode surfaces (512) are recessed relative to a flat tissue engagement surface (522) of clamp pad (520). Blade (530) of this example includes a generally flat upper surface (532), a pair of generally flat outer surfaces (534), and a lower cutout (536). While surfaces (532, 534) are generally flat, and surfaces (534) are perpendicular to surface (532), blade (530) provides curved transitions from surface (532) to surfaces (534) in this example. Thus, the upper region of blade (530) (i.e., the region that faces clamp arm (510)) has rounded corners instead of sharp corners. It should also be understood that surfaces (534) may be curved, angled, or have any other suitable surface geometry.

In the present example, the lateral portions of electrode surface (512) terminate laterally at the same vertical planes defined by surfaces (534) of blade (530). In other words, the width of clamp arm (510) is equal to the width of blade (530). End effector (500) is configured to compress tissue between surface (532) and clamp pad (520), and thereby ultrasonically sever the tissue in a region that is laterally positioned between electrode surfaces (512). End effector (500) is further operable to provide ultrasonic and RF electrosurgical sealing of tissue in regions of tissue that are contacted by electrode surfaces (512), which would include tissue that is laterally outward from the cut line formed by upper surface (532) and clamp pad (520).

E. End Effector with Clamp Pad Having Rounded Contact Surface

Figure 19:
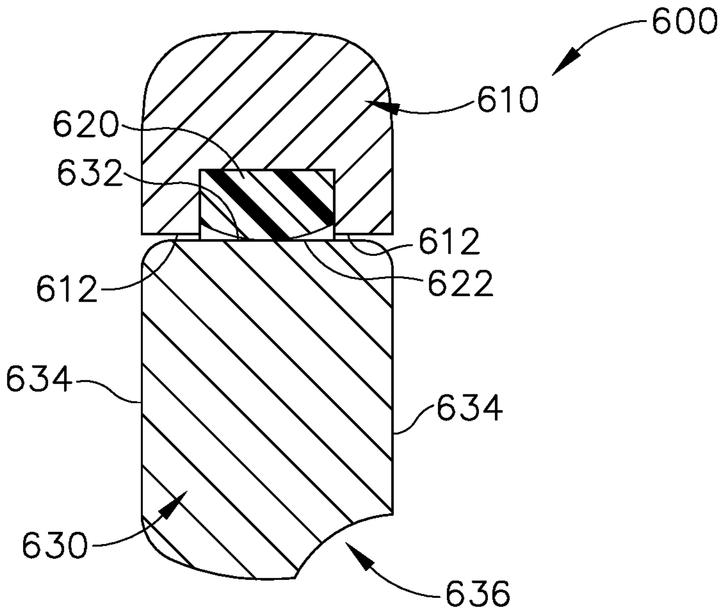
FIG. 19 depicts a cross-sectional end view of another exemplary end effector that may be incorporated into the instrument of FIG. 1, with the end effector in a closed configuration.

FIG. 19 shows another exemplary end effector (600) that may be readily incorporated into instrument (110) in place of end effector (140). End effector (600) of this example comprises a clamp arm (610) and an ultrasonic blade (630). Clamp arm (610) is operable to pivot toward and away from blade (630) in the manner described above. Clamp arm (610) of this example comprises a clamp pad (620) and electrode surfaces (612) that are laterally outboard of clamp pad (620). Clamp pad (620) is also proud relative to electrode surfaces (612), such that electrode surfaces (612) are recessed relative a portion of the tissue engagement surface (622) of clamp pad (620). In particular, tissue engagement surface (622) of this example is curved such that the peak of the curve (at the laterally central region of surface (622)) is proud relative to electrode surfaces (612); while the laterally outer regions of surface (622) are recessed relative to electrode surfaces (612). Blade (630) of this example includes a generally flat upper surface (632), a pair of generally flat outer surfaces (634), and a lower cutout (636). While surfaces (632, 634) are generally flat, and surfaces (634) are perpendicular to surface (632), blade (630) provides curved transitions from surface (632) to surfaces (634) in this example. Thus, the upper region of blade (630) (i.e., the region that faces clamp arm (610)) has rounded corners instead of sharp corners. It should also be understood that surfaces (634) may be curved, angled, or have any other suitable surface geometry.

In the present example, the lateral portions of electrode surface (612) terminate laterally at the same vertical planes defined by surfaces (634) of blade (630). In other words, the width of clamp arm (610) is equal to the width of blade (630). End effector (600) is configured to compress tissue between surface (632) and clamp pad (620), and thereby ultrasonically sever the tissue in a region that is laterally positioned between electrode surfaces (612). End effector (600) is further operable to provide ultrasonic and RF electrosurgical sealing of tissue in regions of tissue that are contacted by electrode surfaces (612), which would include tissue that is laterally outward from the cut line formed by upper surface (632) and clamp pad (620).

F. End Effector with Oblique Electrode Surfaces and Flat Contact Region

Figure 20:
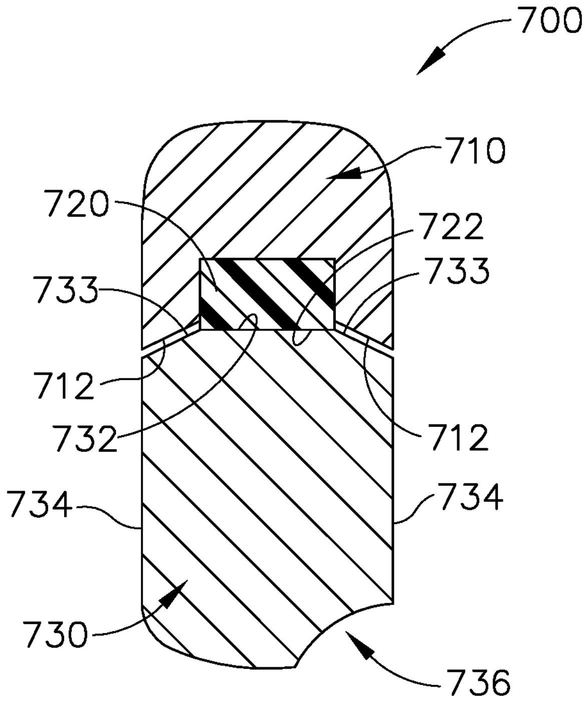
FIG. 20 depicts a cross-sectional end view of another exemplary end effector that may be incorporated into the instrument of FIG. 1, with the end effector in a closed configuration.

FIG. 20 shows another exemplary end effector (700) that may be readily incorporated into instrument (110) in place of end effector (140). End effector (700) of this example comprises a clamp arm (710) and an ultrasonic blade (730). Clamp arm (710) is operable to pivot toward and away from blade (730) in the manner described above. Clamp arm (710) of this example comprises a clamp pad (720) and electrode surfaces (712) that are laterally outboard of clamp pad (720). In the present example, electrode surfaces (712) are obliquely oriented such that the laterally outboard edges of electrode surfaces (712) are positioned lower than the laterally inboard edges of electrode surfaces (712). Clamp pad (720) is proud relative to the laterally inboard edges of electrode surfaces (712), such that the laterally inboard edges of electrode surfaces (712) are recessed relative to the flat tissue engagement surface (722) of clamp pad (720). However, the laterally outboard edges of electrode surfaces (712) are proud relative to the flat tissue engagement surface (722) of clamp pad (720). Blade (730) of this example includes a generally flat upper surface (732) flanked by a pair of oblique surfaces (733), a pair of generally flat outer surfaces (734), and a lower cutout (736). The width of flat upper surface (732) corresponds to the width of tissue engagement surface (722). Similarly, the width and angle of surfaces (733) correspond to the width and angle of electrode surfaces (712). It should also be understood that surfaces (734) may be curved, angled, or have any other suitable surface geometry.

In the present example, the lateral portions of electrode surfaces (712) terminate laterally at the same vertical planes defined by surfaces (734) of blade (730). In other words, the width of clamp arm (710) is equal to the width of blade (730). End effector (700) is configured to compress tissue between surface (732) and clamp pad (720), and thereby ultrasonically sever the tissue in a region that is laterally positioned between electrode surfaces (712). End effector (700) is further operable to provide ultrasonic and RF electrosurgical sealing of tissue in regions of tissue that are contacted by electrode surfaces (712), which would include tissue that is laterally outward from the cut line formed by upper surface (732) and clamp pad (720).

G. End Effector with Oblique Electrode Surfaces and Peaked Contact Region

Figure 21:
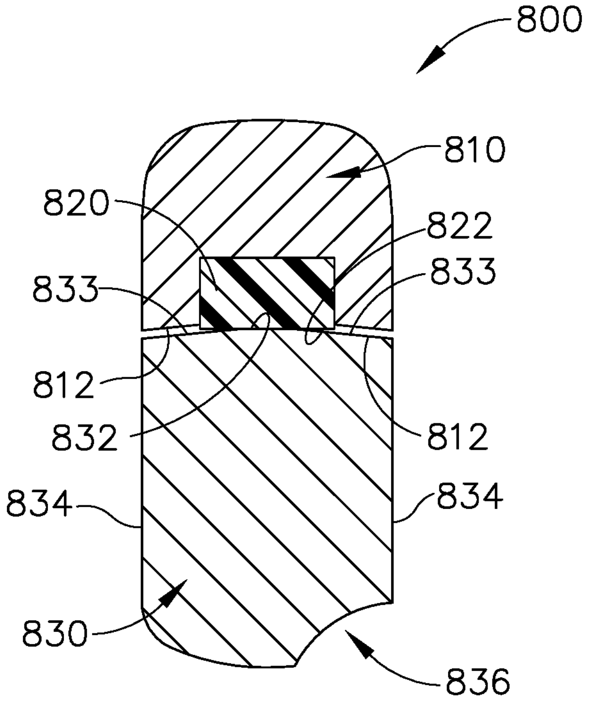
FIG. 21 depicts a cross-sectional end view of another exemplary end effector that may be incorporated into the instrument of FIG. 1, with the end effector in a closed configuration.

FIG. 21 shows another exemplary end effector (800) that may be readily incorporated into instrument (110) in place of end effector (140). End effector (800) of this example comprises a clamp arm (810) and an ultrasonic blade (830). Clamp arm (810) is operable to pivot toward and away from blade (830) in the manner described above. Clamp arm (810) of this example comprises a clamp pad (820) and electrode surfaces (812) that are laterally outboard of clamp pad (820). In the present example, electrode surfaces (812) are obliquely oriented such that the laterally outboard edges of electrode surfaces (812) are positioned lower than the laterally inboard edges of electrode surfaces (812). Clamp pad (820) is proud relative to the laterally inboard edges of electrode surfaces (812), such that the laterally inboard edges of electrode surfaces (812) are recessed relative to the flat tissue engagement surface (822) of clamp pad (820). However, the laterally outboard edges of electrode surfaces (812) are proud relative to the flat tissue engagement surface (822) of clamp pad (820). Blade (830) of this example includes a pair of oblique surfaces (833) that converge at a peak (832), a pair of generally flat outer surfaces (834), and a lower cutout (836). In the present example, peak (832) is formed as a curved transition from one oblique surface (833) to the other oblique surface (833). In some other versions, peak (832) is formed as a sharp transition or a flat transition. The width and angle of surfaces (833) corresponds to the angle of electrode surfaces (812). It should also be understood that surfaces (834) may be curved, angled, or have any other suitable surface geometry.

In the present example, the lateral portions of electrode surfaces (812) terminate laterally at the same vertical planes defined by surfaces (834) of blade (830). In other words, the width of clamp arm (810) is equal to the width of blade (830). End effector (800) is configured to compress tissue between clamp pad (820) and peak (832) (and adjacent regions of surfaces (833), and thereby ultrasonically sever the tissue in a region that is laterally positioned between electrode surfaces (812). End effector (800) is further operable to provide ultrasonic and RF electrosurgical sealing of tissue in regions of tissue that are contacted by electrode surfaces (812), which would include tissue that is laterally outward from the cut line formed by peak (832) and clamp pad (820).

H. End Effector with Single Electrode Insert within Clamp Pad

Figure 32:
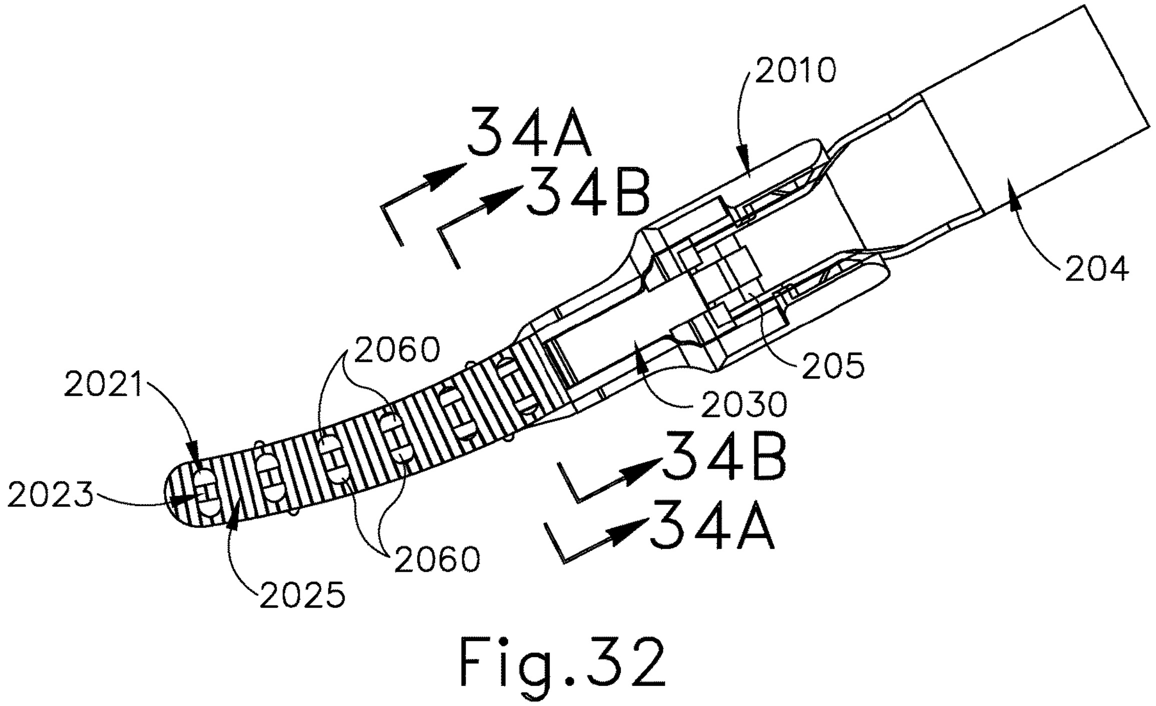
FIG. 32 depicts a bottom view of the clamp arm assembly of FIG. 31.
Figure 33:
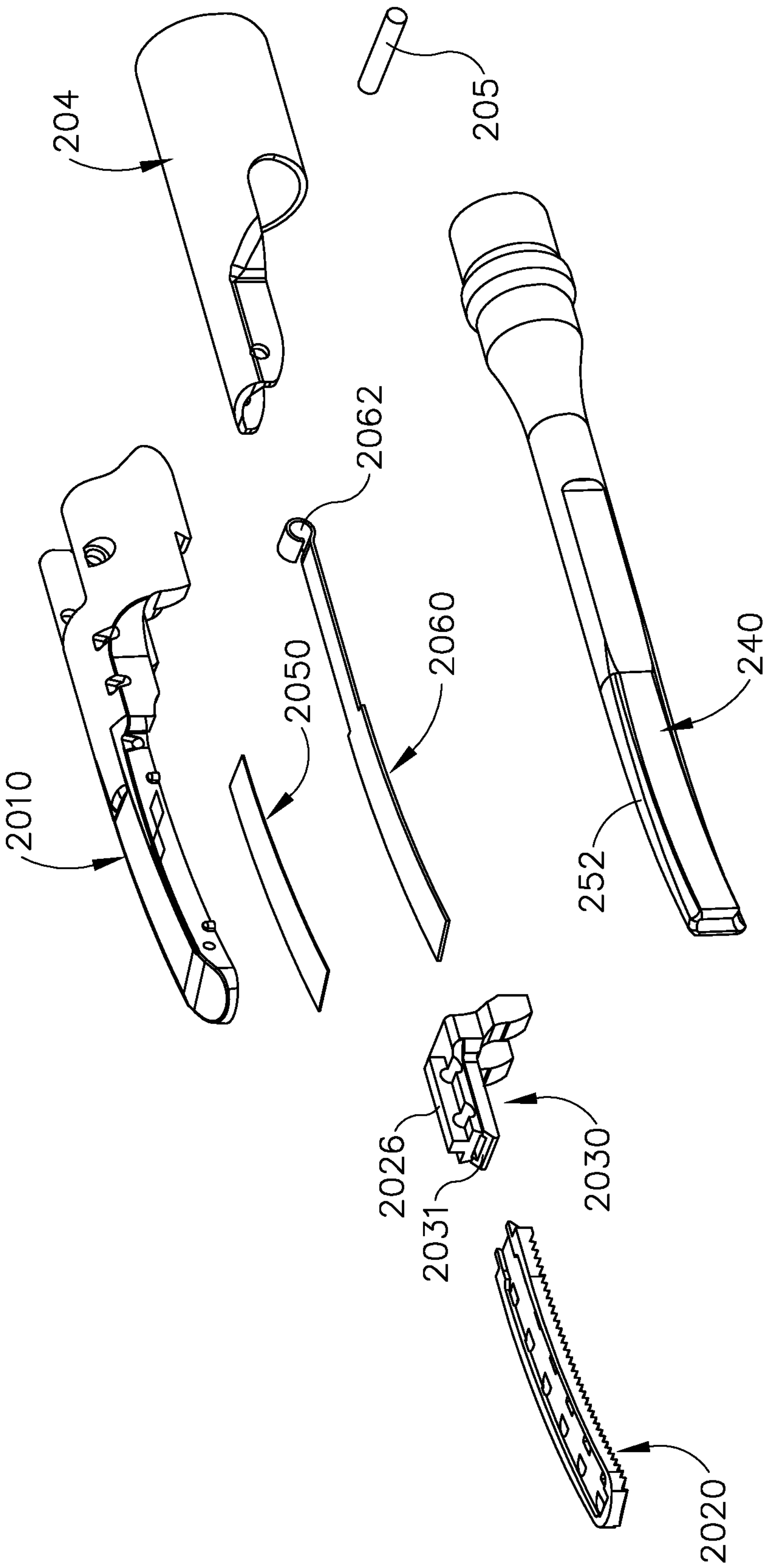
FIG. 33 depicts an exploded view of the end effector of FIG. 31.

FIGS. 31-34B show another exemplary end effector (2000) that may be readily incorporated into instrument (110) in place of end effector (140). End effector (2000) of this example comprises a clamp arm (2010) and an ultrasonic blade (240). Clamp arm (2010) connects with inner tube (204) via pin (205) and is operable to pivot toward and away from blade (240) in the manner described above. Referring to FIG. 33, clamp arm (2010) of this example comprises a distal clamp pad (2020), proximal clamp pad (2030), insulator (2050), and electrode (2060). In some versions, distal clamp pad (2020) is part of a laminate structure that isolates clamp arm (2010) from electrode (2060). In some other versions, clamp arm (2010) itself provides an integral electrode that projects downwardly toward blade (240). In the present example, proximal clamp pad (2030) is retained in clamp arm (2010) with a dovetail or similar feature. Proximal clamp pad (2030) and distal clamp pad (2020) could be formed of the same material(s) or of different material(s).

Referring to FIG. 32, clamp pad (2020) comprises openings (2021) that provide access to electrode (2060). In the present example, openings (2021) are configured as pairs of opposing semi-circle shapes that are separated by a first portion (2023) of clamp pad (2020). The pairs of openings (2021) are spaced apart from each other along the length of clamp pad (2020). In this configuration, each pair of openings (2021) is separated by second portion (2025) of clamp pad (2020). This configuration provides regions of accessible electrode (2060) alternating with regions of inaccessible electrode (2060) that are concealed by clamp pad (2020). Furthermore, this configuration also provides for continuous clamping surface along a centerline region of clamp pad (2020). In the present example, the centerline region may be understood as the center-most region of clamp pad (2020) extending along the length of clamp pad (2020) and including the alternating first and second portions (2023, 2025) of clamp pad (2020). In versions with a curved clamp pad, as is the case with clamp pad (2020), the centerline region comprises the same or similar curvature. In this configuration there is continuous clamp pad (2020) adjacent upper surface (252) of blade (240). In view of the teachings herein, other configurations for openings (2021) in clamp pad (2020) to provide access to electrode (2060) will be apparent to those of ordinary skill in the art.

In the present example, electrode (2060) comprises proximal end (2062) configured to receive pin (205). Pin (205) also extends through openings in inner tube (204) and clamp arm (2010). In this manner, clamp arm (2010), electrode (2060), and inner tube (204) connect about a common axis defined by pin (205). In the present example, pin (205) is electrically isolated at the locations where pin (205) contacts clamp arm (2010). In particular, the free ends of pin (205) are coated with (or otherwise provided with) an electrically insulative material. By way of example only, such a material may comprise parylene, xylan, etc. Alternatively, the full length of pin (205) may be coated with (or otherwise provided with) an electrically insulative material. As another merely illustrative alternative, the openings in clamp arm (2010) that receive pin (205) may be coated with (or otherwise provided with) an electrically insulative material. As yet another merely illustrative alternative, the entire body of clamp arm (2010) that may be coated with (or otherwise provided with) an electrically insulative material.

Insulator (2050) is positioned between clamp arm (2010) and electrode (2060) such that when electrode (2060) is activated, clamp arm (2010) remains neutral due to the insulative coating. Proximal clamp pad (2030) is configured with an opening (2031) through which electrode (2060) passes. In this manner, proximal clamp pad (2030) separates electrode (2060) from the proximal portion of clamp arm (2010) to insulate clamp arm (2010) from electrode (2060). In some versions, electrode (2060) is activated through its connection with pin (205) and inner tube (204). For example, inner tube (204) may receive electrical power and then transmit that to electrode (2060). Inner tube (204) may then be coated with an insulating material or shielded by outer tube to protect a user of instrument (110). In the present example, blade (240) serves as a negative pole while electrode (2060) serves as a positive pole. In this manner, bipolar RF electrosurgical energy can be communicated through tissue that is positioned between (and in contact with) electrode (2060) and blade (240). In view of the teachings herein, other ways to provide electrical communication to electrode (2060) while insulating clamp arm (2010), and/or to provide electrical communication to blade (240), will be apparent to those of ordinary skill in the art.

In some versions, when fabricating end effector (2000), proximal clamp pad (2030) is formed in a first molding step. In this step proximal clamp pad (2030) is molded over electrode (2060) and joined with clamp arm (2010) through molded rail (2026). Rail (2026) is received within a complementary shaped recess within clamp arm (2010) as described in other versions above. Distal clamp pad (2020) is then formed in a second molding step and joined with clamp arm (2010). In versions where clamp pads (2020, 2030) are formed of the same material, clamp pads (2020, 2030) may be formed and joined simultaneously. Openings (2021) are machined in molded distal clamp pad (2020) to expose areas of electrode (2060). In some versions, proximal clamp pad (2030) and/or distal clamp pad (2020) are molded and/or machined separate from clamp arm (2010) and electrode (2060) and then assembled with clamp arm (2010) and electrode (2060) after molding and/or machining. In view of the teachings herein, other ways to fabricate and assemble end effector (2000) will be apparent to those of ordinary skill in the art.

Figure 34A:
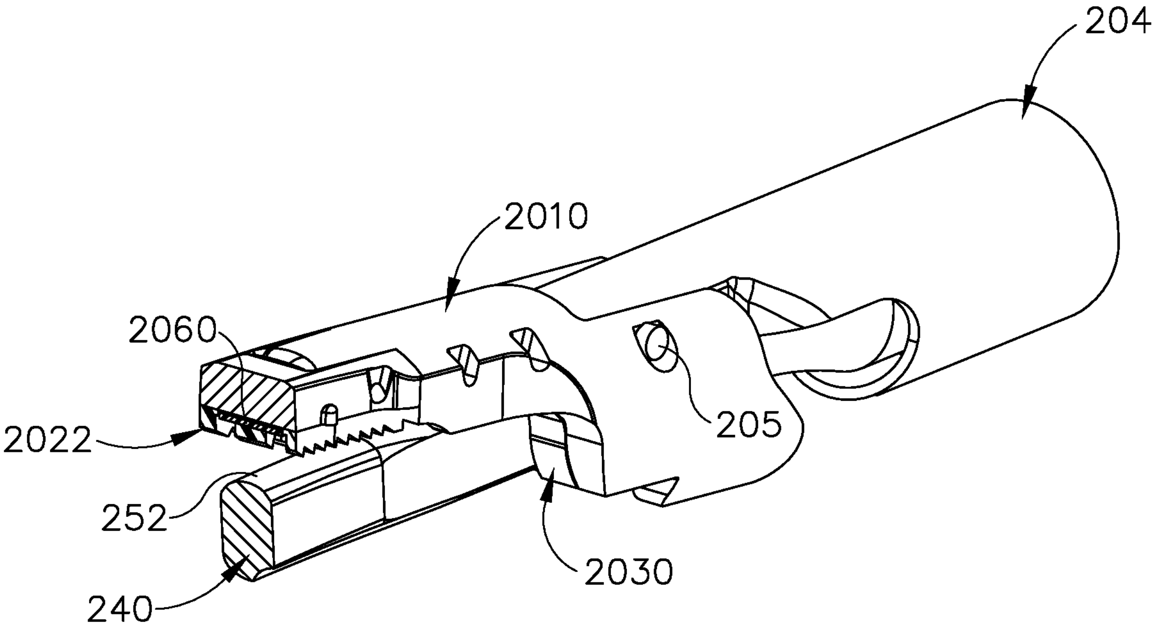
FIG. 34A depicts a perspective cross-sectional view of the end effector of FIG. 31, with the cross-section taken along line 34A-34A of FIG. 32.
Figure 34B:
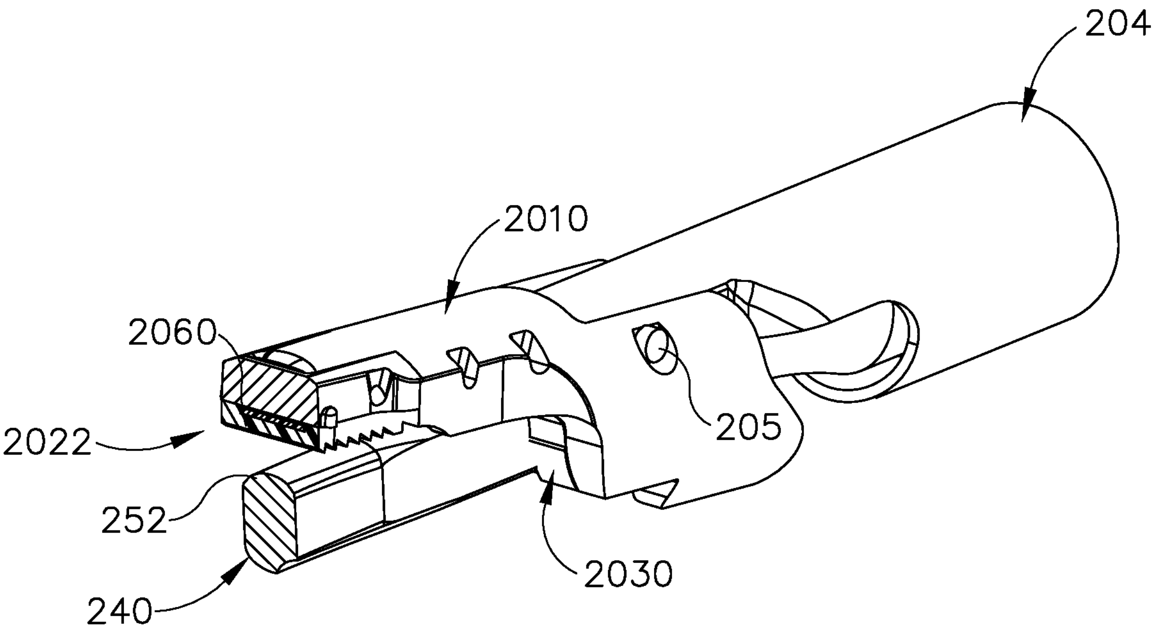
FIG. 34B depicts a perspective cross-sectional view of the end effector of FIG. 31, with the cross-section taken along line 34B-34B of FIG. 32.

Referring to FIGS. 34A and 34B, clamp pad (2020) comprises teeth (2022) as described above. As also described above, end effector (2000) is configured for tissue engagement between blade (240) and the toothed surface of clamp pad (2020). Clamp pad (2020) remains proud relative the surface of electrode (2060), such that the surface of electrode (2060) is recessed relative to the tissue-engaging toothed surface of clamp pad (2020) by a predetermined initial starting gap (e.g., ranging from approximately 0.004" to approximately 0.012"). In those regions having openings (2021), when tissue is compressed between clamp pad (2020) and blade (240), tissue can fill openings (2021) and thereby contact electrode (2060). In this manner, a conductive pathway is established through the tissue between electrode (2060) and blade (240). With tissue compressed between clamp pad (2020) and blade (240), ultrasonic energy can be imparted to waveguide (242) and thereby ultrasonically sever the tissue along the continuous centerline region of clamp pad (2020). On each side of the cut line, ultrasonic sealing occurs as described above. In addition, end effector (2000) is further operable to provide RF electrosurgical sealing of tissue along the conductive pathways described above, which would include tissue that is laterally outward from the cut line formed between upper surface (252) of blade (240) and the centerline region of clamp pad (2020). In some versions, the spacing of openings (2021) is such that the RF electrosurgical sealing occurs not only at the openings (2021), but between openings (2021) as well. In this manner, RF electrosurgical sealing may be obtained along the length of clamp pad (2020) and thus the length of the tissue cut line. In other versions, RF electrosurgical sealing is not required to be continuous along each side of the cut line, and instead may occur at multiple points along each side of the cut line in a discontinuous fashion.

Figure 35:
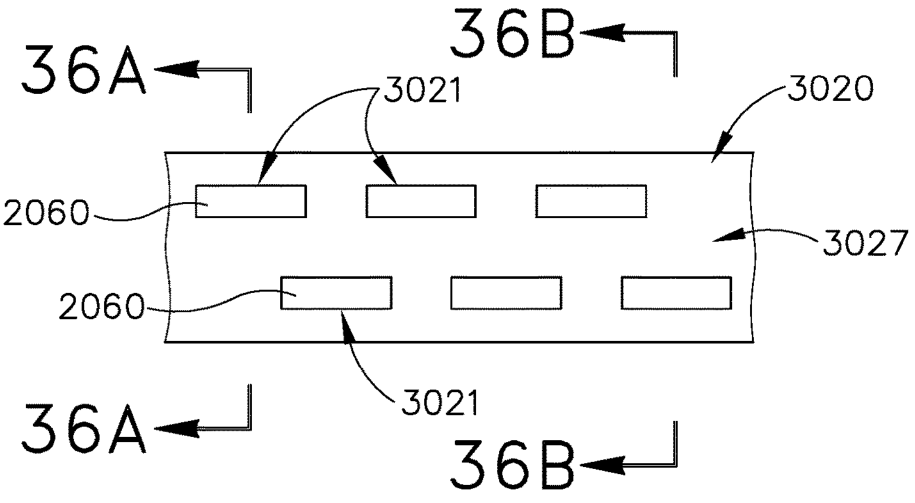
FIG. 35 depicts a bottom view of another exemplary end effector, shown without the blade, that may be incorporated into the instrument of FIG. 1.
Figure 36A:
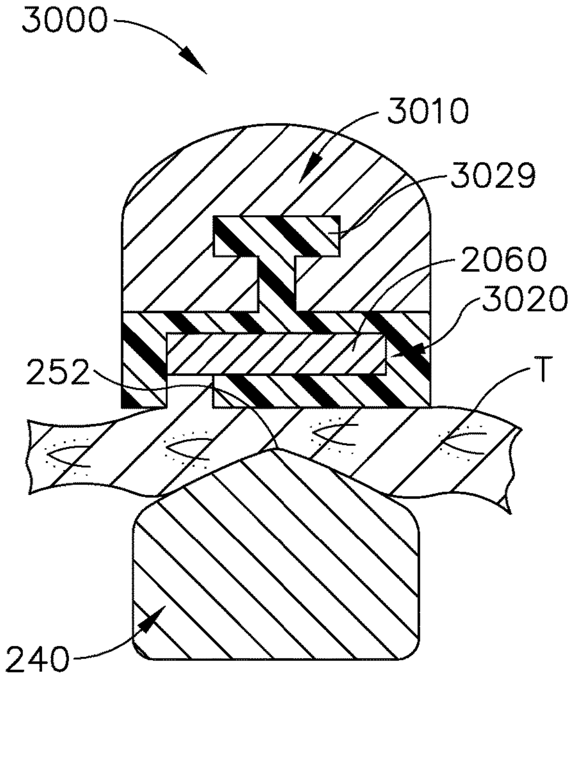
FIG. 36A depicts a cross-sectional view of the end effector of FIG. 35 taken along line 36A-36A as shown in FIG. 35.
Figure 36B:
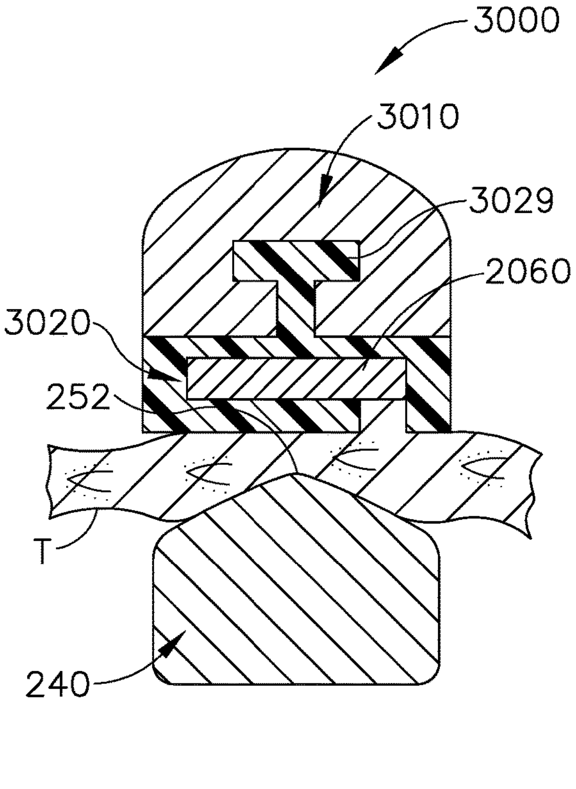
FIG. 36B depicts a cross-sectional view of the end effector of FIG. 35 taken along line 36B-36B as shown in FIG. 35.

FIGS. 35-36B show another exemplary end effector (3000) that may be readily incorporated into instrument (110) in place of end effector (140). End effector (3000) is similar to end effector (2000) described above. However, end effector (3000) comprises clamp pad (3020) having openings (3021) configured with rectangular shapes where openings (3021) are spaced apart longitudinally along each side of a centerline region (3027) of clamp pad (3020). Similar to clamp pad (2020), clamp pad (3020) also provides for maintaining a continuous clamping surface or region of clamp pad (3020) along centerline region (3027). In the present example, blade (240) aligns along centerline region (3027) such that when tissue (T) is compressed between blade (240) and clamp pad (3020), ultrasonic energy may be provided to sever the tissue (T) along a cut line that coincides with the aligned upper surface (252) of blade (240) and centerline region (3027) of clamp pad (3020). While the present example illustrates end effector (3000) and associated clamp pad (3020) as having straight configurations, in other versions end effector (3000) and associated clamp pad (3020) are curved similarly to the curvature of end effector (2000) and clamp pad (2020) for example.

In the present example, openings (3021) on a first side of centerline region (3027) are staggered or longitudinally offset compared to openings (3021) on a second opposite side of centerline region (3027). Similar to end effector (2000) described above, openings (3021) in end effector (3000) provide access to or expose electrode (2060). Referring to FIGS. 36A and 36B, with this configuration, when tissue (T) is compressed between blade (240) and clamp pad (3020), tissue (T) can at least partially fill openings (3021) to contact electrode (2060) at alternating locations along the length of clamp pad (3020). In this manner, a conductive pathway is established through the tissue (T) between electrode (2060) and blade (240). With tissue (T) compressed between clamp pad (3020) and blade (240), ultrasonic energy can be imparted to waveguide (242) and thereby ultrasonically sever the tissue (T) along the continuous centerline region (3027) of clamp pad (3020). On each side of the cut line, ultrasonic sealing occurs as described above. In addition, end effector (3000) is further operable to provide RF electrosurgical sealing of tissue (T) along the conductive pathways described above, which would include tissue (T) that is laterally outward from the cut line formed between upper surface (252) of blade (240) and the centerline region (3027) of clamp pad (3020). In some versions, the spacing of openings (3021) is such that the RF electrosurgical sealing occurs not only at the openings (3021), but between longitudinally adjacent openings (3021) as well. In this manner, RF electrosurgical sealing may be obtained along the length of clamp pad (3020) and thus the length of the tissue cut line. In other versions, RF electrosurgical sealing is not required to be continuous along each side of the cut line, and instead may occur at multiple points along each side of the cut line in a discontinuous fashion.

Another difference between end effector (3000) and end effector (2000) pertains to the orientation of the clamp pads (2020, 3020) with respect to electrode (2060). With end effector (2000), electrode (2060) is positioned on top of clamp pad (2020) as shown in FIG. 33. With end effector (3000), electrode (2060) is positioned within a channel of clamp pad (3020) as shown in FIGS. 36A and 36B. In the present example, but not required in all versions, this configuration for clamp pad (3020) and electrode (2060) is achieved by molding clamp pad (3020) around electrode (2060) and then machining clamp pad (3020) to form openings (3021). In the molding process, clamp pad (3020) is also attached with clamp arm (3010) using complementary engagement features, e.g. a molded rail (3029) of clamp pad (3020) engages a complementary shaped recess in clamp arm (3010). In some other versions, clamp arm (3010) has a rail machined/molded into it and clamp pad (3020) has a complementary matching rail machined/molded into it. Clamp arm (3010) and clamp arm (3010) pad can now be installed along the length of the rail instead of being molded as a single component. In view of the teachings herein, other configurations for orienting electrode (2060) with respect to clamp pad (3020) will be apparent to those of ordinary skill in the art. By way of example only, clamp pad (3020) may be modified in some versions such that electrode (2060) is positioned on top of clamp pad (3020) similar to clamp pad (2020). Separately or in addition, clamp pad (3020) may be modified to use various alternate configurations for openings (3021) as will be understood in view of the teachings herein.

Figure 37:
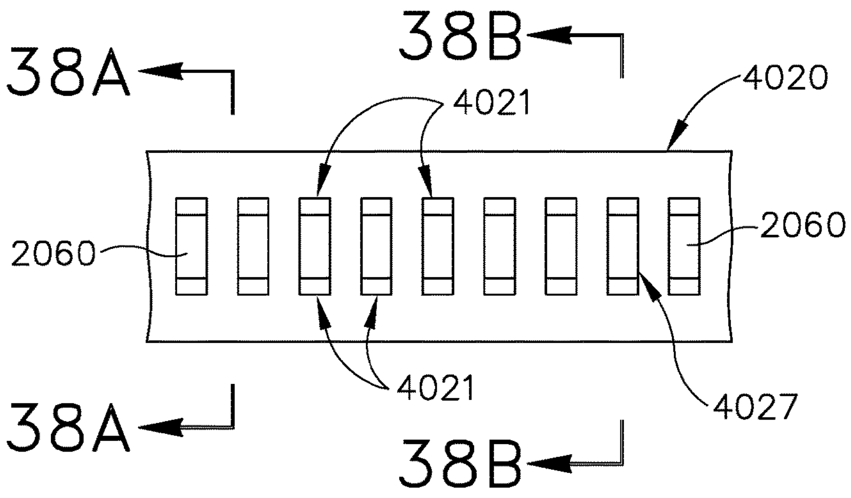
FIG. 37 depicts a bottom view of another exemplary end effector, shown without the blade, that may be incorporated into the instrument of FIG. 1.
Figure 38A:
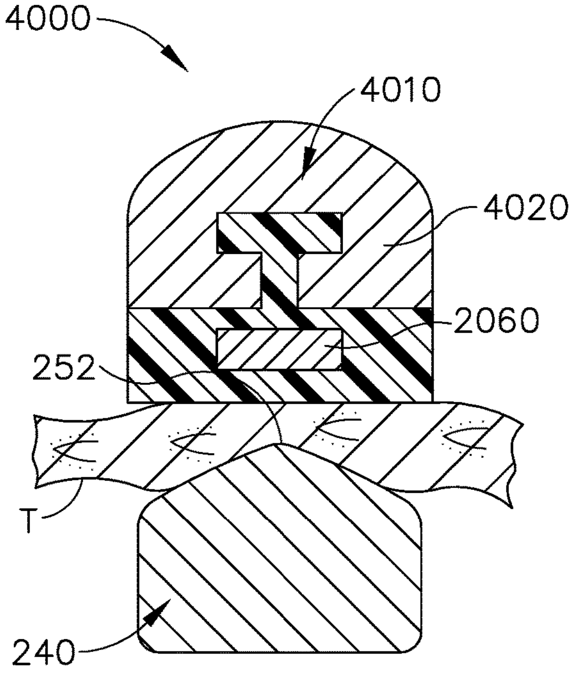
FIG. 38A depicts a cross-sectional view of the end effector of FIG. 37 taken along line 38A-38A as shown in FIG. 37.
Figure 38B:
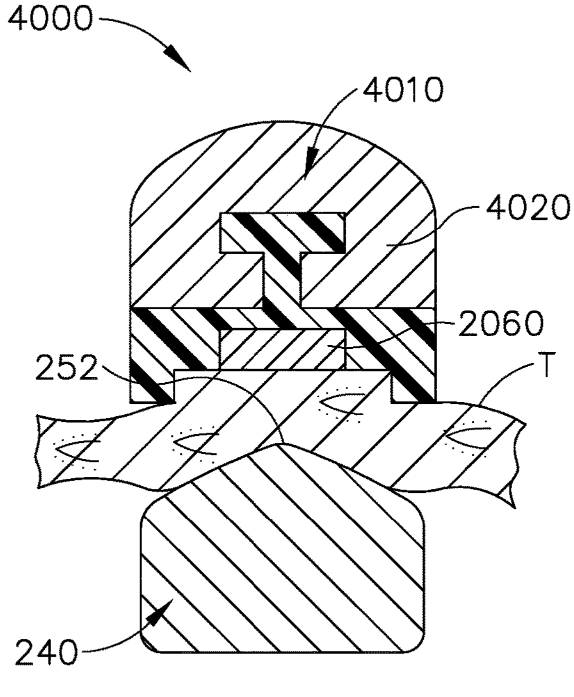
FIG. 38B depicts a cross-sectional view of the end effector of FIG. 37 taken along line 38B-38B as shown in FIG. 37.

FIGS. 37-38B show another exemplary end effector (4000) that may be readily incorporated into instrument (110) in place of end effector (140). End effector (4000) is similar to end effector (2000) described above. However, end effector (4000) comprises clamp arm (4010) and clamp pad (4020) having openings (4021) configured with rectangular shapes, where openings (4021) extend laterally across clamp pad (4020). This configuration provides for end effector (4000) having a centerline region (4027) of clamp pad (4020) with electrode (2060) partially accessible or exposed. In the present example, blade (240) aligns along centerline region (4027) such that when tissue (T) is compressed between blade (240) and clamp pad (4020), ultrasonic energy may be provided to sever the tissue (T) along a cut line that coincides with the aligned upper surface (252) of blade (240) and centerline region (4027) of clamp pad (4020). In the present configuration, clamp pad (4020) contacts tissue (T) intermittently or in a discontinuous fashion when end effector (4000) is in a closed configuration gripping tissue (T) because openings (4021) interrupt centerline region (4027) aligned with blade (240). However, the spacing of openings (4021) and the ultrasonic energy applied are configured such that a continuous cut of tissue (T) is made over the length of clamp pad (4020) even without continuous contact between clamp pad (4020) and tissue (T) along centerline region (4027). While the present example illustrates end effector (4000) and associated clamp pad (4020) as having straight configurations, in other versions end effector (4000) and associated clamp pad (4020) are curved similarly to the curvature of end effector (2000) and clamp pad (2020) for example.

In the present example, openings (4021) in end effector (4000) provide access to or expose electrode (2060). Referring to FIGS. 38A and 38B, with this configuration, when tissue (T) is compressed between blade (240) and clamp pad (4020), tissue (T) can at least partially fill openings (4021) to contact electrode (2060) at locations along the length of clamp pad (4020). In this manner, a conductive pathway is established through the tissue (T) between electrode (2060) and blade (240). With tissue (T) compressed between clamp pad (4020) and blade (240), ultrasonic energy can be imparted to waveguide (242) and thereby ultrasonically sever the tissue (T) along the length of clamp pad (4020) as discussed above. On each side of the cut line, ultrasonic sealing occurs as described above. In addition, with portions of electrode (2060) exposed along the centerline region (4027) of clamp pad (4020)—and thus along the tissue cut line—end effector (4000) is further operable to provide RF electrosurgical sealing of tissue (T) along the conductive pathways described above, which would include tissue (T) that is along the cut line formed between upper surface (252) of blade (240) and centerline region (4027) of clamp pad (4020). In some versions, the spacing of openings (4021) is such that the RF electrosurgical sealing occurs not only at the openings (4021), but between openings (4021) as well. In this manner, RF electrosurgical sealing may be obtained along the length of clamp pad (4020) and thus the length of the tissue cut line. In other versions, RF electrosurgical sealing is not required to be continuous along each side of the cut line, and instead may occur at multiple points along each side of the cut line in a discontinuous fashion.

End effector (4000) uses a similar orientation for clamp pad (4020) and electrode (2060) as shown and described above with respect to end effector (3000), e.g. having electrode (2060) within clamp pad (4020) instead of being on top of clamp pad (4020). In view of the teachings herein, other configurations for orienting electrode (2060) with respect to clamp pad (4020) will be apparent to those of ordinary skill in the art. By way of example only, clamp pad (4020) may be modified in some versions such that electrode (2060) is positioned on top of clamp pad (4020) similar to clamp pad (2020). Additionally, electrode (2060) could be part of clamp arm (4010), and clamp pad (4020) could be molded to clamp arm (4010). Separately or in addition, clamp pad (4020) may be modified to use various alternate configurations for openings (4021) as will be understood in view of the teachings herein.

Figure 39:
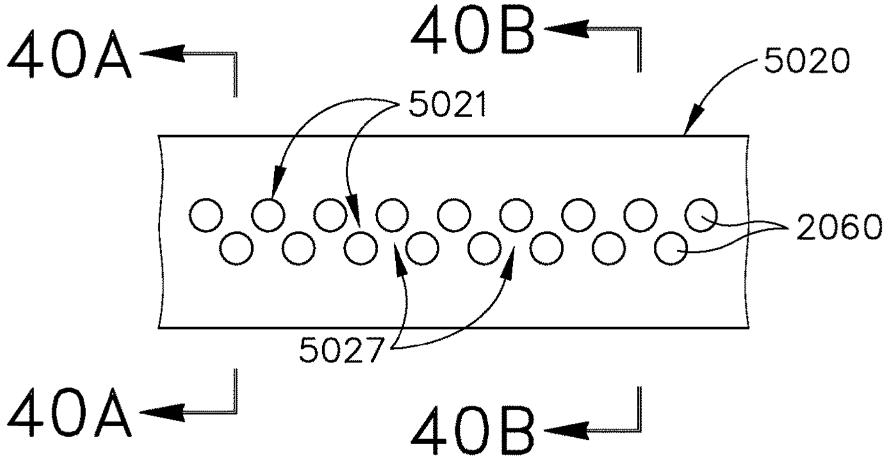
FIG. 39 depicts a bottom view of another exemplary end effector, shown without the blade, that may be incorporated into the instrument of FIG. 1.
Figure 40A:
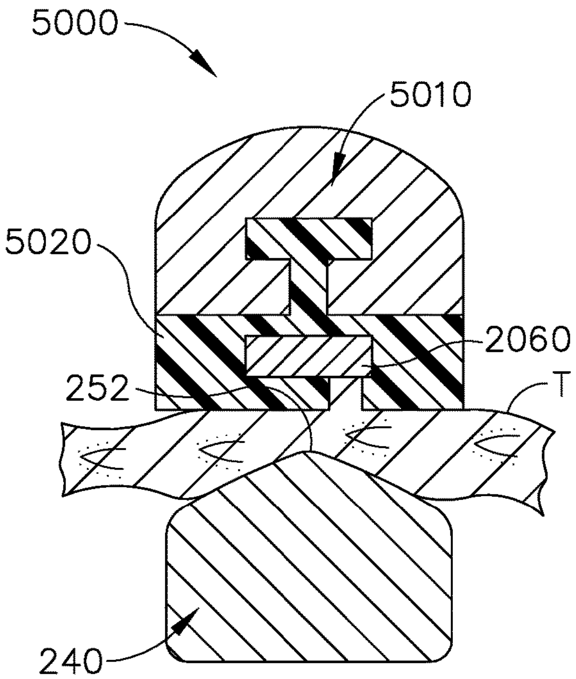
FIG. 40A depicts a cross-sectional view of the end effector of FIG. 39 taken along line 40A-40A as shown in FIG. 39.
Figure 40B:
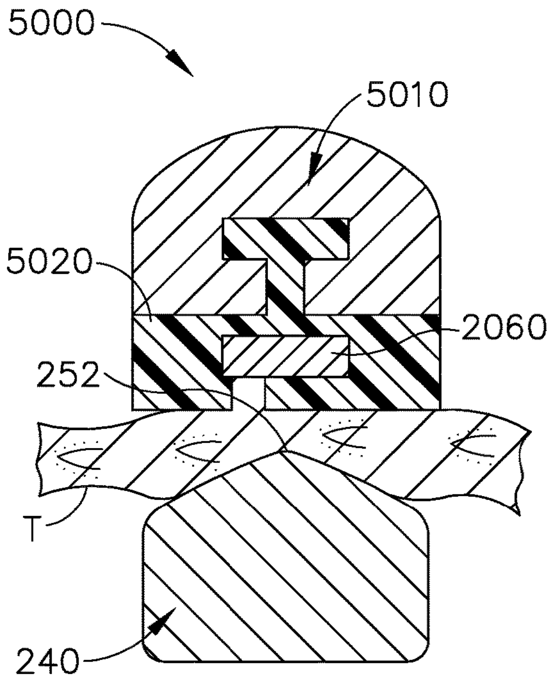
FIG. 40B depicts a cross-sectional view of the end effector of FIG. 39 taken along line 40B-40B as shown in FIG. 39.

FIGS. 39-40B show another exemplary end effector (5000) that may be readily incorporated into instrument (110) in place of end effector (140). End effector (5000) is similar to end effector (2000) described above. However, end effector (5000) comprises clamp arm (5010) and clamp pad (5020) having openings (5021) configured with circular shapes, where openings (5021) extend along the length of clamp pad (5020) in two offset rows extending along the length of clamp pad (5020). This configuration provides for end effector (5000) having a centerline region (5027) of clamp pad (5020) with electrode (2060) partially accessible or exposed. In the present example, blade (240) aligns along centerline region (5027) such that when tissue (T) is compressed between blade (240) and clamp pad (5020), ultrasonic energy may be provided to sever the tissue (T) along a cut line that coincides with the aligned upper surface (252) of blade (240) and centerline region (5027) of clamp pad (5020). In the present configuration clamp pad (5020) contacts tissue (T) intermittently or in a discontinuous fashion when end effector (5000) is in a closed configuration gripping tissue (T) because openings (5021) interrupt centerline region (5027). However, the spacing of openings (5021) and the ultrasonic energy applied are configured such that a continuous cut of tissue (T) is made over the length of clamp pad (5020) even without continuous contact between clamp pad (5020) and tissue (T) along centerline region (5027). While the present example illustrates end effector (5000) and associated clamp pad (5020) as having straight configurations, in other versions end effector (5000) and associated clamp pad (5020) are curved similarly to the curvature of end effector (2000) and clamp pad (2020) for example.

In the present example, openings (5021) in end effector (5000) provide access to or expose electrode (2060). Referring to FIGS. 40A and 40B, with this configuration, when tissue (T) is compressed between blade (240) and clamp pad (5020), tissue (T) can at least partially fill openings (5021) to contact electrode (2060) at alternating locations along the length of clamp pad (5020). In this manner, a conductive pathway is established through the tissue (T) between electrode (2060) and blade (240). With tissue (T) compressed between clamp pad (5020) and blade (240), ultrasonic energy can be imparted to waveguide (242) and thereby ultrasonically sever the tissue (T) along the length of clamp pad (5020) as discussed above. On each side of the cut line, ultrasonic sealing occurs as described above. In addition, with portions of electrode (2060) exposed along the centerline region (5027) of clamp pad (5020)—and thus along the tissue cut line—end effector (5000) is further operable to provide RF electrosurgical sealing of tissue (T) along the conductive pathways described above, which would include tissue (T) that is along the cut line formed between upper surface (252) of blade (240) and centerline region (5027) of clamp pad (5020). In some versions, the spacing of openings (5021) is such that the RF electrosurgical sealing occurs not only at the openings (5021), but between openings (5021) as well. In this manner, RF electrosurgical sealing may be obtained along the length of clamp pad (5020) and thus the length of the tissue cut line. In other versions, RF electrosurgical sealing is not required to be continuous along each side of the cut line, and instead may occur at multiple points along each side of the cut line in a discontinuous fashion.

End effector (5000) uses a similar orientation for clamp pad (5020) and electrode (2060) as shown and described above with respect to end effector (3000), e.g. having electrode (2060) within clamp pad (5020) as opposed to on top of clamp pad (5020). In some other versions, electrode (2060) is provided as a unitary feature of clamp arm (5010), and clamp pad (5020) is overmolded to provide a gap between clamp pad (5020) and electrode (2060). In view of the teachings herein, other configurations for orienting electrode (2060) with respect to clamp pad (5020) will be apparent to those of ordinary skill in the art. By way of example only, clamp pad (5020) may be modified in some versions such that electrode (2060) is positioned on top of clamp pad (5020) similar to clamp pad (2020). Separately or in addition, clamp pad (5020) may be modified to use various alternate configurations for openings (5021) as will be understood in view of the teachings herein.

I. End Effector with Dual Electrode Insert within Clamp Pad

Figure 41:
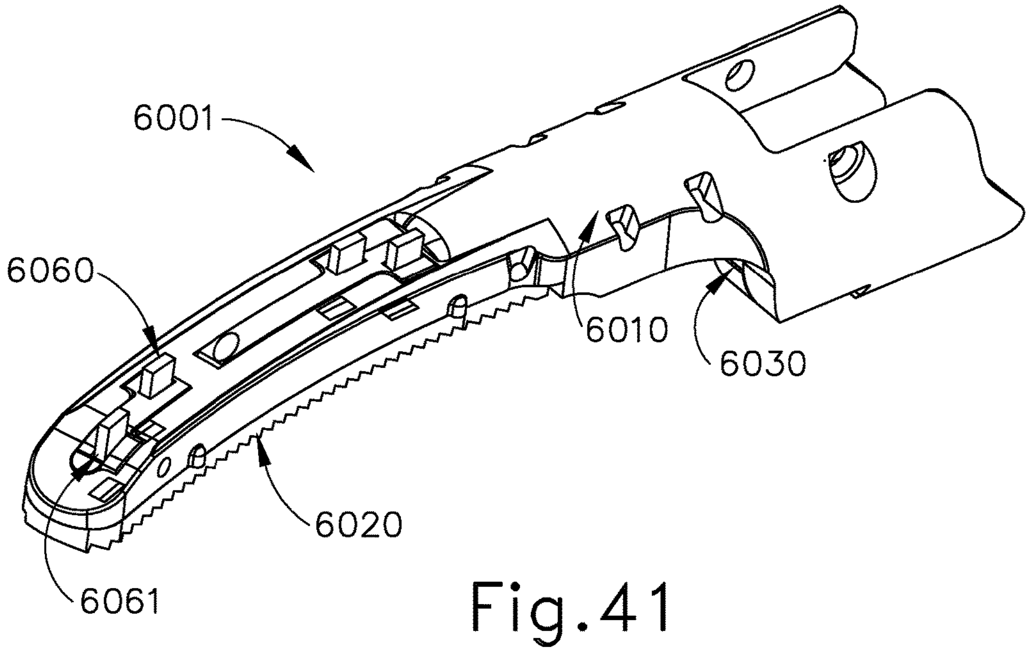
FIG. 41 depicts a perspective view of another exemplary clamp arm assembly of an end effector that may be incorporated into the instrument of FIG. 1.
Figure 42:
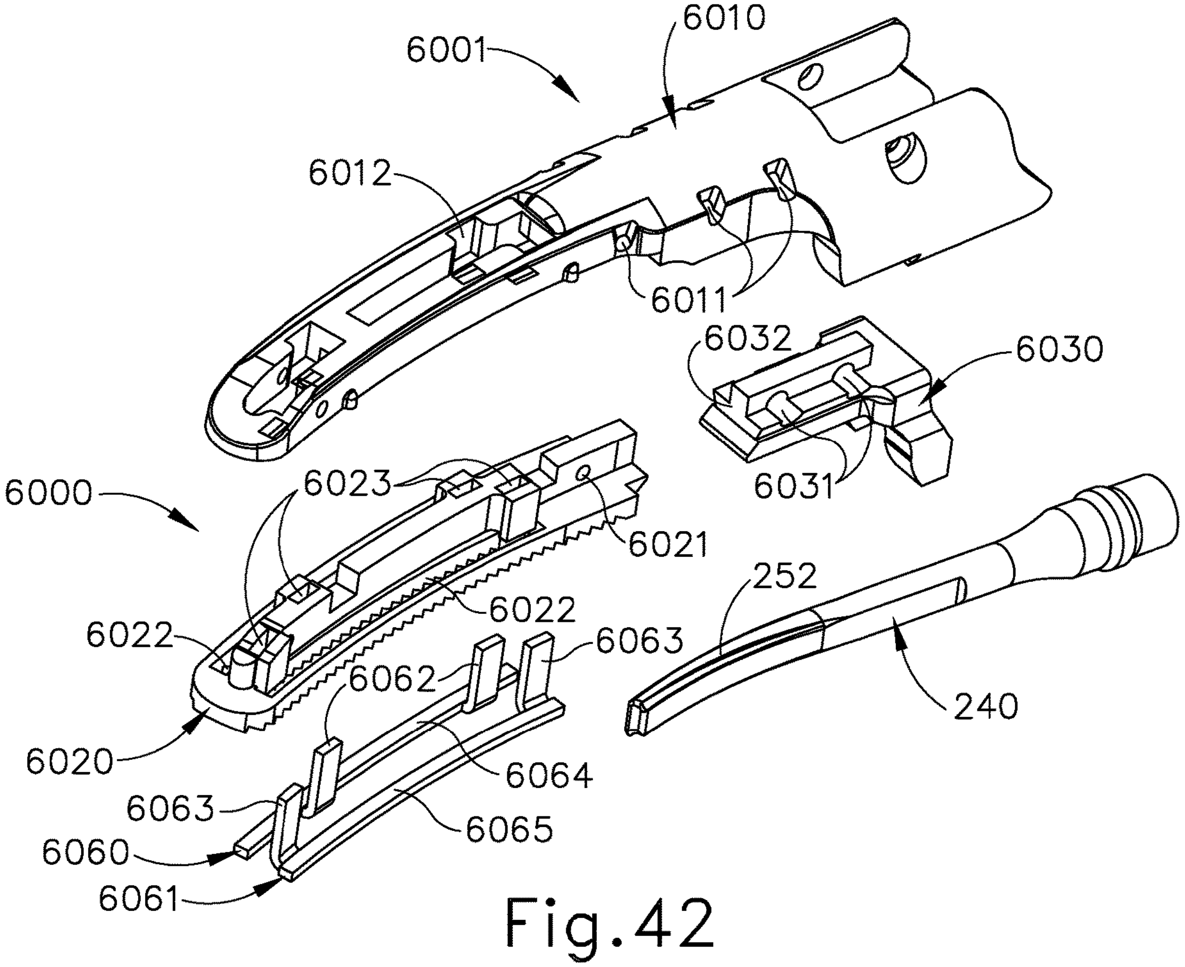
FIG. 42 depicts an exploded view of the clamp arm assembly of FIG. 41 and an ultrasonic blade that forms an end effector with the clamp arm assembly of FIG. 41.

FIGS. 41-46 show portions of other exemplary end effectors that may be readily incorporated into instrument (110) in place of end effector (140). More specifically, FIG. 41 shows a clamp arm assembly (6001) of end effector (6000) shown in FIG. 42. In the present example, a blade of end effector (6000) is the same as blade (240) as described above, while other blade configurations may be used in other examples. End effector (6000) further comprises a clamp arm (6010), a clamp pad (6020), a clamp pad retainer member (6030), a first electrode (6060), and a second electrode (6061).

Clamp arm (6010) is configured with multiple bores (6011) that align with corresponding bores (6021) of clamp pad (6020) and corresponding bores (6031) of retainer member (6030). Clamp arm (6010) comprises an opening (6012) that is shaped to receive clamp pad (6020), which is formed with corresponding features that are shaped to fit within opening (6012). Similarly, retainer member (6030) is formed with features that are shaped to engage with corresponding features of clamp arm (6010). For example, retainer member (6030) includes a rail (6032) similar to rail (226) described above, with rail (6032) engaging a recess within clamp arm (6010) that is shaped to receive rail (6032). With clamp pad (6020) and retainer member (6030) positioned within clamp arm (6010), multiple pins may be used to secure clamp pad (6020) and retainer member (6030) to clamp arm (6010) by inserting the pins through the aligning bores (6011, 6021, 6031). By way of example only, this method of assembly could be achieved by overmolding clamp pad (6020) and retainer member (6030) to clamp arm (6010) while capturing electrodes (6060, 6061).

First electrode (6060) comprises a pair of contacts or terminals (6062), while second electrode (6061) also comprises a pair of contacts or terminals (6063). In some other versions, the pair of contacts may be modified or replaced such that each electrode (6060, 6061) comprises only a single contact or terminal. First and second electrodes (6060, 6061) also comprise respective body portions (6064, 6065). The pairs of terminals (6062, 6063) extend from their respective body portions (6064, 6065) in a manner such that pairs of terminals (6062, 6063) are generally orthogonal with respect to their respective body portions (6064, 6065).

Figure 43:
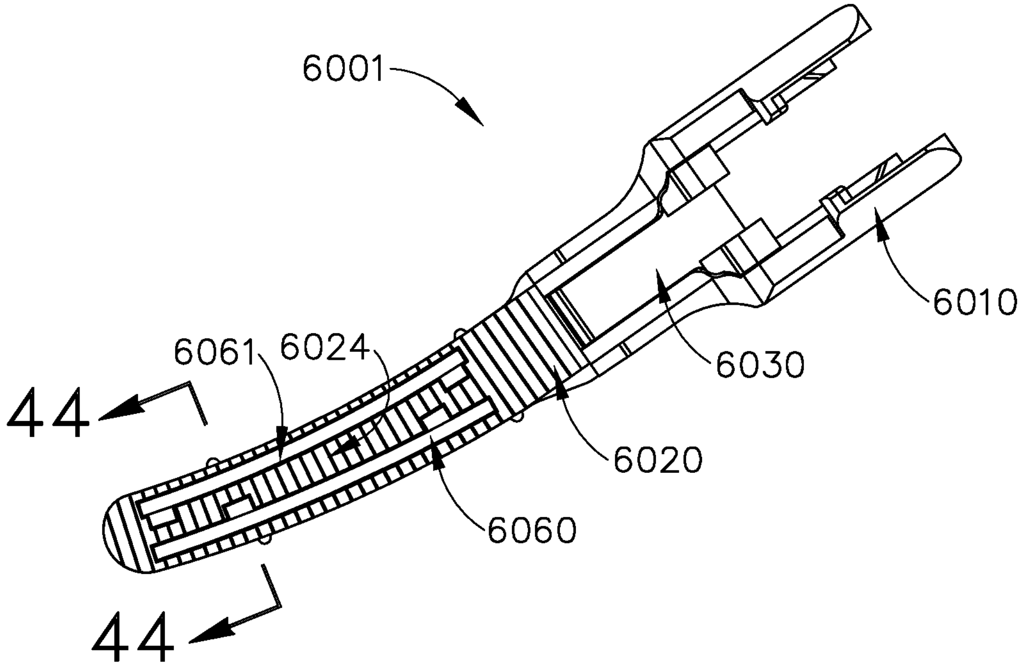
FIG. 43 depicts a bottom view of the clamp arm assembly of FIG. 41.
Figure 44:
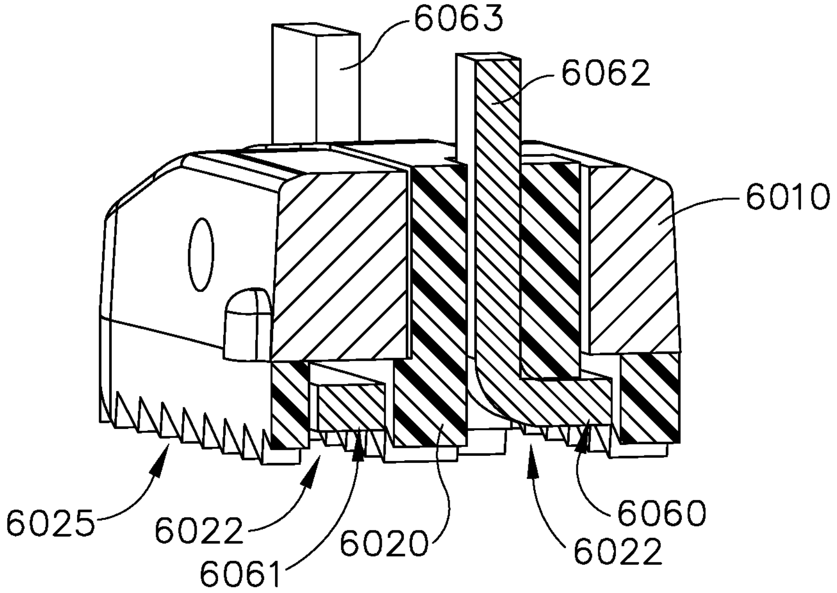
FIG. 44 depicts a perspective cross-sectional view of the clamp arm assembly of FIG. 43 taken along line 44-44 of FIG. 43.

Referring now also to FIGS. 43 and 44, in the connection with clamp arm assembly (6001), first electrode (6060) is received within clamp pad (6020), with pair of terminals (6062) extending through clamp pad (6020) such that pair of terminals (6062) are exposed and accessible from a top outer region of clamp arm (6010) as seen in FIG. 41. Second electrode (6061) connects with clamp arm assembly (6001) in the same manner as first electrode (6060). To accommodate first and second electrodes (6060, 6061), clamp pad (6020) comprises a pair of longitudinal slots (6022) for receiving body portions (6064, 6065) of electrodes (6060, 6061). Clamp pad (6020) also comprises bores (6023) that allow pairs of terminals (6062, 6063) of electrodes (6060, 6061) to pass through clamp pad (6020) for access from the top outer region of clamp arm (6010). In some other versions, these exposed terminals (6062, 6063) bend 90° and terminate into the proximal end of clamp pad (6020); and connect to an insulated wire.

Referring to FIGS. 43 and 44, clamp pad (6020) comprises teeth (6025) as described above. As also described above, end effector (6000) is configured for tissue engagement between blade (240) and the toothed surface of clamp pad (6020). Clamp pad (6020) remains proud relative to the surfaces of electrodes (6060, 6061), such that the surfaces of electrodes (6060, 6061) are recessed relative to the tissue engaging toothed surface of clamp pad (6020). In those regions with longitudinal slots (6022), when tissue is held between clamp pad (6020) and blade (240), tissue can at least partially fill slots (6022) contacting electrodes (6060, 6061). In this manner, a conductive pathway is established through the tissue between electrodes (6060, 6061) and blade (240). Blade (240) is aligned with a centerline region (6024) of clamp pad (6020) that extends between first and second electrodes (6060, 6061). With tissue compressed between clamp pad (6020) and blade (240), ultrasonic energy can be imparted to waveguide (242) and thereby ultrasonically sever the tissue along the continuous centerline region (6024) of clamp pad (6020). On each side of the cut line, ultrasonic sealing occurs as described above. In addition, end effector (6000) is further operable to provide RF electrosurgical sealing of tissue along the conductive pathways described above, which would include tissue that is laterally outward from the cut line formed between upper surface (252) of blade (240) and centerline region (6024) of clamp pad (6020). With the continuously exposed electrodes (6060, 6061) along a majority of the length of clamp pad (6020), RF electrosurgical sealing may be obtained along each side of the length of the tissue cut line.

Figure 45:
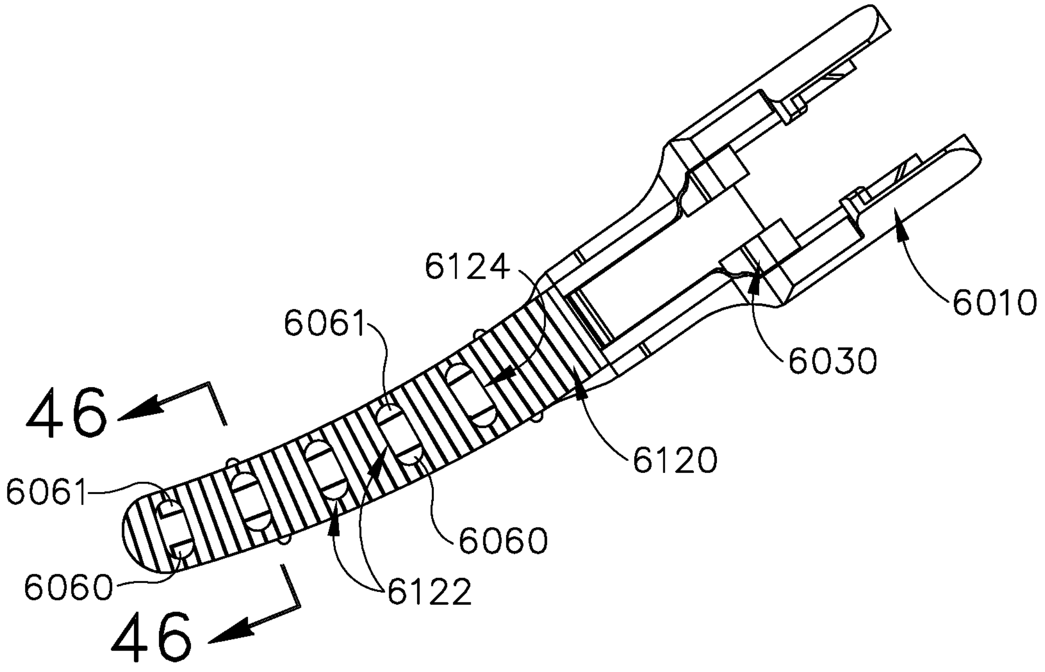
FIG. 45 depicts a bottom view of another exemplary clamp arm assembly of an end effector that may be incorporated into the instrument of FIG. 1.
Figure 46:
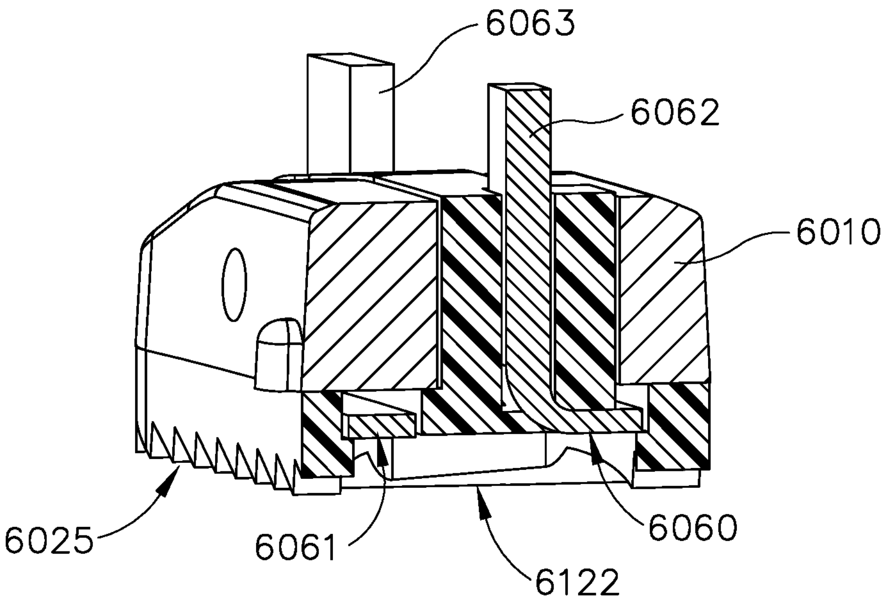
FIG. 46 depicts a perspective cross-sectional view of the clamp arm assembly of FIG. 45 taken along line 46-46 of FIG. 45.

Referring to FIGS. 45 and 46, in other versions, RF electrosurgical sealing is not required to be continuous along each side of the cut line, and instead may occur at multiple points along each side of the cut line in a discontinuous fashion. As shown in FIG. 45, clamp pad (6120) may replace clamp pad (6020). Clamp pad (6120) comprises transverse oval shaped openings (6122) as opposed to longitudinal slots (6022) of clamp pad (6020). Openings (6122) extend across centerline region (6124) of clamp pad (6120) such that centerline region (6124) of clamp pad (6120) is not continuous pad material along the length of centerline region (6124) as opposed to the configuration with clamp pad (6020) having continuous centerline region (6024).

In the example shown in FIGS. 45 and 46, ultrasonic energy may be provided to sever the tissue along a cut line that coincides with the aligned upper surface (252) of blade (240) and centerline region (6124) of clamp pad (6120). In the present configuration clamp pad (6120) contacts gripped tissue intermittently or in a discontinuous fashion because openings (6122) interrupt centerline region (6124). However, the spacing of openings (6122) and the ultrasonic energy applied are configured such that a continuous cut of the tissue is made over the length of clamp pad (6120) even without continuous contact between clamp pad (6120) and the tissue along centerline region (6124).

Openings (6122) in clamp pad (6120) provide access to or expose electrodes (6060, 6061). With this configuration, when the tissue is compressed between blade (240) and clamp pad (6120), the tissue can at least partially fill openings (6122) to contact electrodes (6060, 6061) at locations along the length of clamp pad (6120). In this manner, a conductive pathway is established through the tissue between electrodes (6060, 6061) and blade (240). With the tissue compressed between clamp pad (6120) and blade (240), ultrasonic energy can be imparted to waveguide (242) and thereby ultrasonically sever the tissue along the length of clamp pad (6120) as discussed above. On each side of the cut line, ultrasonic sealing occurs as described above. In addition, the end effector with clamp pad (6120) is further operable to provide RF electrosurgical sealing of tissue along the conductive pathways described above, which would include tissue that is laterally outward from the cut line formed between upper surface (252) of blade (240) and centerline region (6124) of clamp pad (6120). In some versions using openings (6122) the RF electrosurgical sealing occurs at those locations on each side of the cut line corresponding to the locations of respective openings (6122). In some versions, the spacing of openings (6122) is such that the RF electrosurgical sealing occurs not only at the openings (6122), but between openings (6122) as well. In this manner, RF electrosurgical sealing may be obtained along the length of clamp pad (6120) and thus along each side of the length of the tissue cut line. In view of the teachings herein, other configurations for openings (6122) to provide RF electrosurgical sealing will be apparent to those of ordinary skill in the art.

In the examples discussed above with respect to FIGS. 41-46, pairs of terminals (6062, 6063) connect to an electrical source such that each electrode (6060, 6061) has the same polarity, with blade (240) having the opposite polarity such that the conductive pathways exist between each of electrodes (6060, 6061) and blade (240). In other versions, blade (240) is electrically neutral and electrode (6060) has an opposite polarity to electrode (6061). In such examples with two oppositely polarized electrodes (6060, 6061) and a neutral blade (240), pairs of terminals (6062, 6063) connect to electrical sources such that one of electrodes (6060, 6061) has positive polarity and the other has negative polarity. With this configuration, the conductive pathways are established through the tissue between electrodes (6060, 6061). With these conductive pathways, the RF electrosurgical sealing occurs laterally across the tissue cut line. In versions using clamp pad (6020), the RF electrosurgical sealing may be continuous along the length of clamp pad (6020) and the tissue cut line. In versions using clamp pad (6120), the RF electrosurgical sealing may be discontinuous along the length of clamp pad (6120) and the tissue cut line. In view of the teachings herein, other ways to configure electrodes (6060, 6061) and clamp pads (6020, 6120) to achieve a desired conductive pathway for RF electrosurgical sealing will be apparent to those of ordinary skill in the art.

J. End Effector with Dual Electrode Molded within Clamp Pad

Figure 47A:
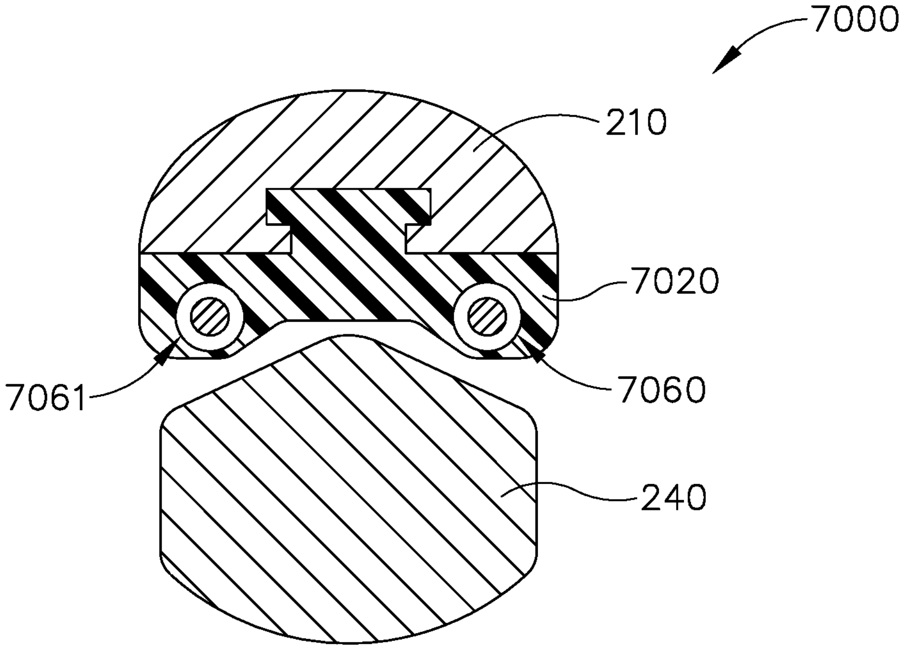
FIG. 47A depicts a cross-sectional view of another exemplary end effector that may be incorporated into the instrument of FIG. 1, with the cross-sectional view taken prior to machining.
Figure 47B:
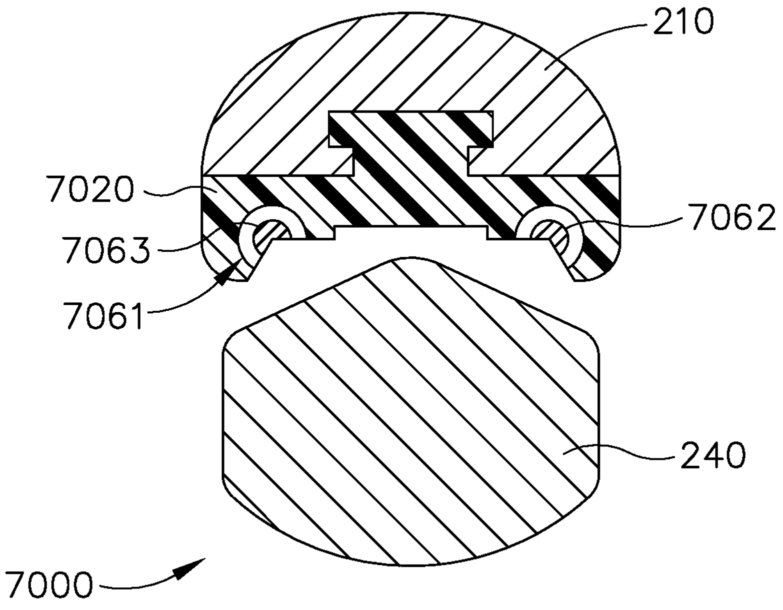
FIG. 47B depicts a cross-sectional view of the end effector of FIG. 47A taken after machining.

FIGS. 47A-48B show exemplary end effectors (7000, 7100) that may be readily incorporated into instrument (110) in place of end effector (140). FIGS. 47A and 47B show end effector (7000), which comprises clamp arm (210), a clamp pad (7020), blade (240), and first and second wires (7060, 7061). FIG. 47A shows a first state of manufacture for end effector (7000), prior to machining clamp pad (7020). FIG. 47B shows a second state of manufacture for end effector (7000), after machining clamp pad (7020) to expose electrodes (7062, 7063) within wires (7060, 7061), which have an insulating material surrounding electrodes (7062, 7063). In the present example, clamp pad (7020) is formed in a molding process such that clamp pad (7020) is formed with clamp arm (210) and molded over wires (7060, 7061). In other examples, clamp pad (7020) may be formed separate from clamp arm (210) and/or wires (7060, 7061) and then later combined with clamp arm (210) and/or wires (7060, 7061). After combining wires (7060, 7061), clamp pad (7020), and clamp arm (210), clamp pad (7020) is machined such that portions of clamp pad (7020) are cut away along with insulator portions of wires (7060, 7061) to expose electrodes (7062, 7063). In some instances, it is not necessary to combine clamp pad (7020) and wires (7060, 7061) with clamp arm (210) prior to machining assembled clamp pad (7020) and wires (7060, 7061).

In the present example, each of wires (7060, 7061) have the same polarity with blade (240) having the opposite polarity. With identically polarized wires (7060, 7061) positioned opposite to oppositely polarized blade (240), this can be considered an opposing or offset electrode configuration. In some versions, wires (7060, 7061) each serve as a positive pole while blade (240) serves as a negative pole. In this configuration the conductive pathway is created through tissue between wires (7060, 7061) and blade (240). It should also be understood that, in some other versions, wires (7060, 7061) may have opposing polarity while blade (240) is electrically neutral.

Furthermore, as will be apparent to those of ordinary skill in the art in view of the teachings herein, the configuration of the machined cutouts, and the resulting openings created in clamp pad (7020) to expose electrodes (7062, 7063) will impact the configuration of the conductive pathways and the resulting RF electrosurgical sealing. By way of example only, and not limitation, clamp pad (7020) and wires (7060, 7061) may be machined such that there are continuous openings along clamp pad (7020) exposing electrodes (7062, 7063) in a continuous fashion along the length of clamp pad (7020). In other versions, clamp pad (7020) and wires (7060, 7061) may be machined such that there are intermittent openings along clamp pad (7020) exposing electrodes (7062, 7063) intermittently along the length of clamp pad (7020). In either approach, clamp pad (7020) and blade (240) are configured such that after machining clamp pad (7020), a sufficient gap is maintained between electrodes (7062, 7063) and blade (240) to prevent short circuiting as discussed above. In use, ultrasonic cutting, ultrasonic sealing, and RF electrosurgical sealing occur in the same or similar manner as described above and will be apparent to those of ordinary skill in the art in view of the teachings herein.

Figure 48A:
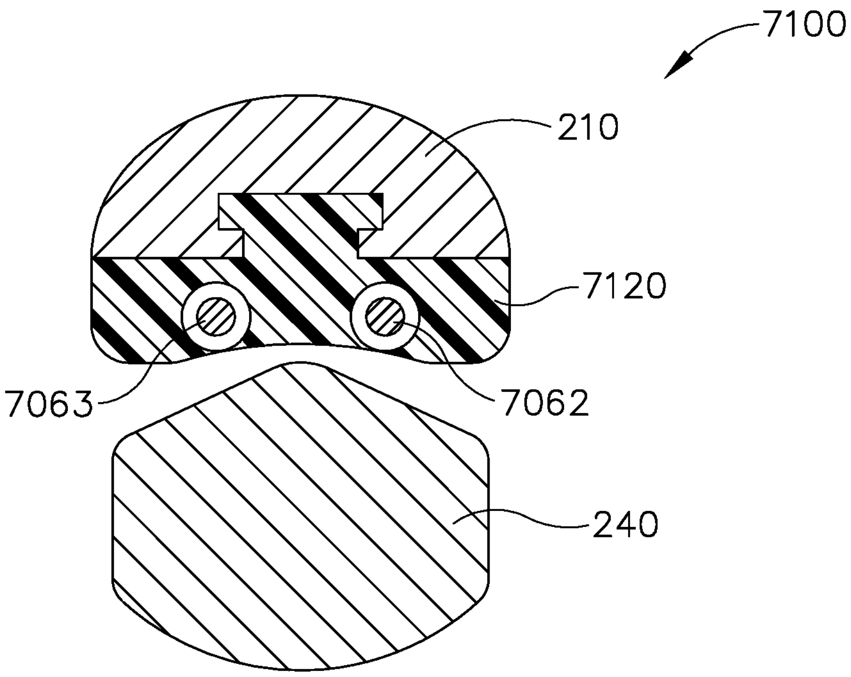
FIG. 48A depicts a cross-sectional view of another exemplary end effector that may be incorporated into the instrument of FIG. 1, with the cross-sectional view taken prior to machining.
Figure 48B:
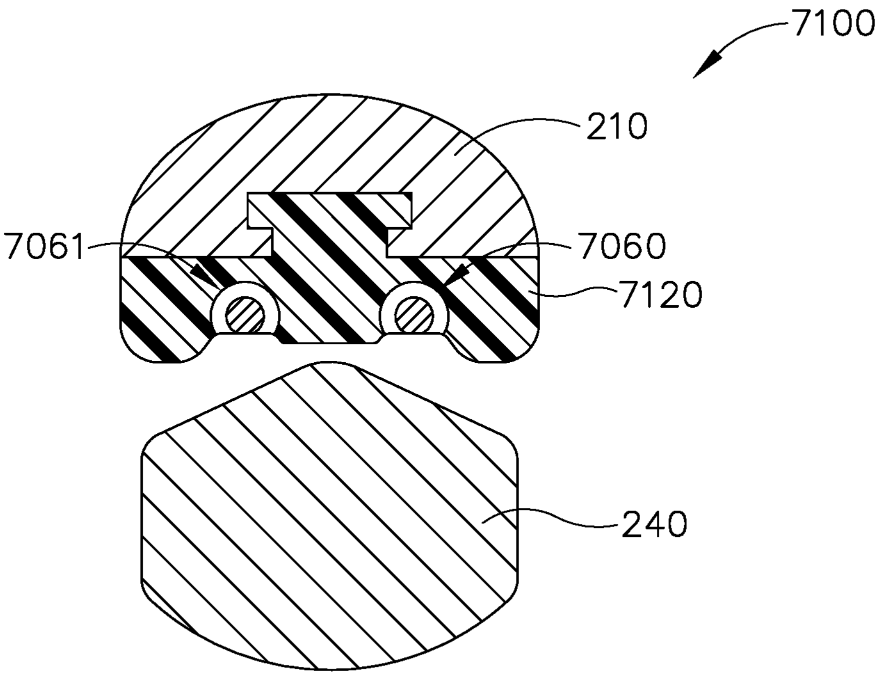
FIG. 48B depicts a cross-sectional view of the end effector of FIG. 47A taken after machining.
Figure 49:
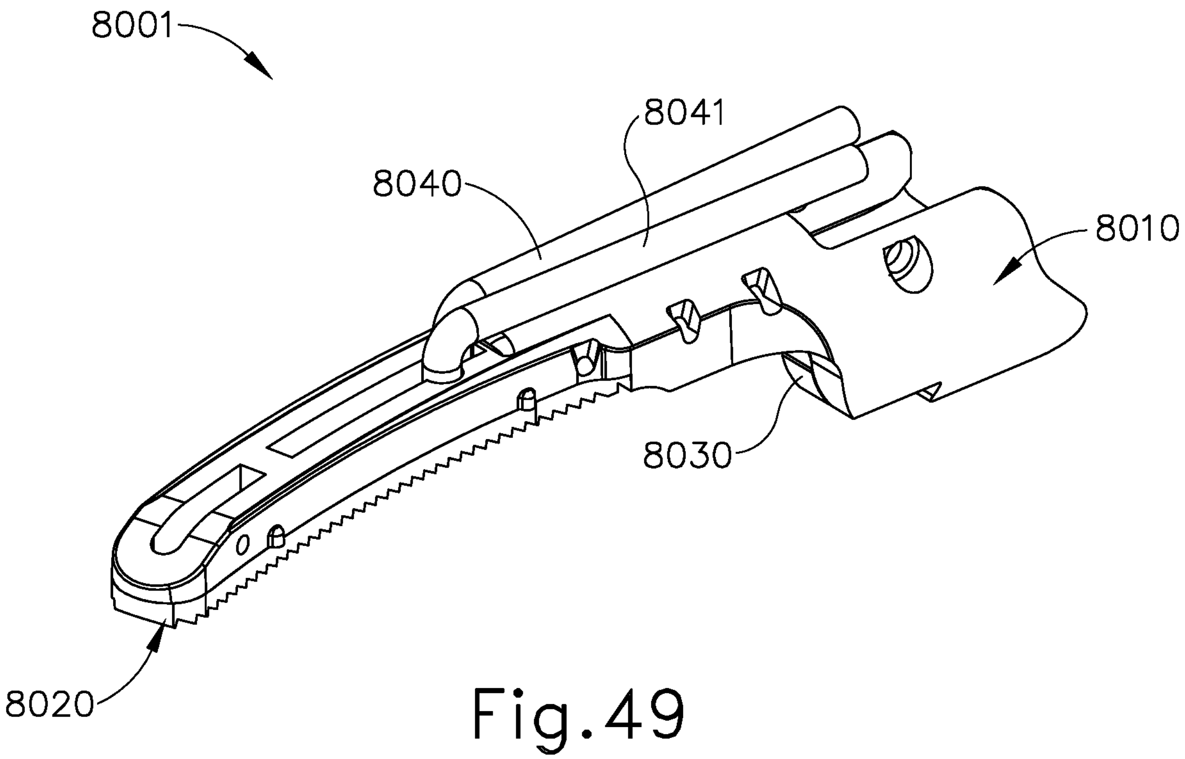
FIG. 49 depicts a perspective view of another exemplary clamp arm assembly of an end effector that may be incorporated into the instrument of FIG. 1.

FIGS. 48A and 48B show end effector (7100), which comprises clamp arm (210), a clamp pad (7120), blade (240), and first and second wires (7060, 7061). FIG. 48A shows a first state of manufacture for end effector (7100), prior to machining clamp pad (7120). FIG. 48B shows a second state of manufacture for end effector (7100), after machining clamp pad (7120) to expose electrodes (7062, 7063) within wires (7060, 7061), which have an insulating material surrounding electrodes (7062, 7063). In the present example, clamp pad (7120) is formed in a molding process such that clamp pad (7120) is formed with clamp arm (210) and molded over wires (7060, 7061). In other examples, clamp pad (7120) may be formed separate from clamp arm (210) and/or wires (7060, 7061) and then later combined with clamp arm (210) and/or wires (7060, 7061). After combining wires (7060, 7061), clamp pad (7120), and clamp arm (210), clamp pad (7120) is machined such that portions of clamp pad (7120) are cut away along with insulator portions of wires (7060, 7061) to expose electrodes (7062, 7063). In some instances, it is not necessary to combine clamp pad (7120) and wires (7060, 7061) with clamp arm (210) prior to machining assembled clamp pad (7120) and wires (7060, 7061).

In the present example, each wire (7060, 7061) has an opposite polarity with blade (240) being neutral. With oppositely polarized wires (7060, 7061) positioned offset from one another within clamp pad (7120), this can be considered an offset electrode configuration. In a configuration where wire (7060) serves as a positive pole and wire (7061) serves as a negative pole, the conductive pathway is created from electrode (7062) of wire (7060), through the gripped tissue, and to electrode (7063) of wire (7061). To facilitate this conductive pathway, wires (7060, 7061) are positioned closer together compared to the arrangement shown in FIGS. 47A and 47B. In view of the teachings herein, other positions for wires (7060, 7061) relative to clamp pad (7120) to achieve a desired conductive pathway through tissue will be apparent to those of ordinary skill in the art. It should also be understood that end effector (7100) may be modified such that electrodes (7062, 7063) both provide one pole (e.g., a positive pole) while blade (240) provides an opposite pole (e.g., a negative pole).

Furthermore, as will be apparent to those of ordinary skill in the art in view of the teachings herein, the configuration of the machined cutouts, and the resulting openings created in clamp pad (7120) to expose electrodes (7062, 7063) will impact the configuration of the conductive pathways and the resulting RF electrosurgical sealing. By way of example only, and not limitation, clamp pad (7120) and wires (7060, 7061) may be machined such that there are continuous openings along clamp pad (7120) exposing electrodes (7062, 7063) in a continuous fashion along the length of clamp pad (7120). In other versions, clamp pad (7120) and wires (7060, 7061) may be machined such that there are intermittent openings along clamp pad (7120) exposing electrodes (7062, 7063) intermittently along the length of clamp pad (7120). In either approach, although blade (240) is neutral, clamp pad (7120) and blade (240) may be configured such that after machining clamp pad (7120), a sufficient gap is maintained between electrodes (7062, 7063) and blade (240) to prevent short circuiting as discussed above. In use, ultrasonic cutting, ultrasonic sealing, and RF electrosurgical sealing occur in the same or similar manner as described above and will be apparent to those of ordinary skill in the art in view of the teachings herein. Furthermore, in some versions end effector (7100) may be configured such that electrodes (7062, 7063) have the same polarity and are used with blade (240) having an opposite polarity, similar to the description above with respect to end effector (7000).

K. End Effector with Dual Nested Electrode within Clamp Pad

FIGS. 49-54B show clamp assemblies (8001, 8101, 8201) of three other exemplary end effectors that may be readily incorporated into instrument (110) in place of end effector (140). Each end effector of these examples comprises the same clamp arm (8010), clamp pad retainer member (8030), wires (8040, 8041), insulators (8050, 8051), electrodes (8060, 8061), and blade (240). However, each end effector of these examples comprises a different configuration for clamp pads (8020, 8120, 8220) as will be described in greater detail below.

Referring to FIGS. 49 and 51-52B, the end effector of this example comprises a clamp arm assembly (8001). Clamp arm assembly (8001) is operable to pivot toward and away from blade (240) in the manner described above. Clamp arm assembly (8001) comprises clamp arm (8010), clamp pad (8020), clamp pad retainer member (8030), wires (8040, 8041), insulators (8050, 8051), and electrodes (8060, 8061). Clamp pad retainer member (8030) operates similar to clamp pad retainer member (230) discussed above. Clamp pad (8020) comprises openings (8021) that provide access to electrodes (8060, 8061). In the present example, openings (8021) are configured as rectangular shapes, where openings (8021) extend laterally across clamp pad (8020). This configuration provides for a centerline region (8027) of clamp pad (8020) with electrodes (8060, 8061) partially accessible or exposed. In the present example, blade (240) aligns along centerline region (8027) such that when tissue is compressed between blade (240) and clamp pad (8020), ultrasonic energy may be provided to sever the tissue along a cut line that coincides with the aligned upper surface (252) of blade (240) and centerline region (8027) of clamp pad (8020). In the present configuration clamp pad (8020) provides intermittent contact with the tissue along centerline region (8027) when the end effector is in a closed configuration gripping the tissue because openings (8021) interrupt centerline region (8027).

Openings (8021) in clamp pad (8020) provide access to or expose electrodes (8060, 8061). Electrodes (8060, 8061) each comprise projections (8062, 8063) that extend from respective body portions (8064, 8065) of electrodes (8060, 8061). Furthermore, electrodes (8060, 8061) each comprise spaces (8066, 8067) between respective projections (8062, 8063) of electrodes (8060, 8061). Projections (8062) and spaces (8066) are offset along the length of electrode (8060) relative to projections (8063) and spaces (8067) of electrode (8061). With this offset configuration, electrodes (8060, 8061) have a nested, interdigitated arrangement as best seen in FIG. 51, where projections (8062) are positionable within spaces (8067), and projections (8063) are positionable within spaces (8066). As seen in FIG. 51, although nested, electrodes (8060, 8061) maintain a space or gap from one another such that they are not in contact. Electrodes (8060, 8061) are connectable with wires (8040, 8041) such that electrodes (8060, 8061) can serve as positive and negative poles. While wires (8040, 8041) are shown as being exposed above clamp arm (8010) in FIGS. 49-51, 52B, 53B, and 54B, it should be understood that this is an exaggerated representation of wires (8040, 8041). In practical contexts, wires (8040, 8041) may in fact be disposed in clamp pad (8020) and retainer member (8030) such that wires (8040, 8041) are not exposed above clamp arm (8010).

Insulators (8050, 8051) are positioned between clamp arm (8010) and electrodes (8060, 8061) such that clamp arm (8010) remains electrically neutral. In the present example, blade (240) can be coated such that blade (240) remains electrically neutral also. The coating used with blade (240) can also provide non-stick features that help prevent tissue from sticking to blade (240).

With this configuration, when the tissue is compressed between blade (240) and clamp pad (8020), the tissue can at least partially fill openings (8021) to contact electrodes (8060, 8061) at locations along the length of clamp pad (8020). Moreover, at least some of the tissue that fills openings (8021) can at least partially fill spaces (8066, 8067) between electrodes (8060, 8061). In this manner, a conductive pathway is established through the tissue between electrodes (8060, 8061). With the tissue compressed between clamp pad (8020) and blade (240), ultrasonic energy can be imparted to waveguide (242) and thereby ultrasonically sever the tissue along the length of clamp pad (8020) as discussed above. On each side of the cut line, ultrasonic sealing occurs as described above. In addition, the end effector is further operable to provide RF electrosurgical sealing of the tissue along the conductive pathways described above, which would include RF electrosurgical sealing through tissue from one side of the cut line to tissue on the other side of the cut line since the cut line is generally centered along the nested area of electrodes (8060, 8061). In some versions, the spacing of openings (8021) is such that the RF electrosurgical sealing occurs not only at the openings (8021), but between openings (8021) as well. In this manner, RF electrosurgical sealing may be obtained along the entire length of clamp pad (8020) and thus the entire length of the tissue cut line. In other versions, RF electrosurgical sealing is not required to be continuous along the cut line, and instead may occur at multiple points along the cut line in a discontinuous fashion as described above.

In some other versions using an end effector as configured as shown in FIGS. 49 and 51-52B, the end effector may be modified such that each electrode (8060, 8061) has the same polarity and with the blade (240) having the opposite polarity from the electrodes (8060, 8061). In this configuration, and where the electrodes (8060, 8061) serve as positive poles and blade (240) serves as the negative pole, the conductive path will extend from each of the electrodes (8060, 8061), through the tissue, and to the blade (240). As will be understood by those of ordinary skill in the art in view of the teachings herein, the RF electrosurgical sealing will then occur as described above with respect to those versions using a polarized blade.

Figure 50:
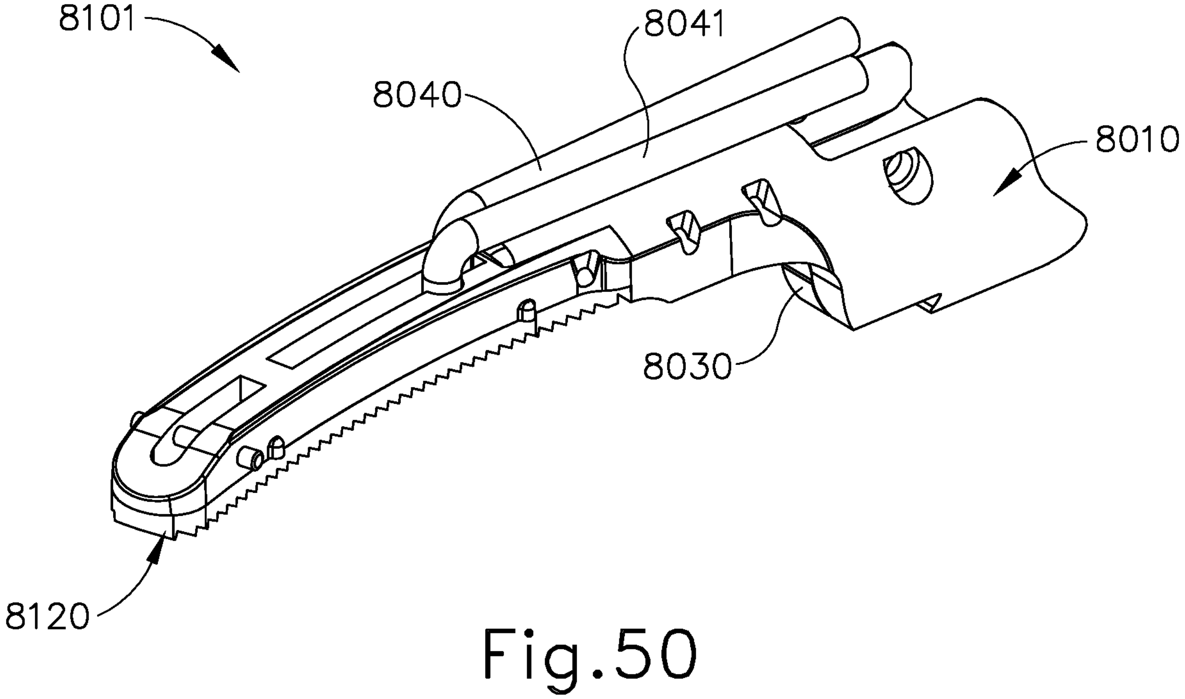
FIG. 50 depicts a perspective view of another exemplary clamp arm assembly of an end effector that may be incorporated into the instrument of FIG. 1.
Figure 51:
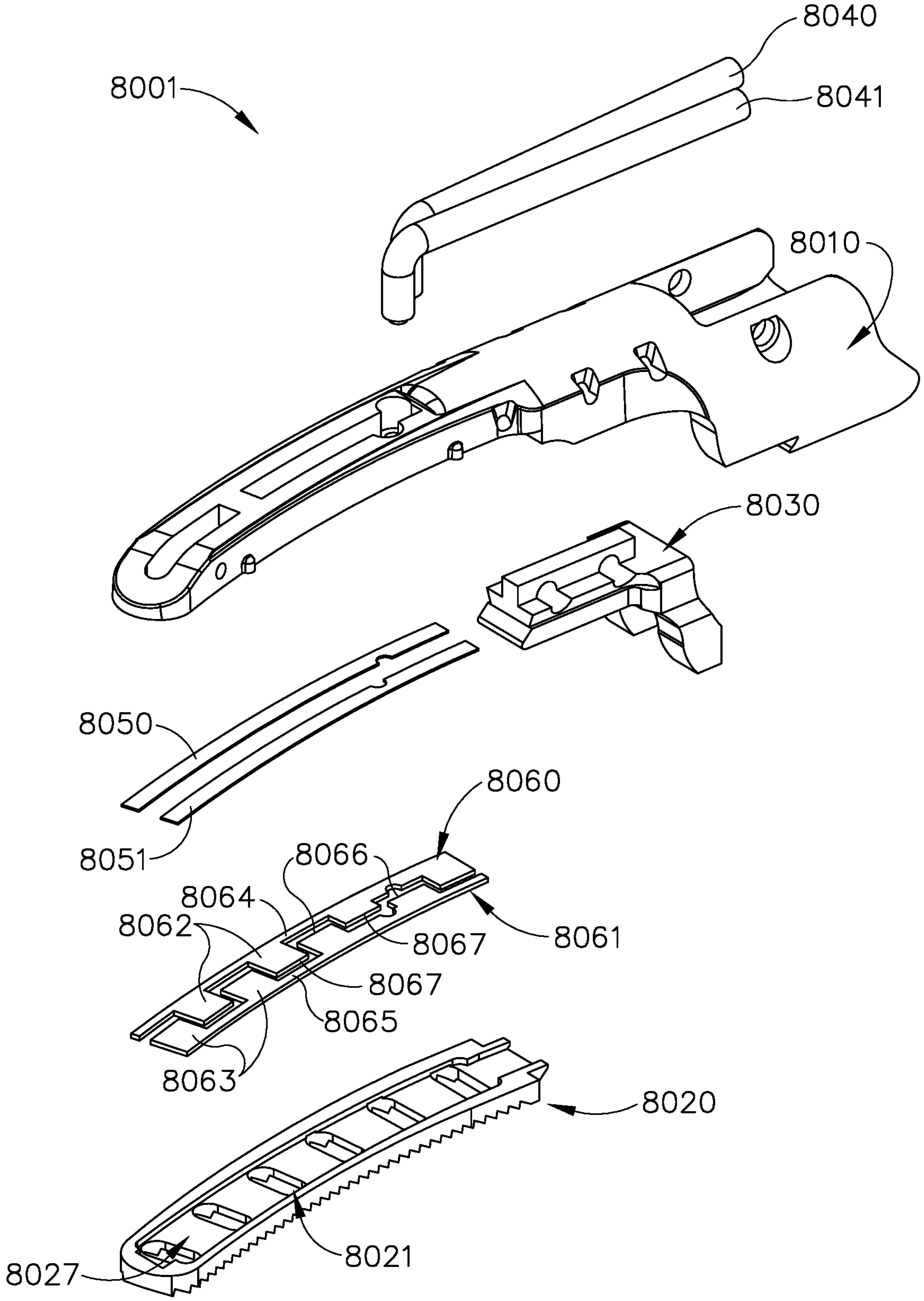
FIG. 51 depicts an exploded view of the clamp arm assembly of FIG. 49.
Figure 52A:
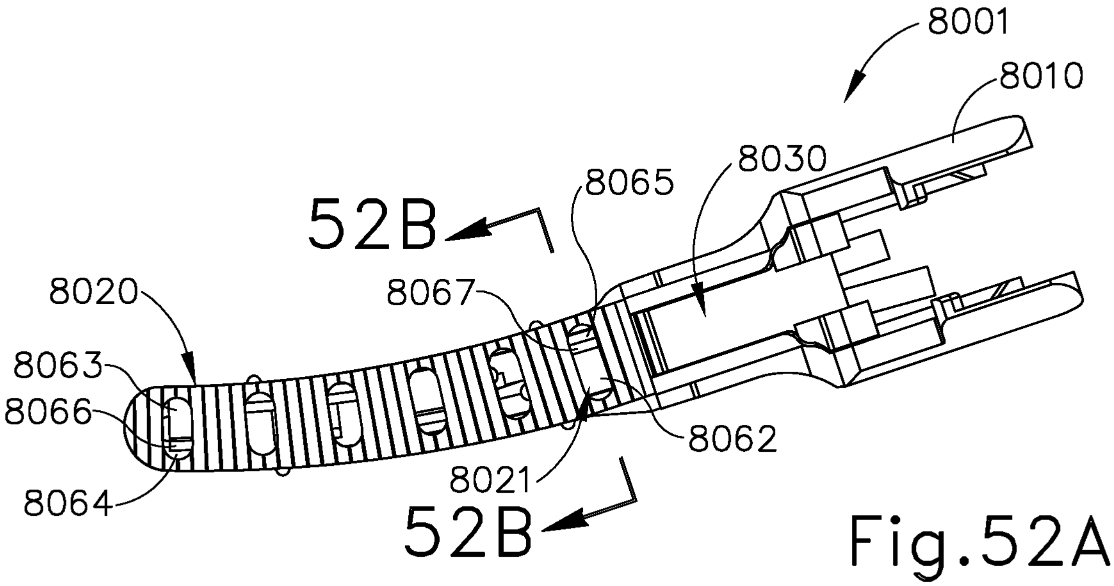
FIG. 52A depicts a bottom view of the clamp arm assembly of FIG. 49.
Figure 53A:
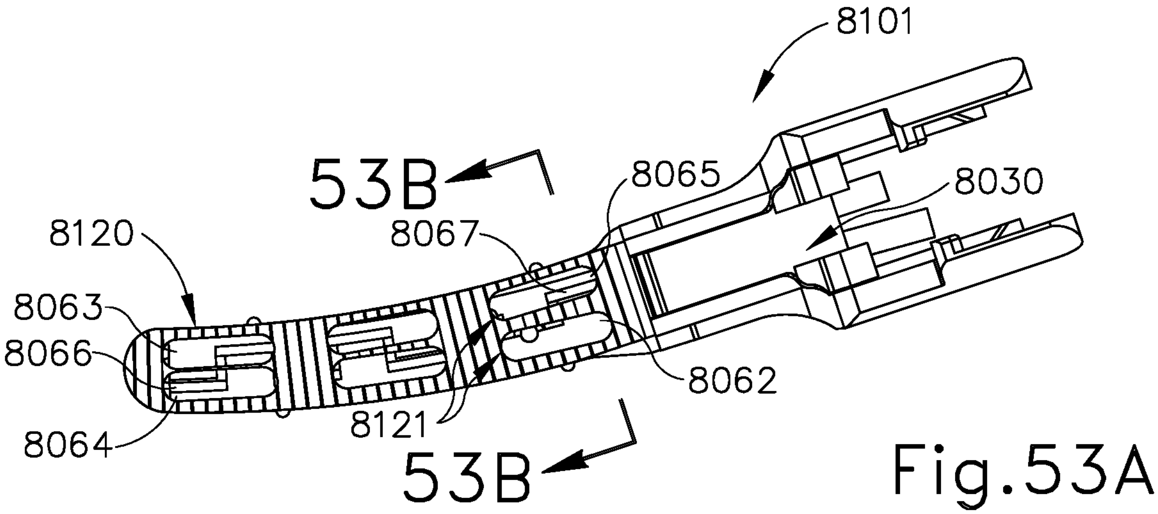
FIG. 53A depicts a bottom view of another exemplary clamp arm assembly of an end effector that may be incorporated into the instrument of FIG. 1.
Figure 53B:
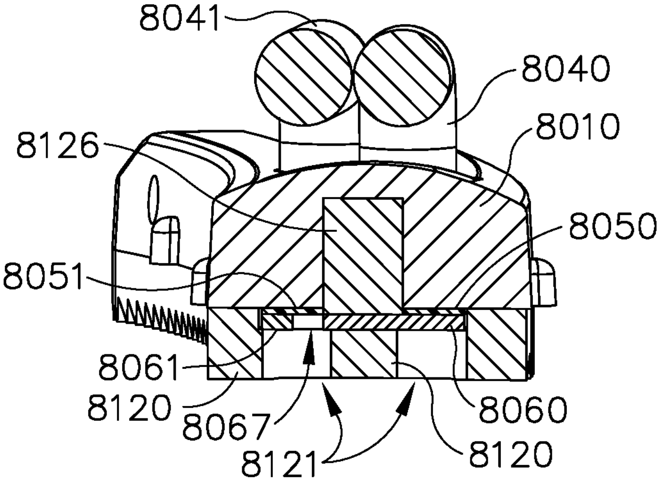
FIG. 53B depicts a perspective cross-sectional view of the clamp arm assembly of FIG. 53A, taken along line 53B-53B of FIG. 53A.

FIGS. 50, 53A, and 53B show a similar end effector that uses clamp arm assembly (8101), which incorporates clamp pad (8120). As mentioned above, clamp arm assembly (8101) includes many of the same components and operates similarly to clamp arm assembly (8001) described above. One difference is with clamp arm assembly (8101), clamp pad (8120) is formed with a rail (8126) for engaging with clamp arm (8010). Rail (8126) is structurally and operably similar to rail (226) described above. Another difference with clamp arm assembly (8101) is that clamp pad (8120) comprises openings (8121) that are shaped as pairs of longitudinally elongated circles that repeat along the length of clamp pad (8120). With this alternate opening configuration for clamp pad (8120), the pattern of the RF electrosurgical sealing may differ from that described above with respect to clamp pad (8020) and openings (8021). As described above, this end effector using clamp arm assembly (8101) may be configured such that an electrically neutral blade (240) is used with oppositely polarized electrodes (8060, 8061); or in other versions each electrode (8060, 8061) may have the same polarity, with blade (240) being oppositely polarized. The gap between openings (8121) may vary to ensure there is material to engage blade (240) for the ultrasonic functionality. For instance, distal openings (8121) may be smaller out at the tapered end of clamp arm (8010). Alternatively, blade (240) may be reconfigured to contact outside of the centerline to allow a cut along the entire length of clamp arm (8010).

Figure 54A:
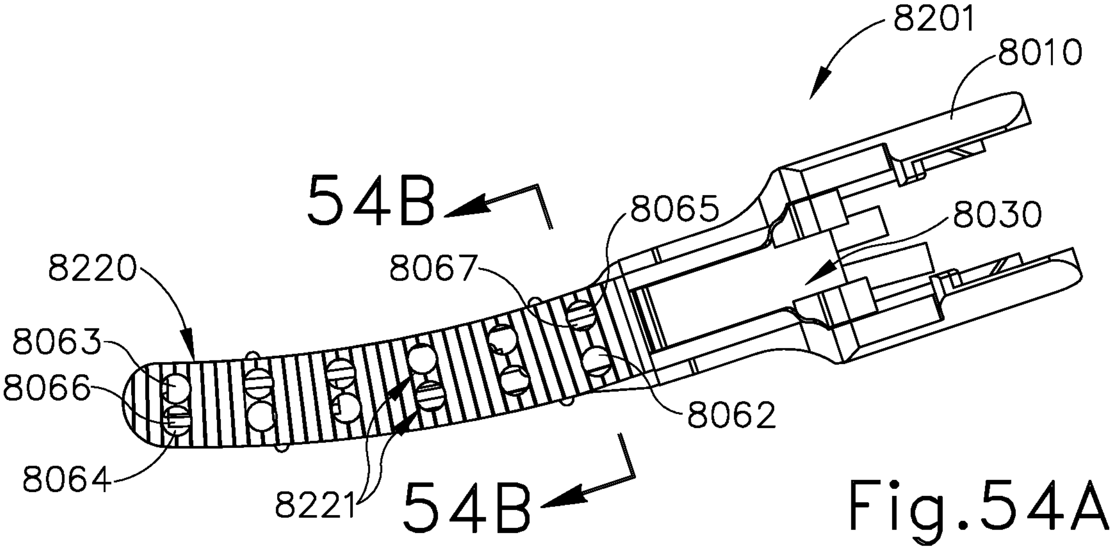
FIG. 54A depicts a bottom view of another exemplary clamp arm assembly of an end effector that may be incorporated into the instrument of FIG. 1.
Figure 52B:
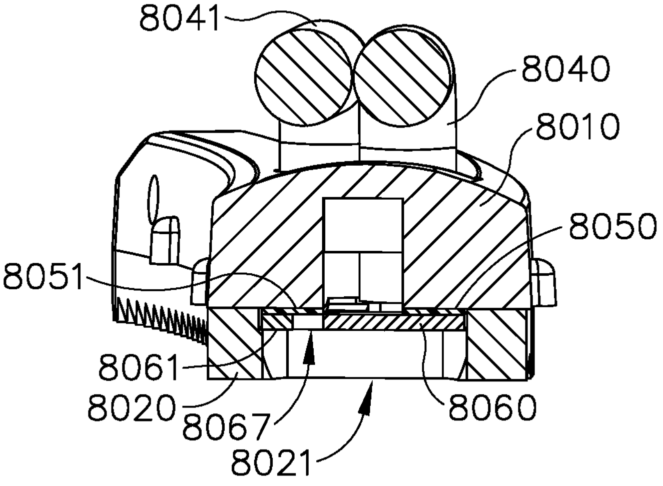
FIG. 52B depicts a perspective cross-sectional view of the clamp arm assembly of FIG. 52A, taken along line 52B-52B of FIG. 52A.
Figure 54B:
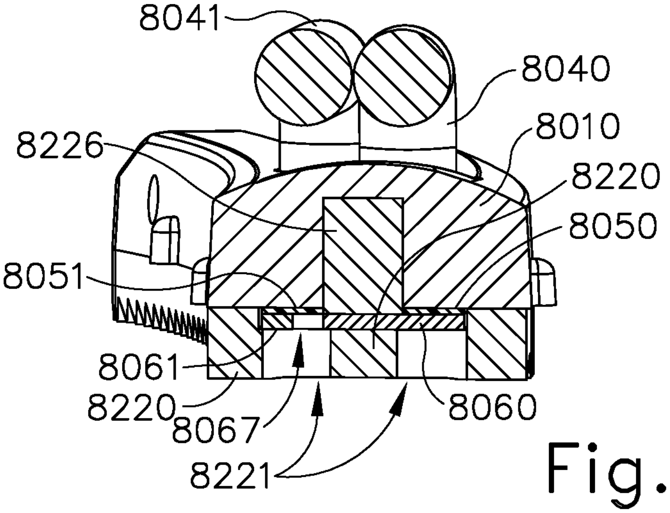
FIG. 54B depicts a perspective cross-sectional view of the clamp arm assembly of FIG. 54A, taken along line 54B-54B of FIG. 54A.

FIGS. 54A and 54B show a similar end effector that uses clamp arm assembly (8201), which incorporates clamp pad (8220). As mentioned above, clamp arm assembly (8201) includes many of the same components and operates similarly to clamp arm assembly (8001) described above. One difference with clamp arm assembly (8201) is that clamp pad (8220) is formed with a rail (8226) for engaging with clamp arm (8010). Rail (8226) is structurally and operably similar to rail (226) described above. Another difference with clamp arm assembly (8201) is that clamp pad (8220) comprises openings (8221) that are shaped as pairs of circles that repeat along the length of clamp pad (8220). With this alternate opening configuration for clamp pad (8220), the pattern of the RF electrosurgical sealing may differ from that described above with respect to clamp pad (8020) and openings (8021). As described above, this end effector using clamp arm assembly (8201) may be configured such that an electrically neutral blade (240) is used with oppositely polarized electrodes (8060, 8061); or in other versions each electrode (8060, 8061) may have the same polarity with blade (240) being oppositely polarized.

While the above version illustrate electrodes (8060, 8061) as flat conductors, such as stamped metal, etc., in some other versions electrodes (8060, 8061) can be wire structures. For example, a pair of wires may be configured in a close nested arrangement, similar to the nested arrangement shown for electrodes (8060, 8061) in FIG. 51. The wires may then have opposite polarity and be used with a neutral blade (240) or the wires may have the same polarity and be used with an oppositely polarized blade (240) as described above. In view of the teachings herein, other nested structures and arrangements for electrodes (8060, 8061) will be apparent to those of ordinary skill in the art.

L. End Effector with Patterned Clamp Arm Electrode

Figure 55:
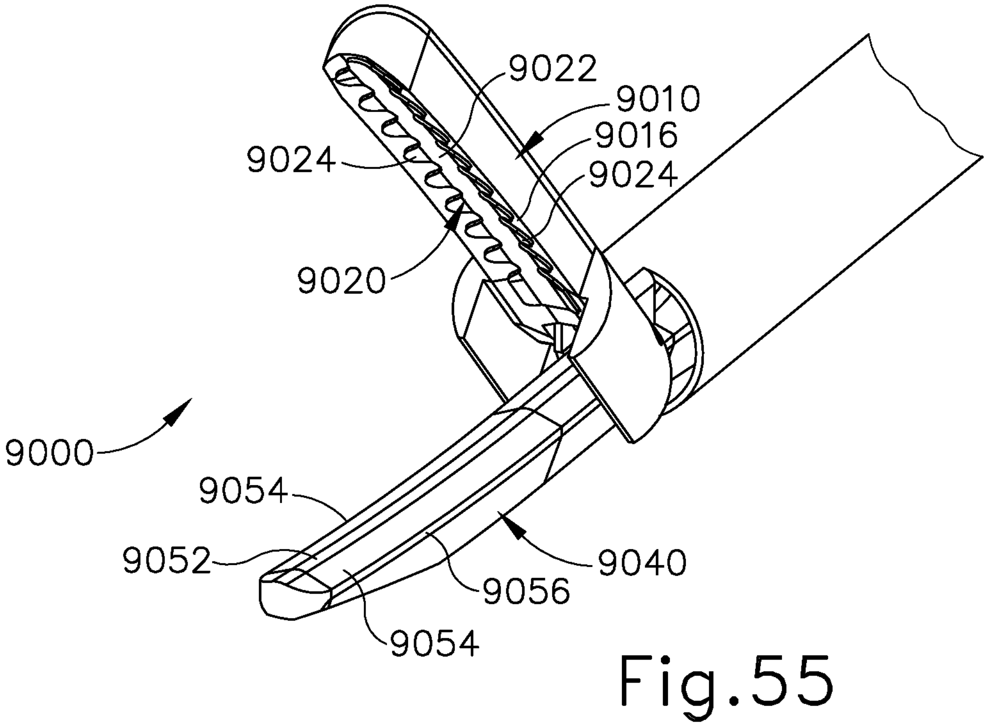
FIG. 55 depicts a perspective view of another exemplary end effector that may be incorporated into the instrument of FIG. 1, with the end effector in an open configuration.
Figure 56:
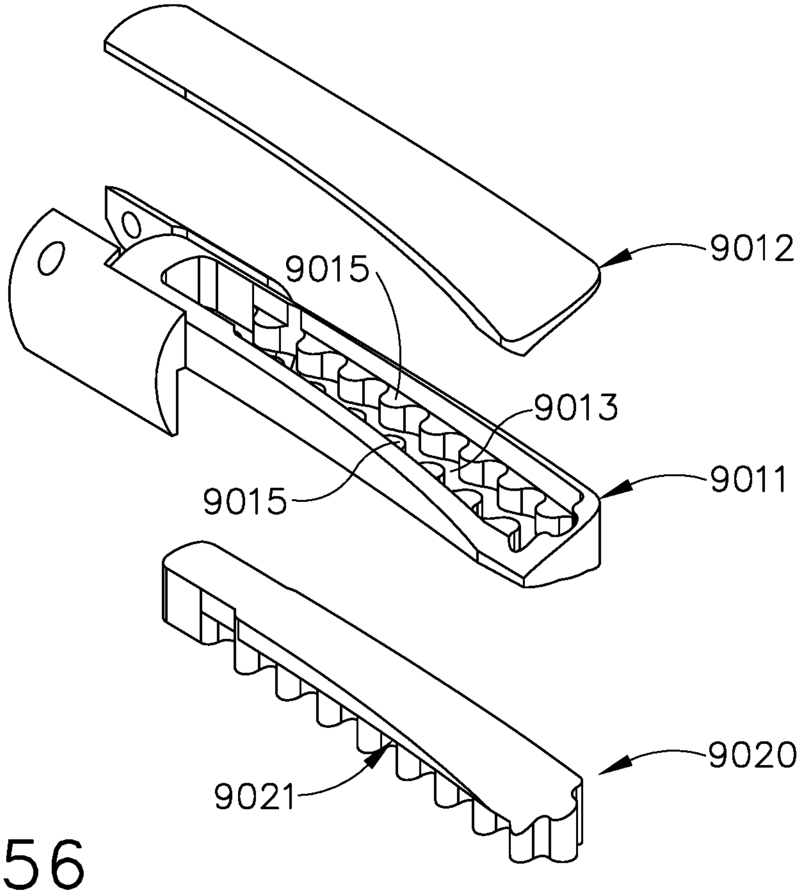
FIG. 56 depicts an exploded view of the clamp arm assembly of the end effector of FIG. 55.

FIGS. 55-60B show other exemplary end effectors that may be readily incorporated into instrument (110) in place of end effector (140). FIG. 55 shows end effector (9000), which comprises blade (9040), clamp arm (9010), and clamp pad (9020). Referring to FIG. 56, clamp arm (9010) includes body (9011) and cap (9012). Body (9011) is configured with a patterned opening (9013) that in the present example represents a mirrored sinusoidal shape. Opening (9013) extends along the length of body (9011). Cap (9012) is configured to attach with a top surface of body (9011) to cover and close off opening (9013). Clamp pad (9020) comprises a shape that is configured to fit within patterned opening (9013) of clamp arm (9010). In the present example, clamp pad (9020) comprises a mirrored sinusoidal shape such that when clamp pad (9020) is positioned within clamp arm (9010), clamp pad (9020) fits within opening (9013). Clamp pad (9020) is further configured with shelf portions (9021) along each side. When clamp pad (9020) is inserted within body (9011) from the top side, shelf portions (9021) contact an upper surface (9015) of body (9011) outlining opening (9013). In this configuration, clamp pad (9020) can only be installed within clamp arm (9010) from one side, and furthermore clamp pad (9020) cannot pass entirely through opening (9013). With clamp pad (9020) positioned within body (9011), cap (9012) can be installed to secure clamp pad (9020) in place.

Figure 57A:
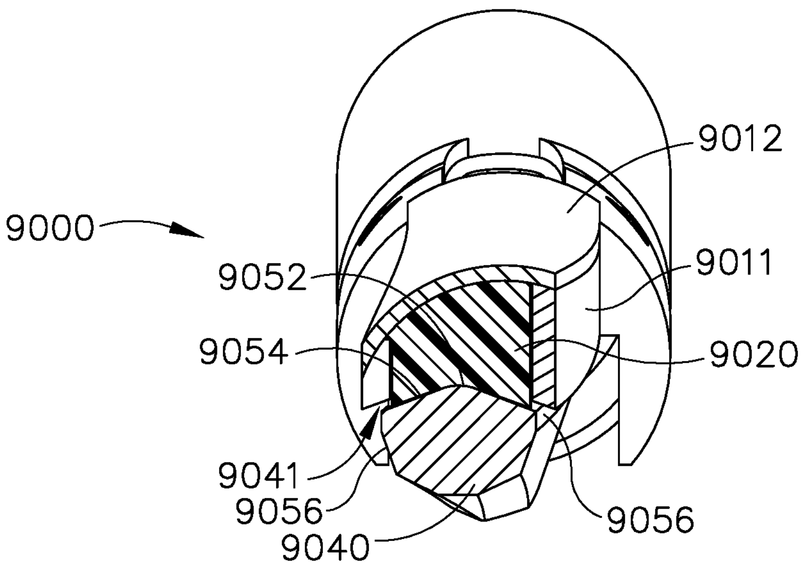
FIG. 57A depicts a perspective cross-sectional view of the end effector of FIG. 55, shown in a closed configuration at a first position along the length of the end effector.
Figure 57B:
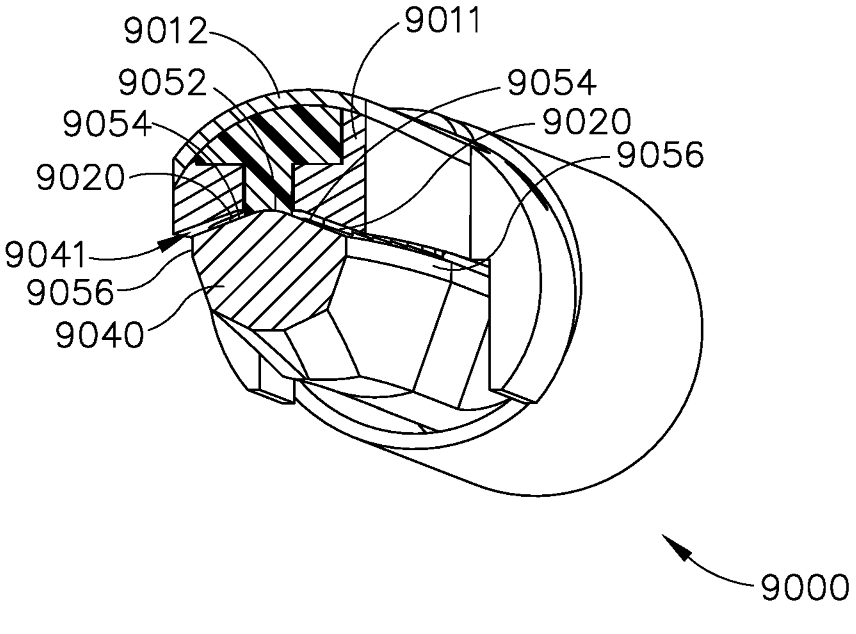
FIG. 57B depicts a perspective cross-sectional view of the end effector of FIG. 55, shown in a closed configuration at a second position along the length of the end effector.
Figure 58:
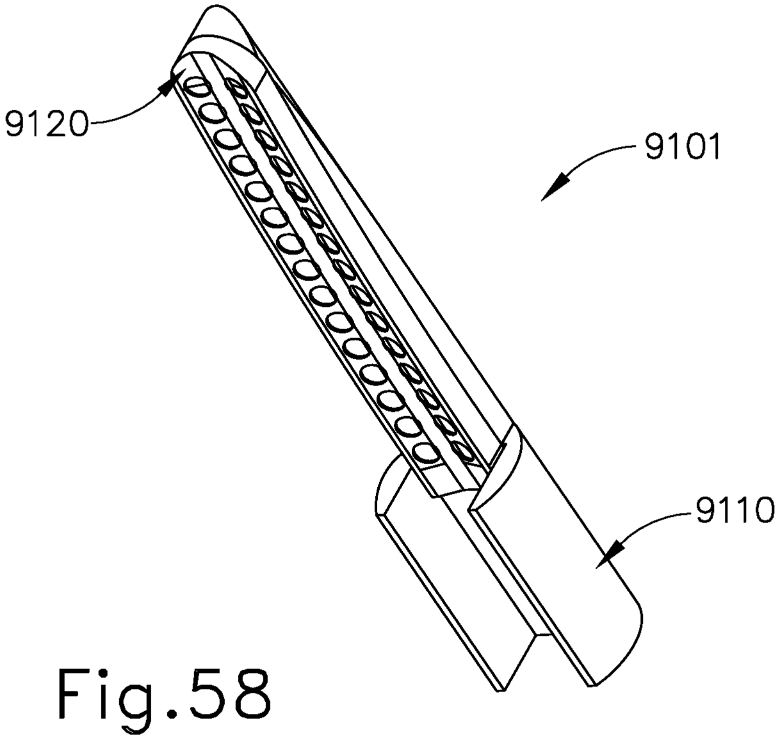
FIG. 58 depicts a perspective view of another exemplary clamp arm assembly of an end effector that may be incorporated into the instrument of FIG. 1.
Figure 59:
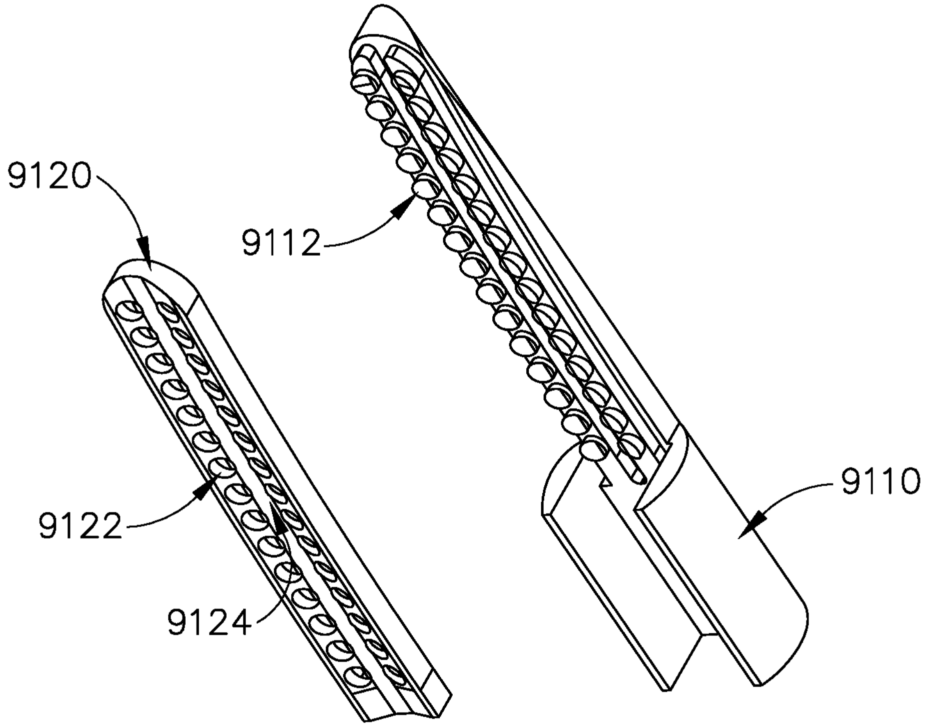
FIG. 59 depicts an exploded view of the clamp arm assembly of FIG. 58.

Referring to FIGS. 57A and 57B, clamp pad (9020) is proud of body (9011) such that when end effector (9000) is in a closed configuration without tissue between blade (9040) and clamp arm (9010), blade (9040) contacts clamp pad (9020) and not body (9011). In this manner, a gap (9041) is maintained between blade (9040) and clamp arm (9010). In some versions, in the absence of gripped tissue between clamp pad (9020) and blade (9040), the degree of contact between clamp pad (9020) and blade (9040) may vary along the length of clamp pad (9020) in an alternating fashion due to the mirrored sinusoidal shape of clamp pad (9020). For instance, as seen in FIG. 57A, a cross-section along mirrored peaks of the sinusoidal shape of clamp pad (9020) shows that blade (9040) has maximum contact with clamp pad (9020) at those points. On the contrary, as seen in FIG. 57B, a cross-section along mirrored valleys of the sinusoidal shape of clamp pad (9020) shows that blade (9040) has a minimum contact with clamp pad (9020) at those points. However, in both instances, gap (9041) is maintained so that blade (9040) does not contact clamp arm (9010).

In still other versions, the angled surfaces of blade (9040) and the angled surfaces of clamp pad (9020) are configured such that, in the absence of gripped tissue between clamp pad (9020) and blade (9040), the degree of contact between clamp pad (9020) and blade (9040) is constant along the length of clamp pad (9020). In some such versions, an upper contact surface (9052) of blade (9040) contacts only a lower contact surface (9022) of clamp pad (9020), while oblique surfaces (9054) of blade (9040) and oblique surfaces (9024) of clamp pad (9020) remain out of contact, e.g. by the angles of these surfaces differing so that they diverge when end effector (9000) is in the closed configuration.

As seen in FIGS. 55, 57A, and 57B, blade (9040) includes an upper contact surface (9052) flanked by a pair of oblique surfaces (9054); as well as a pair of laterally presented surfaces (9056). In some versions, upper contact surface (9052) is flat. In some other versions, upper contact surface (9052) is curved. Oblique surfaces (9054) may be flat, though other versions may have oblique surfaces (9054) that are curved or have some other surface geometry. Laterally presented surfaces (9056) are also flat in this example, though other versions may have surfaces (9056) that are curved, angled, or have some other surface geometry. In some versions, blade (9040) may be configured with a concave cutout similar to concave cutout (258) described above.

In the present example, clamp pad (9020) includes a lower contact surface (9022) flanked by a pair of oblique surfaces (9024). In some versions, lower contact surface (9022) is flat. In some other versions, lower contact surface (9022) is curved. Oblique surfaces (9024) may be flat, though other versions may have oblique surfaces (9024) that are curved or have some other surface geometry. As best seen in FIGS. 57A and 57B, with the shapes of blade (9040) and clamp pad (9020) as described above, blade (9040) and clamp pad (9020) have complementary profiles.

When grasping tissue within end effector (9000) for sealing and/or cutting, the compression forces on the tissue are focused in the region between upper contact surface (9052) of blade (9040) and lower contact surface (9022) of clamp pad (9020). These compression forces are directed mainly along the same vertical plane along which clamp arm (9010) pivots toward blade (9040). The tissue is also contacted by oblique surfaces (9054) of blade (9040) and oblique surfaces (9024) of clamp pad (9020). However, the compression provided by oblique surfaces (9054, 9024) is lower than the compression provided by upper and lower contact surfaces (9052, 9022). Moreover, the compression forces imposed on the tissue by oblique surfaces (9054, 9022) are directed obliquely outwardly, mainly toward surfaces of clamp arm (9010). It should be understood that the above-described manner in which end effector (9000) engages tissue may provide ultrasonic severing of the tissue in the region between upper contact surface (9052) of blade (9040) and lower contact surface (9022) of clamp pad (9020); with ultrasonic sealing of the tissue in the regions between oblique surfaces (9054, 9024). Additionally, RF electrosurgical sealing can be provided as described below.

In the present example, clamp arm (9010) serves as a positive pole while blade (9040) serves as a negative pole. Thus in the present example, clamp arm (9010) serves as one electrode while blade (9040) serves as the other electrode in a bipolar arrangement. Clamp pad (9020) is constructed of an insulating material and so remains electrically neutral. To provide the polarity to clamp arm (9010), in some versions, clamp arm (9010) attaches with outer tube (202) and/or inner tube (204) as described above, and electrical power is transmitted to clamp arm (9010) using outer tube (202) and/or inner tube (204). As also described above, inner and/or outer tubes (204, 202) can be coated or covered to protect a user from exposure to electrical power and also prevent a short circuit when using instrument (110). Similarly, select portions of clamp arm (9010) can be coated or covered so as to maintain electrical power in desired areas of clamp arm (9010) while shielding other areas and preventing short circuits. In view of the teachings herein, other ways to provide electrical communication to clamp arm (9010) and/or blade (9040) will be apparent to those of ordinary skill in the art.

With this configuration, when the tissue is compressed between blade (9040) and clamp pad (9020), the tissue contacts perimeter surface (9016) of clamp arm (9010) that surrounds clamp pad (9020). With clamp arm (9010) being electrically activated, perimeter surface (9016) serves as one electrode with blade (9040) being the other electrode. In this manner, a conductive pathway is established through the tissue between perimeter surface (9016), and blade (9040). In addition to the ultrasonic cutting and ultrasonic sealing as described above, end effector (9000) is further operable to provide RF electrosurgical sealing of the tissue along the conductive pathways described above, which would include RF electrosurgical sealing through tissue on each side of the cut line.

Figure 60B:
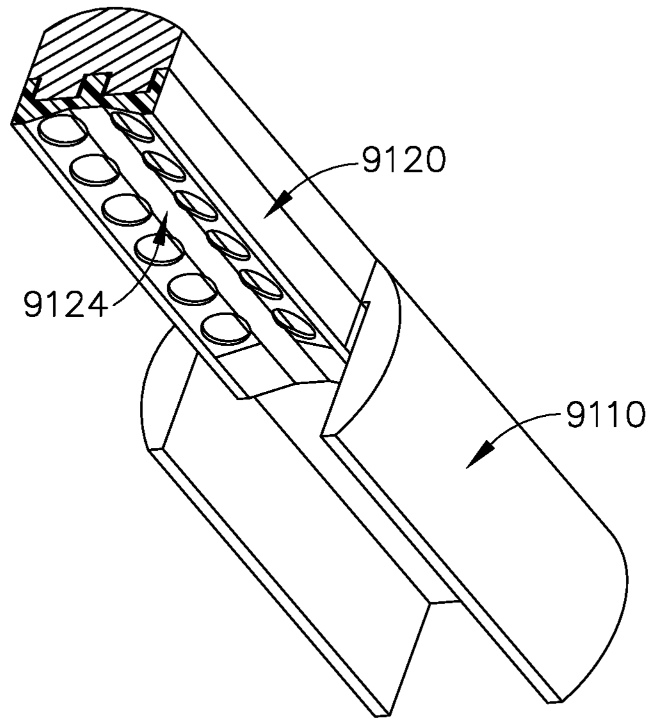
FIG. 60B depicts a perspective cross-sectional view of the clamp arm assembly of FIG. 58.
Figure 60A:
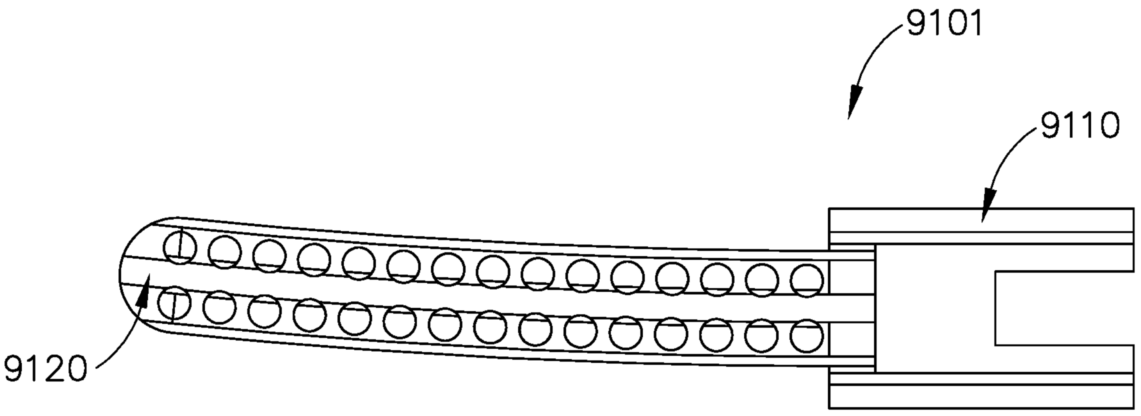
FIG. 60A depicts a bottom view of the clamp arm assembly of FIG. 58.
Figure 61:
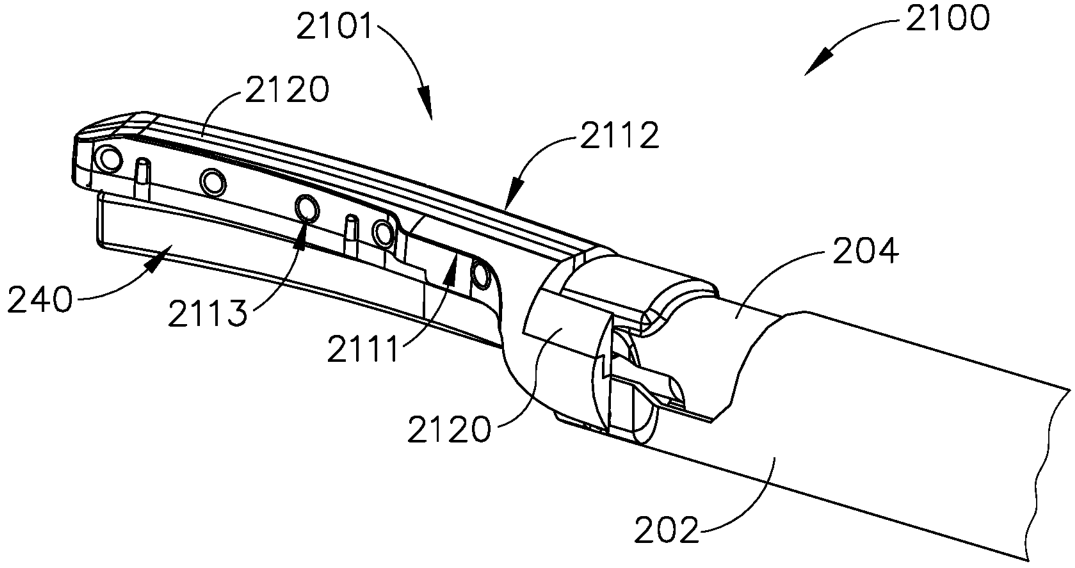
FIG. 61 depicts a perspective view of another exemplary end effector that may be incorporated into the instrument of FIG. 1, with the end effector in a closed configuration.
Figure 62:
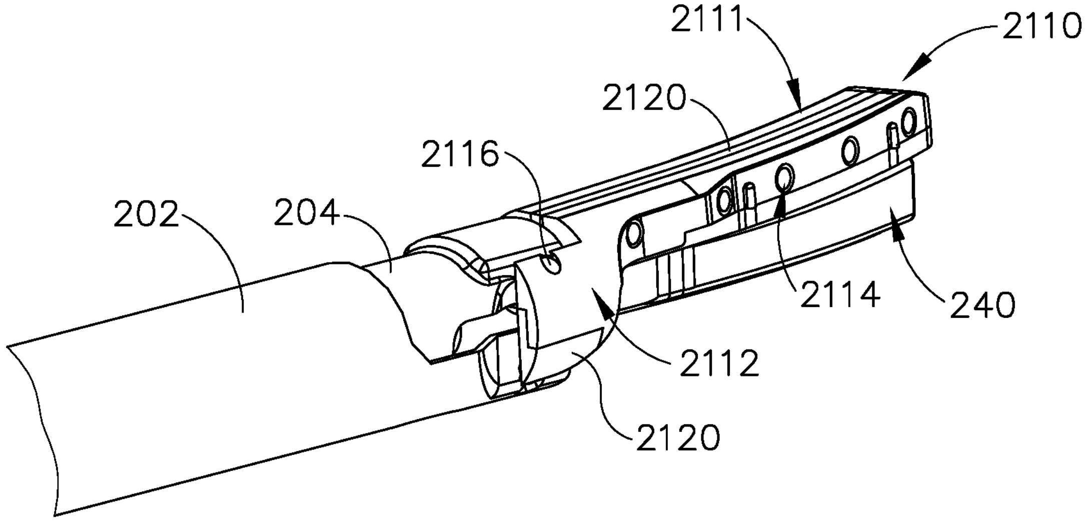
FIG. 62 depicts another perspective view of the end effector of FIG. 61.
Figure 63:
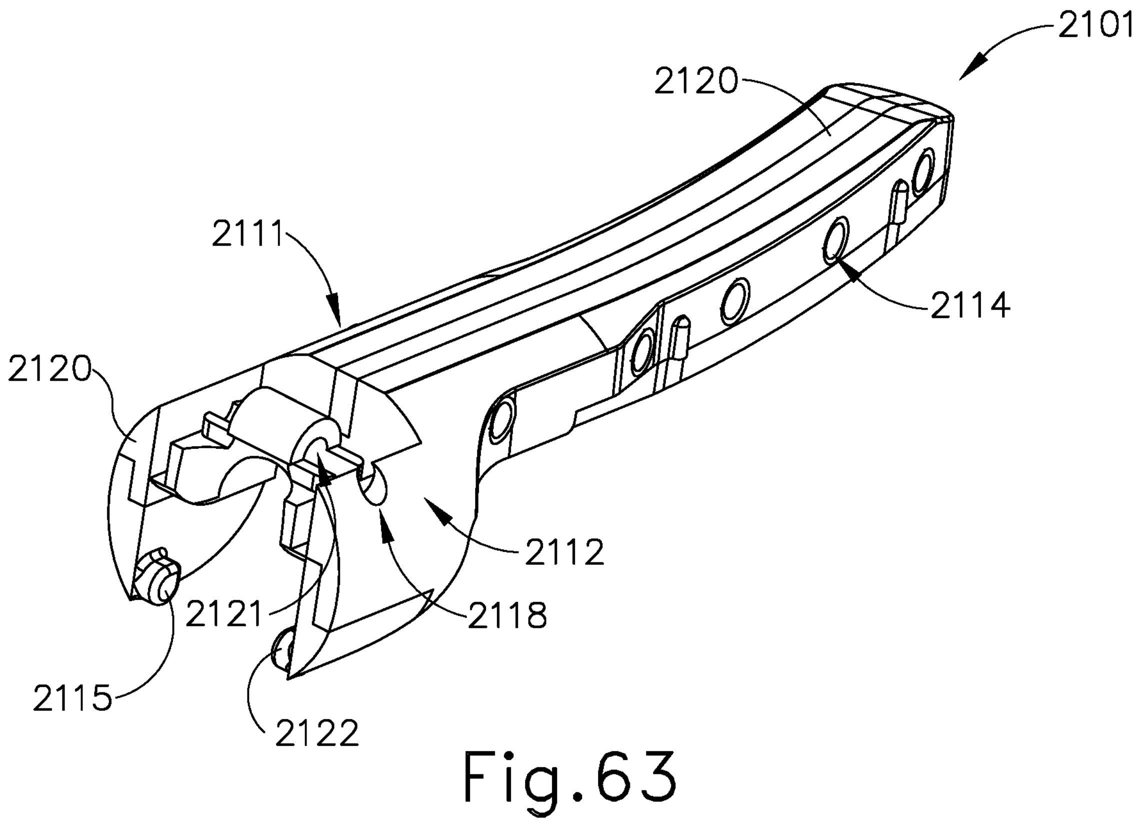
FIG. 63 depicts a perspective view of the clamp arm assembly of FIG. 61.

FIGS. 58-60B show an alternate version of end effector (9000), having a different clamp arm assembly (9101) with a different clamp arm (9110) and different clamp pad (9120). In this alternate version of end effector (9000) clamp arm (9110) is configured to serve as one electrode, and blade (9040) is oppositely configured to serve as the other electrode to provide the bipolar RF electrosurgical sealing. However, clamp arm (9110) comprises cylindrical protrusions (9112), while clamp pad (9120) comprises openings (9122) that are configured to receive cylindrical protrusions (9112). Clamp pad (9120) connects with clamp arm (9110) using suitable fastening structures such as adhesive or other mechanical fastening structures (e.g., overmolding). As seen in FIG. 60B, when clamp pad (9120) is attached with clamp arm (9110), clamp pad (9120) is proud of cylindrical protrusions (9112) such that cylindrical protrusions (9112) are recessed within openings (9122). This configuration prevents contact between cylindrical protrusions (9112) and blade (9040) to avoid short circuits to the desired conductive pathway.

When tissue is held between clamp pad (9120) and blade (9040), tissue can fill openings (9122) contacting cylindrical protrusions (9112). In this manner, a conductive pathway is established through the tissue between cylindrical protrusions (9112) and blade (9040). With tissue compressed between clamp pad (9120) and blade (9040), ultrasonic energy can be imparted to waveguide (242), and thus to blade (9040), and thereby ultrasonically sever the tissue, e.g., along a continuous centerline region (9124) of clamp pad (9120). On each side of the cut line, ultrasonic sealing occurs as described above. In addition, alternate end effector (9000) is further operable to provide RF electrosurgical sealing of tissue along the conductive pathways described above, which would include tissue that is laterally outward from the cut line formed between upper surface (9052) of blade (9040) and centerline region (9124) of clamp pad (9120). In some versions, the spacing of openings (9122) is such that the RF electrosurgical sealing occurs not only at the openings (9122), but between openings (9122) as well. In this manner, RF electrosurgical sealing may be obtained along the entire length of clamp pad (9120) and thus the entire length of the tissue cut line. In other versions, RF electrosurgical sealing is not required to be continuous along each side of the cut line, and instead may occur at multiple points along each side of the cut line in a discontinuous fashion.

M. End Effector with Split Clamp Arm Electrodes

FIGS. 61-65B show another exemplary end effector (2100) that may be readily incorporated into instrument (110) in place of end effector (140). End effector (2100) comprises a clamp arm (2110), blade (240), and a pad (2120). Clamp arm (2110) has a split configuration where clamp arm (2110) comprises a first body (2111) and a second body (2112). As will be discussed further below, first body (2111) and second body (2112) each have opposite polarity and serve as electrodes for RF electrosurgical sealing.

Figure 64:
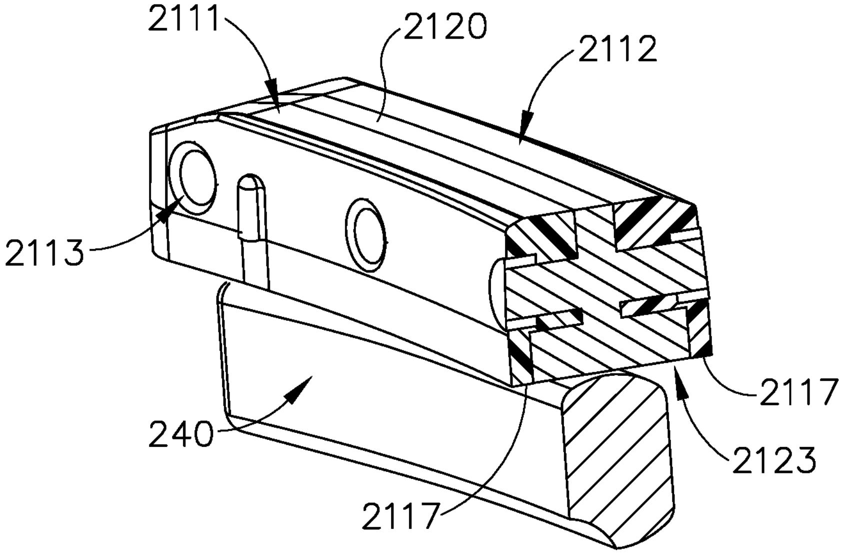
FIG. 64 depicts a perspective cross-sectional view of the end effector of FIG. 61.
Figure 65A:
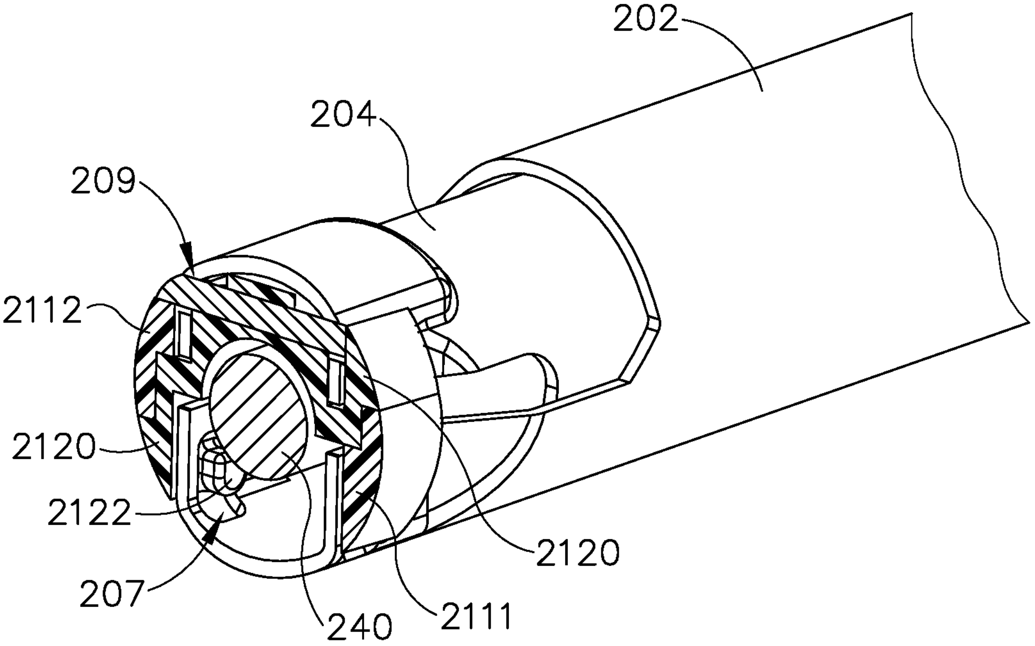
FIG. 65A depicts another perspective cross-sectional view of the end effector of FIG. 61.
Figure 65B:
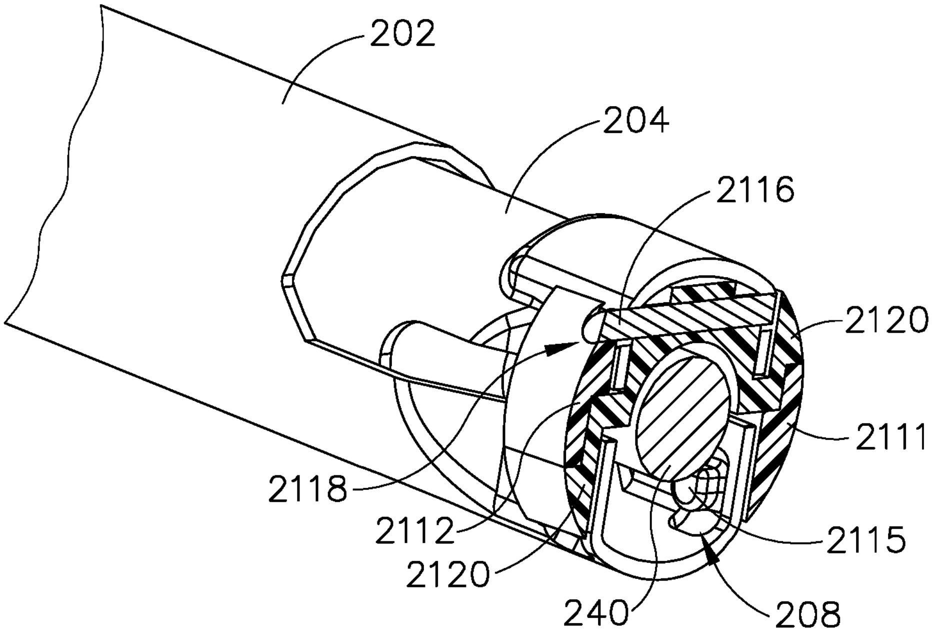
FIG. 65B depicts another perspective cross-sectional view of the end effector of FIG. 61.

Positioned between first body (2111) and second body (2112) of clamp arm (2110) is an electrically insulating clamp pad (2120). In the present example, clamp pad (2120) is molded and formed between first and second bodies (2111, 2112). First body (2111) comprises bores (2113) that are configured to receive portions of molded clamp pad (2120) to secure clamp pad (2120) with first body (2111). Similarly, second body (2112) comprises bores (2114) that are also configured to receive portions of molded clamp pad (2120) to secure clamp pad (2120) with first body (2111). As shown in FIG. 64, molded clamp pad (2120) extends within bores (2113, 2114), connecting first body (2111) and second body (2112) together. Collectively, first body (2111), second body (2112), and clamp pad (2120) make up clamp arm assembly (2101). While the present example shows bores (2113) and bores (2114) generally aligned across from each other, such alignment is not required in all versions. In assembling clamp arm (2110), clamp pad (2120) is formed between first body (2111) and second body (2112) such that first body (2111) and second body (2112) do not directly contact one another. In this manner, with first body (2111) oppositely polarized from second body (2112), short circuits can be avoided. In view of the teachings herein, other ways to configure clamp arm (2110) and clamp pad (2120) to achieve a multi part clamp arm that provides both positive and negative polarity will be apparent to those of ordinary skill in the art.

In the present example, clamp arm assembly (2101) connects with inner tube (204) and outer tube (202). Clamp arm assembly (2101) is operable to open and close to grip tissue in the same manner to that described above with respect to end effector (200). In the present example, first body (2111) makes connects with outer tube (202) by way of a post (2115) engaging an opening (208) in outer tube (202). Post (2115) is directly formed as part of first body (2111) such that post (2115) provides a path for electrical communication between outer tube (202) and first body (2111). Second body (2112) connects with inner tube (204) by way of a pin (2116) engaging an opening (209) in inner tube (204). Pin (2116) extends through an opening (2118) in second body (2112), which aligns with opening (209) in inner tube (204). Pin (2116) is comprised of a conductive material such that pin (2116) provides a path for electrical communication between inner tube (204) and second body (2112).

To provide electrical isolation between outer tube (202) and inner tube (204), first body (2111) does not directly connect with inner tube (204). Instead, pin (2116) extends through a molded bore (2121) in clamp pad (2120), which is securely attached with first body (2111) as described above. Similarly, second body (2112) does not directly connect with outer tube (202), but instead clamp pad (2120) is formed with a post (2122) that engages an opening (207) in outer tube (202). With this configuration, clamp arm assembly (2101) has a pivoting connection with inner tube (204) as well as a pivoting connection with outer tube (202) such that clamp arm assembly (2101) is operable to open and close in response to translating movement of outer and/or inner tubes (202, 204) as described above. Moreover, clamp arm assembly (2101) is operable to open and close while maintaining two sides of clamp arm (2110) having opposite polarity. In view of the teachings herein, other ways to connect clamp arm assembly (2101) with inner and outer tubes (204, 202) for open/close operability, while maintaining the polarity configuration descried above, will be apparent to those of ordinary skill in the art.

Referring to FIG. 64, with its split configuration, clamp arm (2110) includes a split U-shaped electrode surface (2117) formed by first and second bodies (2111, 2112). Clamp pad (2120) includes a plurality of teeth (2123) that assist in gripping tissue that is clamped between clamp arm (2110) and blade (240). Electrode surface (2117) extends around clamp arm (2110), surrounding the outer perimeter of clamp pad (2120) except where clamp pad (2120) separates first body (2111) from second body (2112) at the distal-most end of clamp arm (2110). In the present example, electrode surface (2117) is flush with the ridges of teeth (2123), such that valleys of teeth (2123) are recessed relative to electrode surface (2117). In some alternative versions, the ridges of teeth (2123) are recessed relative to electrode surface (2117). In some other alternative versions, the ridges of teeth (2123) are proud relative to electrode surface (2117), such that electrode surface is recessed relative to the ridges of teeth (2123). Other suitable relationships will be apparent to those of ordinary skill in the art in view of the teachings herein.

End effector (2100) may capture a single layer of tissue or two or more layers of tissue may be captured in some examples. As similarly described above with respect to end effector (200), the compression forces on the tissue with end effector (2100) are focused in the region between upper contact surface (252) of blade (240) and clamp pad (2120). These compression forces are directed mainly along the same vertical plane along which clamp arm (2110) pivots toward blade (240). The tissue is also contacted by oblique surfaces (254) of blade (240). However, the compression provided by oblique surfaces (254) is lower than the compression provided by upper contact surface (252). Moreover, the compression forces imposed on the tissue by oblique surfaces (254) are directed obliquely outwardly, mainly toward electrode surface (2117). It should be understood that the above-described manner in which end effector (2100) engages tissue may provide ultrasonic severing of tissue in the region between upper contact surface (252) and clamp pad (2120); with combined ultrasonic sealing of tissue in the regions between oblique surfaces (254) and clamp pad (2120) and/or electrode surface (2117).

Additionally, with oppositely polarized first body (2111) and second body (2112) of clamp arm (2110), when end effector (2100) captures tissue in a closed configuration, a conductive pathway is created between the positive pole of e.g. first body (2111), laterally through the captured tissue, and the negative pole of e.g. second body (2112). Of course in other versions the polarity of first and second bodies (2111, 2112) may be switched such that the conductive pathway would be similar but flow from second body (2112), through the tissue, and to first body (2111). In the present example, RF electrosurgical sealing occurs along the conductive pathway described above, which includes RF electrosurgical sealing laterally through the compresses tissue along and across the cut line of the tissue. In this example, blade (240) may be neutral or blade (240) may be electrically conductive.

N. End Effector with Selectively Coated Blade and/or Pad

Figure 66:
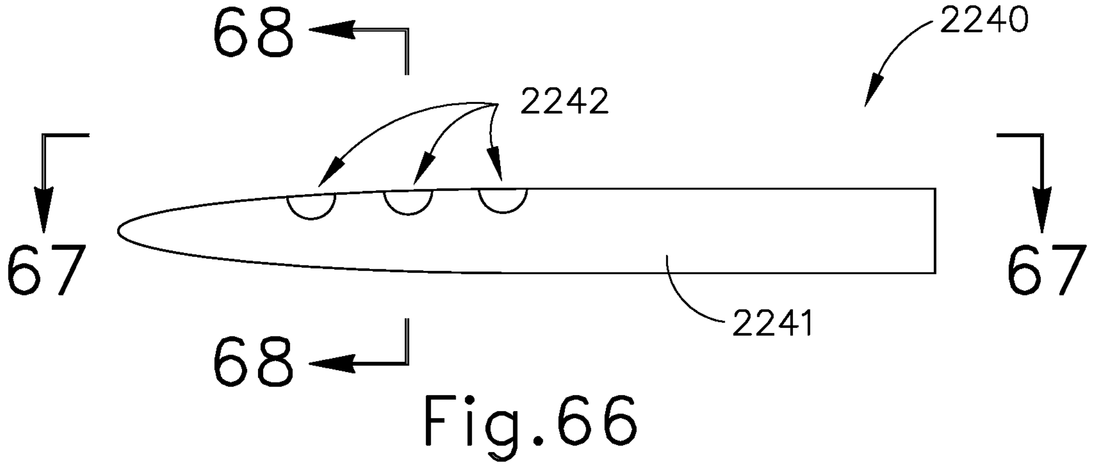
FIG. 66 depicts a side view of another blade of an end effector that may be incorporated into the instrument of FIG. 1.
Figure 67:
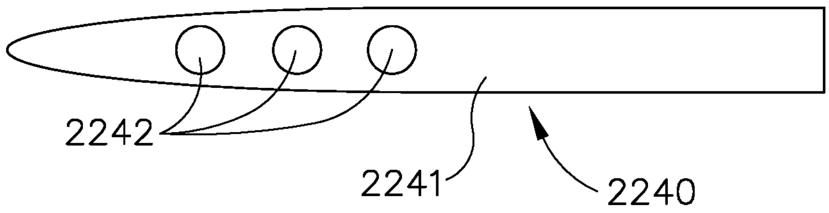
FIG. 67 depicts a top view of the blade of FIG. 66 taken along the line 67-67 of FIG. 66.
Figure 68:
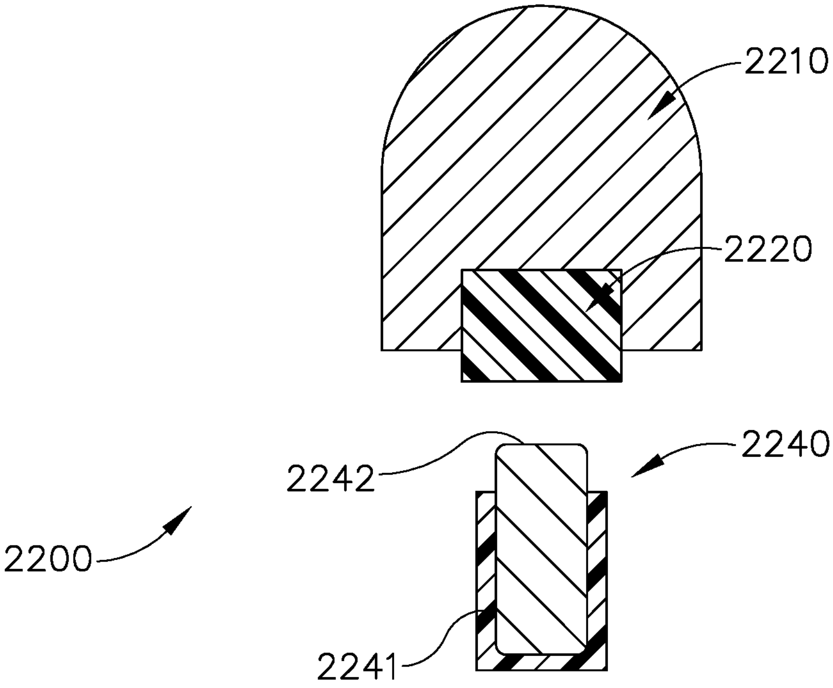
FIG. 68 depicts a cross-section view of the exemplary end effector incorporating the blade of FIG. 66, taken along line 68-68 of FIG. 66.

FIGS. 66-73 show other exemplary end effectors that may be readily incorporated into instrument (110) in place of end effector (140). FIGS. 66-68 show end effector (2200), or portions of end effector (2200). End effector (2200) comprises clamp arm (2210), clamp pad (2220), and blade (2240). In the present example, clamp arm (2210) is configured to serve as a positive pole. In view of the teachings herein, various ways to provide electrical communication to clamp arm (2210) will be apparent to those of ordinary skill in the art. Clamp pad (2220) comprises a nonconductive material and thus remains electrically neutral. Blade (2240) is configured to serve as a negative pole. Again, in view of the teachings herein, various ways to provide electrical communication to blade (2240) will be apparent to those of ordinary skill in the art. Blade (2240) further includes a selectively placed nonconductive coating (2241). Where applied, coating (2241) electrically insulates portions of blade (2240), such that only the uncoated portions of blade (2240) provide a negative pole to cooperate with clamp arm (2210) for communication of bipolar RF electrosurgical energy through contacted tissue. Referring to FIGS. 66-68, coating (2241) is applied to blade (2240) except in circular shaped uncoated regions (2242). In the present example, uncoated areas (2242) are located along blade (2240) such that uncoated areas (2242) align with clamp pad (2220).

End effector (2200) may capture a single layer of tissue or two or more layers of tissue may be captured in some examples. As described above with respect to other end effectors, the compression forces on the tissue with end effector (2200) are focused in the region between blade (2240) and clamp pad (2220). These compression forces are directed mainly along the same vertical plane along which clamp arm (2210) pivots toward blade (2240). With this configuration, end effector (2200) engages tissue to provide ultrasonic severing of tissue in the region between blade (2240) and clamp pad (2220); with combined ultrasonic sealing of tissue in the regions of tissue adjacent the cut line.

Additionally, with oppositely polarized clamp arm (2210) and uncoated areas (2242) of blade (2240), when end effector (2200) captures tissue in a closed configuration, a conductive pathway is created through the tissue captured between clamp arm (2210) and uncoated areas (2242) of blade (2240). Of course in other versions the polarity of clamp arm (2210) and blade (2240) may be switched such that the conductive pathway would be similar. In the present example, RF electrosurgical sealing occurs along the conductive pathways described above, which includes RF electrosurgical sealing along the cut line of the tissue at those locations of uncoated areas (2242). In some versions, the spacing of uncoated areas (2242) is such that the RF electrosurgical sealing occurs not only at uncoated areas (2242), but between uncoated areas (2242) as well. In this manner, RF electrosurgical sealing may be obtained along the entire length of the combined uncoated areas (2242) of blade (2240). In some versions, this entire length of the combined uncoated areas (2242) is the same as, or approximates, the entire length of the tissue cut line such that RF electrosurgical sealing is obtained along the entire length of the cut line. In other versions, RF electrosurgical sealing is not required to be continuous along the cut line, and instead may occur at multiple points along the cut line in a discontinuous fashion, e.g. those points contacting the locations of uncoated areas (2242). The pattern of these uncoated areas could range from a percentage of approximately 20% to approximately 85%, and various patterns are possible to include various shapes and sizes.

Figure 69:
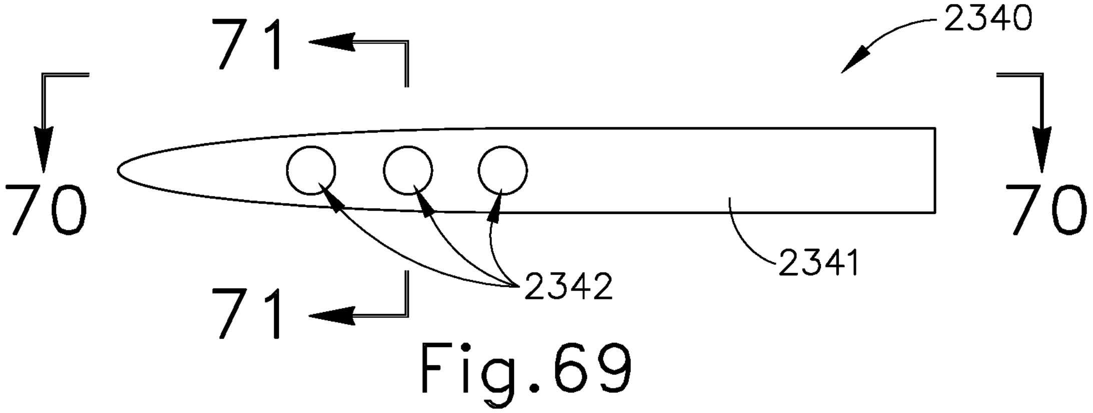
FIG. 69 depicts a side view of another blade of an end effector that may be incorporated into the instrument of FIG. 1.
Figure 70:
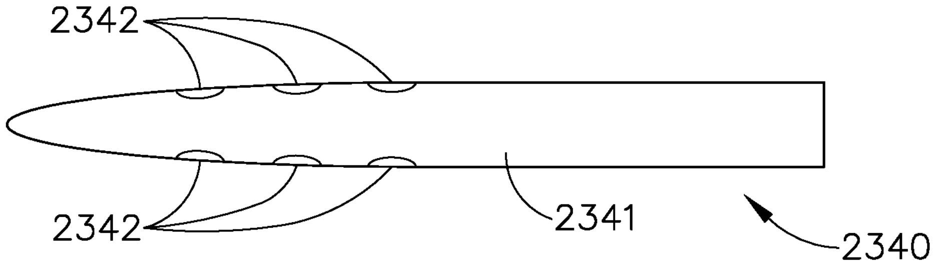
FIG. 70 depicts a top view of the blade of FIG. 69 taken along the line 70-70 of FIG. 69.
Figure 71:
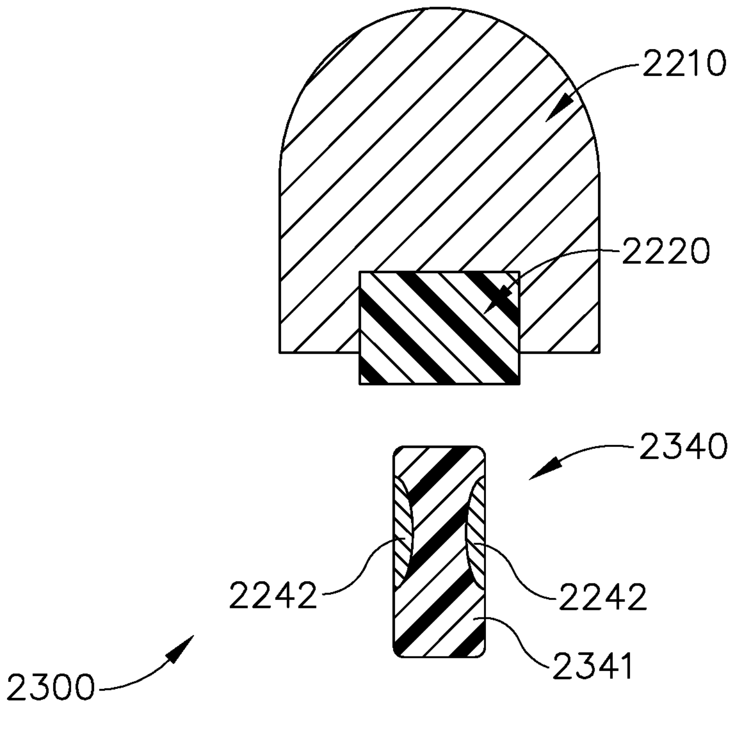
FIG. 71 depicts a cross-section view of the exemplary end effector incorporating the blade of FIG. 69, taken along line 71-71 of FIG. 69.

FIGS. 69-71 show another exemplary end effector (2300), similar to end effector (2200) descried above, that may be readily incorporated into instrument (110) in place of end effector (140). In this example, a blade (2340) serves as a negative pole and again includes a coating (2341) that is selectively applied to blade (2340) such that portions of blade (2340) are shielded while other portions are exposed. As shown in FIGS. 69-71, uncoated areas (2342) exposing polarized portions of blade (2340) are located along each side of blade (2340) instead of along the top surface as was the example with blade (2240) of end effector (2200). End effector (2300) further comprises clamp arm (2210) and clamp pad (2220) as described above. In the present example, clamp arm (2210) is electrically neutral while clamp pad (2220) serves as a positive pole; and blade (2340) serves as a negative pole. In other versions, this polarity arrangement may be reversed. Also, in the present example the entire tissue contacting surface of clamp pad (2220) serves as a positive pole electrode, though in other versions modified clamp pads may be used that using various techniques described above to provide an electrode that contacts tissue in discrete regions forming a particular pattern.

End effector (2300) may capture a single layer of tissue or two or more layers of tissue may be captured in some examples. As described above with respect to other end effectors, the compression forces on the tissue with end effector (2300) are focused in the region between blade (2340) and clamp pad (2220). These compression forces are directed mainly along the same vertical plane along which clamp arm (2210) pivots toward blade (2340). With this configuration, end effector (2300) engages tissue to provide ultrasonic severing of tissue in the region between blade (2340) and clamp pad (2220); with combined ultrasonic sealing of tissue in the regions of tissue adjacent the cut line.

Additionally, with oppositely polarized clamp arm (2210) and uncoated areas (2342) of blade (2340), when end effector (2300) captures tissue in a closed configuration, a conductive pathway is created through the tissue captured between clamp pad (2220) and uncoated areas (2342) of blade (2340). Of course in other versions the polarity of clamp pad (2220) and blade (2340) may be switched. In the present example, RF electrosurgical sealing occurs along the conductive pathways described above, which includes RF electrosurgical sealing along each side of the cut line of the tissue at those locations of uncoated areas (2342). In some versions, the spacing of uncoated areas (2342) is such that the RF electrosurgical sealing occurs not only at uncoated areas (2342), but between adjacent uncoated areas (2342) as well. In this manner, RF electrosurgical sealing may be obtained along the entire length of the combined uncoated areas (2342) on each side of blade (2340). In some versions, this entire length of the combined uncoated areas (2342) on each side of blade (2340) is the same as, or approximates, the entire length of the tissue cut line such that RF electrosurgical sealing is obtained lateral to the cut line yet along the entire length of the cut line. In other versions, RF electrosurgical sealing is not required to be continuous lateral to and along the length of the cut line, and instead may occur at multiple points lateral to and along the length of the cut line in a discontinuous fashion, e.g. those points contacting the locations of uncoated areas (2342).

While the uncoated areas shown for end effectors (2100, 2200) have a general circular configuration, in other version uncoated areas (2242, 2342) can have other shapes and patterns to locate areas of exposed electrode surfaces in a desired fashion. In view of the teachings herein, such other shapes and patterns for uncoated areas (2242, 2342) will be apparent to those of ordinary skill in the art.

Figure 72:
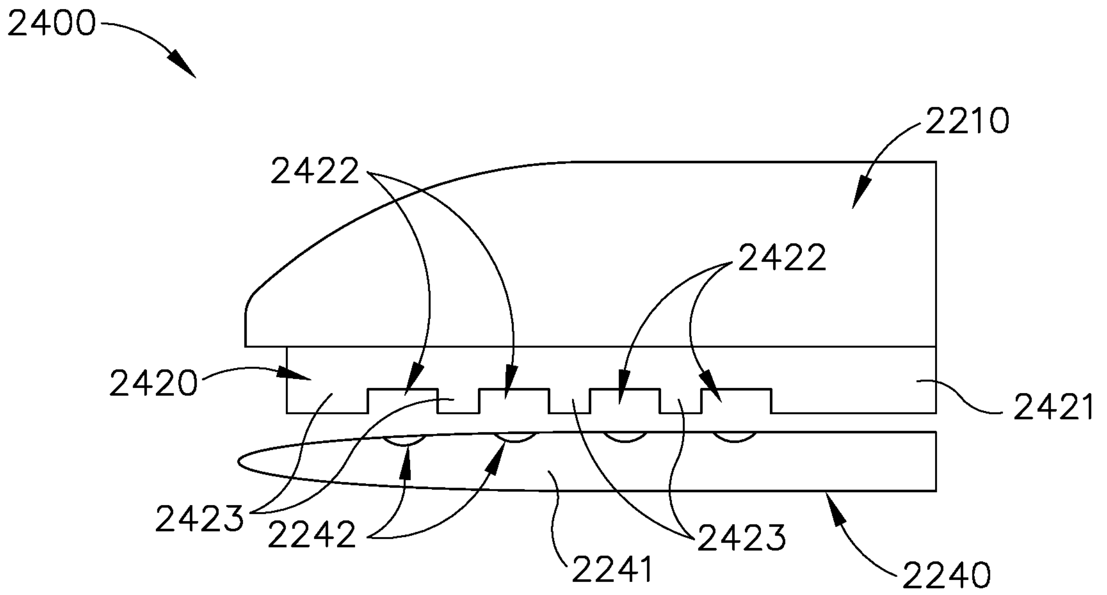
FIG. 72 depicts a side view of another exemplary clamp arm assembly for use with the blade of FIG. 66.
Figure 73:
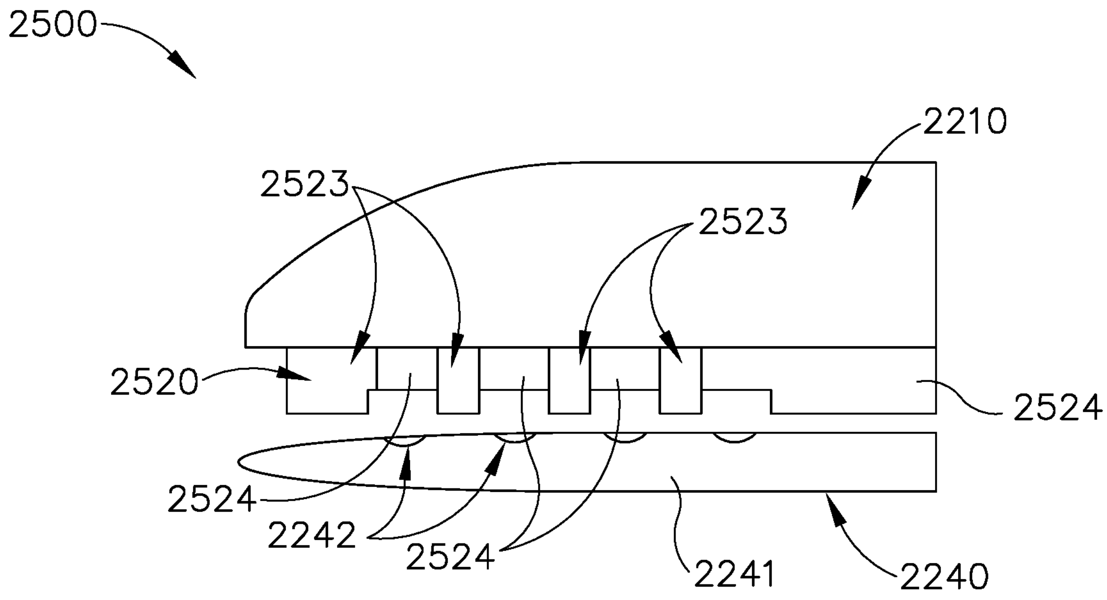
FIG. 73 depicts a side view of another exemplary clamp arm assembly for use with the blade of FIG. 66.

FIGS. 72 and 73 show other exemplary end effectors (2400, 2500), similar to end effectors (2200, 2300) described above, that may be readily incorporated into instrument (110) in place of end effector (140). Each end effector (2400, 2500) comprises blade (2240) as described above with selective coating (2241) and uncoated areas (2242). Each end effector (2400, 2500) further comprises clamp arm (2210) as described above. With each end effector (2400, 2500), clamp arm (2210) is electrically neutral.

Referring to FIG. 72, end effector (2400) further comprises clamp pad (2420) that is coated with a conductive coating (2421) such that clamp pad (2420) can be configured to provide a polarity using the techniques described above. In the present example, the conductive coating (2421) is applied uniformly to at least the surface of clamp pad (2420) contacting tissue captured between clamp pad (2420) and blade (2240); but may be applied to the entire outer surface of clamp pad (2420). To prevent short circuits between clamp pad (2420) and exposed uncoated areas (2242) of blade (2240), clamp pad (2420) comprises cutouts (2422) that recess portions of clamp pad (2420) that align above uncoated areas (2242) of blade (2240). In the present example, cutouts (2422) are machined into clamp pad (2420) or formed with clamp pad (2420) prior to coating clamp pad (2420) with conductive coating (2421). In other examples, clamp pad (2420) may be coated and then cutouts (2422) machined into clamp pad (2420). In the configuration described above, in the absence of tissue between blade (2240) and clamp pad (2420), when end effector (2400) is closed and blade (2240) contacts clamp pad (2420), conductively coated projections (2423) of clamp pad (2420) only contact areas of blade (2240) with nonconductive coating (2241) and do not contact any uncoated areas (2242) of blade (2240).

When tissue is compressed between blade (2240) and clamp pad (2420), tissue contacts clamp pad (2420) and uncoated areas (2242) of blade (2240). In this manner, conductive pathways are established through the tissue between clamp pad (2420) and uncoated areas (2242) of blade (2240). With tissue compressed between clamp pad (2420) and blade (2240), ultrasonic energy can be imparted to waveguide (242) and thereby ultrasonically sever the tissue along the length of clamp pad (2420), with ultrasonic sealing as well, as discussed above. End effector (2400) is further operable to provide RF electrosurgical sealing of the tissue along the conductive pathways described above, which would include tissue that is along the cut line formed between blade (2240) and clamp pad (2420). In some versions, the spacing of uncoated areas (2242) and coated projections (2423) is such that the RF electrosurgical sealing occurs along the entire length of clamp pad (2420) and thus the entire length of the tissue cut line. In other versions, RF electrosurgical sealing is not required to be continuous along the cut line, and instead may occur at multiple points along the cut line in a discontinuous fashion.

FIG. 73 shows end effector (2500), which is similar in structure and operability to end effector (2400), but which comprises clamp pad (2520). A conductive coating is applied selectively to clamp pad (2520), such that clamp pad (2520) can be configured with areas (2523) using the techniques described above. In this configuration, clamp pad (2520) comprises areas (2523) having conductive coating, and neutral areas (2524) without conductive coating.

To prevent short circuits between areas (2523) of clamp pad (2520) and uncoated areas (2242) of blade (2240), clamp pad (2520) is configured such that areas (2523) with the conductive coating do not align with uncoated areas (2242) of blade (2240). When end effector (2500) is closed with blade (2240) contacting clamp pad (2520), areas (2523) of clamp pad (2520) only contact the neutral areas of blade (2240), which are covered by nonconductive coating (2241) as described above. Similarly, any areas of blade (2240), i.e. uncoated areas (2242), will not contact areas (2523) of clamp pad (2520). Instead, uncoated areas (2242) of blade (2240) are offset longitudinally in alignment with areas (2523) of clamp pad (2520) with the conductive coating. In this configuration, uncoated areas (2242) of blade (2240) are aligned with neutral areas (2524) of clamp pad (2520), which are the uncoated areas of clamp pad (2520). In some variations, clamp pad (2520) itself is conductive. By way of example only, clamp pad (2520) may be formed of a molded, carbon filled polytetrafluoroethylene, etc.

Additionally, in the present example, neutral areas (2524) of clamp pad (2520) are recessed relative to areas (2523) of clamp pad (2520). In some instances this recessed configuration may be attributable to the thickness of the conductive coating on areas (2523). In some instances this recessed configuration may be created through molding or machining techniques when forming clamp pad (2520). In one example, cutouts are machined into clamp pad (2520) or formed with clamp pad (2520) prior to coating clamp pad (2520) with the conductive coating. In other examples, clamp pad (2520) may be coated and then cutouts machined into clamp pad (2520).

When tissue is compressed between blade (2240) and clamp pad (2520), tissue contacts areas (2523) of clamp pad (2520) and uncoated areas (2242) of blade (2240). In this manner, conductive pathways are established through the tissue between electrode areas (2523) of clamp pad (2520) and uncoated areas (2242) of blade (2240). With tissue compressed between clamp pad (2520) and blade (2240), ultrasonic energy can be imparted to waveguide (242) and thereby ultrasonically sever the tissue along the length of clamp pad (2520), with ultrasonic sealing as well, as discussed above. End effector (2500) is further operable to provide RF electrosurgical sealing of the tissue along the conductive pathways described above, which would include tissue that is along the cut line formed between blade (2240) and clamp pad (2520). In some versions, the spacing of uncoated areas (2242) and areas (2523) with conductive coating is such that the RF electrosurgical sealing occurs along the entire length of clamp pad (2520) and thus the entire length of the tissue cut line. In other versions, RF electrosurgical sealing is not required to be continuous along the cut line, and instead may occur at multiple points along the cut line in a discontinuous fashion.

O. End Effector with Molded Projections for Short Circuit Protection

Figure 74:
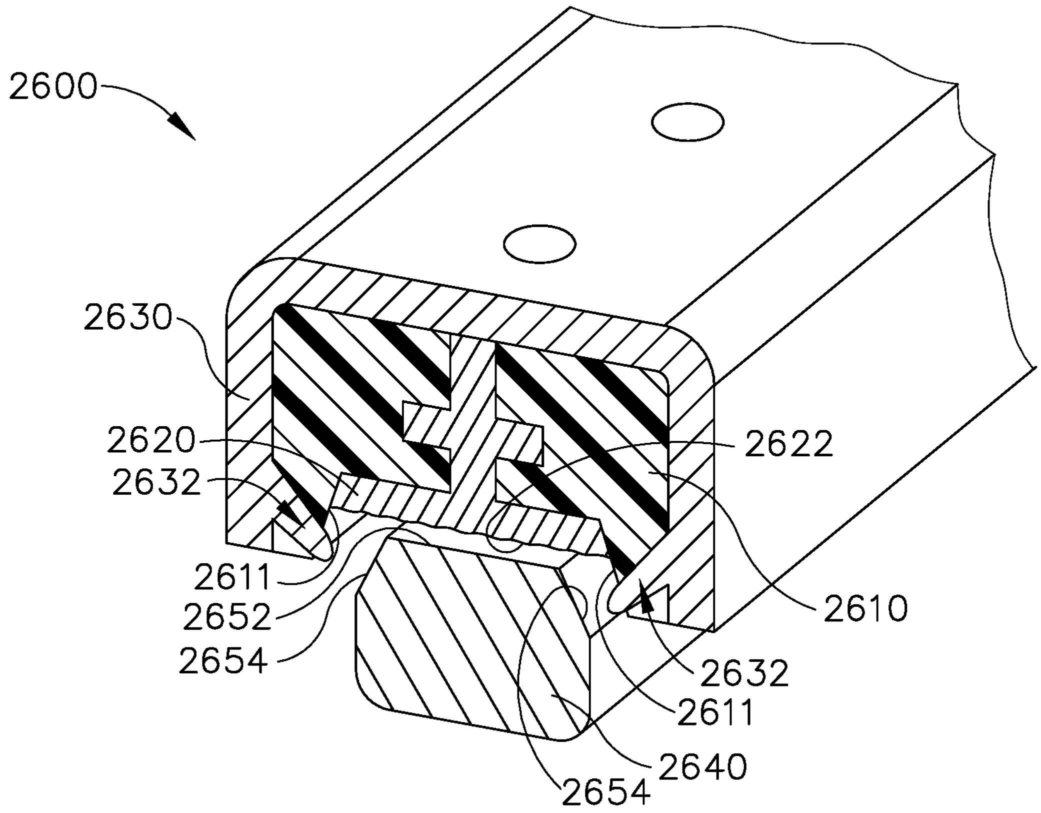
FIG. 74 depicts a perspective cross-section view of another exemplary end effector that may be incorporated into the instrument of FIG. 1, with the end effector in a partially closed configuration.
Figure 75:
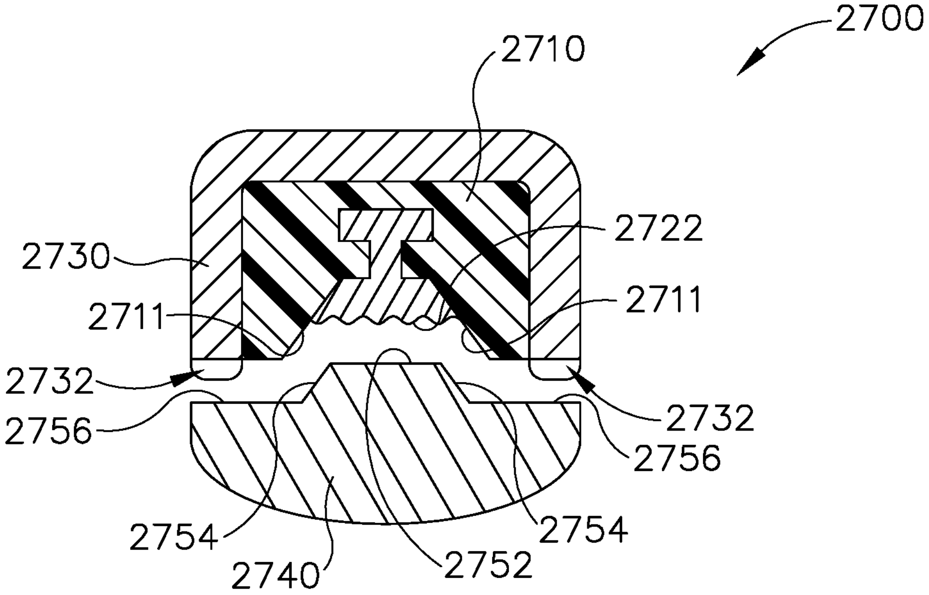
FIG. 75 depicts a cross-section view of another exemplary end effector that may be incorporated into the instrument of FIG. 1, with the end effector in a partially closed configuration.

FIGS. 74 and 75 show other exemplary end effectors (2600, 2700) that may be readily incorporated into instrument (110) in place of end effector (140). Referring to FIG. 74, end effector (2600) comprises clamp arm (2610), clamp pad (2620), blade (2640), and sheath (2630). Blade (2640) comprises upper contact surface (2652) and oblique surfaces (2654) on each side of upper contact surface (2652). In the present example, clamp arm (2610) comprises oblique surfaces (2611) that have a generally corresponding surface angle with oblique surfaces (2654) of blade (2640). Clamp pad (2620) is molded with clamp arm (2610) and clamp pad (2620) comprises contact surface (2622) that extends between oblique surfaces (2611) of clamp arm (2610). Contact surface (2622) is aligned above upper contact surface (2652) of blade (2640) such that when end effector (2600) captures tissue and is closed, tissue will be compressed between contact surface (2622) of clamp pad (2620) and upper contact surface (2652) of blade (2640). Tissue may also be compressed between oblique surfaces (2654) of blade (2640) and oblique surfaces (2611) of clamp arm (2610).

In the present example, a second molding process connects sheath (2630) with clamp arm (2610). Sheath (2630) is molded over combined clamp arm (2610) with clamp pad (2620), with sheath (2630) covering an outer surface of clamp arm (2610). In this configuration, sheath (2630) is operable to insulate clamp arm (2610) such that any heat build-up during use is not transferred to surrounding tissue or organs. Additionally, sheath (2630) is molded with inwardly projecting protruding members (2632) that extend toward oblique surfaces (2654) of blade (2640). Protruding members (2632) are operable to serve as gap setting structures that prevent blade (2640) from contacting clamp arm (2610). While the present example uses two separate molding steps to form clamp pad (2620) and sheath (2630), in some other versions greater or fewer separate molding steps can be used to form clamp pad (2620) and sheath (2630).

In some configurations, end effector (2600) is configured for RF electrosurgical sealing where clamp arm (2610) serves as a positive pole and blade (2640) serves as a negative pole. With tissue compressed between blade (2640) and clamp pad (2620), the tissue contacts clamp arm (2610) and blade (2640), which results in a conductive pathway through the tissue between clamp arm (2610) and blade (2640). As discussed in greater detail above, RF electrosurgical sealing occurs along this conductive pathway. In some versions, ultrasonic severing of the tissue may also occur along the region where tissue is compressed between upper contact surface (2652) of blade (2640) and contact surface (2622) of clamp pad (2620) as described in greater detail above.

Over time, clamp pad (2620) can wear with use. When clamp pad (2620) is not yet worn, end effector (2600) is configured such that when end effector (2600) captures tissue between blade (2640) and clamp pad (2620), blade (2640) will not make contact with clamp arm (2610). Furthermore, when clamp pad (2620) is new or not yet worn down, protruding members (2632) approach blade (2640) but do not contact blade (2640). As clamp pad (2620) wears, protruding members (2632) are configured to serve as gap setting structures that prevent blade (2640) from contacting clamp arm (2610) and thereby creating a short circuit to the desired RF electrosurgical sealing pathway. It should be understood that, when end effector (2600) is first used, protruding members (2632) do not necessarily contact tissue or blade (2640). Instead, protruding members (2632) may be fully contained within clamp pad (2620) when end effector (2600) is first used; and the tips of protruding members (2632) may eventually be exposed relative to clamp pad (2620) after clamp pad (2620) has encountered wear due to use.

In one example of end effector (2600), protruding members (2632) are formed on each side of clamp arm (2610) at the distal end of clamp arm (2610). In other examples, clamp arm (2610) comprises openings extending through oblique surfaces (2611) along its length such that when molding sheath (2630) over clamp arm (2610), protruding members (2632) are formed in multiple locations along the length of clamp arm (2610). In view of the teachings herein, other ways to provide protruding members on an end effector to prevent short circuits by acting to maintain a gap between an oppositely polarized blade and clamp arm will be apparent to those of ordinary skill in the art.

Referring to FIG. 75, end effector (2700) comprises clamp arm (2710), clamp pad (2720), blade (2740), and sheath (2730). Blade (2740) comprises upper contact surface (2752), oblique surfaces (2754) on each side of upper contact surface (2752), and lateral surfaces (2756) on each side of oblique surfaces (2754). In the present example, clamp arm (2710) comprises oblique surfaces (2711) that have a generally corresponding surface angle with oblique surfaces (2754) of blade (2740). Clamp pad (2720) is molded with clamp arm (2710) and clamp pad (2720) comprises contact surface (2722) that extends between oblique surfaces (2711) of clamp arm (2710). Contact surface (2722) is aligned above upper contact surface (2752) of blade (2740) such that when end effector (2700) captures tissue and is closed, tissue will be compressed between contact surface (2722) of clamp pad (2720) and upper contact surface (2752) of blade (2740). Tissue may also be compressed between oblique surfaces (2754) of blade (2740) and oblique surfaces (2711) of clamp arm (2710), and also between lateral surfaces (2756) of blade (2740) and clamp arm (2710).

In the present example, a second molding process connects sheath (2730) with clamp arm (2710). Sheath (2730) is molded over combined clamp arm (2710) with clamp pad (2720), with sheath (2730) covering an outer surface of clamp arm (2710). In this configuration, sheath (2730) is operable to insulate clamp arm (2710) such that any heat build-up during use is not transferred to surrounding tissue or organs. Additionally, sheath (2730) is molded with protruding members (2732) that extend toward lateral surfaces (2656) of blade (2740). Protruding members (2732) are operable to serve as gap setting structures that prevent blade (2740) from contacting clamp arm (2710) as pad (2720) wears when ultrasonic energy is applied over time. While the present example uses two separate molding steps to form clamp pad (2720) and sheath (2730), in some other versions greater or fewer separate molding steps can be used to form clamp pad (2720) and sheath (2730).

In some configurations, end effector (2700) is configured for RF electrosurgical sealing where clamp arm (2710) serves as a positive pole and blade (2740) serves as a negative pole. With tissue compressed between blade (2740) and clamp pad (2720), the tissue contacts clamp arm (2710) and blade (2740), which results in a conductive pathway through the tissue between clamp arm (2710) and blade (2740). As discussed in greater detail above, RF electrosurgical sealing occurs along this conductive pathway. In some versions, ultrasonic severing of the tissue may also occur along the region where tissue is compressed between upper contact surface (2752) of blade (2740) and contact surface (2722) of clamp pad (2720) as described in greater detail above.

Over time, clamp pad (2720) can wear with use. When clamp pad (2720) is not yet worn, end effector (2700) is configured such that when end effector (2700) captures tissue between blade (2740) and clamp pad (2720), blade (2740) will not make contact with clamp arm (2710). Furthermore, when clamp pad (2720) is new or not yet worn down, protruding members (2732) approach blade (2740) but do not contact blade (2740). As clamp pad (2720) wears, protruding members (2732) are configured to serve as gap setting structures that prevent blade (2740) from contacting clamp arm (2710) and thereby creating a short circuit to the desired RF electrosurgical sealing pathway.

In one example of end effector (2700), protruding members (2732) are formed along each side of clamp arm (2710) at the distal end of clamp arm (2710). In other examples, protruding members (2732) are formed continuously along the length of each side of clamp arm (2710). Still in other examples, protruding members (2732) are formed in a repeating configuration along the length of each side of clamp arm (2710). In view of the teachings herein, other ways to provide protruding members on an end effector to prevent short circuits by acting to maintain a gap between an oppositely polarized blade and clamp arm will be apparent to those of ordinary skill in the art.

P. End Effector with Clamp Pad Flow Control

Figure 76:
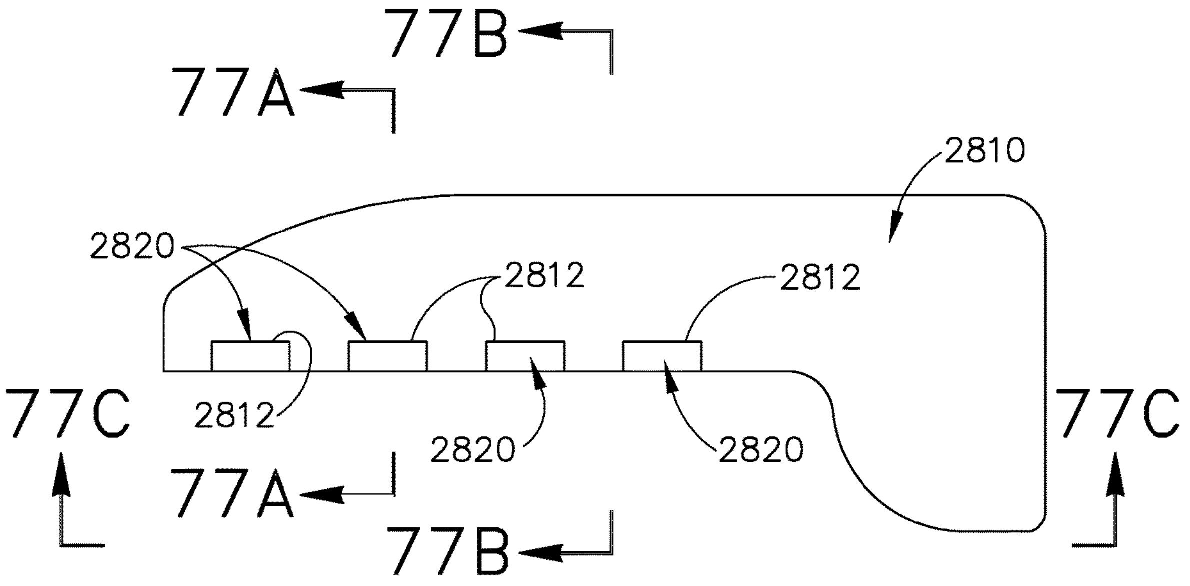
FIG. 76 depicts a side view of another exemplary end effector, shown without the blade, that may be incorporated into the instrument of FIG. 1.
Figure 77A:
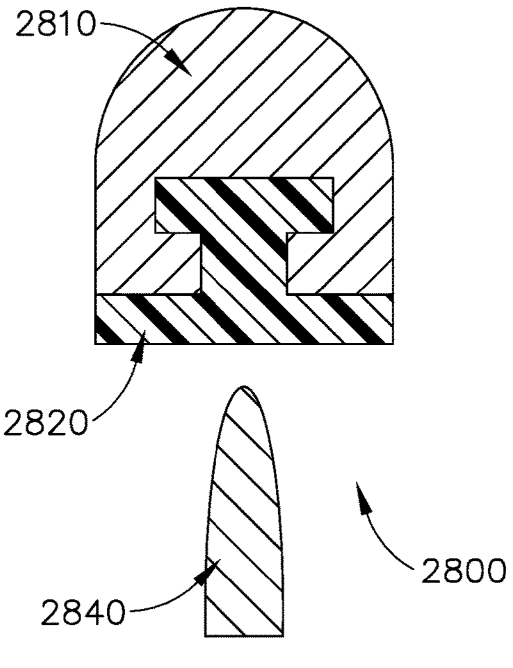
FIG. 77A depicts a cross-section view of the end effector of FIG. 76 taken along line 77A-77A of FIG. 76.
Figure 77B:
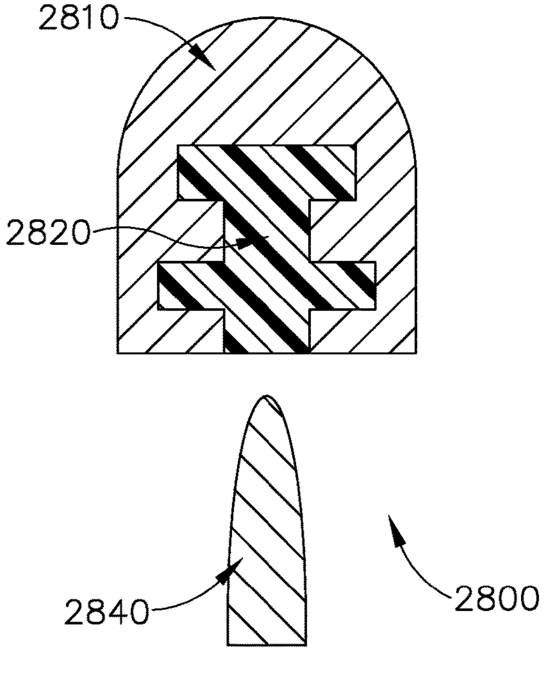
FIG. 77B depicts a cross-section view of the end effector of FIG. 76 taken along line 77B-77B of FIG. 76.
Figure 77C:
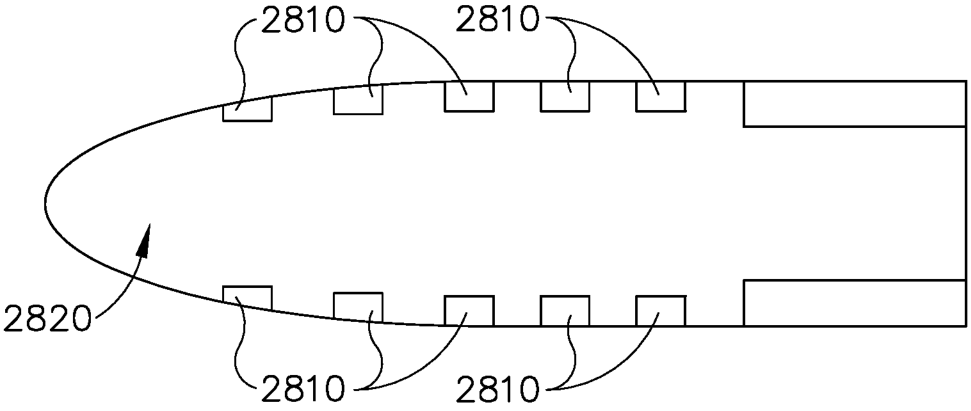
FIG. 77C depicts a bottom view of the end effector of FIG. 76 taken along line 77C-77C of FIG. 76.
Figure 78:
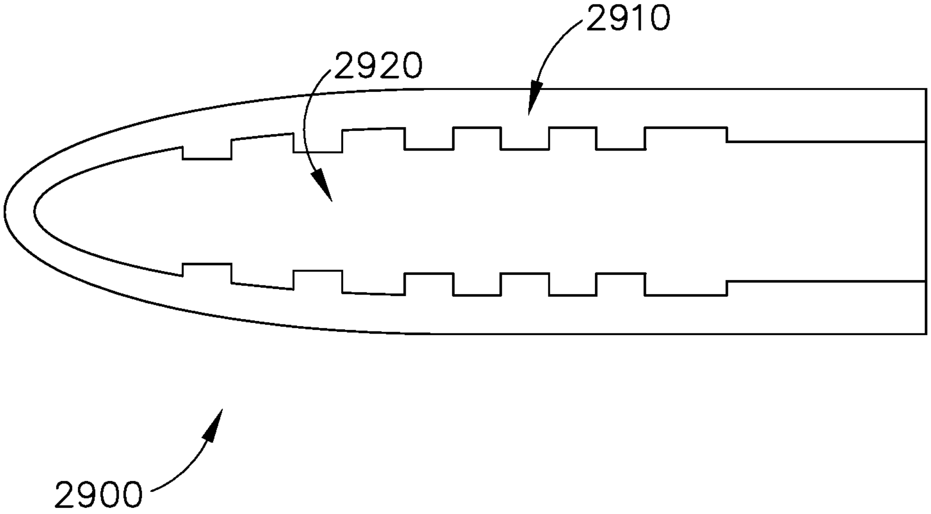
FIG. 78 depicts a bottom view of another exemplary end effector, shown without the blade, that may be incorporated into the instrument of FIG. 1.

FIGS. 76-78 show other exemplary end effectors (2800, 2900) that may be readily incorporated into instrument (110) in place of end effector (140). End effectors (2800, 2900) include clamp pads and clamp arms. There may be concern that, as the clamp pad material wears, there will be need to be a path for the clamp pad material to flow. Thus, the clamp pads of the following examples include features that guide flow of the clamp pad material when degradation occurs so that this clamp pad flow will not interfere with the consistent gap desired between electrode poles of respective end effectors (2800, 2900). A consistent gap between electrode poles promotes consistent RF electrosurgical sealing.

Referring to FIGS. 76-77C, end effector (2800) comprises clamp arm (2810), clamp pad (2820), and blade (2840). In the present example, blade (2840) has serves as a negative pole and thereby serves as one of the electrodes for RF electrosurgical sealing. Furthermore, clamp arm (2810) serves as a positive pole and thereby serves as the other electrode for RF electrosurgical sealing. End effector (2800) is configured initially with a desired gap between the electrodes—in the present example, between blade (2840) and clamp arm (2810). Similarly to previously described end effector versions, end effector (2800) is operable to capture, ultrasonically sever, ultrasonically seal, and RF electrosurgical seal tissue that is compressed between blade (2840) and clamp pad (2820). These processes can create a heat build-up that can deform clamp pad (2820). This deformation can cause clamp pad (2820) to flow outwardly away from areas of compression with blade (2820). Deformed portions of clamp pad (2820), can move out laterally where there are not electrodes protruding downwardly from clamp arm (2810). This deformation, flow, and deposit of clamp pad material can alter the desired initial gap between the electrodes—in the present example, between blade (2840) and clamp arm (2810).

With end effector (2800), clamp arm (2810) comprises electrodes (2812) along its perimeter such that clamp arm (2810) has a castellated appearance as shown in FIG. 76. Clamp pad (2820) is formed within electrodes (2812) of clamp arm (2810) as seen by comparing the cross-section views of FIGS. 77A and 77B. With this configuration, when clamp pad (2820) degrades and begins to flow, the clamp pad material can flow outwardly between electrodes (2812) in clamp arm (2810) since clamp pad (2820) is not completely bound by clamp arm (2812). This outward flow of degraded clamp pad material prevents such degraded clamp material from depositing on tissue-contacting surfaces of clamp arm (2810), or other tissue contacting surfaces of clamp pad (2820). In this manner a constant gap is maintained between conductive blade (2840) and conductive clamp arm (2810) along those portions of clamp arm (2810) having a conductive pathway from clamp arm (2810), through captured tissue, and to blade (2840), as shown in FIG. 77B.

FIG. 78 shows an alternate clamp arm (2900) having an electrode (2910) and clamp pad (2920) configured to provide pad material flow control similarly as described above. In this example, electrode (2910) is continuous around the perimeter of clamp arm (2900) and extends inwardly toward the center line along the length of clamp arm (2900). The body of clamp arm (2900) defines recesses or chambers into which the material of clamp pad (2920) may flow as clamp pad (2920) degrades. Such recesses or chambers may be located above electrodes (2910) (i.e., further into the page in the view of FIG. 78), such that as the material of clamp pad (2920) degrades and is pushed upwardly, the material will not flow out over clamp arm (2900) and thereby block electrode (2910) from maintaining electrical continuity with the tissue.

In view of the teachings herein, other ways to configure clamp arms and clamp pads to provide for flow control of degraded clamp pad material will be apparent to those of ordinary skill in the art.

Q. End Effector with Conductive Pad and Clamp Arm

Figure 79:
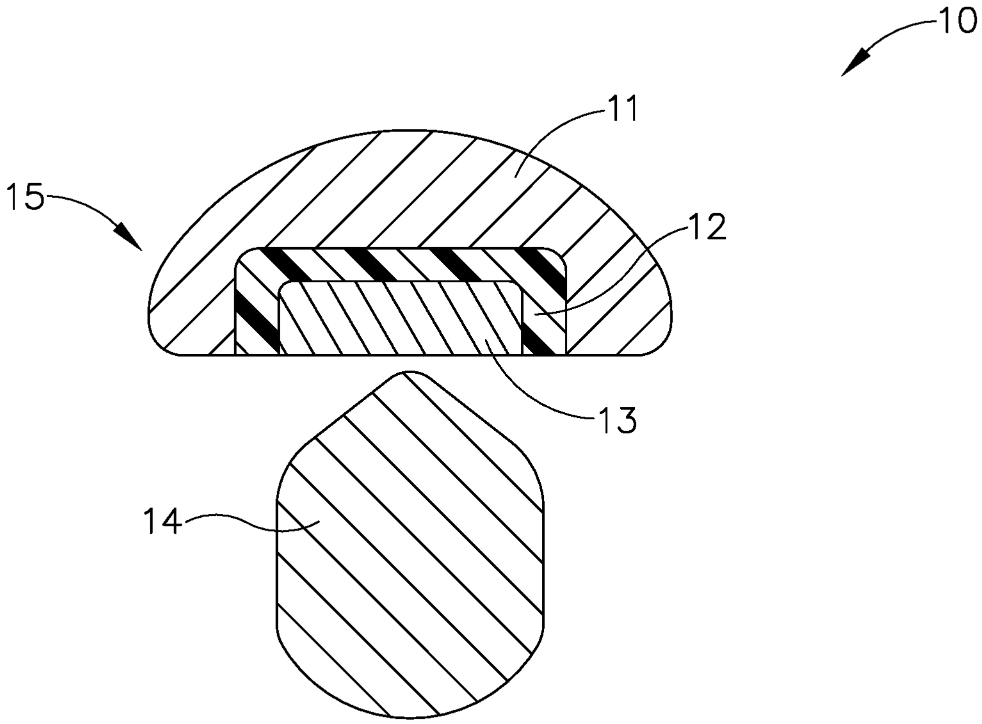
FIG. 79 depicts a cross-section view of another exemplary end effector that may be incorporated into the instrument of FIG. 1, with the end effector in a closed configuration.
Figure 80:
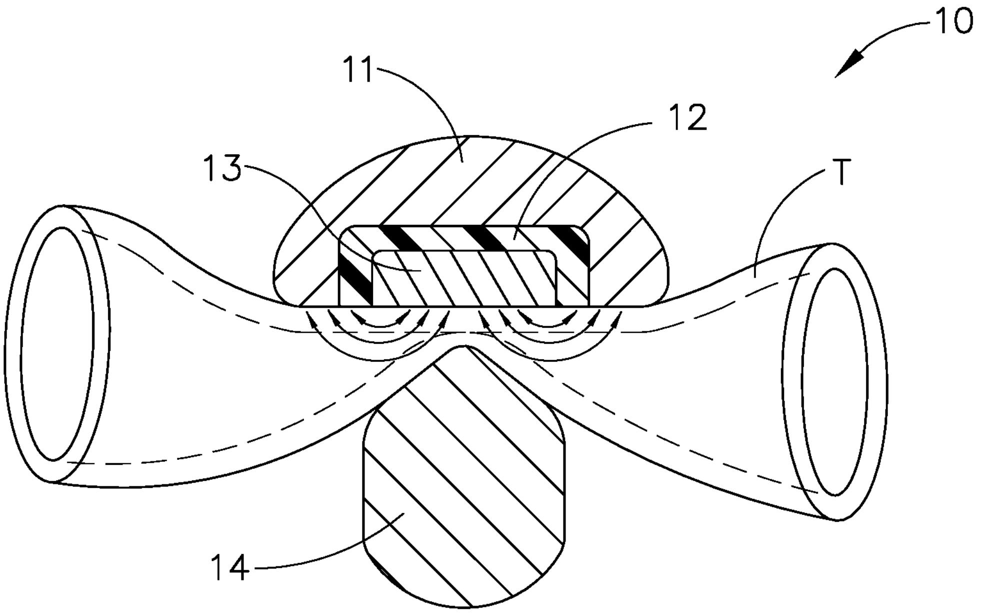
FIG. 80 depicts an end view of the end effector of FIG. 79, with the end effector compressing tissue between the clamp arm and the ultrasonic blade.

FIGS. 79-80 show another exemplary end effector (10) that may be readily incorporated into instrument (110) in place of end effector (140). End effector (10) is configured such that a single treatment region can be defined for both ultrasonic cutting and electrosurgical sealing. End effector (10) of this example comprises an ultrasonic blade (14) and a clamp arm assembly (15). Clamp arm assembly (15) comprises a clamp arm (11), an insulator (12), and a clamp pad (13). Clamp arm (11) connects with inner tube (204) via pin (205) and is operable to pivot toward and away from blade (14) in the manner described above. In this way, instrument (110) is operable to provide ultrasonic cutting when tissue is compressed between blade (14) and clamp arm assembly (15), and blade (14) is activated to oscillate ultrasonically as described further herein.

End effector (10) also provides electrosurgical sealing by delivering electrosurgical energy from one electrical pole to another. In the present example, clamp pad (13) comprises one of the electrical poles while clamp arm (11) comprises the other of the electrical poles. In this manner both clamp pad (13) and clamp arm (11) are conductive and thereby configured to apply electrical energy, with clamp pad (13) having an opposite polarity to that of clamp arm (11). In some versions of end effector (10), clamp pad (13) comprises a custom formulated pad having metallic alloy particles that are electrically activated. In some other versions, clamp pad (13) may be formulated with carbon particles, graphene, and/or other conductive fillers instead of or in addition to metallic alloy particles. Still in other versions, clamp pad (13) may comprises a positive temperature coefficient (PTC) material, which is both conductive and temperature reactive. In view of the teachings herein, other materials and ways to configure clamp pad (13) such that clamp pad (13) is electrically conductive will be apparent to those of ordinary skill in the art. Conductive clamp pad (13) connects with an electrical source, such as generator (116), via a cable or other electrical pathway to electrically activate clamp pad (13).

Clamp arm (11) is also formed of a conductive material as mentioned above. In the present example, clamp arm (11) is coated with an insulating material on its outer surface, which faces away from clamped tissue. The inner surface of clamp arm (11), which faces the clamped tissue, is not coated with an insulating material such that the clamped tissue is exposed to the electrically conductive surface of clamp arm (11) when end effector (10) is providing electrosurgical sealing. Conductive clamp arm (11) connects with an electrical source, such as generator (116), via a cable or other electrical pathway to provide electrical polarity to clamp arm (11). In the present example, clamp arm (11) is isolated from clamp pad (13) by way of insulator (12). This isolation using insulator (12) is configured so that any flow of electrical energy from clamp pad (13) to clamp arm (11), or vice versa, when clamping tissue, must be by the electrical energy flowing through the clamped tissue.

In the present example, blade (14) comprises a coating on at least a portion of blade (14) such that in the region for ultrasonic cutting and RF electrosurgical sealing blade (14) is electrically isolated from electrically activated clamp arm (11) and clamp pad (13). In some versions, the coating used on blade (14) may comprises parylene, xylan, or other suitable coatings that electrically isolate blade (14) from the RF circuit.

During cutting and sealing, clamp arm assembly (15) is actuated to the closed position such that tissue (T) is compressed between clamp arm assembly (15) and blade (14) as shown in FIG. 80. To provide ultrasonic cutting, vibrational energy is applied to blade (14), which oscillates ultrasonically to sever clamped tissue (T) at the region where tissue (T) is compressed between blade (14) and clamp pad (13). To provide RF electrosurgical sealing, with tissue (T) in the clamped and compressed state, RF electrosurgical energy is provided from an electrical source, such as generator (116). The electrical current travels from the positive pole though the tissue (T) and to the negative pole. In the present example, clamp pad (13) comprises the positive pole and clamp arm (11) comprises the negative pole. However, in other versions these poles may be reversed. Cutting and sealing operations may be performed in any order or simultaneously. In some instances, only one of the treatment modalities (ultrasonic cutting being one modality and electrosurgical sealing being another) may be used with end effector (10). Where both cutting and sealing modalities are used for a portion of clamped tissue (T), as best understood from FIG. 80, electrosurgical sealing occurs along both sides of the cut line, such that both of the cut ends of the tissue (T) are sealed.

Figure 81:
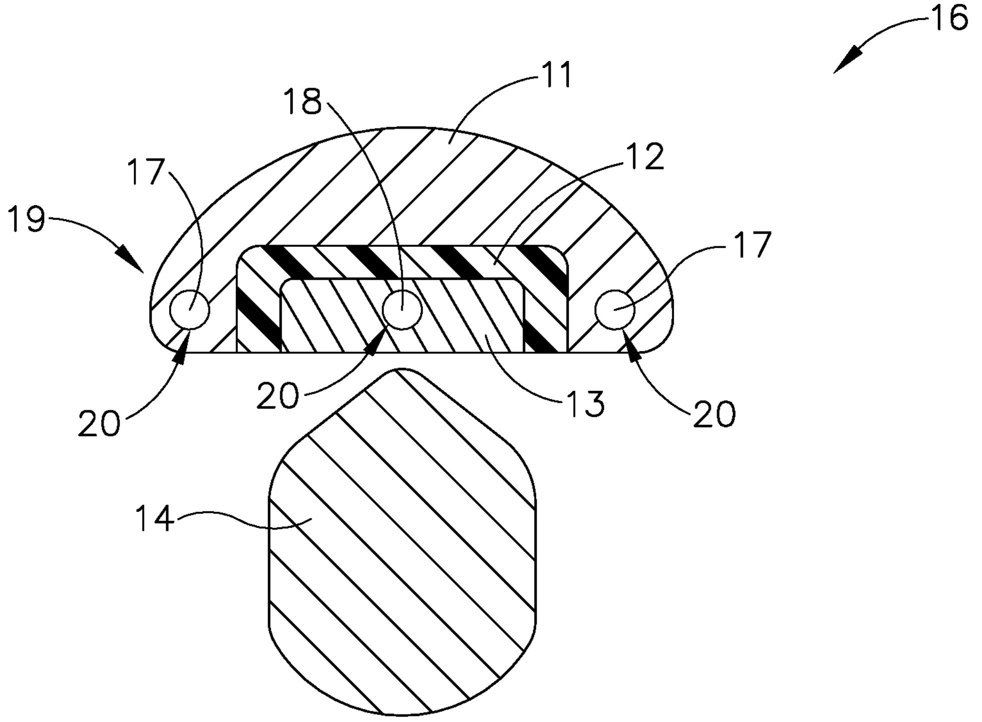
FIG. 81 depicts a cross-section view of another exemplary end effector that may be incorporated into the instrument of FIG. 1, with the end effector in a closed configuration.

FIG. 81 shows another exemplary end effector (16) that may be readily incorporated into instrument (110) in place of end effector (140). End effector (16) is similar to end effector (10) described above. End effector (16) comprises ultrasonic blade (14) and clamp arm assembly (19). With end effector (16), instead of electrically isolating blade (14) by coating blade (14), the electrical energy for clamp arm (11) and clamp pad (13) is provided by running insulated wires (17, 18) through the shaft assembly (130) of instrument (110) in channels (20) positioned within the respective clamp arm (11) and clamp pad (13). Wires (17) are positioned within clamp arm (11) in a manner where wires (17) are located on each side of the clamp arm (11) and spaced away from blade (14) such that there is a portion of clamp arm (11) between wires (17) and blade (14). Similarly, wire (18) is positioned within clamp pad (13) in a manner where wire (18) is spaced away from blade (14) such that there is a portion of clamp pad (13) between wire (18) and blade (14). In this manner, blade (14) is electrically isolated from the RF circuit and the electrosurgical energy is configured to flow through clamped tissue and wires (17, 18). Cutting and sealing operations with end effector (16) occur in the same fashion as explained above with respect to end effector (10).

R. End Effector with Double Coated Blade

Figure 82:
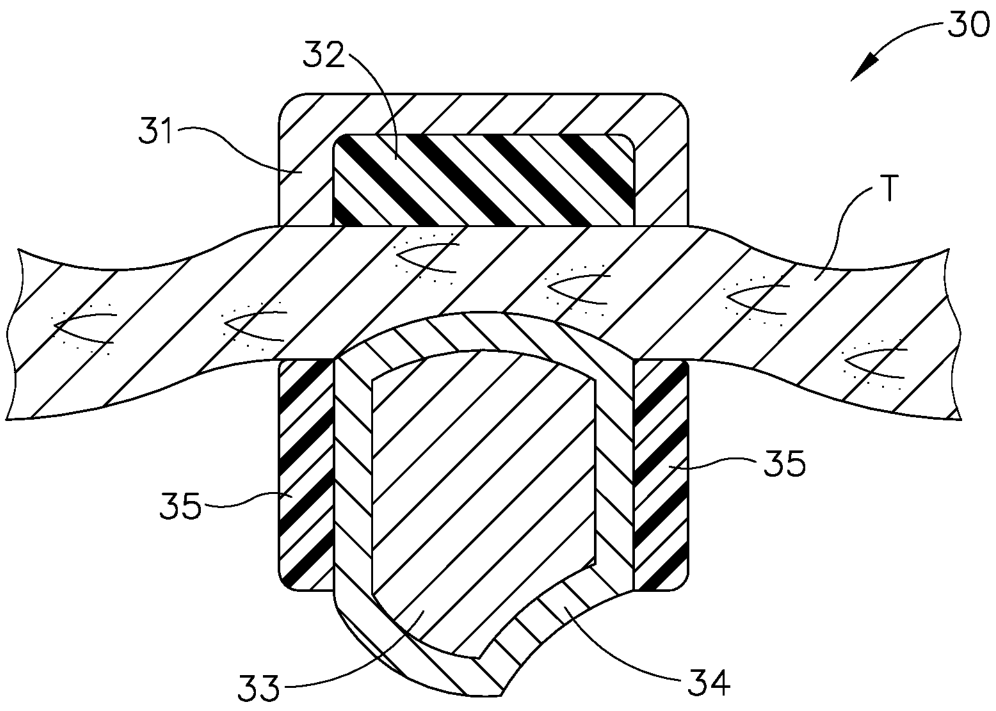
FIG. 82 depicts a cross-section view of another exemplary end effector that may be incorporated into the instrument of FIG. 1.

FIG. 82 shows another exemplary end effector (30) that may be readily incorporated into instrument (110) in place of end effector (140). End effector (30) comprises clamp arm (31), clamp pad (32), and blade (33). In the present example, both clamp arm (31) and clamp pad (32) are nonconductive and are thus not part of the RF electrosurgical circuit or pathway. Blade (33) comprises first coating (34) and second coating (35). First coating (34) surrounds the surface of blade (33) and provides a nonconductive coating for blade (33). As shown in the illustrated version, this nonconductive coating extends over the top surface of blade (33) that is directly beneath the bottom surface of clamp pad (32). Thus, the treatment region for ultrasonic cutting is defined between the nonconductive clamp pad (32) and the nonconductive top surface of blade (33).

Second coating (35) is positioned along each side of blade (33) as shown in the illustrated version. Second coating (35) is conductive and the region where second coating (35) is applied on one side of blade (33) is separate and isolated from the region where second coating (35) is applied on the other or opposite side of blade (33). In the present example, second coating (35) is configured such that one side of blade (33) has a first electrical polarity while the other side of blade (33) has a second electrical polarity.

During cutting and sealing, clamp arm (31) is actuated to the closed position such that tissue (T) is compressed between clamp arm (31), clamp pad (32), and blade (33) as shown in FIG. 82. To provide ultrasonic cutting, vibrational energy is applied to blade (33), which oscillates ultrasonically to sever the clamped tissue (T) at the region where the tissue (T) is compressed between blade (33) and clamp pad (32). To provide RF electrosurgical sealing, with tissue (T) in the clamped and compressed state, RF electrosurgical energy is provided from an electrical source, such as generator (116). The electrical current travels through the tissue (T) between the opposing poles provided by second coating (35). In the present example, second coating (35) on one side of blade (33) provides an active pole and second coating (35) on the other side of blade (33) provides return pole. Cutting and sealing operations may be performed in any order or simultaneously. In some instances, only one of the treatment modalities (ultrasonic cutting being one modality and electrosurgical sealing being another) may be used with end effector (30). Where both cutting and sealing modalities are used for a portion of clamped tissue (T), as best understood from FIG. 82, electrosurgical sealing occurs along and through both sides of the cut line, such that both of the cut ends of the tissue (T) are sealed.

S. End Effector with Two Pole Blade Guard

Figure 83:
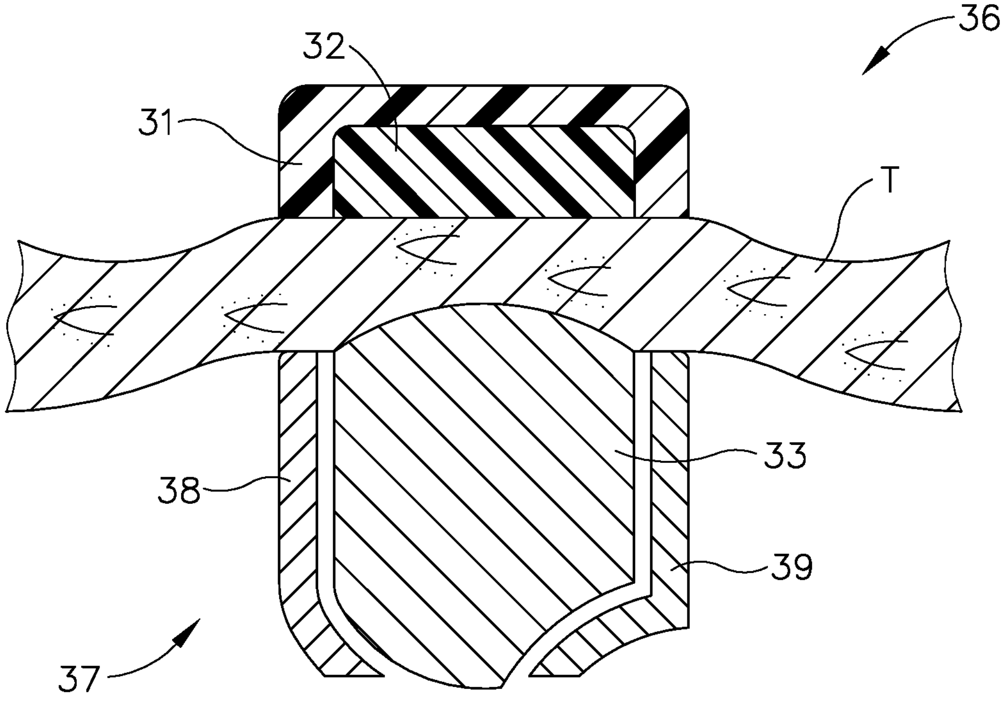
FIG. 83 depicts a cross-section view of another exemplary end effector that may be incorporated into the instrument of FIG. 1.

FIG. 83 shows another exemplary end effector (36) that may be readily incorporated into instrument (110) in place of end effector (140). End effector (36) comprises clamp arm (31), clamp pad (32), and blade (33). In the present example, both clamp arm (31) and clamp pad (32) are nonconductive and are thus not part of the RF electrosurgical circuit or pathway. Blade (33) comprises a split blade guard (37) with a first portion (38) on one side of blade (33) and a second portion (39) on the other side of blade (33). In the present example, split blade guard (37) is spaced away from blade (33) and thus blade (33) remains isolated from the RF electrosurgical circuit or pathway. While blade (33) may be coated in the present example with an insulating material and/or a nonstick material, coating of blade (33) is not required. First and second portions (38, 39) of split blade guard (37) are conductive, with first portion (38) of split blade guard (37) being separate and electrically isolated from the second portion (39) of split blade guard (37). In the present example, first and second portions (38, 39) of split blade guard (37) are oppositely polarized such that the RF electrosurgical circuit or pathway is defined as extending between first portion (38) and second portion (39) of split blade guard (37).

During cutting and sealing, clamp arm (31) is actuated to the closed position such that tissue (T) is compressed between clamp arm (31), clamp pad (32), and blade (33) as shown in FIG. 83. To provide ultrasonic cutting, vibrational energy is applied to blade (33), which oscillates ultrasonically to sever the clamped tissue at the region where the tissue is compressed between a top surface of blade (33) and clamp pad (32). To provide RF electrosurgical sealing, with tissue (T) in the clamped and compressed state, RF electrosurgical energy is provided from an electrical source, such as generator (116). The electrical current travels through tissue (T) between first portion (38) of split blade guard (37) and second portion (39) of split blade guard (37). Cutting and sealing operations may be performed in any order or simultaneously. In some instances, only one of the treatment modalities (ultrasonic cutting being one modality and electrosurgical sealing being another) may be used with end effector (36). Where both cutting and sealing modalities are used for a portion of clamped tissue (T), as best understood from FIG. 83, electrosurgical sealing occurs along and through both sides of the cut line, such that both of the cut ends of the tissue (T) are sealed.

Figure 84:
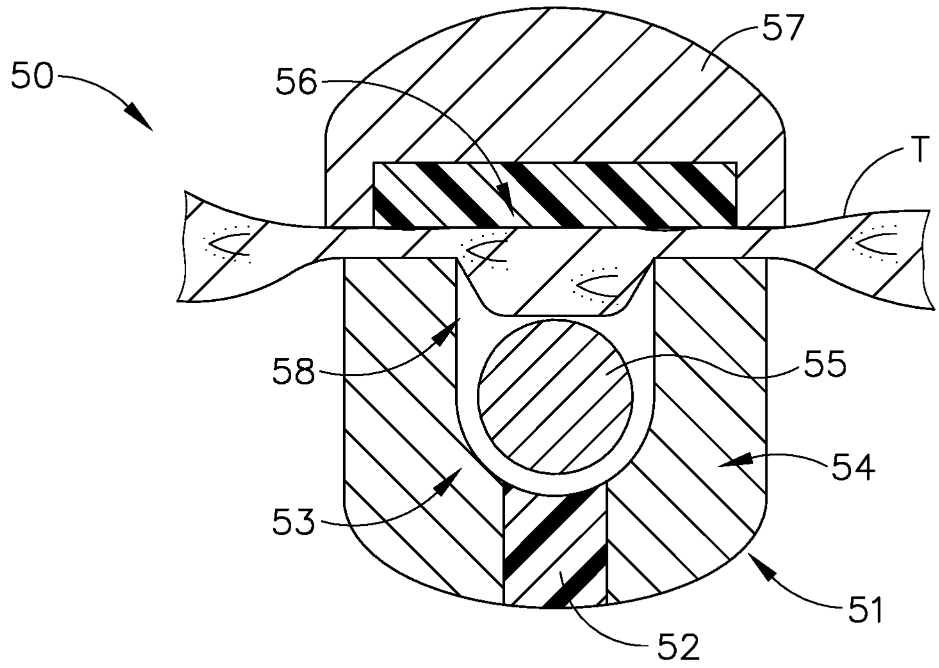
FIG. 84 depicts a cross-section view of another exemplary end effector that may be incorporated into the instrument of FIG. 1.
Figure 85:
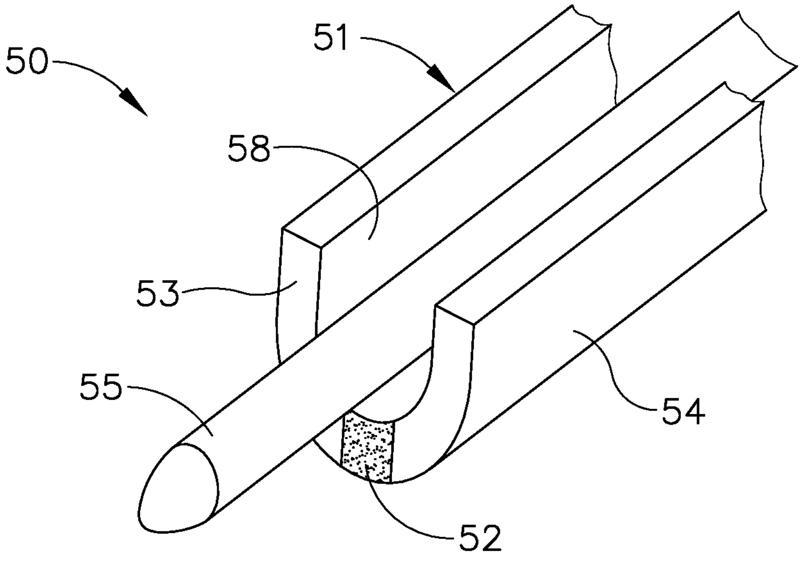
FIG. 85 depicts a partial perspective view of the end effector of FIG. 84.

FIGS. 84 and 85 show another exemplary end effector (50) that may be readily incorporated into instrument (110) in place of end effector (140). End effector (50) is similar to end effector (36). However, end effector (50) of this example comprises a blade guard (51) that includes an insulator (52), which connects a first portion (53) with a second portion (54) of blade guard (51) yet electrically isolates portions (53, 54) relative to each other. Blade guard (51) extends around at least a distal region of a blade (55) of end effector (50). Blade guard (51) further extends in a fashion such that first and second sides of blade (55), as well as the underside of blade (55), are protected by blade guard (51). Blade guard (510) is further configured to have an open side extending along the top surface of blade (55) so that the top surface of blade (55) is accessible for contacting tissue for ultrasonic cutting. As shown in FIGS. 84 and 85, blade guard (51) comprises a profile having a U-shape. However, it should be understood that other profile shapes may be used such as e.g. a V-shape.

Similar to blade guard (37), first portion (53) and second portion (54) of blade guard (51) are conductive. For example, first and second portions (53, 54) of blade guard (51) are oppositely polarized such that the RF electrosurgical circuit or pathway is defined as extending between first portion (53) and second portion (54) of blade guard (51) through compressed tissue (T) captured between blade (55) and a clamp pad (56) of end effector (50). In the present example, blade (55) is insulated using a coating material so that blade (55) is nonconductive. Blade (55) may instead or additionally be insulated at the transducer. Moreover, clamp pad (56) is also non-conductive and may or may not be coated to provide further electrical isolation from blade guard (51). Clamp pad (56) attaches with clamp arm (57), and clamp arm (57) may also be non-conductive and electrically insulated. In the illustrated version of FIG. 84, blade guard (57) also comprises an inner surface (58) facing blade (55). Inner surface (58) includes a coating with an insulating material to further promote electrical isolation of blade (55) from the conductive blade guard (57); and to provide some degree of protection from blade (55) contacting blade guard (57) during ultrasonic cutting.

During cutting and sealing, clamp arm (57) is actuated to the closed position such that tissue (T) is compressed between clamp pad (56) and blade (55) as shown in FIG. 84. To provide ultrasonic cutting, vibrational energy is applied to blade (55), which oscillates ultrasonically to sever the clamped tissue at the region where the tissue is compressed between a top surface of blade (55) and clamp pad (56). To provide RF electrosurgical sealing, with tissue (T) in the clamped and compressed state, RF electrosurgical energy is provided from an electrical source, such as generator (116). The electrical current travels through tissue (T) between first portion (53) of blade guard (51) and second portion (54) of blade guard (51). Cutting and sealing operations may be performed in any order or simultaneously. In some instances, only one of the treatment modalities (ultrasonic cutting being one modality and electrosurgical sealing being another) may be used with end effector (50). Where both cutting and sealing modalities are used for a portion of clamped tissue (T), as best understood from FIG. 84, electrosurgical sealing occurs along and through both sides of the cut line, such that both of the cut ends of the tissue (T) are sealed.

T. End Effector with Dual Charged Clamp Pads

Figure 86:
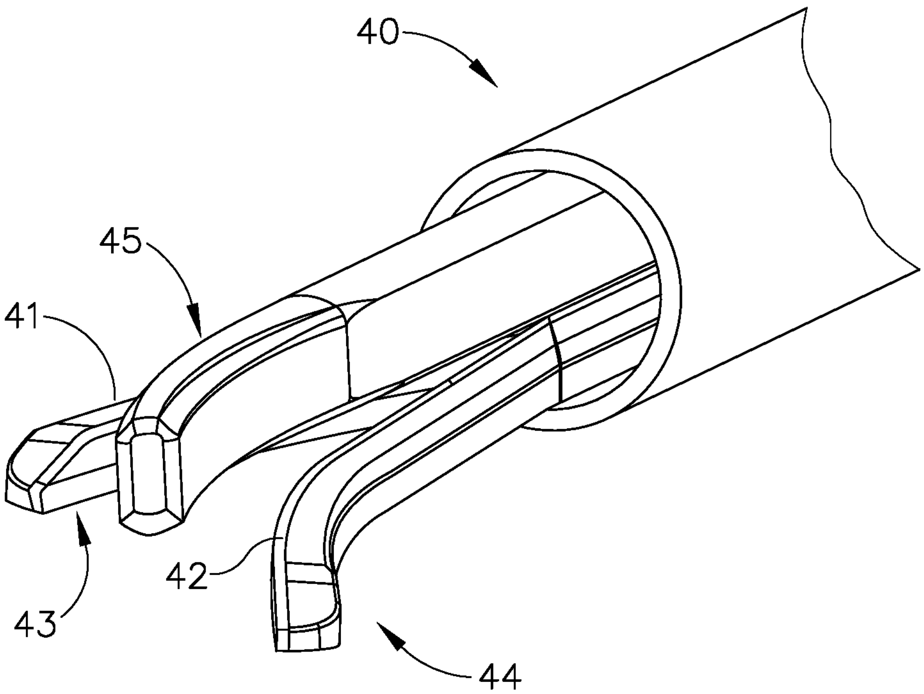
FIG. 86 depicts a perspective view of another exemplary end effector that may be incorporated into the instrument of FIG. 1.
Figure 87:
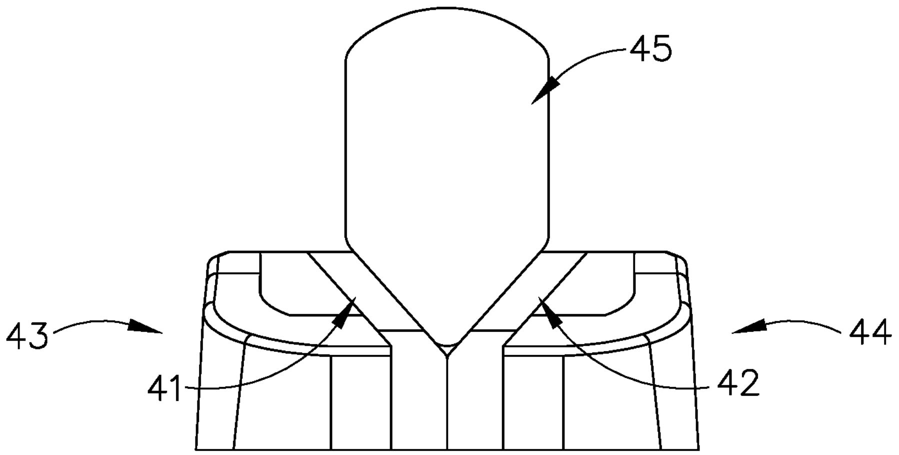
FIG. 87 depicts an end view of a portion of the end effector of FIG. 86.

FIGS. 86 and 87 show another exemplary end effector (40) that may be readily incorporated into instrument (110) in place of end effector (140). End effector (40) comprises a first clamp pad (41), and a second clamp pad (42). Clamp pad (41) is connectable with clamp arm (43), and clamp pad (42) is connectable with clamp arm (44). End effector (40) further comprises blade (45). Each respective clamp arm (43, 44) and attached clamp pad (41, 42) is configured to pivot relative to blade (45) between an open position and a closed position to selectively receive and clamp tissue in end effector (40). In the present example, this pivotal movement occurs in the same or substantially the same manner as the pivoting movement of clamp arm (210) described above. For example, each respective clamp arm (43, 44) is pivotably coupled with an outer tube (202) at one pivot point; and with inner tube (204) at another pivot point. Thus, relative longitudinal movement between tubes (202, 204) provides pivotal movement of clamp arms (43, 44).

In some versions, instrument (110) may be configured with additional tubes or adapters that connect with clamp arms (43, 44) to provide pivotal movement as described herein. Furthermore, clamp arms (43, 44) and their associated clamp pads (41, 42) are configured to move either independently or together. In view of the teachings herein, various ways to configure clamp arms (43, 44) with instrument (110) to provide this pivotal movement will be apparent to those of ordinary skill in the art. By way of example only, clamp arms (43, 44) may be configured and operable to move in accordance with at least some of the teachings of U.S. Pat. No. 9,237,900, entitled "Surgical Instrument with Split Jaw," issued Jan. 19, 2016, the disclosure of which is incorporated by reference herein.

Each clamp pad (41, 42) in the present example is configured with a different polarity so that an RF electrosurgical circuit or pathway is created from clamp pad (41), through captured tissue, to the clamp pad (43), and vice versa. For instance, clamp pad (41) may have a first polarity while clamp pad (42) may have a second polarity. As described above, the conductive nature of clamp pads (41, 42) may be achieved by combining conductive material(s) (46) with the clamp pad material when manufacturing clamp pads (41, 42). The conductive clamp pad (41, 42) are then connectable with an electrical source, such as generator (116), to provide the respective electrical polarity to clamp pads (41, 42). In view of the teachings herein, various ways for connecting conductive clamp pads (41, 42) with generator (116) or another electrical source will be apparent to those of ordinary skill in the art. Also, any of the methods and techniques described above for altering or modifying clamp pad design to shape the electrosurgical circuit or pathway may be used with clamp pads (41, 42) of end effector (40). In view of the teachings herein, such alterations or modification of clamp pads (41, 42) to shape the electrosurgical circuit and resultant sealing will be apparent to those of ordinary skill in the art. Furthermore, each clamp arm (43, 44) is electrically isolated from its respective clamp pad (41, 42) through various insulating materials as will be understood by those of ordinary skill in the art in view of the teachings herein.

In the example where clamp arms (43, 44) move independently relative to blade (45), either or both clamp arms (43, 44) can be moved to the closed position to compress tissue between the respective clamp pad (41, 42) and blade (45). Blade (45) can be activated to oscillate such that compressed tissue will be ultrasonically severed along the regions where tissue is compressed between clamp pads (41, 42) and blade (45). Because each clamp pad (41, 42) in the present example has a different polarity, to achieve RF electrosurgical sealing, both clamp pads (41, 42) are moved so that they contact the captured tissue. This is accomplished by moving each clamp arm (43, 44), containing clamp pads (41, 42) respectively, to the closed position. With both clamp arms (43, 44) closed, RF electrosurgical sealing can be provided via clamp pads (41, 42) either before, during, or after the ultrasonic cutting process.

U. End Effector with Outriggers with Selective Insulation

Figure 88:
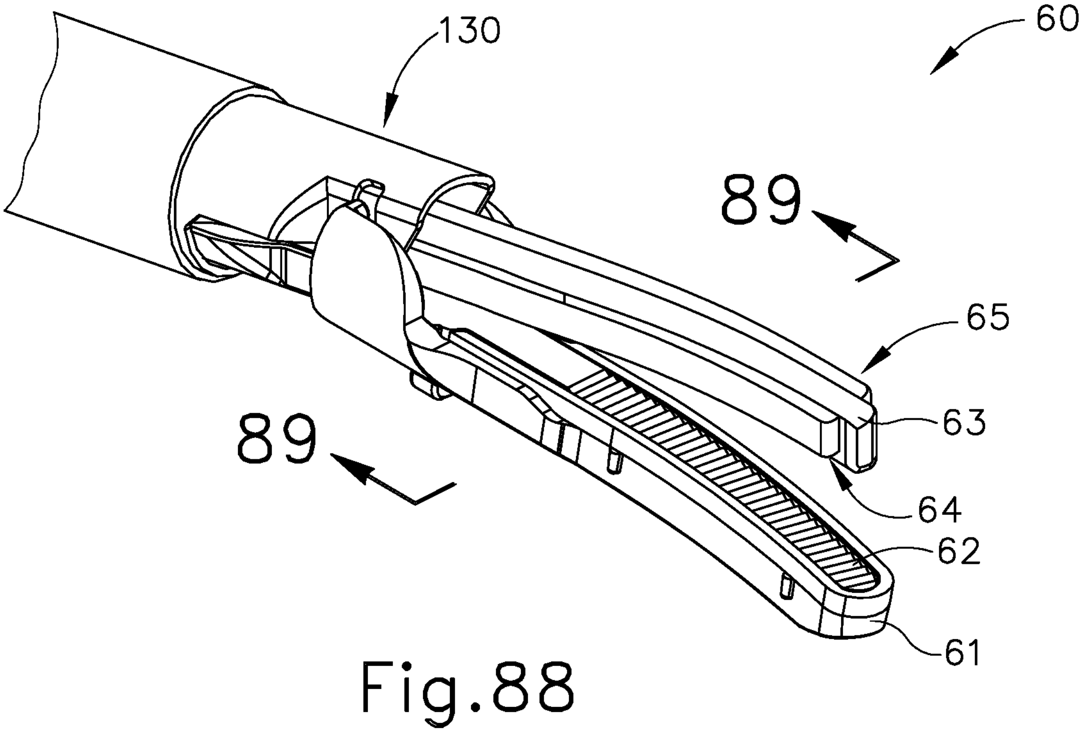
FIG. 88 depicts a perspective view of another exemplary end effector that may be incorporated into the instrument of FIG. 1.
Figure 89:
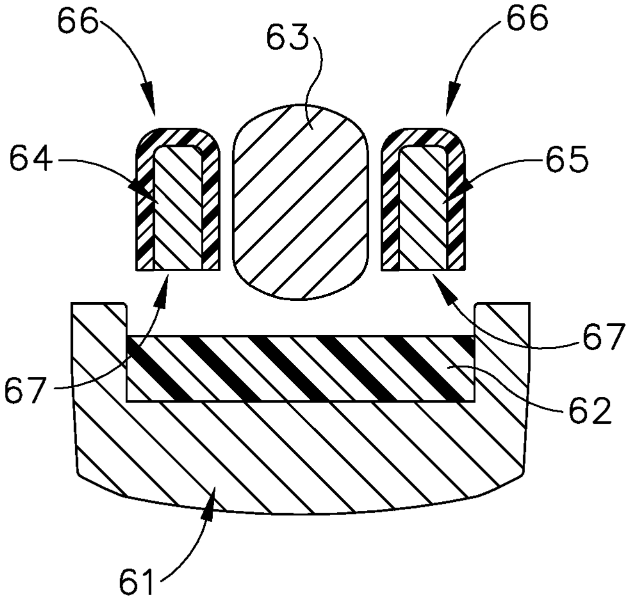
FIG. 89 depicts a cross-section view of the end effector of FIG. 88, taken along line 89-89 of FIG. 88.

FIGS. 88 and 89 show another exemplary end effector (60) that may be readily incorporated into instrument (110) in place of end effector (140). End effector (60) comprises clamp arm (61), clamp pad (62), and blade (63), which are all nonconductive in the present example. Ultrasonic cutting with end effector (60) occurs in the manner described above, where tissue is compressed between blade (63) and clamp pad (62) with blade (63) being activated to oscillate ultrasonically to thereby sever clamped and compressed tissue.

To provide RF electrosurgical sealing in a way where blade (63) remains neutral or nonconductive, and may be coated with xylan or another suitable coating, end effector (60) further comprises a first and second outrigger (64, 65) that each extend from shaft assembly (130). In some other versions, first and second outriggers (64, 65) may extend from blade (63). In the present example, outriggers (64, 65) include a coating (66). Coating (66) is applied selectively to outriggers (64, 65). As shown in the illustrated version of FIG. 89, the selective coating (66) is applied around all sides of outriggers (64, 65) except for an exposed surface (67) of each outrigger (64, 65), which faces or is adjacent to clamp pad (62).

Coating (66) is configured such that coating (66) prevents blade (63) from contacting outriggers (64, 65) directly. Coating (66) also provides insulating properties so as to inhibit the transfer of electrical energy from outriggers (64, 65) to blade (63) or clamp arm (61) thereby causing a short circuit to the RF electrosurgical path as discussed below. In some versions coating (66) may comprise polytetrafluoroethylene, but other coating materials may be used as will be apparent to those of ordinary skill in the art in view of the teachings herein.

In the present example, each of outriggers (64, 65) are conductive. Furthermore, outriggers (64, 65) have opposite polarities. With this configuration, when tissue is clamped between clamp arm (61) and blade (63), a RF electrosurgical circuit or path is defined that extends from one of outriggers (64,65) through the clamped tissue, to the other of outriggers (64, 65). As shown in the illustrated version, exposed surfaces (67) of outriggers (64, 65), which are closest to or facing clamp pad (62), are uncoated thereby allowing electrosurgical energy to flow through the tissue contacting outriggers (64, 65).

In some versions, selective coating (66) is applied such that the exposed surfaces (67) of outriggers (64, 65) are uncoated and thus exposed to clamp pad (62) and clamped tissue along the length of clamp pad (62). In some other versions, selective coating (66) may be applied to outriggers (64, 65) in a pattern so as to alter the pathway of the RF electrosurgical energy flow and thus the electrical field and the resultant sealing shape or pattern. By way of example only, and not limitation, several such features and techniques for altering or manipulating the pathway of the RF electrosurgical energy are described herein with respect to other end effector versions. In view of these teachings, such modifications to the pattern of selective coating (66) on outriggers (64, 65) to alter the RF electrosurgical pathways and the resulting sealing patterns will be apparent to those of ordinary skill in the art. For example, in some versions, instead of exposed surfaces (67) being uncoated along the length of clamp pad (62), selective coating (66) may be applied such that exposed surfaces (67) comprise alternating regions of coating and uncoated areas.

V. End Effector with Embedded Pole in Blade

Figure 90:
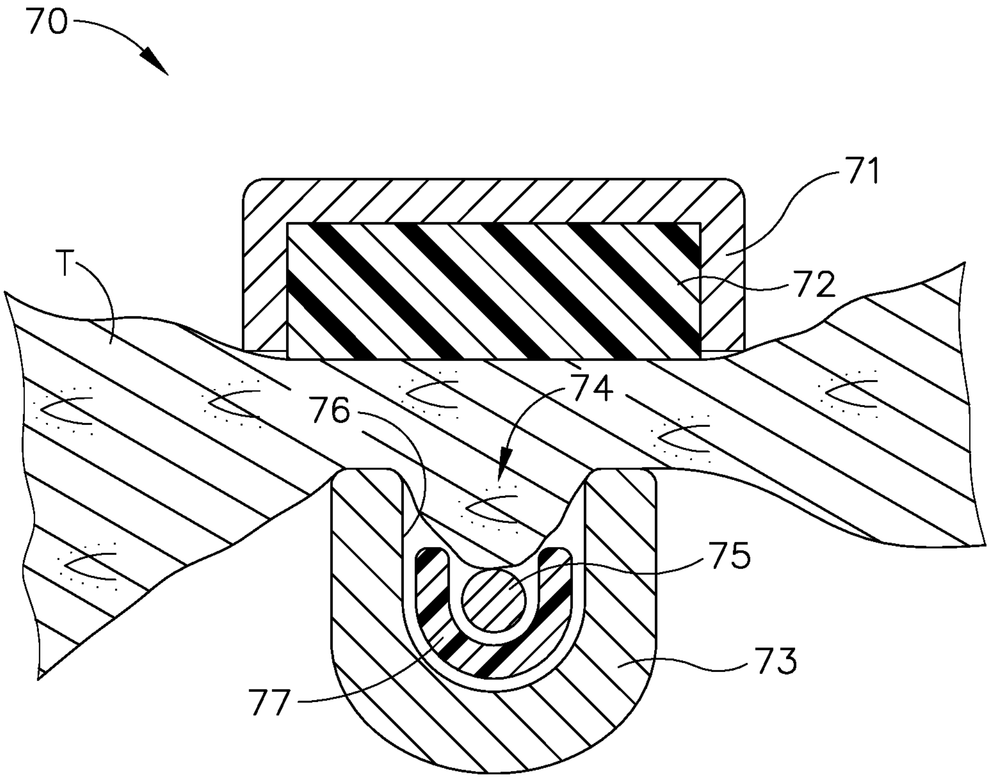
FIG. 90 depicts a cross-section view of another exemplary end effector that may be incorporated into the instrument of FIG. 1.

FIG. 90 shows another exemplary end effector (70) that may be readily incorporated into instrument (110) in place of end effector (140). End effector (70) comprises clamp arm (71), clamp pad (72), and blade (73). Blade (73) is configured with a groove (74). A conductive wire (75) is positioned within groove (74). Between conductive wire (75) and an inner surface (76) of blade (73) is an insulator (77) that electrically isolates blade (73) from conductive wire (75). In some versions, insulator (77) and wire (75) are glued to inner surface (77) of blade (75) defined by groove (74). In some other examples, insulator (77) and wire (75) may be embedded within groove (74) of blade (75) by other suitable fastening features that will be apparent to those of ordinary skill in the art in view of the teachings herein.

Clamp pad (72) of end effector (70) is configured to be electrically conductive. Clamp pad (72) is further configured to have opposite polarity to the polarity of conductive wire (75). Various features and techniques described above are usable with end effector (70) and in particular with clamp pad (72) to provide clamp pad (72) with conductive properties. Conductive clamp pad (72) and conductive wire (75) connect with an electrical source, such as generator (116). Clamp arm (71) is electrically isolated from clamp pad (72), and blade (73) is coated with an insulating material to provide further electrical isolation from conductive clamp pad (72) and wire (75). Groove (74) in blade (73) is sufficiently deep such that when end effector (70) is in a closed position, with or without clamping tissue (T), clamp pad (72) and wire (75) do not contact one another. In this way, any short circuit by such contact between clamp pad (72) and wire (75) is prevented. With this configuration, blade (73) is considered to be proud of wire (75) along at least the clamping region of end effector (70).

When tissue (T) is clamped and compressed between clamp pad (72) and blade (73), two harmonic zones are defined where blade (73) compresses tissue (T) against clamp pad (72). These harmonic zones may be located at longitudinal positions corresponding to anti-nodes associated with resonant ultrasonic vibrations communicated through blade (73). Along these two harmonic zones, when blade (73) is activated, ultrasonic cutting occurs to sever the tissue in two corresponding locations. Between the ultrasonic cut lines is an RF electrosurgical zone defined by the electrical path that extends through tissue (T) between clamp pad (72) and to wire (75). As described above, the RF electrosurgical energy provide for sealing of tissue (T). With this configuration, the harmonic treatment zones are outside of the RF electrosurgical treatment zone.

W. End Effector with Clamp Arm with Overmolded Electrodes

Figure 91:
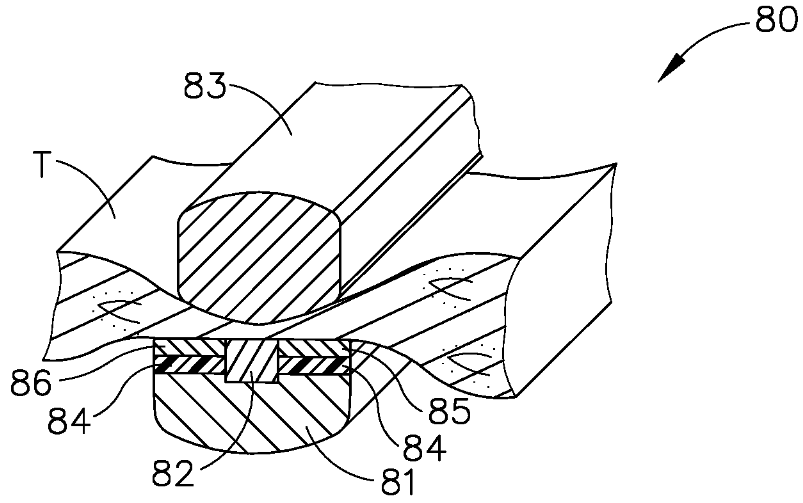
FIG. 91 depicts a cross-section view of another exemplary end effector that may be incorporated into the instrument of FIG. 1.

FIG. 91 shows another exemplary end effector (80) that may be readily incorporated into instrument (110) in place of end effector (140). End effector (80) comprises clamp arm (81), clamp pad (82), and blade (83). In the present example, blade (83) is nonconductive and may be coated with an insulating and/or nonstick material or coating. Clamp pad (82) is also nonconductive in the present example. With tissue (T) compressed between clamp pad (82) and blade (83) when end effector (80) is in a closed position, blade (83) may be activated and tissue (T) ultrasonically cut or severed.

In the present example, RF electrosurgical sealing features are incorporated into clamp arm (81). For instance, clamp arm (81) comprises an insulator (84) that extends along clamp arm (81) along each side of clamp pad (82). Insulator (84) is overmolded onto clamp arm (81), but may be connected with clamp arm (81) other ways that will be apparent to those of ordinary skill in the art in view of the teachings herein. First and second electrodes (85, 86) are each located on and along insulator (84) along each side of clamp pad (82). In this configuration, clamp arm (81) is electrically isolated from first and second electrodes (85, 86) by insulator (84). As will be discussed in greater detail below, each of first and second electrodes (85, 86) are conductive and first electrode (85) has an oppositely polarity from second electrode (86). With this configuration, an RF electrosurgical path is defined extending through tissue (T) between electrodes (85, 86).

Figure 92:
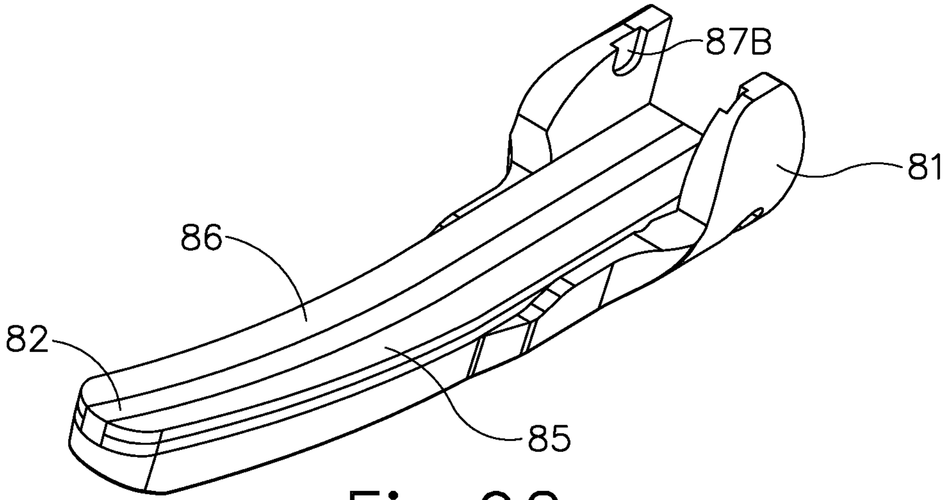
FIG. 92 depicts a perspective view of the clamp arm of the end effector of FIG. 91.
Figure 93:
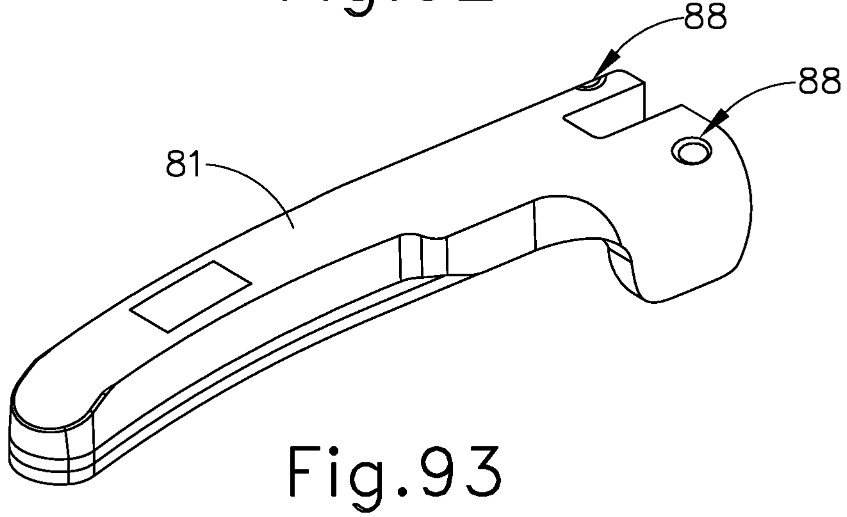
FIG. 93 depicts another perspective view of the clamp arm of the end effector of FIG. 91.
Figure 94:
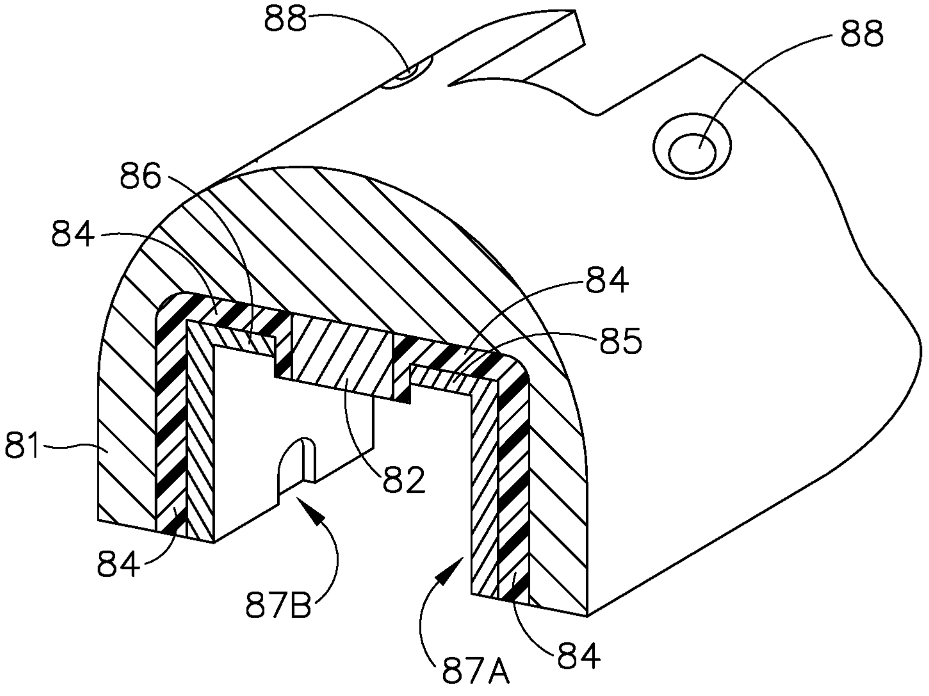
FIG. 94 depicts another cross-section view of the clamp arm of the end effector of FIG. 91.

FIGS. 92-94 show other views of clamp arm (81) and the RF electrosurgical sealing features incorporated therein. As seen in the illustrated version of FIGS. 92 and 94, in addition to clamp pad (82) and first and second electrodes (85, 86), clamp arm (81) includes pull slots (87A, 87B) on each side of clamp arm (81). Pull slots (87A, 87B) are configured to connect with a tube of shaft assembly (130) to provide pivoting movement of clamp arm (81) for opening and closing end effector (80) as described above. In the present example, pull slot (87A) is formed with and/or connects with first electrode (85). Similarly, pull slot (87B) is formed with and/or connects with second electrode (86). In exemplary versions where pull slots (87A, 87B) are formed with respective first and second electrodes (85, 86), each of first and second electrodes (85, 86) comprise a respective longitudinally extending portion and a respective transversely extending portion. In particular, the transversely extending portion comprises the pull slot (87A, 87B) and the longitudinally extending portion extends along the length of clamp arm (81) on top of insulator (84). It should further be understood, as shown in FIG. 94, that insulator (84) also extends transversely, in addition to extending longitudinally, such that clamp arm (81) is fully isolated from first and second electrodes (85, 86). With pull slots (87A, 87B) connecting with first and second electrodes (85, 86) respectively, and with pull slots (87A, 87B) connectable with a tube of shaft assembly (130), as will be described further below, one or more tubes of shaft assembly (130) can be configured to deliver the electrical energy to first and second electrodes (85, 86).

FIG. 93 shows another view of clamp arm (81), with clamp arm (81) comprising openings (88) at each side of a top side of clamp arm (81). Openings (88) are also visible in FIG. 94. Openings (88) are configured to connect with one or more tubes of shaft assembly (130). In the present example, openings (88) connect with corresponding pins or posts located on outer tube of shaft assembly (130). Pull slots (87A, 87B) connect with corresponding pins or posts located on inner tube of shaft assembly (130). In this manner, as described above, clamp arm (81) is pivotable to open and close by translating inner and outer tubes relative to one another. In the present example, openings (88) are isolated from first and second electrodes (85, 86). For example, openings (88) comprise an overmolded plastic insulating material in the present example. With this insulating material, outer tube connecting with openings (88) is also isolated from first and second electrodes (85, 86).

Figure 95:
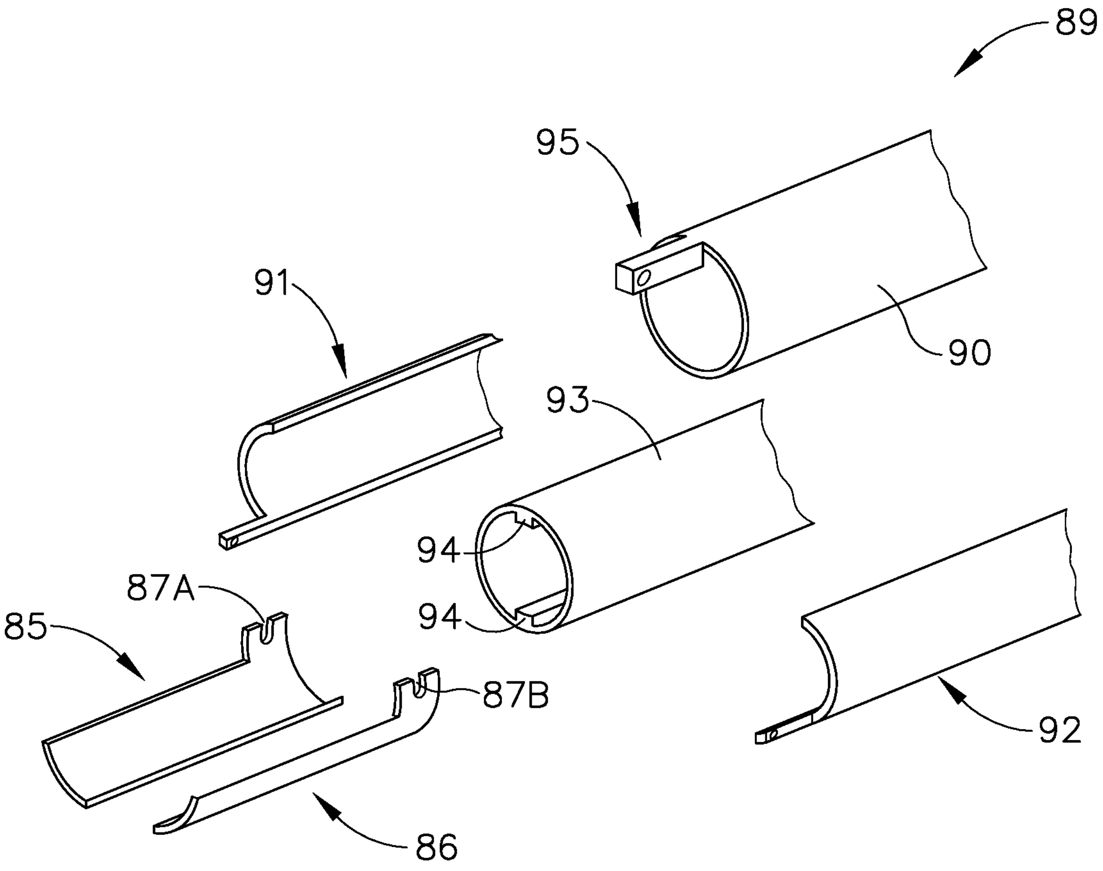
FIG. 95 depicts a partial exploded view of the end effector of FIG. 91, with a tube assembly that may be incorporated into the shaft assembly of FIG. 1 and used with the end effector of FIG. 91.
Figure 96:
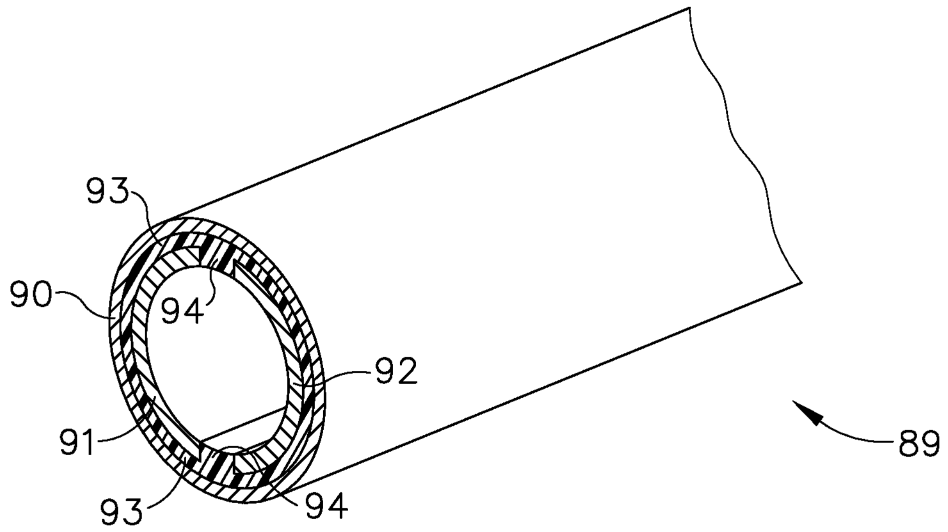
FIG. 96 depicts a cross-section view of the tube assembly of FIG. 95.

FIGS. 95-96 show a tube assembly (89) with first and second electrodes (85, 86). Tube assembly (89) comprises outer tube (90), first half inner tube (91), second half inner tube (92), and insulator tube (93). Tube assembly (89) may replace outer tube (202) and inner tube (204) described above, such that shaft assembly (130) is usable with end effector (80) as further described herein. In the assembled state for tube assembly (89), insulator tube (93) sits within outer tube (90). First half inner tube (91) and second half inner tube (92) each sit within insulator tube (93). Insulator tube (93) comprises dividers (94) that separate first and second half inner tubes (91, 92) such that first and second half inner tubes (91, 92) do not directly contact one another. Insulator tube (93) further separates outer tube (90) from first and second half inner tubes (91, 92) such that outer tube (90) does not directly contact first and/or second half inner tubes (91, 92).

In the present example, outer tube (90) is nonconductive while first and second half inner tubes (91, 92) are conductive. First and second half inner tubes (91, 92) respectively connect with pull slots (87A, 87B) of first and second electrodes (85, 86) as described above. First half inner tube (91) is configured to provide a first electrical polarity to first electrode (85) through its connection with pull slot (87A). Second half inner tube (92) is configured to provide a second electrical polarity to second electrode (86) through its connection with pull slot (87B).

As described above, insulator (84) electrically isolates clamp arm (81) from first and second electrodes (85, 86). Additionally, openings (88) are insulated as mentioned. Outer tube (90) includes elongated member (95) having pins or posts that connect with openings (88) in clamp arm (81). With this configuration, clamp arm (81) of end effector (80) connects with both outer tube (90) and with first and second half inner tubes (91, 92). First and second half inner tubes (91, 92) are configured to translate in unison. As described above, with translational movement of first and second half inner tubes (91, 92) relative to outer tube (90), clamp arm (81) opens and closes with a pivoting action. In other versions outer tube may translate relative to first and second half inner tubes (91, 92) to pivot clamp arm (81).

In the configuration described above, an RF electrosurgical path is defined as extending through tissue (T) between electrodes (85, 86). When tissue (T) is clamped between clamp arm (81) and blade (83), tissue (T) can be ultrasonically cut along the region between clamp pad (82) and blade (83). Furthermore, tissue (T) can be sealed along each side of the cut line where tissue (T) contacts first and second electrodes (85, 86).

Figure 97:
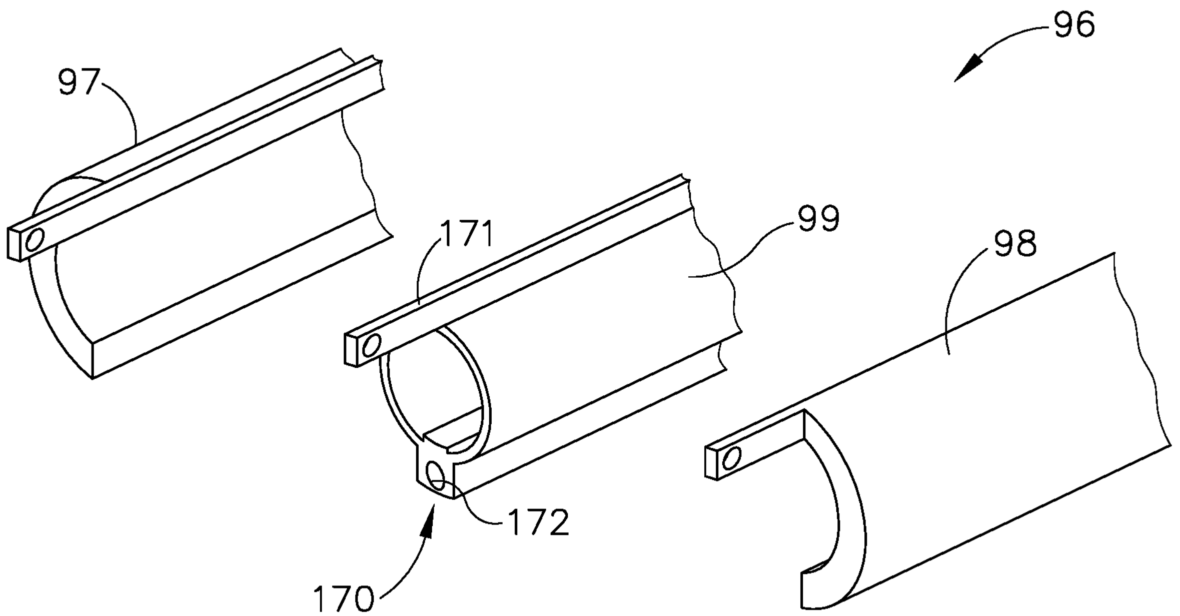
FIG. 97 depicts an exploded view of another exemplary tube assembly that may be incorporated into the shaft assembly of FIG. 1 and used with the end effector of FIG. 91.
Figure 98:
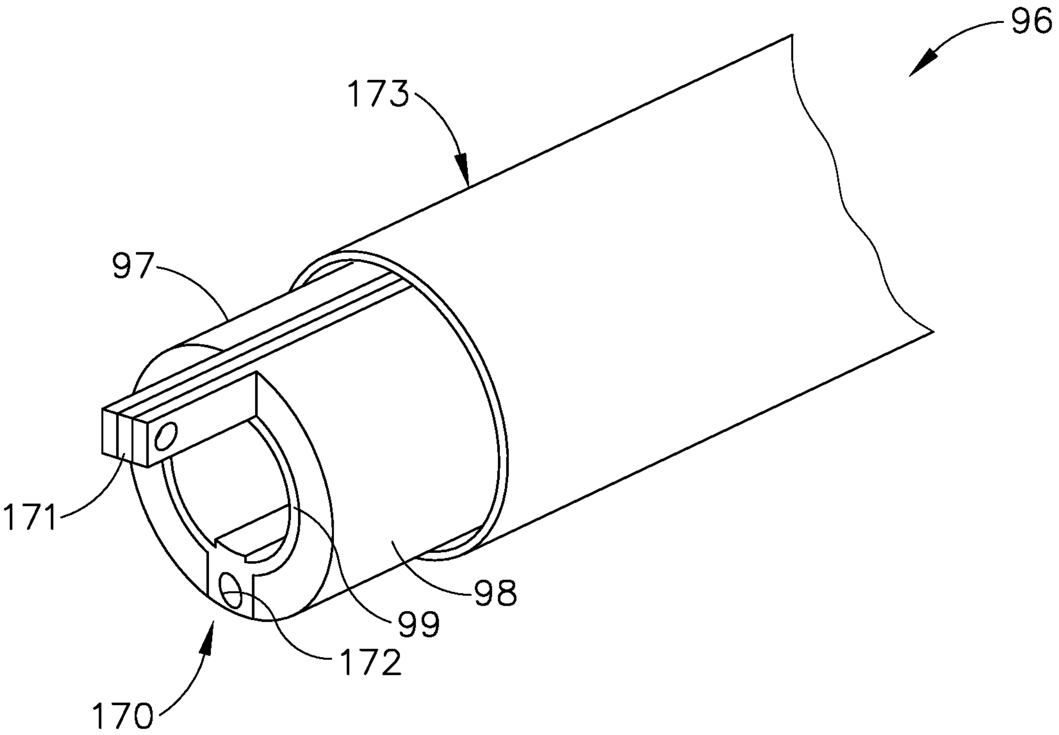

FIGS. 97 and 98 show another tube assembly (96) that may be used with end effector (80) instead of tube assembly (89). Tube assembly (96) is similar to tube assembly (89). However, tube assembly (96) of this example is configured such that the outer tube provides the electrical energy to first and second electrodes (85, 86) instead of the inner tube as in tube assembly (89).

Tube assembly (96) comprises first half outer tube (97), second half outer tube (98), insulator tube (99), and inner tube (not shown). Tube assembly (96) may replace outer tube (202) and inner tube (204) described above, such that shaft assembly (130) is usable with end effector (80) as further described herein. In the assembled state for tube assembly (96), insulator tube (99) sits within first and second half outer tubes (97, 98). Inner tube (not shown) sits within insulator tube (99). Insulator tube (99) comprises dividers (170, 171) that separate first and second half outer tubes (97, 98) such that first and second half outer tubes (97, 98) do not directly contact one another. Insulator tube (99) further separates inner tube from first and second half outer tubes (97, 98) such that inner tube does not directly contact first and/or second half outer tubes (97, 98). Divider (170) of insulator tube (99) defines a bore (172) that is configured such that wires or cables can pass through bore (172) to extend through instrument (110). Such wires and/or cables can be used to provide electrical energy to first and second electrodes (85, 86) in some versions instead of providing electrical energy through inner or outer tube structures. It should also be understood that wires and/or cables can be used for electrical grounding.

In the present example, inner tube is nonconductive while first and second half outer tubes (97, 98) are conductive. First and second half outer tubes (97, 98) respectively connect with openings (88). In the present example using tube assembly (96), clamp arm (81) and first and second electrodes (85, 86) are modified such that electrical energy may be communicated through openings (88) to first and second electrodes (85, 86) instead of through pull slots (87A, 87B) as described above. In view of the teachings herein, such modifications to clamp arm (81) to transfer electrical energy to first and second electrodes (85, 86) by way of openings (88) instead of pull slots (87A, 87B) will be apparent to those of ordinary skill in the art. In this manner, first half outer tube (97) is configured to provide a first electrical polarity to first electrode (85) through its connection, and second half outer tube (98) is configured to provide a second electrical polarity to second electrode (86). As shown in FIG. 98, a heat shrink tube (173) can surround first and second half outer tubes (97, 98) to isolate other components of shaft assembly (130) and instrument (110) from conductive first and second outer tube halves (97, 98).

As described above, insulator (84) electrically isolates clamp arm (81) from first and second electrodes (85, 86). In the present example using tube assembly (96), insulator (84) and clamp arm (81) are also modified such that clamp arm (81) remains electrically isolated from first and second half outer tubes (97, 98). In view of the teachings herein, such modifications to insulator (84) and clamp arm (81) to maintain electrical isolation of clamp arm (81) will be apparent to those of ordinary skill in the art. Additionally, with tube assembly (96) pull slots (87A, 87B) are insulated such that inner tube remains electrically isolated from first and second electrodes (85, 86). With this configuration, clamp arm (81) of end effector (80) connects with both inner tube and with first and second half outer tubes (97, 98). First and second half outer tubes (97, 98) are configured to translate in unison. As described above, with translational movement of first and second half outer tubes (97, 98) relative to inner tube, clamp arm (81) opens and closes with a pivoting action. In some other versions, inner tube may translate relative to first and second half outer tubes (97, 98) to pivot clamp arm (81).

In the configuration described above with tube assembly (96), an RF electrosurgical path is defined as extending through tissue (T) between electrodes (85, 86). When tissue (T) is clamped between clamp arm (81) and blade (83), tissue (T) can be ultrasonically cut along the region between clamp pad (82) and blade (83). Furthermore, tissue (T) can be sealed along each side of the cut line where tissue (T) contacts first and second electrodes (85, 86).

Figure 99:
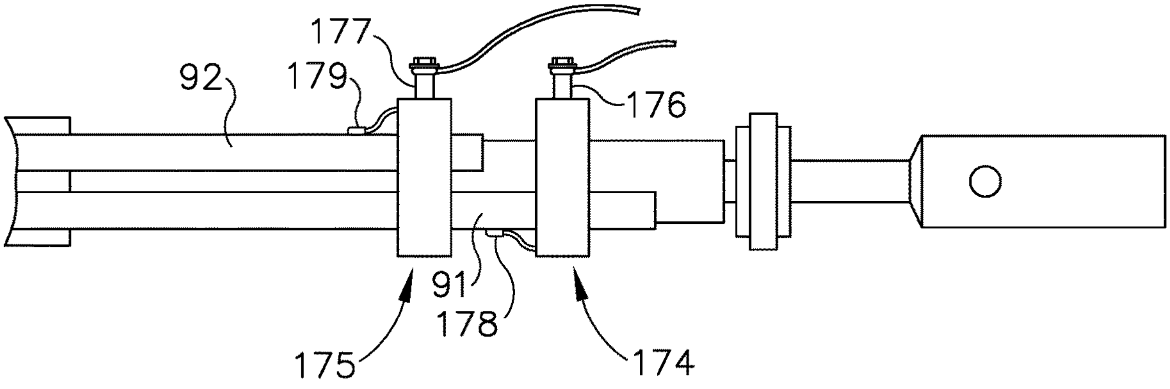
Figure 100:
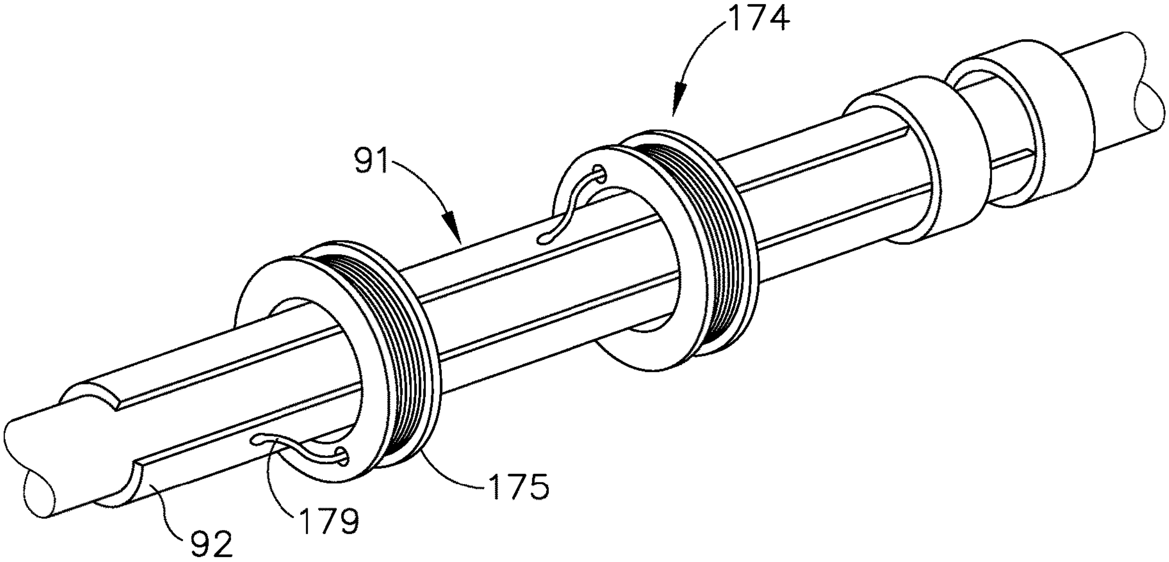

FIGS. 99 and 100 show further proximal portions of tube assembly (89), and in particular connections of first and second half inner tubes (91, 92) with first and second rings (174, 175) to provide RF electrical energy to first and second half inner tubes (91, 92), and ultimately to first and second electrodes (85, 86). In the present example, first half inner tube (91) connects with first ring (174), and second half inner tube (92) connects with second ring (175). Ring (174) further connects with ring contact (176), which connects with one of the cables that connects with generator (116) to provide the electrical energy. Ring (175) further connects with ring contact (177), which connects with the other of the cables that connects with generator (116) to provide the electrical energy. In one version, ring contacts (176, 177) comprise contact springs.

First ring (174) and second ring (175) comprise respective connection members (178, 179). Connection member (178) contacts first half inner tube (91) to provide electrical continuity with first half inner tube (91). Connection member (179) contact second half inner tube (92) to provide electrical continuity with second half inner tube (92). In the present example, first ring (174) and second ring (175) are welded or otherwise fixedly attached to respective first and second half inner tubes (91, 92). In this manner, shaft assembly (130) is rotatable 360 degrees and electrical contact is maintained between first and second rings (174, 175) and respective first and second half inner tubes (91, 92). In some versions, rings (174, 175) are rotatable relative to respective first and second ring contacts (176, 177), such that when shaft assembly rotates, rings (174, 175) rotate also based on their fixed connection with respective first and second half inner tubes (91, 92). This rotation of rings (174, 175) is relative to ring contacts (176, 177). However, ring contacts (176, 177) remain in electrical contact with respective rings (174, 175), thereby providing electrical continuity from respective cables to respective first and second half inner tubes (91, 92), and ultimately to respective first and second electrodes (85, 86). With rings (174, 175) rotatable relative to ring contacts (176, 177), cables within instrument (110) that connect with ring contacts (176, 177) can remain generally stationary when the shaft assembly is rotated.

Figure 101:
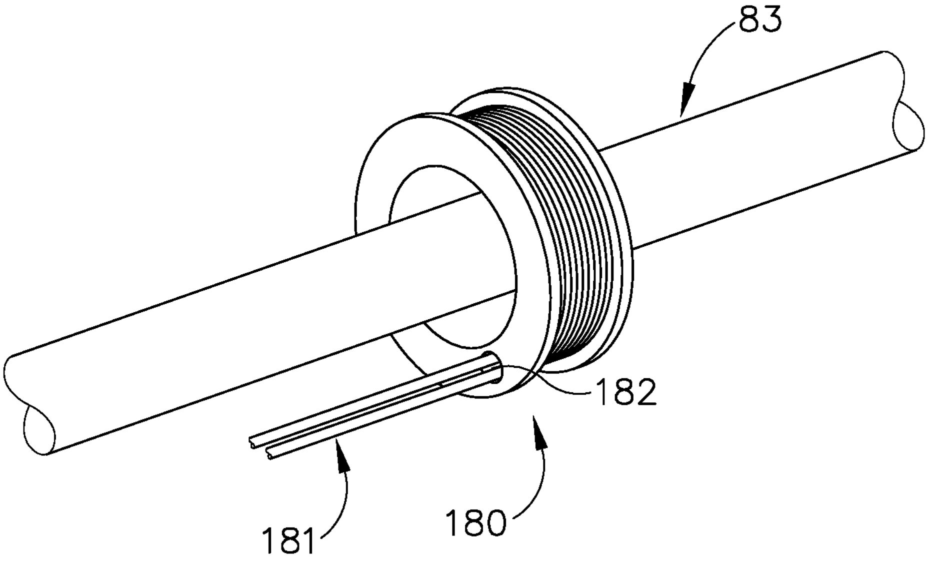

FIG. 101 shows actuation ring (180) with blade (83) passing through actuation ring (180). In the present example, actuation ring (180) is configured to connect with first inner half tube (91) and second inner half tube (92) to translate inner half tubes (91, 92) relative to outer tube (90) so as to pivot clamp arm (81) to open and close clamp arm (81). Actuation ring (180) is connectable with trigger (128) such that clamp arm (81) is pivotable toward ultrasonic blade (83) in response to pivoting of trigger (128) toward pistol grip (124); and such that clamp arm (81) is pivotable away from ultrasonic blade (83) in response to pivoting of trigger (128) away from pistol grip (124). Various suitable ways in which actuation ring (180) may be coupled with inner half tubes (91, 92) and trigger (128) will be apparent to those of ordinary skill in the art in view of the teachings herein. In some versions, actuation ring (180) may be connectable with outer tube (90) instead of with inner half tubes (91, 92) to provide the translation necessary to pivot clamp arm (81) between open and closed positions. As shown in FIG. 101, actuation ring (180) may be configured with a bore (182) that allows wires (181) to pass through actuation ring (180) in some versions.

X. End Effector with Conductive Pad with Two Poles

Figure 102:
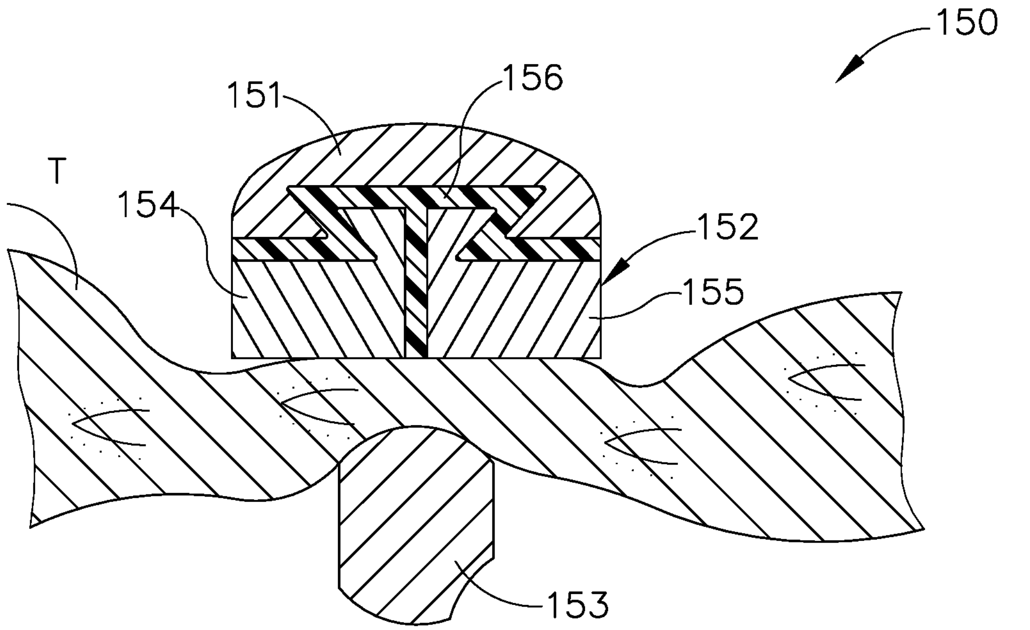

FIG. 102 shows another exemplary end effector (150) that may be readily incorporated into instrument (110) in place of end effector (140). End effector (150) comprises clamp arm (151), clamp pad (152), and blade (153). Clamp pad (152) comprises first portion (154) and second portion (155). An insulator (156) separates first and second portions (154, 155). Insulator (156) also separates respective first and second portions (154, 155) of clamp (152) from clamp arm (151).

Figure 103:
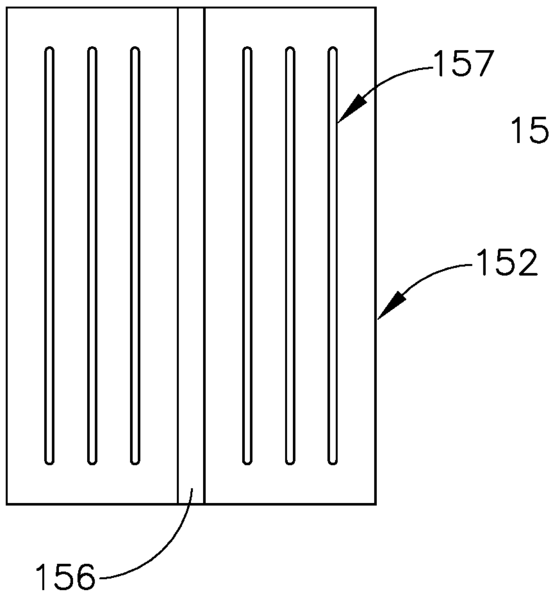
Figure 104:
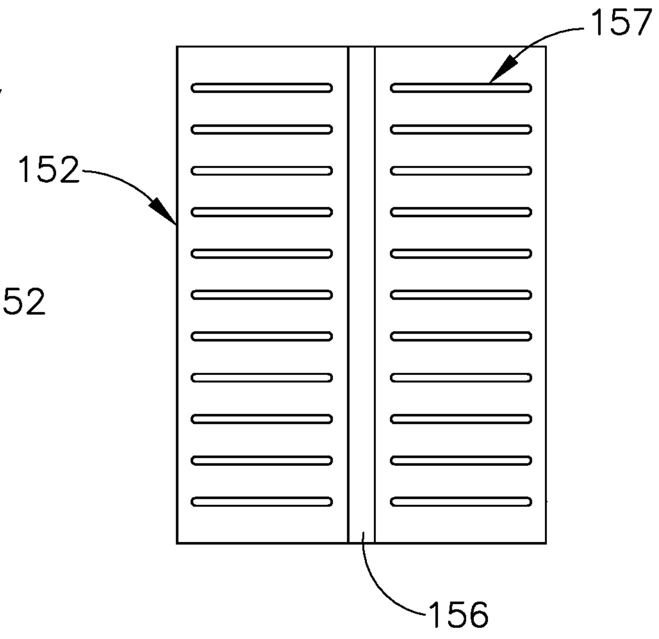

Clamp pad (152) is constructed from conductive material (157) such that first and second portion (154, 155) are each electrically conductive. Furthermore, each conductive first and second portions (154, 155) of clamp pad (152) connect either directly or indirectly with respective cables that lead to generator (116) or another source of RF electrosurgical power. First and second portions (154, 155) of clamp pad (152) are oppositely polarized. In some versions, conductive material (157) within clamp pad (152) comprises conductive fibers that are formed in clamp pad (152). These fibers may be oriented longitudinally along clamp pad (152) as shown in FIG. 103. Alternatively, these fibers may be oriented transversely along clamp pad (152) as shown in FIG. 104. Any other suitable fiber orientation may be used.

As yet another merely illustrative variation, conductive material (157) comprises metal that is impregnated within rubber during clamp pad (152) construction. This metal may also be oriented longitudinally, transversely, or otherwise along clamp pad (152), or in any other suitable pattern including a random orientation. Some exemplary metals that may be used with clamp pad (152) to impart conductivity to clamp pad (152) include, but are not limited to, silver, silver-plated aluminum, silver-plated copper, silver-plated glass, nickel-plated graphite, among others. Another exemplary conductive material (157) usable with clamp pad (152) includes black carbon. In view of the teachings herein, other materials that may be used with clamp pad (152) to make clamp pad (152) conductive, as well as techniques for incorporating such materials with clamp pad (152), will be apparent to those of ordinary skill in the art.

With the orientation of insulator (156) as described above, end effector (150) first and second portions (154, 155) of conductive pad (152) provide oppositely polarized electrodes of an RF electrosurgical pathway or circuit. Furthermore, the electrically conductive portions of clamp pad (152) are isolated from one another and from clamp arm (151). With this configuration, a single treatment region is defined between clamp pad (152) and blade (153), and both ultrasonic cutting and RF electrosurgical sealing of tissue sealing can be provided within the single treatment region.

In some versions, clamp pad (152) is configured as a disposable clamp pad (152) that wears away gradually as heat is generated by blade (153). With this configuration, conductive material (157) within clamp pad (152) may be configured to wear away such that RF electrosurgical sealing becomes less effective and thereby serves to indicate the time is right to replace clamp pad (152).

When end effector (150) is used with instrument (110) to cut and seal tissue (T), as mentioned above a single treatment region is defined by tissue (T) compressed between blade (153) and clamp pad (152). With tissue (T) compressed and blade (153) activated, ultrasonic cutting of tissue (T) occurs along this compressed region of tissue (T). Additionally, or separately, RF electrosurgical sealing occurs in this single treatment region. More specifically, with tissue (T) clamped between blade (153) and pad (152), an RF electrosurgical pathway or circuit is defined as extending through tissue between first portion (154) of clamp pad (152) and second portion (155) of clamp pad (152). In this exemplary RF electrosurgical circuit, first portion (154) is provided at a first electrical polarity while second portion (155) is provided at a second electrical polarity. When using end effector (150) for ultrasonic cutting and RF electrosurgical sealing, these modalities may be used in any order, or at the same time. Furthermore, just one of these modalities may be used in some applications, such that it is not necessary in all circumstances to use both modalities with end effector (150).

Y. End Effector with Dual Lengthwise Sections

FIG. 105 shows another exemplary end effector (450) configured for use with a shears device (451). While the present example illustrates shears device (451), in view of the teachings herein, the features and techniques pertaining to the ultrasonic cutting and RF electrosurgical sealing are also applicable to instrument (110) and one or more of the end effectors described herein that are readily usable with instrument (110).

In certain procedure, e.g. solid organ procedures, it may be desirable to crush tissues to divide the parenchymous tissues without disturbing the vessels and ducts lying within. By way of example only, this may occur in procedures where a portion of a patient's liver is removed. After crushing the parenchyma, the exposed vessels and ducts can then be sealed and cut. In some instances, larger jaw or clamp arm devices are used with such procedures. Some such larger jaw or clamp arm devices may include shears like shears (451) shown in FIG. 105. It should therefore be understood that the same shears (451) may be used to crush the parenchyma, sever the exposed vessels and ducts, and seal the severed vessels and ducts. In view of the teachings herein, other devices usable in such procedures as described here will be apparent to those of ordinary skill in the art. Such other devices include, but are not limited to, instrument (110) and end effectors readily usable with instrument (110), including end effectors incorporating modifications based on the teachings described and shown here with respect to end effector (450).

Referring to FIGS. 105-109, end effector (450) comprises clamp arm (452), clamp pad (453), blade (454), and blade cover (455). End effector (450) further comprises two sections that extend lengthwise along clamp arm (452). The two lengthwise sections comprise a proximal section (456) and a distal section (457). In the present example, proximal section (456) is configured for clamping tissue without or with minimal energy-based cutting. Instead of being configured for energy-based cutting, proximal section (456) is configured to provide mechanical crushing of tissue as described above; and/or to deliver bipolar electrosurgical energy to seal tissue. Distal section (457) is configured for cutting tissue by delivering ultrasonic and/or bipolar electrosurgical energy, where the tissue is cut by way of ultrasonic energy. While the energy-based cutting section is distal section (457) in the present example, in some other versions, the functions of the proximal and distal sections (456, 457) may be reversed such that the energy-based cutting occurs at proximal section (456), while the bipolar coagulation and sealing occurs at the distal section (457).

In the present example, proximal section (456) for sealing and coagulation includes opposing clamping electrode surfaces that deliver bipolar electrosurgical energy to clamped tissue. For instance, the clamp arm side comprises a first electrode (458) and blade side comprises a second electrode (459). In some versions, first electrode (458) is configured with clamp arm (452) such that clamp arm (452) provides a first polarity in the bipolar RF electrosurgical circuit. In some other versions, first electrode (458) is configured with clamp pad (453) such that clamp pad (453) provides a first polarity in the bipolar RF electrosurgical circuit. In still other versions, first electrode (458) comprises a conductive plate connectable with clamp arm (452) and/or clamp pad (453), where the conductive plate is configured to provide a first polarity in the bipolar RF electrosurgical circuit. In view of the teachings herein, other various ways to provide first electrode (458) on clamp arm side of end effector (450) will be apparent to those of ordinary skill in the art.

In some versions, second electrode (459) is configured with blade (454) such that blade (454) provides a second polarity of the bipolar RF electrosurgical circuit. In some other versions, second electrode (459) is configured with blade cover (455) such that blade cover (455) provides the second polarity of the bipolar RF electrosurgical circuit. In still other versions, second electrode (459) comprises a conductive plate connectable with blade (454) or blade cover (455), where the conductive plate provides the second polarity of the bipolar RF electrosurgical circuit. In examples where second electrode (459) is formed by blade (454), second electrode (459) can be ultrasonically active even though present in proximal section (456). In examples where second electrode (459) is formed by separate components not part of blade (454), second electrode (459) is not ultrasonically active. Furthermore, even where second electrode (459) is formed as part of blade (454) and thus is ultrasonically active, the displacement of blade (454) in proximal section (456) is about 70% less than the displacement that occurs at the distal tip of blade (454). In view of the teachings herein, other various ways to provide second electrode (459) on blade side of end effector (450) will be apparent to those of ordinary skill in the art.

In the present example, distal section (457) for ultrasonic cutting includes clamp pad (453) and blade (454) such that tissue can be clamped between and severed by ultrasonic cutting when blade (454) is activated to oscillate ultrasonically. Distal section (457) can optionally include opposing clamping electrode surfaces that deliver bipolar energy to clamped tissue so that sealing and coagulation can be provided in distal section (457) also. For instance, in an example that includes RF electrosurgical sealing in distal section (457), the clamp arm side comprises a third electrode (460) and blade side comprises a fourth electrode (461). In some versions, third electrode (460) is configured with clamp arm (452) such that clamp arm (452) provides a first polarity of the bipolar RF electrosurgical circuit. In some other versions, third electrode (460) is configured with clamp pad (453) such that clamp pad (453) provides the first polarity of the bipolar RF electrosurgical circuit. In still other versions, third electrode (460) comprises a conductive plate connectable with clamp arm (452) and/or clamp pad (453), where the conductive plate provides the first polarity of the bipolar RF electrosurgical circuit. In some versions, first electrode (458) and third electrode (460) may be the same structure that spans both proximal and distal sections (456, 457) of end effector (450). In view of the teachings herein, other various ways to provide third electrode (460) on clamp arm side of end effector (450) will be apparent to those of ordinary skill in the art.

In some versions, fourth electrode (461) is configured with blade (454) such that blade (454) provides the second polarity of the bipolar RF electrosurgical circuit. In some other versions, fourth electrode (461) is configured with blade cover (455) such that blade cover (455) provides the second polarity of the bipolar RF electrosurgical circuit. In still other versions, fourth electrode (461) comprises a conductive plate connectable with blade (454) or blade cover (455), where the conductive plate provides the second polarity of the bipolar RF electrosurgical circuit. In some versions, second electrode (459) and fourth electrode (461) may be the same structure that spans both proximal and distal sections (456, 457) of end effector (450). In view of the teachings herein, other various ways to provide fourth electrode (461) on blade side of end effector (450) will be apparent to those of ordinary skill in the art.

Figure 106:
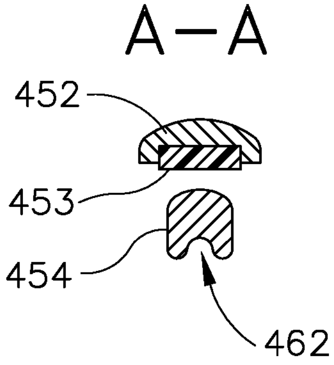
Figure 107:
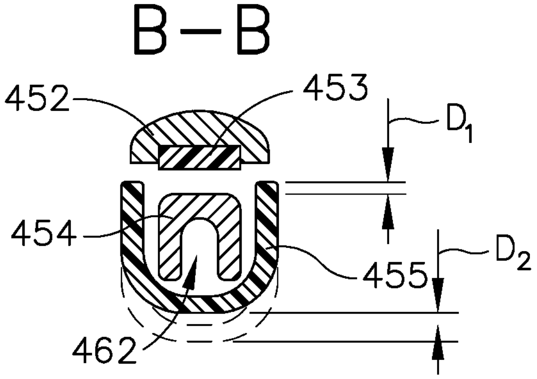

FIGS. 106 and 107 show exemplary cross-sections of a version of end effector (450) where clamp arm (452) provides the first polarity of the bipolar RF electrosurgical circuit. In distal section (457) shown in FIG. 106, tissue can be clamped between clamp pad (453) and blade (454). Blade (454) oscillates ultrasonically to sever the tissue. Furthermore, in the present example blade (454) provides the second polarity of the bipolar RF electrosurgical circuit. Thus, in addition to ultrasonic cutting occurring in distal section (457), RF electrosurgical sealing and coagulation can occur based on the RF electrosurgical pathway extending through tissue between clamp arm (452) and blade (454).

In the illustrated example in FIGS. 106 and 107, blade (454) comprises a groove (462) that extends along its underside. Groove (462) aides in minimizing the thermal capacitance of blade (454) and/or matching the blade's (454) thermal capacitance with that of clamp arm (452). In the present example, groove (462) extends along blade (454) through both distal and proximal sections (457, 456). As seen by comparing blade (454) profile in proximal section (456) versus distal section (457), groove (462) is more pronounced in proximal section (456) where RF electrosurgical sealing occurs.

In proximal section (456) shown in FIG. 107, end effector (450) further includes blade cover (455) that extends along the sides and underside of blade (454). Blade cover (455) is constructed of a nonconductive material in the present example, such as a polymer or ceramic; or coated, dipped, or overmolded stainless steel. As illustrated, the top surfaces of blade cover (455) are raised or elevated relative to the top of blade (454) such that clamp arm (452) engages blade cover (455) when end effector (450) is closed. In the present example the distance that blade cover (455) is raised or elevated relative to blade (454) is represented by D1. Blade cover (455) is also configured such that when clamp arm (452) engages blade cover (455), blade cover (455) deflects. The deflection distance in the present example is represented by D2. The deflection distance is configured to be less than the elevated distance D1 so that blade cover (455) will prevent electrically energized clamp arm (452) from contacting electrically energized blade (454) and thereby short circuiting the desired RF electrosurgical pathway.

Figure 108:
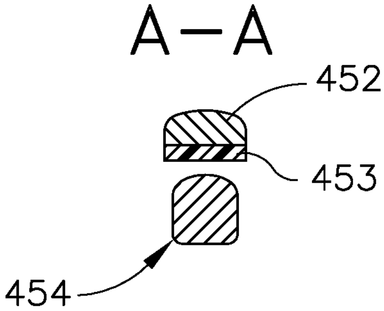
Figure 109:
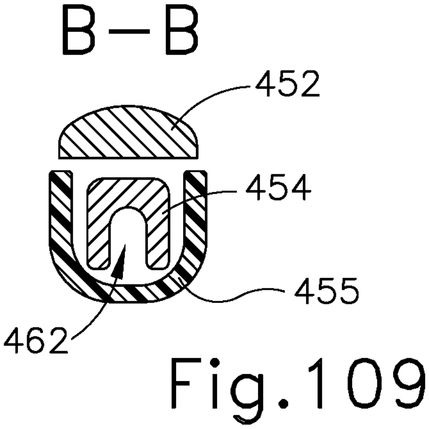

FIGS. 108-109 show other exemplary cross-sections of a version of end effector (450). With this example, distal section (457) is configured for ultrasonic cutting without RF electrosurgical sealing or coagulation. Furthermore, blade (454) lacks groove (462) along distal section (457). Proximal section (456) in this example is similar to that described with respect to FIG. 107. However, clamp pad (453) is omitted along proximal section (456). Again, blade cover (455) extends above the top of blade (454) to prevent contact between clamp arm (452) and blade (454) when end effector (450) is closed.

FIGS. 110 and 111 show exemplary views of a version of end effector (450) where the poles of the RF electrosurgical circuit are provided by two conductive plates. FIG. 110 shows distal section (457) defining one lengthwise section of the clamping area, and in particular the region where ultrasonic cutting occurs. In the present example, third electrode (460) sits atop of clamp pad (453). A molded top holder (463) is positioned above first electrode (458) and electrically isolates clamp arm (452) from first electrode (458). On the blade side in distal section (457), a top surface of blade (454) is exposed and accessible for contacting clamp pad (453) when end effector (450) is closed. As discussed above, this configuration provides for ultrasonic cutting of clamped tissue. At distal section (457), blade cover (455) extends along the bottom and sides of blade (454), but does not cover the top surface of blade (454).

Referring to FIG. 111, in proximal section (456) blade cover (455) surrounds blade (454) on all sides. Second electrode (459) is positioned on top of blade cover (455) and beneath clamp pad (453). Furthermore, first electrode (458) extends above and along the sides of second electrode (459). With this configuration, clamp pad (453) in proximal section (456) prevents first electrode (458) and second electrode (459) from directly contacting each other when end effector (450) is in a closed position and thus preventing a short circuit. As described above, when tissue is clamped within proximal section (456), RF electrosurgical sealing and coagulation can be delivered through RF electrosurgical energy flowing through the tissue between electrodes (458, 459).

With the configuration of end effector (450) described in the above examples, a larger jaw or clamp can be used while minimizing the power needed for ultrasonic cutting since cutting is limited to only a portion of the entire length of the jaw or clamp. This also reduces the amount of heat generation associated with larger jaw or clamp devices. Furthermore, because of the reduced power need, smaller and/or lightweight transducers can be used.

Z. End Effector with Dual Charged Clamp Arms

FIG. 112 shows another exemplary end effector (550) that may be readily incorporated into instrument (110) in place of end effector (140). End effector (550) comprises a first clamp arm (551), and a second clamp arm (552). Clamp arm (551) is connectable with clamp pad (553), and clamp arm (552) is connectable with clamp pad (554). End effector (550) further comprises blade (555). Each respective clamp arm (551, 552) and attached clamp pad (553, 554) is configured to pivot relative to blade (555) between an open position and a closed position to selectively receive and clamp tissue (T) in end effector (550).

In the present example, the pivotal movement of clamp arms (551, 552) occurs in the same or substantially the same manner as the pivoting movement of clamp arm (210) described above. For example, each respective clamp arm (551, 552) is pivotably coupled with an outer tube (202) at one pivot point; and with inner tube (204) at another pivot point. Thus, relative longitudinal movement between tubes (202, 204) provides pivotal movement of clamp arms (551, 552). In some versions, instrument (110) may be configured with additional tubes or adapters that connect with clamp arms (551, 552) to provide pivotal movement as described herein. Furthermore, clamp arms (551, 552) and their associated clamp pads (553, 554) are configured to move either independently or together. In view of the teachings herein, various ways to configure clamp arms (551, 552) with instrument (110) to provide this pivotal movement will be apparent to those of ordinary skill in the art.

Each clamp arm (551, 552) in the present example is provided with a different polarity so that an RF electrosurgical circuit or pathway is created through tissue captured between from clamp arms (551, 552). For instance, clamp arm (551) may have a first electrical polarity while clamp arm (552) may have a second electrical polarity. As described above, the conductive nature of clamp arms (551, 552) may be achieved by combining conductive material(s) (46) with clamp arms (551, 552). The conductive clamp arms (551, 552) are then connectable with an electrical source, such as generator (116), to deliver the electrical energy to clamp arms (551, 552). In view of the teachings herein, various ways for connecting conductive clamp arms (551, 552) with generator (116) or another electrical source will be apparent to those of ordinary skill in the art. Also, any of the methods and techniques described above for altering or modifying clamp arm design to shape the electrosurgical circuit or pathway may be used with clamp arms (551, 552) of end effector (550). In view of the teachings herein, such alterations or modification of clamp arms (551, 552) to shape the electrosurgical circuit and resultant sealing will be apparent to those of ordinary skill in the art. Furthermore, each clamp pad (553, 554) is electrically isolated from its respective clamp arm (551, 552) through various insulating materials as will be understood by those of ordinary skill in the art in view of the teachings herein.

In the example where clamp arms (551, 552) move independently relative to blade (555), either or both clamp arms (551, 552) can be moved to the closed position to compress tissue between the respective clamp pad (553, 554) and blade (555). Blade (555) can be activated to oscillate such that compressed tissue will be ultrasonically severed along the regions where tissue is compressed between clamp pads (553, 554) and blade (555). Because each clamp arm (551, 552) in the present example has a different polarity, to achieve RF electrosurgical sealing, both clamp arms (551, 552) are moved to the closed position so that they contact the captured tissue. With both clamp arms (551, 552) closed, RF electrosurgical sealing can be provided either before, during, or after the ultrasonic cutting process.

FIG. 113 shows another exemplary end effector (560) that may be readily incorporated into instrument (110) in place of end effector (140). End effector (560) comprises a first clamp arm (561), a second clamp arm (562), a first clamp pad (563), a second clamp pad (564), and a blade (565). End effector (560) operates the same or similar to end effector (550), and thus the discussion above regarding end effector (550) should be understood to apply also to end effector (560). A difference between end effector (560) and end effector (550) pertains to clamp pads (563, 564). With end effector (560), clamp pads (563, 564) each extend inwardly toward a centerline longitudinal axis of blade (565). In this configuration, clamp arms (561, 562) contact clamped tissue at each outer portion of clamp arms (561, 562). Accordingly, the RF electrosurgical pathway from one clamp arm (561) to the other clamp arm (562) extends only from the outer surface of one clamp arm (561) to the outer surface of the other clamp arm (562). Comparing back to end effector (550), clamp arms (551, 552) are each in contact with clamped tissue on both sides of clamp arms (551, 552). Therefore, with end effector (550) there are four RF electrosurgical pathways from one clamp arm (551) through clamped tissue (T), and to the other clamp arm (552).

FIG. 114 shows another exemplary end effector (570) that may be readily incorporated into instrument (110) in place of end effector (140). End effector (570) comprises split clamp arm (571) having a first portion (572) and a second portion (573) that are each oppositely polarized and isolated from one another by pad (574). End effector (570) further comprises nonconductive blade (575). With the split clamp arm configuration, ultrasonic cutting occurs in the same manner as described above with other single clamp arm end effectors. RF electrosurgical sealing occurs similarly to such sealing described above with respect to end effector (560) shown in FIG. 113, there being a single RF electrosurgical pathway from first portion (572) to second portion (573).

FIGS. 115-117 show additional clamp pad (584, 594, 596) to clamp arm (581, 591, 595) configurations. For example, FIGS. 115 and 116 show configurations where clamp arms (581, 591) each include two extending portions that may be used to define RF electrosurgical pathways for sealing. FIG. 117 shows a clamp arm (595) attached with a clamp pad (596) where clamp pad (596) comprises multiple capillaries that can be filled with conductive gel to provide RF electrosurgical energy. In view of the teachings herein, other modifications to clamp arm and clamp pad to achieve a desired RF electrosurgical pathway arrangement will be apparent to those of ordinary skill in the art.

III. Exemplary Handle Assembly Configurations

As noted above, handle assembly (120) provides operator control over ultrasonic and/or RF electrosurgical activation of end effector (140) via buttons (125, 126). It may be desirable to provide an operator with additional forms of control over ultrasonic and/or RF electrosurgical activation of end effector (140). The following description relates to several merely illustrative examples of alternative forms that handle assembly (120) may take. It should therefore be understood that the handle assemblies described below may be readily incorporated into instrument (110) in place of handle assembly (120). It should also be understood that the handle assemblies described below may be readily combined with any of the various end effectors described herein, including but not limited to end effector (140) and the variations of end effector (140) described above.

A. Handle Assembly with Three Discrete Buttons

Figure 22:
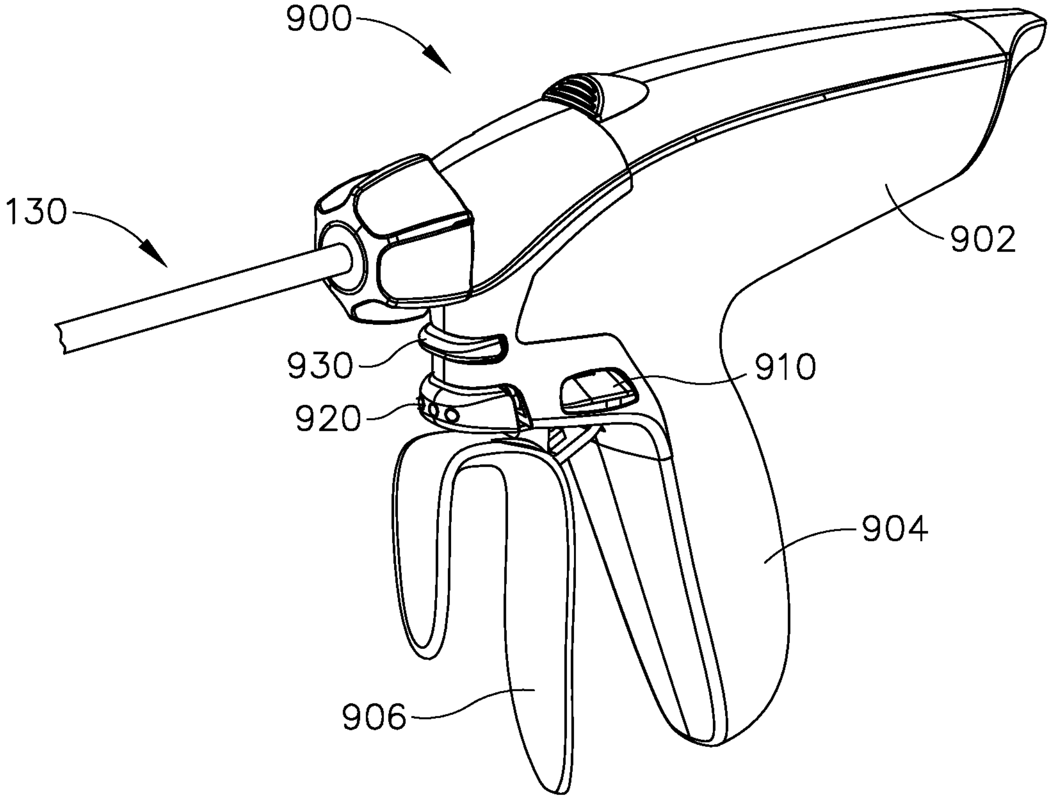
FIG. 22 depicts a perspective view of an exemplary alternative handle assembly that may be incorporated into the instrument of FIG. 1.
Figure 23:
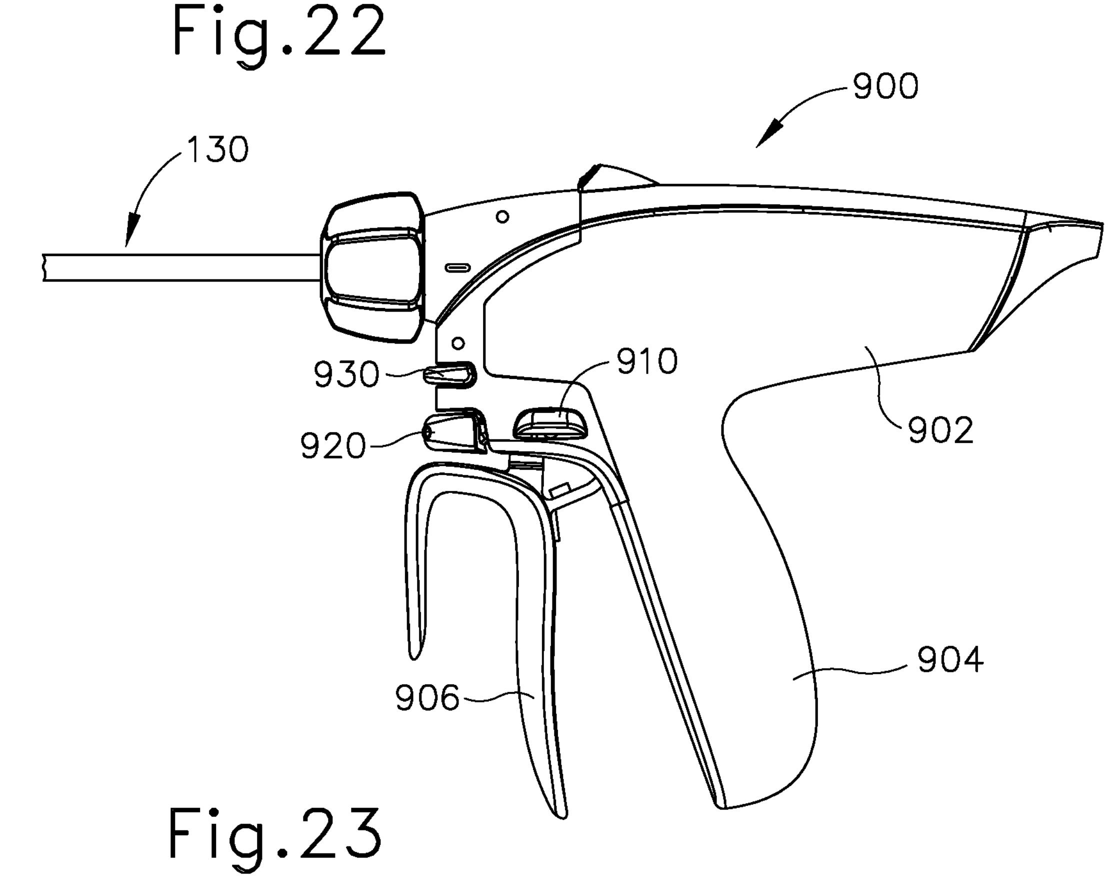
FIG. 23 depicts a side elevational view of the handle assembly of FIG. 22.
Figure 24:
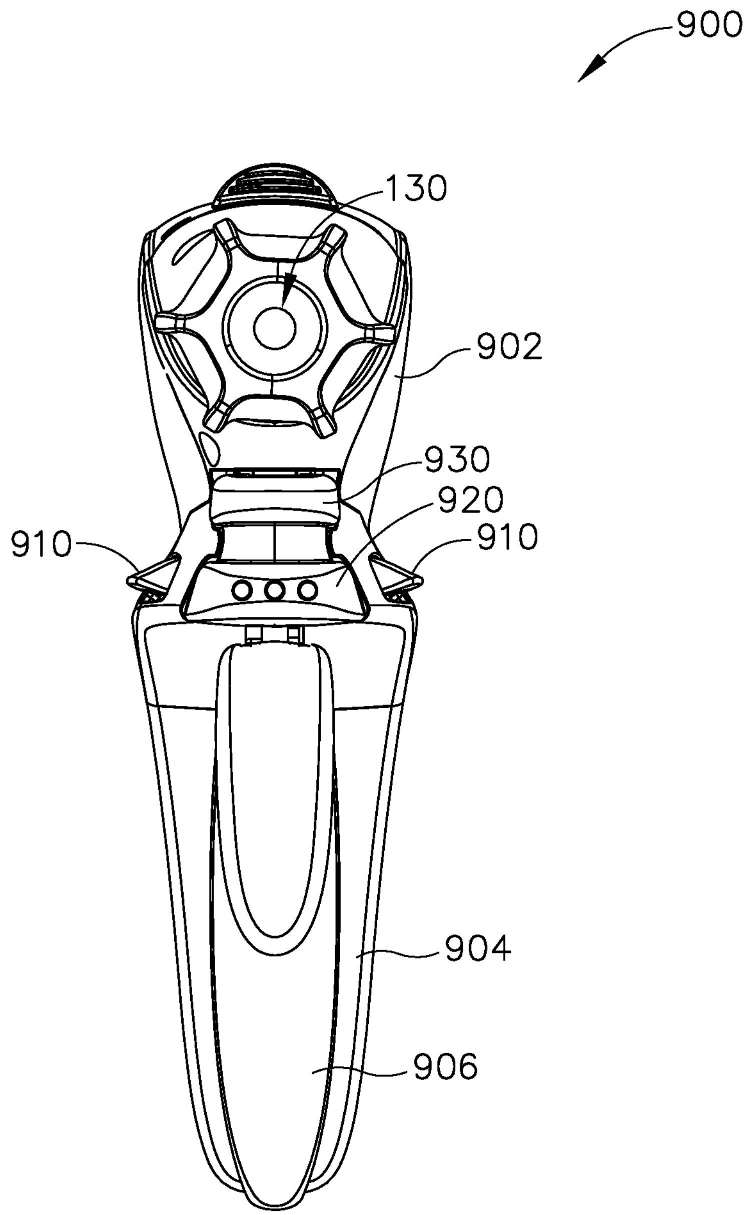
FIG. 24 depicts a front end view of the handle assembly of FIG. 22.
Figure 25:
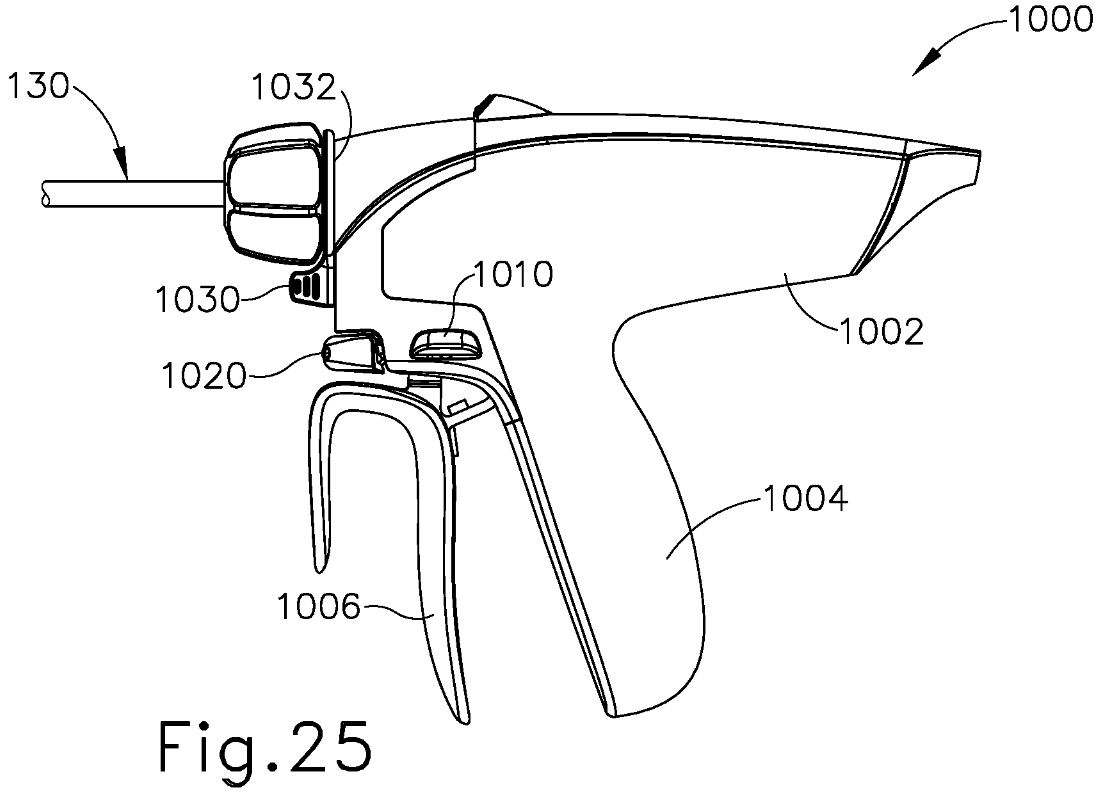
FIG. 25 depicts a side elevational view of another exemplary alternative handle assembly that may be incorporated into the instrument of FIG. 1.
Figure 26A:
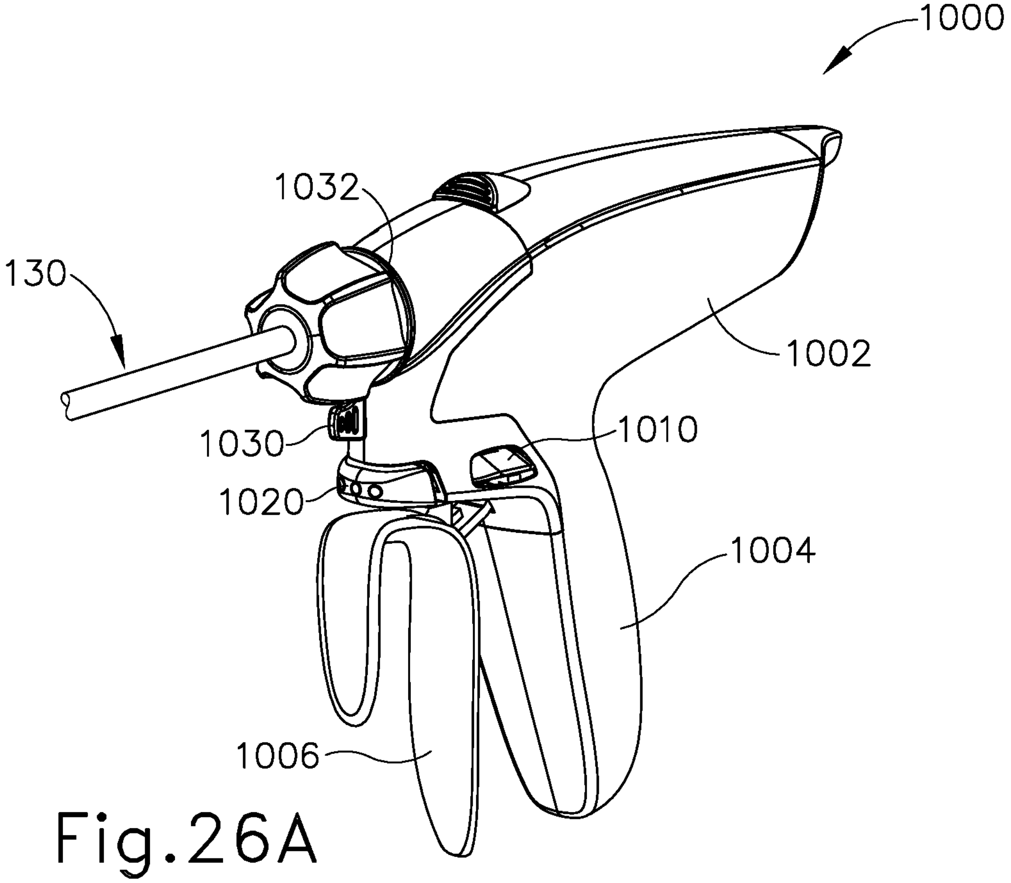
FIG. 26A depicts a perspective view of the handle assembly of FIG. 25, with an activation paddle in a centered position.
Figure 26B:
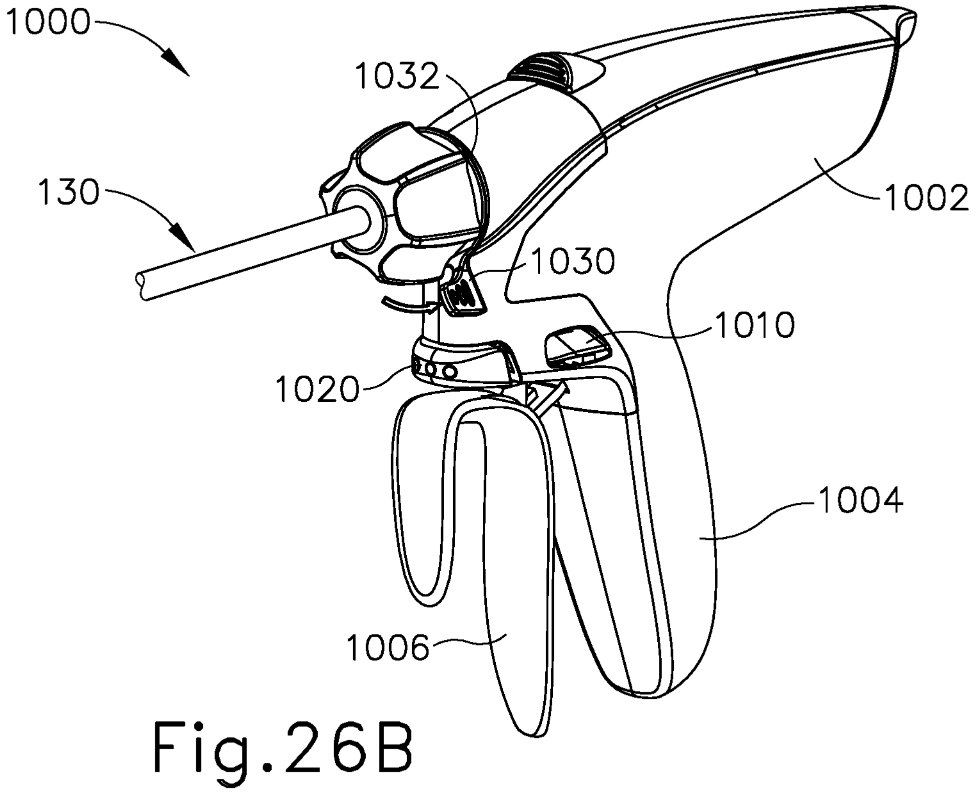
FIG. 26B depicts a perspective view of the handle assembly of FIG. 25, with the activation paddle actuated in a first direction.
Figure 26C:
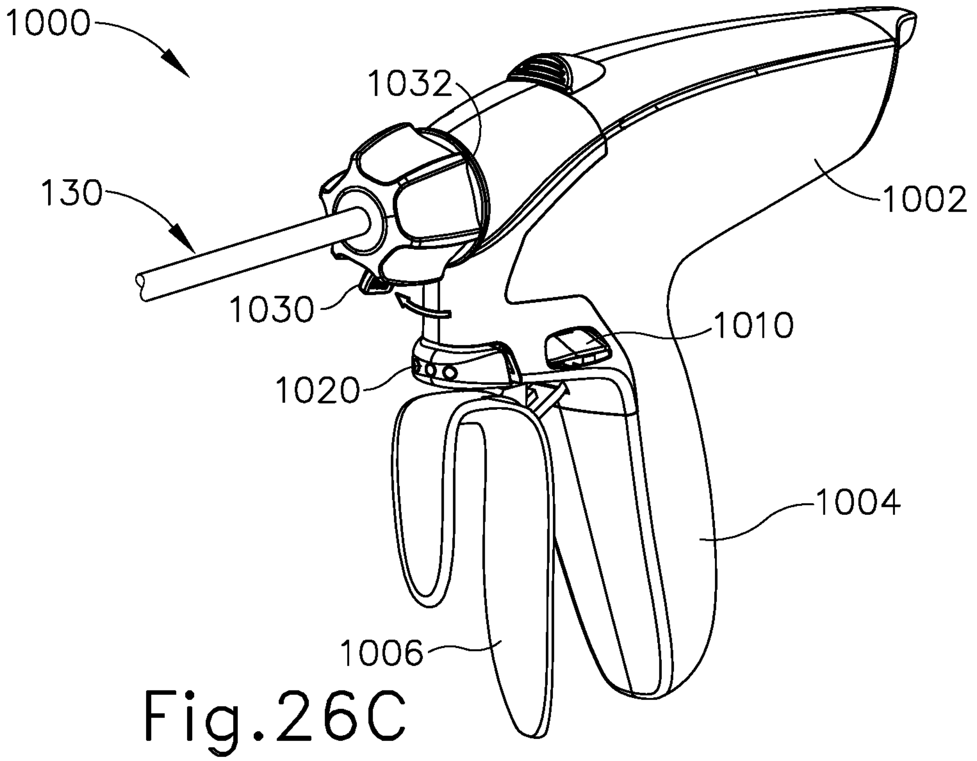
FIG. 26C depicts a perspective view of the handle assembly of FIG. 25, with the activation paddle actuated in a second direction.

FIGS. 22-24 show an exemplary handle assembly (900) that may be readily incorporated into instrument (110) in place of handle assembly (120). Handle assembly (900) of this example is substantially identical to handle assembly (120) described above. For instance, handle assembly (900) of this example comprises a body (902) defining a pistol grip (904), with a trigger (906) that is pivotable relative to pistol grip (904). Shaft assembly (130) extends distally from handle assembly (900). Any of the various end effectors described herein may be positioned at the distal end of shaft assembly (130).

Unlike handle assembly (120), handle assembly (900) of this example has three discrete buttons (910, 920, 930). Buttons (910) are provided on both lateral sides of handle assembly (900), as best seen in FIG. 24. Buttons (910) are positioned such that a button (910) is configured to be actuated by the thumb of the hand that grasps pistol grip (904). By having buttons (910) on both lateral sides of handle assembly (900), handle assembly (900) provides easy access to at least one button (910) regardless of whether the operator is grasping pistol grip (904) in the operator's right hand or the operator's left hand. It should be understood that buttons (910) of handle assembly (900) are substantially similar to buttons (125) of handle assembly (120).

Buttons (920, 930) are each positioned such that each button (920, 930) is configured to be actuated by the index finger of the hand that grasps pistol grip (904). Each button (920, 930) may be accessed just as easily regardless of whether the operator is grasping pistol grip (904) in the operator's right hand or the operator's left hand. It should be understood that button (920) of handle assembly (900) is substantially similar to button (126) of handle assembly (120). However, button (930) of handle assembly (900) has no analog in handle assembly (120).

As noted above, buttons (910, 920, 930) may be used to selectively activate the application of ultrasonic and/or RF electrosurgical energy to tissue via the end effector that is coupled with shaft assembly (130). In some versions, buttons (910) are operable to activate an "advanced hemostasis" operation via the end effector. In some such versions, the advanced hemostasis operation includes application of only ultrasonic energy to tissue, with a power profile that is configured to maximize hemostasis in tissue while reducing the cutting speed. By way of example only, this power profile may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. In some versions, the advanced hemostasis operation is configured to seal vessels having a diameter up to approximately 7 mm.

In the present example, button (920) is operable to activate a "max seal and cut" operation via the end effector. By way of example only, an operator may choose this operation to seal and cut vessels having a diameter between approximately 3 mm and approximately 5 mm. In some such versions, the max seal and cut operation includes application of either only ultrasonic energy or a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

In the present example, button (930) is operable to activate a "seal only" operation via the end effector. By way of example only, an operator may choose this operation to seal vessels having a diameter between approximately 3 mm and approximately 7 mm. In some such versions, the seal only operation includes application of a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

Of course, the foregoing examples are merely illustrative examples. Buttons (910, 920, 930) may alternatively be configured to activate any other suitable operations via the end effector. Further examples will be apparent to those of ordinary skill in the art in view of the teachings herein.

B. Handle Assembly with Two Discrete Buttons and Rotary Paddle

FIGS. 25-27C show another exemplary handle assembly (1000) that may be readily incorporated into instrument (110) in place of handle assembly (120). Handle assembly (1000) of this example is substantially identical to handle assembly (120) described above. For instance, handle assembly (1000) of this example comprises a body (1002) defining a pistol grip (1004), with a trigger (1006) that is pivotable relative to pistol grip (1004). Shaft assembly (130) extends distally from handle assembly (1000). Any of the various end effectors described herein may be positioned at the distal end of shaft assembly (130).

Figure 27C:
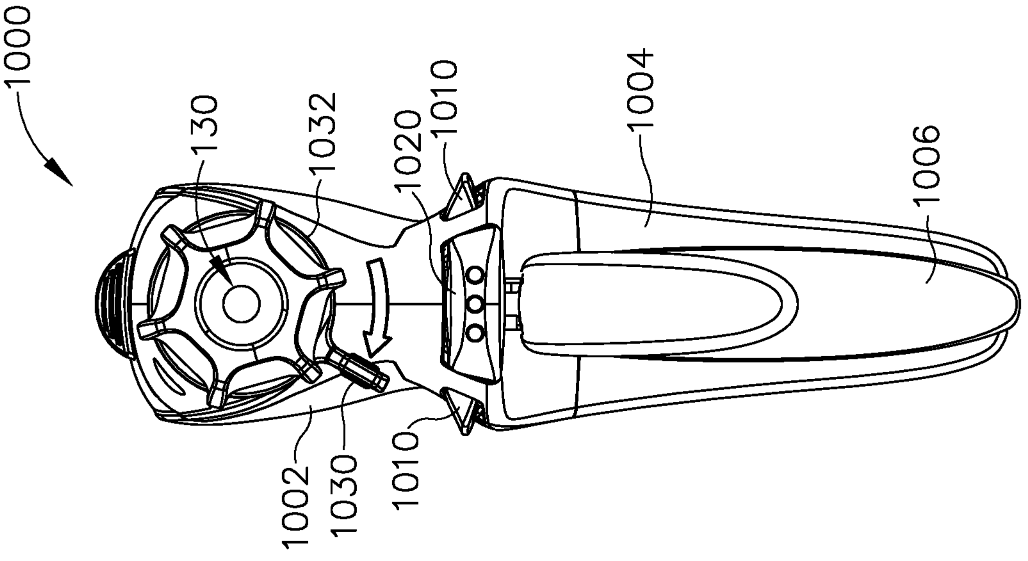
FIG. 27C depicts a front end view of the handle assembly of FIG. 25, with the activation paddle actuated in the second direction.
Figure 27B:
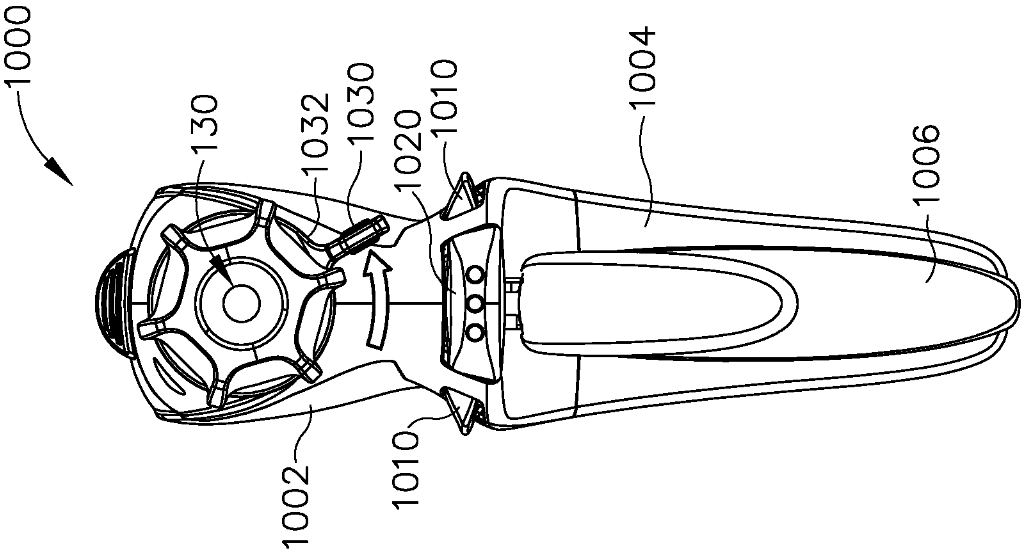
FIG. 27B depicts a front end view of the handle assembly of FIG. 25, with the activation paddle actuated in the first direction.
Figure 27A:
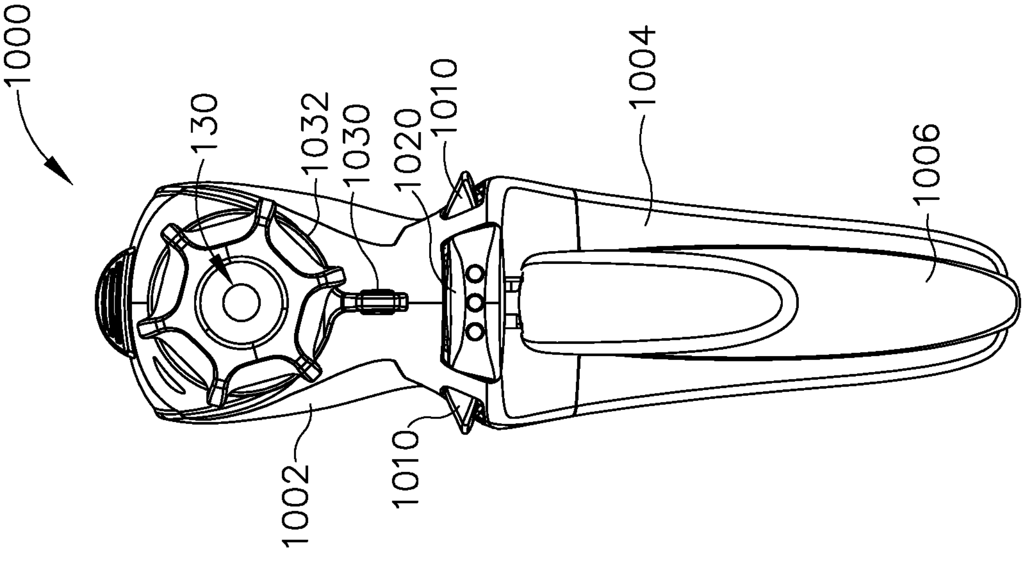
FIG. 27A depicts a front end view of the handle assembly of FIG. 25, with the activation paddle in the centered position.

Unlike handle assembly (120), handle assembly (1000) of this example has two discrete buttons (1010, 1020) in combination with an activation paddle (1030). Buttons (1010) are provided on both lateral sides of handle assembly (1000), as best seen in FIGS. 27A-27C. Buttons (1010) are positioned such that a button (1010) is configured to be actuated by the thumb of the hand that grasps pistol grip (1004). By having buttons (1010) on both lateral sides of handle assembly (1000), handle assembly (1000) provides easy access to at least one button (1010) regardless of whether the operator is grasping pistol grip (1004) in the operator's right hand or the operator's left hand. It should be understood that buttons (1010) of handle assembly (1000) are substantially similar to buttons (125) of handle assembly (120).

Button (1020) is positioned such that button (1020) is configured to be actuated by the index finger of the hand that grasps pistol grip (1004). Button (1020) may be accessed just as easily regardless of whether the operator is grasping pistol grip (1004) in the operator's right hand or the operator's left hand. It should be understood that button (1020) of handle assembly (1000) is substantially similar to button (126) of handle assembly (120).

Activation paddle (1030) extends distally relative to body (1002) and is secured to a ring (1032). Ring (1032) is coaxially disposed about the longitudinal axis of shaft assembly (130). Paddle (1030) of handle assembly (1000) has no analog in handle assembly (120). While buttons (1010, 1020) are configured to be pressed inwardly by the operator to activate a function in the end effector (e.g., as described below); paddle (1030) is configured to be pressed laterally by the operator, thereby rotating ring (1032) about the longitudinal axis of shaft assembly (130), to activate a function in the end effector (e.g., as described below). In particular, paddle (1030) may be pressed laterally in one direction to transition from the neutral state shown in FIGS. 26A and 27A to the deflected state shown in FIGS. 26B and 27B; or in the other lateral direction to transition from the neutral state shown in FIGS. 26A and 27A to the deflected state shown in FIGS. 26C and 27C. It should be understood that the degree of paddle (1030) deflection shown in FIGS. 26B-26C and 27B-27C is exaggerated for purposes of illustration only. In actual versions of handle assembly (1000), paddle (1030) may be configured to move along only a relatively short distance in the directions shown FIGS. 26B-26C and 27B-27C.

Paddle (1030) is positioned such that paddle (1030) is configured to be actuated by the index finger of the hand that grasps pistol grip (1004). Paddle (1030) may be accessed just as easily regardless of whether the operator is grasping pistol grip (1004) in the operator's right hand or the operator's left hand. Right-handed operators may find it easier to depress paddle (1030) in the direction shown in FIGS. 26B and 27B; while left-handed operators may find it easier to depress paddle (1030) in the direction shown in FIGS. 26C and 27C.

As noted above, buttons (1010, 1020) and paddle (1030) may be used to selectively activate the application of ultrasonic and/or RF electrosurgical energy to tissue via the end effector that is coupled with shaft assembly (130). In some versions, buttons (1010) are operable to activate an "advanced hemostasis" operation via the end effector. In some such versions, the advanced hemostasis operation includes application of only ultrasonic energy to tissue, with a power profile that is configured to maximize hemostasis in tissue. By way of example only, this power profile may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

In the present example, button (1020) is operable to activate a "max seal and cut" operation via the end effector. By way of example only, an operator may choose this operation to seal and cut vessels having a diameter between approximately 3 mm and approximately 5 mm. In some such versions, the max seal and cut operation includes application of either only ultrasonic energy or a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

In the present example, paddle (1030) is operable to activate a "seal only" operation via the end effector. By way of example only, an operator may choose this operation to seal vessels having a diameter between approximately 3 mm and approximately 7 mm. In some such versions, the seal only operation includes application of a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

Of course, the foregoing examples are merely illustrative examples. Buttons (1010, 1020) and paddle (1030) may alternatively be configured to activate any other suitable operations via the end effector. Further examples will be apparent to those of ordinary skill in the art in view of the teachings herein. It should also be understood that, since paddle (1030) may be actuated in two different directions from the neutral position of FIGS. 26A and 27A, paddle (1030) may activate different operations via the end effector depending on the direction in which paddle (1030) is deflected.

C. Handle Assembly with Discrete Button and Rocker Assembly

Figure 28:
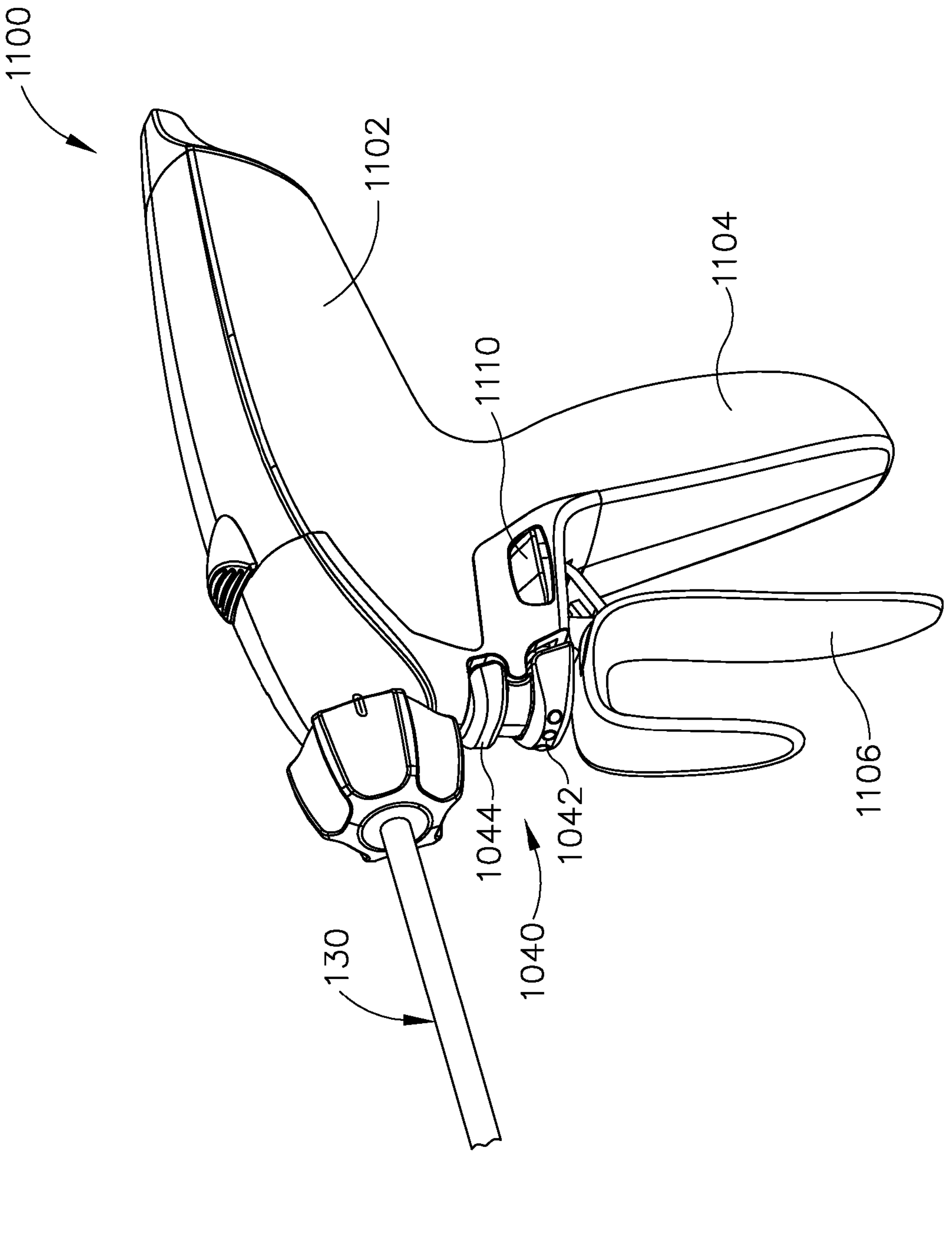
FIG. 28 depicts a perspective view of another exemplary alternative handle assembly that may be incorporated into the instrument of FIG. 1.
Figure 29:
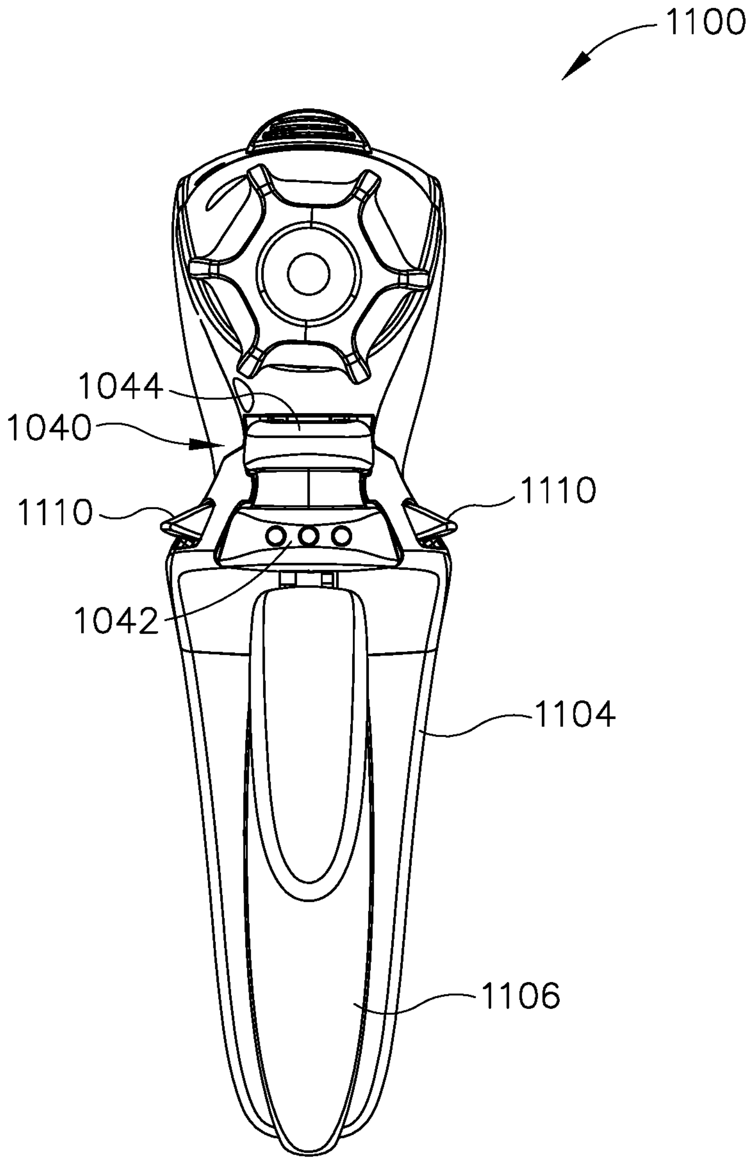
FIG. 29 depicts a front end view of the handle assembly of FIG. 28.
Figure 30:
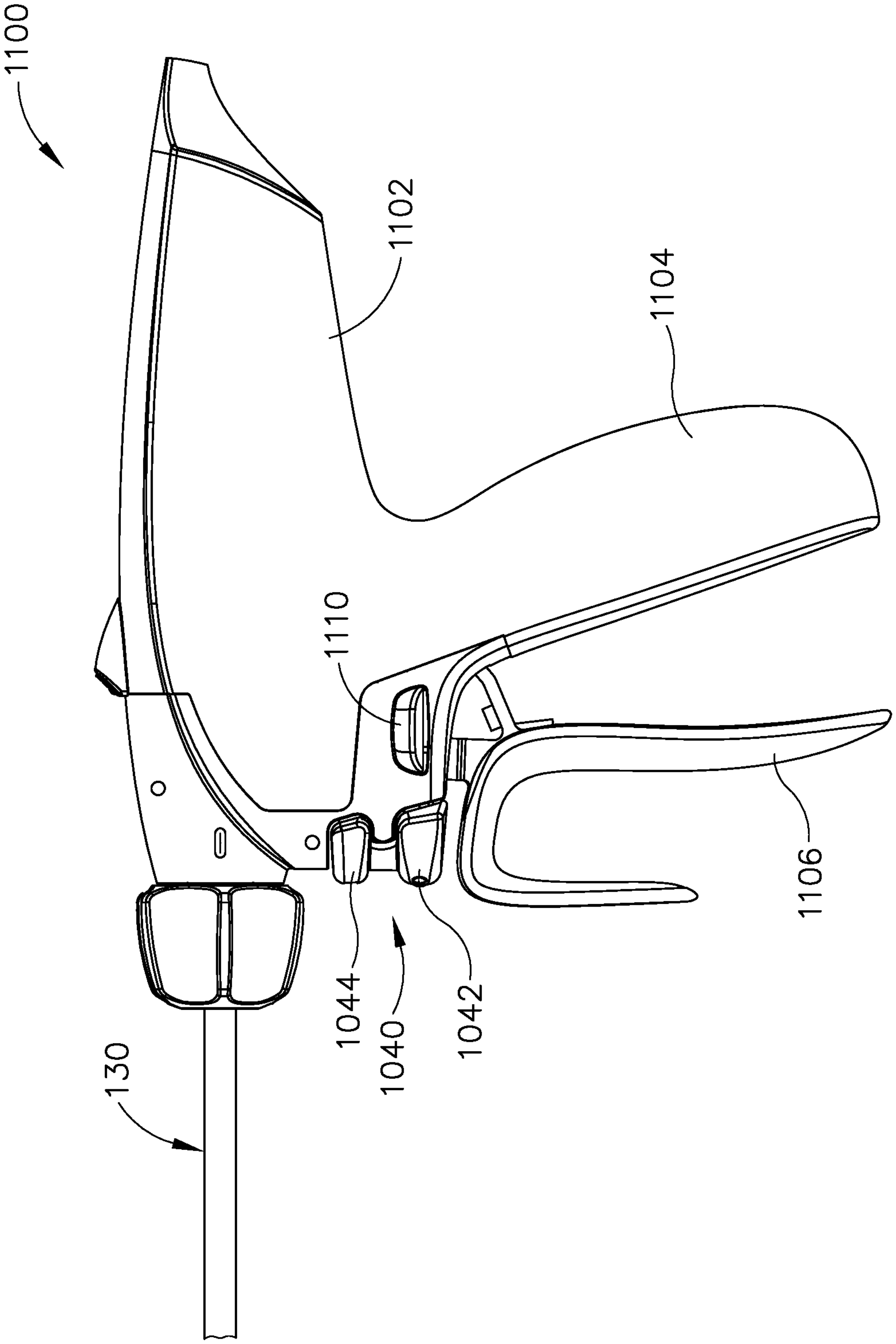
FIG. 30 depicts a side elevational view of the handle assembly of FIG. 28.
Figure 31:
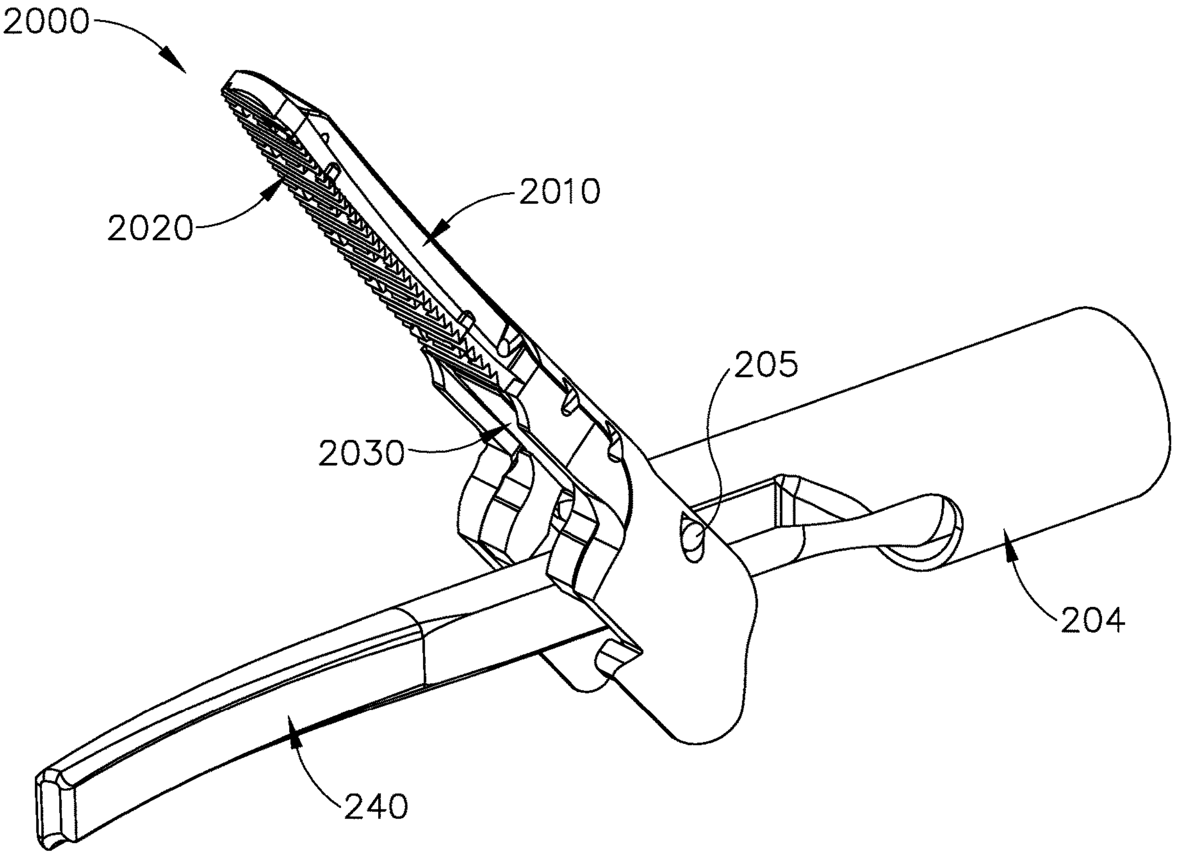
FIG. 31 depicts a perspective view of another exemplary end effector that may be incorporated into the instrument of FIG. 1, with the end effector in an open configuration.

FIGS. 28-30 show another exemplary handle assembly (1100) that may be readily incorporated into instrument (110) in place of handle assembly (120). Handle assembly (1100) of this example is substantially identical to handle assembly (120) described above. For instance, handle assembly (1100) of this example comprises a body (1102) defining a pistol grip (1104), with a trigger (1106) that is pivotable relative to pistol grip (1104). Shaft assembly (130) extends distally from handle assembly (1100). Any of the various end effectors described herein may be positioned at the distal end of shaft assembly (130).

Unlike handle assembly (120), handle assembly (1100) of this example a discrete button (1100) in combination with a rocker assembly (1040). Buttons (1110) are provided on both lateral sides of handle assembly (1100), as best seen in FIG. 29. Buttons (1110) are positioned such that a button (1110) is configured to be actuated by the thumb of the hand that grasps pistol grip (1104). By having buttons (1110) on both lateral sides of handle assembly (1100), handle assembly (1100) provides easy access to at least one button (1110) regardless of whether the operator is grasping pistol grip (1104) in the operator's right hand or the operator's left hand. It should be understood that buttons (1110) of handle assembly (1100) are substantially similar to buttons (125) of handle assembly (120).

Rocker assembly (1040) is positioned such that rocker assembly (1040) is configured to be actuated by the index finger of the hand that grasps pistol grip (1104). Rocker assembly (1040) may be accessed just as easily regardless of whether the operator is grasping pistol grip (1104) in the operator's right hand or the operator's left hand. Rocker assembly (1040) presents an upper button feature (1044) and a lower button feature (1042). Rocker assembly (1040) is pivotably coupled with body (1102) such that rocker (1040) is configured to rock about a laterally oriented axis that is perpendicular to the longitudinal axis of shaft assembly (130). For instance, if an operator depresses upper button feature (1044), rocker assembly (1040) will pivot relative to body (1102) such that upper button feature (1044) will travel proximally relative to body (1102) and lower button feature (1042) will travel distally relative to body (1102). Similarly, if an operator depresses lower button feature (1042), rocker assembly (1040) will pivot relative to body (1102) such that lower button feature (1042) will travel proximally relative to body (1102) and upper button feature (1044) will travel distally relative to body (1102). It should be understood that lower button feature (1042) of handle assembly (1100) is substantially similar to button (126) of handle assembly (120). However, upper button feature (1044) has no analog in handle assembly (120).

As noted above, buttons (1110) and rocker assembly (1040) may be used to selectively activate the application of ultrasonic and/or RF electrosurgical energy to tissue via the end effector that is coupled with shaft assembly (130). In some versions, buttons (1110) are operable to activate an "advanced hemostasis" operation via the end effector. In some such versions, the advanced hemostasis operation includes application of only ultrasonic energy to tissue, with a power profile that is configured to maximize hemostasis in tissue. By way of example only, this power profile may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

In the present example, lower button feature (1042) is operable to activate a "max seal and cut" operation via the end effector. By way of example only, an operator may choose this operation to seal and cut vessels having a diameter between approximately 3 mm and approximately 5 mm. In some such versions, the max seal and cut operation includes application of either only ultrasonic energy or a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

In the present example, upper button feature (1044) is operable to activate a "seal only" operation via the end effector. By way of example only, an operator may choose this operation to seal vessels having a diameter between approximately 3 mm and approximately 7 mm. In some such versions, the seal only operation includes application of a combination of ultrasonic and RF electrosurgical energy. Again, this operation may be provided in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

Of course, the foregoing examples are merely illustrative examples. Buttons (1110) and rocker assembly (1040) may alternatively be configured to activate any other suitable operations via the end effector. Further examples will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of using an instrument, the method comprising: (a) positioning an instrument end effector within a patient, wherein the end effector comprises: (i) an ultrasonic blade, (ii) a clamp pad, and (iii) at least one electrode; (b) positioning the ultrasonic blade against tissue in the patient; (c) activating the ultrasonic blade to vibrate ultrasonically while the ultrasonic blade is positioned against tissue; (d) positioning the at least one electrode against tissue in the patient; and (e) activating the at least one electrode to apply RF electrosurgical energy to tissue against which the at least one electrode is positioned against tissue.

Example 2

The method of Example 1, further comprising compressing tissue between the clamp pad and the ultrasonic blade.

Example 3

The method of Example 2, wherein the act of activating the ultrasonic blade is performed while the tissue is compressed between the clamp pad and the ultrasonic blade.

Example 4

The method of any one or more of Examples 2 through 3, wherein the act of activating the at least one electrode is performed while the tissue is compressed between the clamp pad and the ultrasonic blade.

Example 5

The method of any one or more of Examples 2 through 4, wherein the end effector further comprises a clamp arm, wherein the clamp arm is pivotable relative to the ultrasonic blade, wherein the at least one electrode is supported by the clamp arm, wherein the act of compressing tissue between the clamp pad and the ultrasonic blade comprises pivoting the at least one electrode toward the tissue.

Example 6

The method of any one or more of Examples 1 through 5, wherein the ultrasonic blade provides a return path for the electrode, wherein the act of activating the at least one electrode to apply RF electrosurgical energy to tissue results in the application of bipolar RF electrosurgical energy to the tissue via the at least one electrode and the ultrasonic blade.

Example 7

The method of any one or more of Examples 1 through 6, wherein the clamp pad has a pair of lateral sides, wherein the at least one electrode extends along both lateral sides of the clamp pad, wherein the act of activating the at least one electrode to apply RF electrosurgical energy to tissue comprises applying RF electrosurgical energy to tissue at both lateral sides of the clamp pad.

Example 8

The method of any one or more of Examples 1 through 7, wherein the ultrasonic blade is positioned against tissue extending along a first plane, wherein the at least one electrode is positioned against tissue extending along a second plane, wherein the second plane is substantially parallel with the first plane.

Example 9

The method of any one or more of Examples 1 through 7, wherein the ultrasonic blade is positioned against tissue extending along a first plane, wherein the at least one electrode is positioned against tissue extending along a second plane, wherein the second plane is obliquely oriented relative to the first plane.

Example 10

The method of any one or more of Examples 1 through 9, wherein the end effector further comprises a plurality of stand-off features, wherein the stand-off features prevent the at least one electrode from contacting the ultrasonic blade.

Example 11

The method of any one or more of Examples 1 through 6 and 8 through 10, wherein the end effector further comprises a clamp arm body, wherein the at least one electrode is interposed between the clamp pad and the clamp arm body, wherein the clamp pad defines a plurality of openings, wherein the act of positioning the at least one electrode against tissue comprises pressing the tissue through at least some of the openings to contact the at least one electrode.

Example 12

The method of any one or more of Examples 1 through 4, wherein the end effector further comprises a blade guard, wherein the blade guard extends along at least a portion of the length of the ultrasonic blade, wherein the blade guard is spaced away from the ultrasonic blade, wherein the at least one electrode is positioned on the blade guard, wherein the act of positioning the at least one electrode against tissue comprises urging the blade guard into contact with the tissue.

Example 13

The method of any one or more of Examples 1 through 5 and 7 through 11, wherein the end effector further comprises a clamp arm assembly, wherein the clamp arm assembly comprises the clamp pad and the at least one electrode, wherein the at least one electrode comprises a first electrode and a second electrode, wherein the act of activating the at least one electrode comprises activating the first and second electrodes to apply bipolar RF electrosurgical energy to tissue.

Example 14

The method of any one or more of Examples 1 through 5, 7 through 11, and 13, wherein the at least one electrode comprises a first electrode and a second electrode, wherein the clamp pad is laterally interposed between the first and second electrodes, wherein the act of positioning the at least one electrode against tissue further comprises positioning the first and second electrodes against the tissue while simultaneously positioning the clamp pad against the tissue.

Example 15

The method of Example 14, wherein the act of positioning the first and second electrodes against the tissue while simultaneously positioning the clamp pad against the tissue further comprises compressing the tissue between the clamp pad and the ultrasonic blade.

Example 16

The method of Example 15, wherein the act of activating the ultrasonic blade to vibrate ultrasonically while the ultrasonic blade is positioned against tissue is performed while the tissue is compressed between the clamp pad and the ultrasonic blade.

Example 17

The method of any one or more of Examples 1 through 16, wherein the end effector further comprises a clamp arm body defining a plurality of recesses, wherein at least a portion of the clamp pad flows into at least some of the recesses during one or both of the act of activating the ultrasonic blade to vibrate ultrasonically while the ultrasonic blade is positioned against tissue or the act of activating the at least one electrode to apply RF electrosurgical energy to tissue against which the at least one electrode is positioned.

Example 18

The method of Example 1, wherein the at least one electrode comprises a first electrode and a second electrode, wherein the end effector further comprises a first arm and a second arm, wherein the first electrode is carried by the first arm, wherein the second electrode is carried by the second arm, wherein the act of positioning the at least one electrode against tissue in the patient comprises: (i) pivoting the first arm toward the tissue, and (ii) pivoting the second arm toward the tissue.

Example 19

A method of using an instrument, the method comprising: (a) positioning an instrument end effector within a patient, wherein the end effector comprises: (i) an ultrasonic blade, and (ii) a clamp arm assembly, wherein the clamp arm assembly comprises: (A) a clamp pad, (B) a first electrode, and (C) a second electrode; (b) pivoting the clamp arm assembly toward the ultrasonic blade, thereby compressing tissue between the ultrasonic blade and the clamp pad, and thereby bringing the first and second electrodes into contact with the tissue; and (c) activating one or both of: (i) the ultrasonic blade to vibrate ultrasonically to thereby apply the ultrasonic energy to the tissue, or (ii) the first and second electrodes to thereby apply bipolar RF electrosurgical energy to the tissue.

Example 20

A method of using an instrument, the method comprising: (a) positioning an instrument end effector within a patient, wherein the end effector comprises: (i) an ultrasonic blade, (ii) a clamp arm assembly, (iii) a first conductive arm, wherein the first conductive arm is spaced apart from the ultrasonic blade and from the clamp arm assembly, and (iv) a second conductive arm, wherein the second conductive arm is spaced apart from the ultrasonic blade and from the clamp arm assembly; (b) pivoting the clamp arm assembly toward the ultrasonic blade, thereby compressing tissue between the ultrasonic blade and the clamp arm assembly; and (c) activating one or both of: (i) the ultrasonic blade to vibrate ultrasonically to thereby apply the ultrasonic energy to the tissue, or (ii) the first and second conductive arms to thereby apply bipolar RF electrosurgical energy to the tissue.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a body;
(b) a shaft assembly extending distally from the body, wherein the shaft assembly comprises an acoustic waveguide, wherein the acoustic waveguide is configured to communicate ultrasonic vibrations; and
(c) an end effector, wherein the end effector comprises:
(i) an ultrasonic blade in acoustic communication with the acoustic waveguide, wherein the ultrasonic blade is electrically nonconductive,
(ii) a clamp arm assembly, wherein the clamp arm assembly is pivotable toward and away from the ultrasonic blade,
(iii) a first conductive arm, wherein the first conductive arm is spaced apart from the ultrasonic blade and from the clamp arm assembly, and
(iv) a second conductive arm, wherein the second conductive arm is spaced apart from the ultrasonic blade and from the clamp arm assembly.

2. The apparatus of claim 1, wherein the clamp arm assembly comprises:
(A) a clamp arm body, and
(B) a clamp pad, wherein the clamp pad is configured to compress tissue against the ultrasonic blade.

3. The apparatus of claim 2, wherein the clamp arm body and the clamp pad are each nonconductive.

4. The apparatus of claim 1, wherein the ultrasonic blade is coated with an insulative material.

5. The apparatus of claim 1, wherein the first and second conductive arms each extend from the shaft assembly.

6. The apparatus of claim 1, wherein the first and second conductive arms each extend from the ultrasonic blade.

7. The apparatus of claim 1, wherein the first and second conductive arms are each partially coated with an insulative material.

8. The apparatus of claim 7, wherein the insulative material includes polytetrafluoroethylene.

9. The apparatus of claim 7, wherein each of the first and second conductive arms includes at least one exposed surface, wherein the at least one exposed surface of each of the first and second conductive arms faces the clamp arm assembly.

10. The apparatus of claim 9, wherein the at least one exposed surface of each of the first and second conductive arms extends along a length of the respective conductive arm.

11. The apparatus of claim 9, wherein the at least one exposed surface of each of the first and second conductive arms includes a plurality of exposed surfaces spaced apart from each other in a pattern along a length of the respective conductive arm.

12. The apparatus of claim 1, wherein the first and second conductive arms are connected with an electrical source such that the first conductive arm has a first polarity and such that the second conductive arm has a second polarity opposite the first polarity.

13. The apparatus of claim 1, further comprising first and second outriggers, wherein the first and second outriggers include the first and second conductive arms, respectively.

14. The apparatus of claim 13, wherein the first and second outriggers are spaced apart from each other.

15. The apparatus of claim 13, wherein the first and second outriggers are coupled to the shaft assembly independently of each other.

16. An apparatus comprising:
(a) a body;
(b) a shaft assembly extending distally from the body, wherein the shaft assembly comprises an acoustic waveguide, wherein the acoustic waveguide is configured to communicate ultrasonic vibrations; and
(c) an end effector, wherein the end effector comprises:
(i) an electrically nonconductive ultrasonic blade in acoustic communication with the acoustic waveguide,
(ii) a nonconductive clamp arm assembly, wherein the nonconductive clamp arm assembly is pivotable toward and away from the nonconductive ultrasonic blade,
(iii) a first conductive outrigger, wherein the first conductive outrigger is spaced apart from the nonconductive ultrasonic blade and from the nonconductive clamp arm assembly, and
(iv) a second conductive outrigger, wherein the second conductive outrigger is spaced apart from each of the nonconductive ultrasonic blade, the nonconductive clamp arm assembly, and the first conductive outrigger.

17. The apparatus of claim 16, wherein the first and second conductive outriggers are connected with an electrical source such that the first conductive outrigger has a first polarity and such that the second conductive outrigger has a second polarity opposite the first polarity.

18. An apparatus comprising:
(a) an electrical source;
(b) a body;
(c) a shaft assembly extending distally from the body, wherein the shaft assembly comprises an acoustic waveguide, wherein the acoustic waveguide is configured to communicate ultrasonic vibrations; and
(d) an end effector, wherein the end effector comprises:
(i) an electrically nonconductive ultrasonic blade in acoustic communication with the acoustic waveguide,
(ii) a nonconductive clamp arm assembly, wherein the nonconductive clamp arm assembly is pivotable toward and away from the nonconductive ultrasonic blade,
(iii) a first conductive arm, wherein the first conductive arm is spaced apart from the nonconductive ultrasonic blade and from the nonconductive clamp arm assembly, wherein the first conductive arm is connected with the electrical source such that the first conductive arm has a first polarity, and
(iv) a second conductive arm, wherein the second conductive arm is spaced apart from the nonconductive ultrasonic blade and from the nonconductive clamp arm assembly, wherein the second conductive arm is connected with the electrical source such that the second conductive arm has a second polarity opposite the first polarity.

19. The apparatus of claim 18, wherein the nonconductive clamp arm assembly includes a nonconductive clamp arm body and a nonconductive clamp pad.

* * * * *